(12) United States Patent
McGovern et al.

(10) Patent No.: US 11,981,967 B2
(45) Date of Patent: May 14, 2024

(54) ENGINEERING AAV

(71) Applicant: SANGAMO THERAPEUTICS, INC., Richmond, CA (US)

(72) Inventors: Kyle McGovern, Richmond, CA (US); David S. Ojala, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 951 days.

(21) Appl. No.: 16/858,489

(22) Filed: Apr. 24, 2020

(65) Prior Publication Data

US 2020/0370137 A1  Nov. 26, 2020

Related U.S. Application Data

(60) Provisional application No. 62/939,094, filed on Nov. 22, 2019, provisional application No. 62/915,386, filed on Oct. 15, 2019, provisional application No. 62/839,421, filed on Apr. 26, 2019.

(51) Int. Cl.
| | |
|---|---|
| *C12N 15/86* | (2006.01) |
| *A61K 48/00* | (2006.01) |
| *C07K 7/08* | (2006.01) |
| *C07K 14/005* | (2006.01) |
| *C12N 7/00* | (2006.01) |
| *C12N 7/01* | (2006.01) |
| *C12Q 1/6897* | (2018.01) |
| *C40B 20/04* | (2006.01) |

(52) U.S. Cl.
CPC .............. *C12Q 1/6897* (2013.01); *C07K 7/08* (2013.01); *C12N 15/86* (2013.01); *C40B 20/04* (2013.01); *C12N 2750/14111* (2013.01); *C12Q 2563/185* (2013.01)

(58) Field of Classification Search
CPC ......... C12N 15/86; C12N 2750/14143; C12N 7/00; C12N 15/8645; C07K 14/075
See application file for complete search history.

(56) References Cited

U.S. PATENT DOCUMENTS

| | | | |
|---|---|---|---|
| 5,176,996 A | 1/1993 | Hogan | |
| 5,422,251 A | 6/1995 | Fresco | |
| 6,156,303 A | 12/2000 | Russell | |
| 8,586,526 B2 | 11/2013 | Gregory | |
| 2008/0148432 A1* | 6/2008 | Abad | C07K 14/415 435/468 |

FOREIGN PATENT DOCUMENTS

| | | |
|---|---|---|
| WO | WO1998011244 | 3/1998 |
| WO | WO1999061601 | 12/1999 |
| WO | WO2000028061 | 5/2000 |
| WO | WO2001/55320 * | 8/2001 |
| WO | WO2006/076423 * | 7/2006 |
| WO | WO2013107778 | 7/2013 |
| WO | WO2017/196432 * | 11/2017 |
| WO | WO2018/189244 | 10/2018 |

OTHER PUBLICATIONS

Adachi et al., "A segment of the Mecp2 promoter is sufficient to drive expression in neurons," Human Molecular Genetics, 14(23): 3709-3722 (2005).
Adachi et al., "Drawing a high-resolution functional map of adeno-associated virus capsid by massively parallel sequencing," Nature Communications, 5:3075 (2013) (14 pages).
Bantel-Schaal et al., "Human adeno-associated virus type 5 is only distantly related to other known primate helper-dependent parvoviruses," Journal of Virology, 73(2):939-937 (1999).
Bechtle et al., "AAV Capsids & Trafficking. 394. Rational AAV Capsid Engineering Via Peptide Insertion Reveals Critical Roles of the Underlying Vector Serotype," The American Society of Gene & Cell Therapy, 19(Supplement 1): S153 (2011).
Berens et al., "Gene regulation by tetracyclines," European Journal of Biochemistry, 270(15):3109-3121 (2003).
Buller et al., "Herpes Simplex Virus Types 1 and 2 Completely Help Adenovirus-Associated Virus Replication," Journal of Virology, 40(1):241-241 (1981).
Buning et. al., "Capsid Modifications for Targeting and Improving the Efficacy of AAV Vectors," Molecular Therapy Methods & Clinical Development, 12:248-265 (2019).
Burstein et al., "New CRISPR-Cas systems from uncultivated microbes," Nature, 542(7640):237-241 (2017).
Cebrian-Serrano et al., "CRISPR-Cas orthologues and variants: optimizing the repertoire, specificity and delivery of genome engineering tools," Mammalian Genome, 28(7-8):247-261 (2017).
Chiorini et al., "Cloning of adeno-associated virus type 4 (AAV4) and generation of recombinant AAV4 particles," Journal of Virology, 71(9):6823-6833 (1998).
Chiorini, "Cloning and characterization of adeno-associated virus type 5," Journal of Virology, 73(2):1309-1319 (1999).
Davidsson et. al., "A novel process of viral vector barcoding and library preparation enables high-diversity library generation and recombination-free paired-end sequencing," Scientific Reports. 6:37563 (2016) (18 pages).
Deverman et al., "Cre-dependent selection yields AAV variants for widespread gene transfer to the adult brain," Nature Biotechnology, 34(2):204-209 (2016).
Gao et al., "Novel adeno-associated viruses from rhesus monkeys as vectors for human gene therapy," PNAS, 99(18):11854-11859 (2002).

(Continued)

*Primary Examiner* — Barry A Chestnut
(74) *Attorney, Agent, or Firm* — Snell & Wilmer, L.L.P.; April Wurster

(57) ABSTRACT

The present disclosure provides methods and compositions to develop AAV capsids with a desired characteristic compared to a natural AAV serotype. These capsids are useful, for example, for the delivery of genome engineering molecules and gene therapy molecules for the treatment of a subject in need thereof.

20 Claims, 54 Drawing Sheets

(41 of 54 Drawing Sheet(s) Filed in Color)

Specification includes a Sequence Listing.

(56) References Cited

OTHER PUBLICATIONS

Gibson et al., "Enzymatic assembly of DNA molecules up to several hundred kilobases," Nature Methods, 6(5):343-345 (2009).

Grainger et al., "869. Infectious Titer Assay for Recombinant Adeno-Associated Virus Vectors Using Direct Cell Lysis and Endpoint Taqman PCR," Molecular Therapy, 11:S337 (2005).

Hainsworth et al., "Super-resolution imaging of subcortical white matter using stochastic optical reconstruction microscopy (STORM) and super-resolution optical fluctuation imaging (SOFI)," Neuropathology and Applied Neurobiology, 44(4): 417-426 (2018).

Han et al., "Ligand-directed retroviral targeting of human breast cancer cells," PNAS, 92(21):9747-9751 (1995).

Herrmann et. al., "A Robust and All-Inclusive Pipeline for Shuffling of Adeno-Associated Viruses," ACS Synthetic Biology, 8(1): 194-206 (2018).

Hordeaux et al., "The Neurotropic Properties of AAV-PHP.B Are Limited to C57BL/6J Mice," Molecular Therapy, 26(3):664-668 (2018).

Inaba et al., "Generation of large numbers of dendritic cells from mouse bone marrow cultures supplemented with granulocyte/macrophage colony-stimulating factor," Journal of Experimental Medicine, 176:1693-1702 (1992).

Jacobson et al., "Safety of recombinant adeno-associated virus type 2-RPE65 vector delivered by ocular subretinal injection" Molecular Therapy, 13(6): 1074-1084 (2006).

Kim et al., Highly efficient RNA-guided genome editing in human cells via delivery of purified Cas9 ribonucleoproteins, Genome Research, 24(6):1012-1019 (2014).

Kim et al., "Use of the human elongation factor 1 alpha promoter as a versatile and efficient expression system," Gene, 91(2):217-223 (1990).

Kleinstiver et al., "High-fidelity CRISPR-Cas9 nucleases with no detectable genome-wide off-target effects," Nature, 529(7587):450-455 (2016).

Korbelin et. al., "Pulmonary Targeting of Adeno-associated Viral Vectors by Next-generation Sequencing-guided Screening of Random Capsid Displayed Peptide Libraries," Molecular Therapy, 24(6):1050-1061 (2016).

Krishnaswami et al., "Using single nuclei for RNA-seq to capture the transcriptome of postmortem neurons," Nature Protocols, 11(3):499-524 (2016).

Lee et al., "GFAP promoter elements required for region-specific and asrocyte-specific expression," Glia, 56(5):481-493 (2008).

Leeuw et al., "rAAV-compatible MiniPromoters for restricted expression in the brain and eye," Molecular Brain, 9(1):52 (2016) (13 pages).

Loderio et al., "Transcription from the second heavy-strand promoter of human mtDNA is repressed by transcription factor a in vitro," PNAS, 109(17):6513-6518 (2012).

Lowes et al., "Impact of Age and Motor Function in a Phase 1/2A Study of Infants with SMA Type 1 Receiving Single-Dose Gene Replacement Therapy," Pediatric Neurology, 98:39-45 (2019).

Ma et al., "Cell-specific expression of SERCA, the exogenous Ca2+ transport ATPase, in cardiac myocytes," American Journal of Physiology Cell Physiology, 286(3):C556-564 (2004).

Ma et al., Rational Design of Mini-Cas9 for Transcriptional Activation, ACS Synthetic Biology, 7(4):978-985 (2018).

Marsic et al., "High-accuracy biodistribution analysis of adeno-associated virus variants by double barcode sequencing," Molecular Therapy-Methods & Clinical Development, 2:15041 (2015) (7 pages).

Michelfelder et al., "Peptide Ligands Incorporated into the Three-fold Spike Capsid Domain to Re-Direct Gene Transduction of AAV8 and AAV9 In Vivo," PLOS ONE. 6(8):1-11 (2011).

Miyazaki et al., "Expression vector system based on the chicken beta-actin promoter directs efficient production of interleukin-5," Gene, 79(2):269-277 (1989).

Mori et al., "Two novel adeno-associated viruses from cynomolgus monkey: pseudotyping characterization of capsid protein," Virology, 330(2):375-383 (2004).

Morton et al., "Specific Pathogen-Free Macaques: Definition, History, and Current Production," ILAR Journal, 49(2): 137-144 (2008).

Muramatsu et al., "Nucleotide sequencing and generation of an infectious clone of adeno-associated virus 3," Virology, 221(1)208-217 (1996).

Naidoo et al., "Extensive Transduction and Enhanced Spread of a Modified AAV2 Capsid in the Non-human Primate CNS," Molecular Therapy, 26(10):2418-2430 (2018).

Nance et al., "Perspective on Adeno-Associated Virus Capsid Modification for Duchenne Muscular Dystrophy Gene Therapy," Human Gene Therapy, 26(12):786-800 (2015).

Opie et al., "Identification of amino acid residues in the capsid proteins of adeno-associated virus type 2 that contribute to heparan sulfate proteoglycan binding," Journal of Virology, 77(12):6995-7006 (2003).

Rudeck et al., "A compact unc45b-Promoter Drives Muscle-Specific Expression in Zebrafish and Mouse," Genesis, 54: 431-438 (2016).

Shade et al., "Nucleotide sequence and genome organization of human parvovirus B19 isolated from the serum of a child during aplastic crisis," 58(3):921-936 (1986).

Sheng et al., "Structure-based cleavage mechanism of Thermus thermophilus Argonaute DNA guide strand-mediated DNA target cleavage," PNAS, 111(2): 652-657 (2013).

Singer-Sam et al., "Sequence of the promoter region of the gene for human X-linked 3-phosphoglycerate kinase," Gene, 32(3):409-417 (1984).

Smith et al., "A Simplified Baculovirus-AAV Expression Vector System Coupled with One-step Affinity Purification Yields High-titer rAAV Stocks From Insect Cells," Molecular Therapy, 17(11):1888-1896 (2009).

Srivastava et al., "Nucleotide sequence and organization of the adeno-associated virus 2 genome," Journal of Virology, 45(2):555-564 (1983).

Stinski et al., "Activation of the major immediate early gene of human cytomegalovirus by cis-acting elements in the promoter-regulatory sequence and by virus-specific trans-acting components," Journal of Virology, 55(2):431-441 (1985).

Troung et al., "Development of an intein-mediated split-Cas9 system for gene therapy," Nucleic Acids Research, 43(13):6450-6458 (2015).

Wei et al., "Cloning and characterization of the rat myelin basic protein gene promoter," Gene, 313:161-167 (2003).

Wulff et al., "Partial processing of the neuropeptide Y precursor in transfected CHO cells," FEBS Letters, 261(1): 101-105 (1990).

Xiao et al., "Production of High-Titer Adeno-Associated Virus Vectors in the Absence of Helper Adenovirus," Journal of Virology, 72(3):2224-2232 (1998).

Xiao et al., "Gene therapy vectors based on adeno-associated virus type 1," Journal of Virology, 73(5):3994-4003 (1999).

Yin et al., "Therapeutic genome editing by combined viral and non-viral delivery of CRISPR system components in vivo," Nature Biotechnology, 34(3):328-333 (2016).

Zetsche et al., "A split-Cas9 architecture for inducible genome editing and transcription modulation," Nature Biotechnology, 33(2):139-142 (2015).

Zheng et al., "Evaluation of Promoters for Use in Tissue-Specific Gene Delivery," Methods in Molecular Biology, 434(2):205-219 (2008).

Zolotukhin et al., "Recombinant adeno-associated virus purification using novel methods improves infectious titer and yield," Gene Therapy, 6(6):972-985 (1999).

* cited by examiner

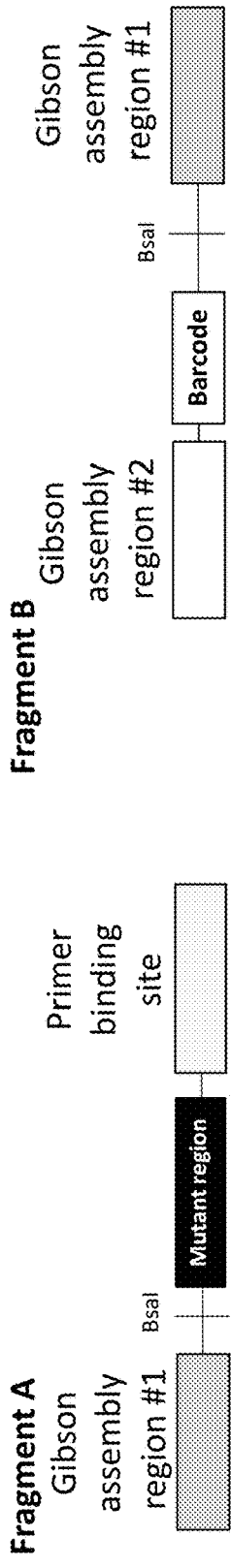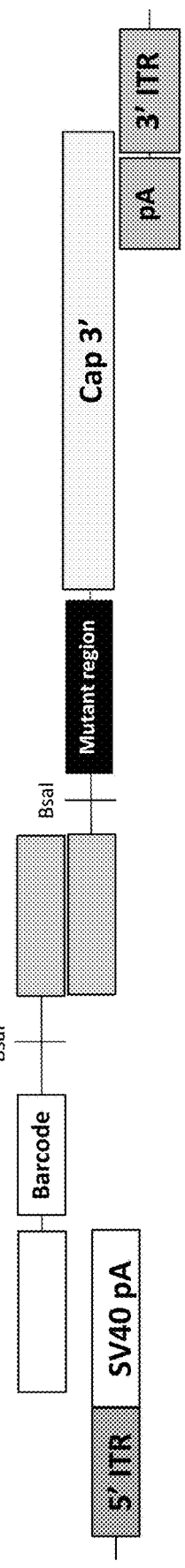
FIG. 4C

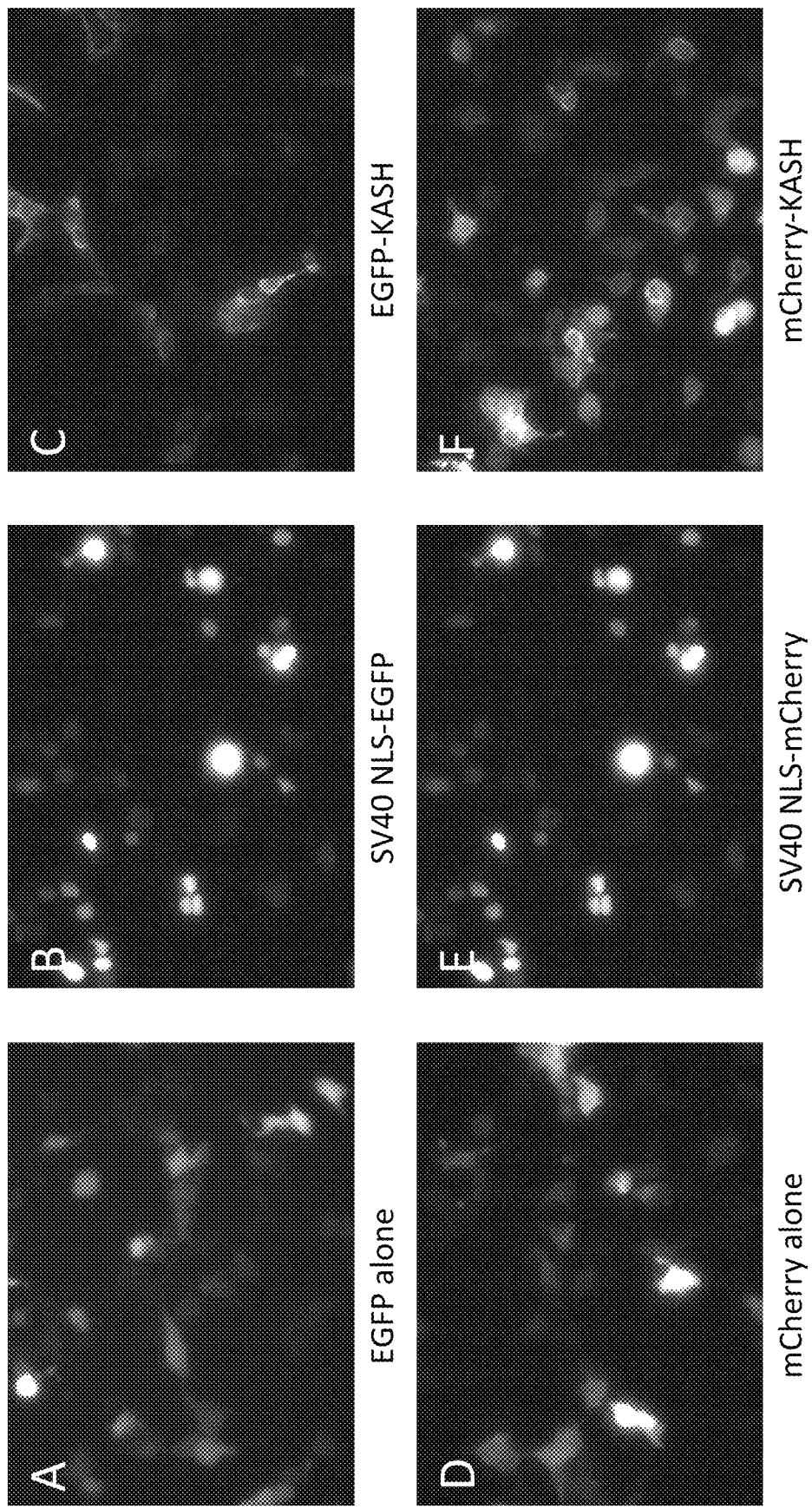

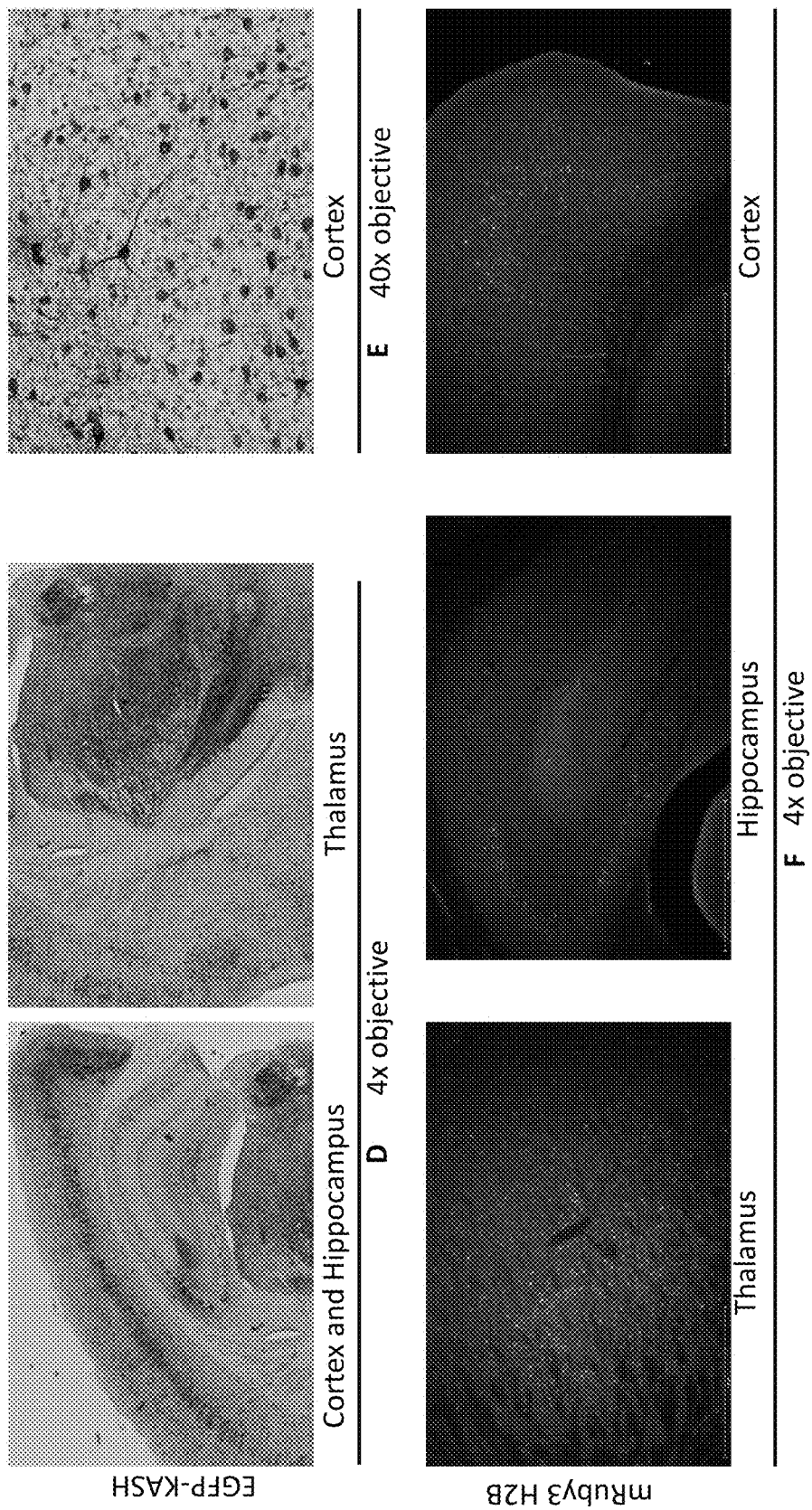

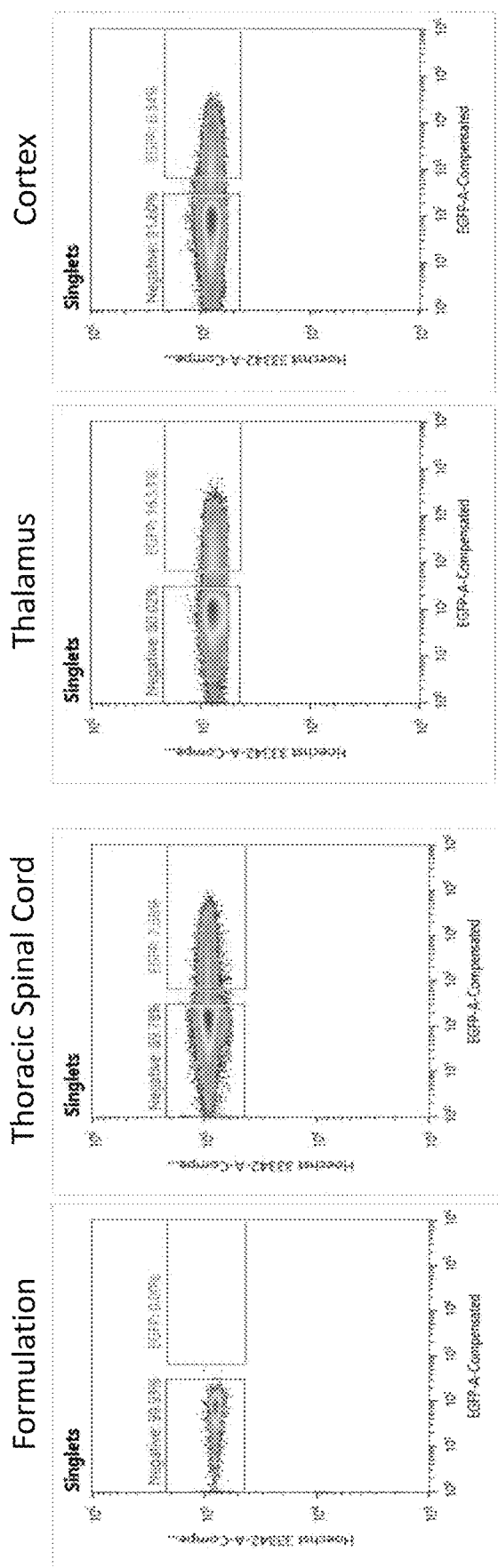
FIG. 11 EGFP-H2B positive nuclei

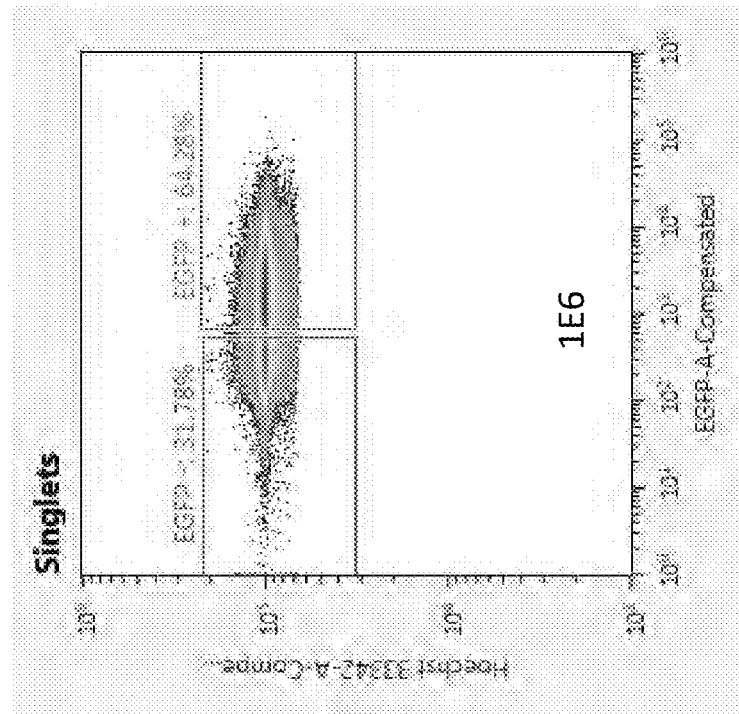
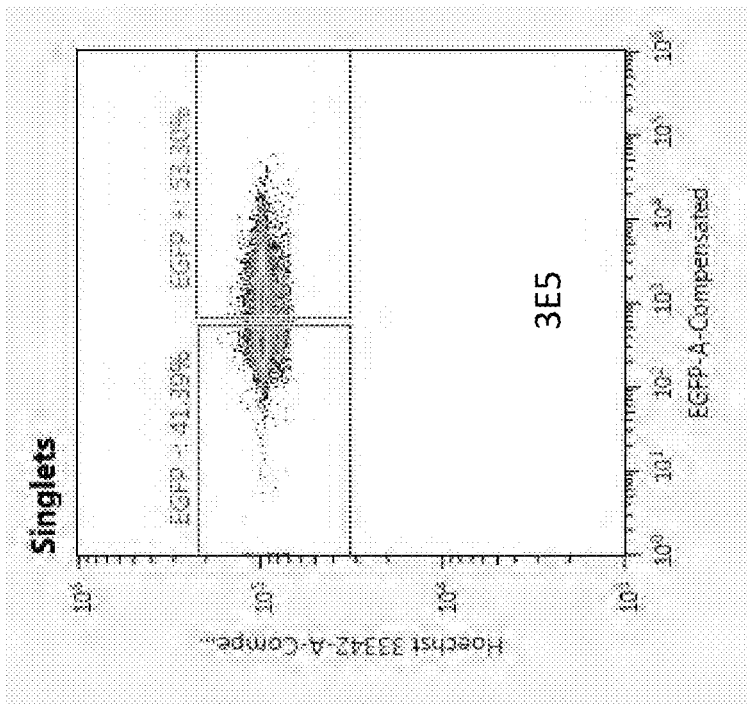
FIG. 15C

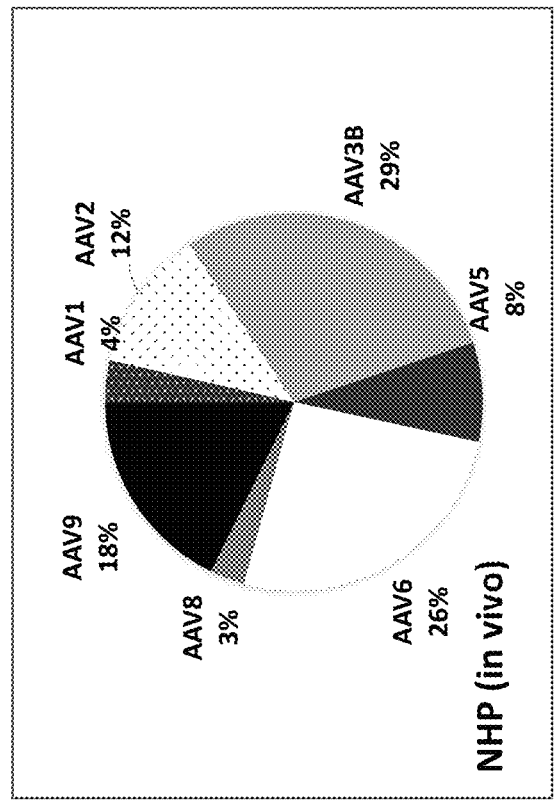
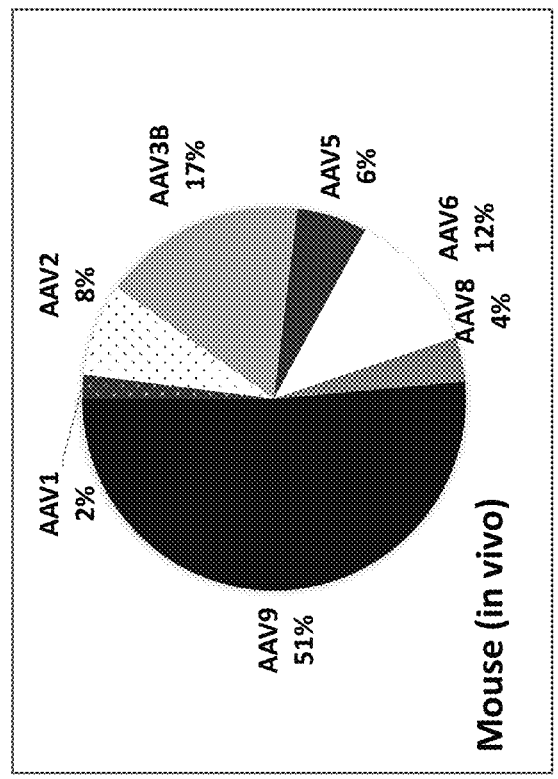
FIG. 17B

FIG. 29A

| Peptide | Parent Serotype | Neuro2A | Primary Mouse Neurons | Human iPSC Neurons | C57BL/6J Mouse (ICV) | NHP AD Regions (DNA) | NHP PSP Regions (DNA) | NHP Spinal Cord (DNA) | NHP AD Regions (RNA) | NHP PSP Regions (RNA) | NHP Spinal Cord (RNA) |
|---|---|---|---|---|---|---|---|---|---|---|---|
| 1. AALRQIR | AAV1 | ● | ● | ● | ● | ● | ● | ● | ● | ● | ● |
| 2. PAIKTYS | AAV1 | ● | ● | ● | ● | ● | ● | ● | ● | ● | ● |
| 3. TQDRISSRTL | AAV1 | ● | ● | ● | ● | ● | ● | ● | ● | ● | ● |
| 4. SVVVSGSSKRPRML | AAV1 | ● | ● | ● | ● | ● | ● | ● | ● | ● | ● |
| 5. VGARLSA | AAV1 | ● | ● | ● | ● | ● | ● | ● | ● | ● | ● |
| 6. IEKPHTSTKK | AAV1 | ● | ● | ● | ● | ● | ● | ● | ● | ● | ● |
| 7. DTVRSKN | AAV1 | ● | ● | ● | ● | ● | ● | ● | ● | ● | ● |
| 8. KELNKAR | AAV1 | ● | ● | ● | ● | ● | ● | ● | ● | ● | ● |
| 9. PVASITG | AAV9 | ● | ● | ● | ● | ● | ● | ● | ● | ● | ● |
| 10. TGAFSST | AAV9 | ● | ● | ● | ● | ● | ● | ● | ● | ● | ● |
| 11. EQFRNLA | AAV9 | ● | ● | ● | ● | ● | ● | ● | ● | ● | ● |
| 12. FNSPVIQ | AAV9 | ● | ● | ● | ○ | ● | ○ | ● | ● | ○ | ● |
| 13. TDFRSPQ | AAV9 | ● | ● | ● | ○ | ● | ● | ● | ● | ● | ● |
| 14. MYSLMED | AAV9 | ● | ● | ● | ○ | ● | ● | ● | ● | ● | ● |

| Peptide | Parent Serotype | Neuro2A | Primary Mouse Neurons | Human iPSC Neurons | C57BL/6J Mouse (ICV) | NHP AD Regions (DNA) | NHP PSP Regions (DNA) | NHP Spinal Cord (DNA) | NHP AD Regions (RNA) | NHP PSP Regions (RNA) | NHP Spinal Cord (RNA) |
|---|---|---|---|---|---|---|---|---|---|---|---|
| 28 PLRNPHE | AAV2 | ● | ● | ● | ● | ● | ● | ● | ● | ● | ● |
| 29 DVGIRPS | AAV2 | ● | ● | ● | ● | ● | ● | ● | ● | ● | ● |
| 30 KDSTAFG | AAV2 | ● | ● | ● | ● | ● | ● | ● | ● | ● | ● |
| 31 YPGRNPD | AAV2 | ● | ● | ● | ● | ● | ● | ● | ● | ● | ● |
| 32 ISGTRIS | AAV2 | ● | ● | ● | ● | ● | ● | ● | ● | ● | ● |
| 33 ENFSKVA | AAV2 | ● | ● | ● | ● | ● | ● | ● | ● | ● | ● |
| 34 RDALGGLRPE | AAV2 | ● | ● | ● | ● | ● | ● | ● | ● | ● | ● |
| 35 LGNGKMTVQP | AAV2 | ● | ● | ● | ● | ● | ● | ● | ● | ● | ● |
| 36 VSMPLNQ | AAV2 | ● | ● | ● | ● | ● | ● | ● | ● | ● | ● |
| 37 LNERGLG | AAV2 | ● | ● | ● | ● | ● | ● | ● | ● | ● | ● |
| 38 GRMTVGLSSA | AAV2 | ● | ● | ● | ● | ● | ● | ● | ● | ● | ● |
| 39 VGHAGMP | AAV2 | ● | ● | ● | ● | ● | ● | ● | ● | ● | ● |
| 40 SRAGTVP | AAV2 | ● | ● | ● | ● | ● | ● | ● | ● | ● | ● |

SEQUENCE LISTING

```
<160> NUMBER OF SEQ ID NOS: 212

<210> SEQ ID NO 1
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Lys Ser Pro Gln Ser Lys Val
1               5

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2
```

Ser Asp Leu Arg Ser Lys Val
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Thr Thr Val Arg Lys Val
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Arg Ser Asp Met Ala Gly
1               5

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Leu Leu Ser Ser Glu Arg Ser
1               5

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Gln Arg Pro Asn Val Ser
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Thr Arg Gln Ile Ser Ser Asp
1               5

```
<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Gly Ala Leu Ala Gln Val
1               5

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Tyr Pro Ser Ser Asn Thr Pro
1               5

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Met Leu Asn Pro Arg Thr Glu
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln Met Arg Thr Arg Asp Glu
1               5

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Met Pro Gly Arg Ala Pro Ile
1               5

<210> SEQ ID NO 13
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Leu Gly Arg Leu Thr Ala Asn
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Ser Thr Ser Arg Ser
1               5

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Thr Arg Pro Ser Ser Thr Asn
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Val Pro Gln Ser Ser Ser Arg
1               5

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Val Ser Arg Ser Tyr Pro Ala
1               5

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                        Synthetic peptide"

<400> SEQUENCE: 18

Gln Arg Ala Arg Pro Asp Thr
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 19

Ser Gln Leu Thr Pro His Ser
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 20

Leu Gly Ser His Leu Pro Ser
1               5

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 21

Tyr Thr Leu Ser Ser Gly Gln
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 22

Ser Ser Arg Ile Pro Pro Asp
1               5

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 23
```

Trp Thr Glu Thr Ile Pro Arg
1               5

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

His Gly Leu Gln Gly Val Ala
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Thr Met Arg Val Ser Asp Gln
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Ser Ser Lys Val Val Met
1               5

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser Ala Leu Asp Arg Gly Val
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Lys Glu Leu Gly Thr Gln Arg
1               5

```
<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Ser Ser Asp Val Gln Arg
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Pro Ser Ala Pro Lys Thr Phe
1               5

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

His Thr Lys Arg Ser Glu Tyr
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ile Lys Gly Ser Asn Leu Pro
1               5

<210> SEQ ID NO 33
<211> LENGTH: 19
<212> TYPE: DNA
<213> ORGANISM: Adeno-associated virus

<400> SEQUENCE: 33
taaccctgtg gccaccgaa                                            19

<210> SEQ ID NO 34
<211> LENGTH: 21
<212> TYPE: DNA
<213> ORGANISM: Adeno-associated virus

<400> SEQUENCE: 34
gacgtgtacc tgcagggtcc c                                         21
```

```
<210> SEQ ID NO 35
<211> LENGTH: 19
<212> TYPE: DNA
<213> ORGANISM: Adeno-associated virus

<400> SEQUENCE: 35
caatcccgtg gctacggag                                                        19

<210> SEQ ID NO 36
<211> LENGTH: 21
<212> TYPE: DNA
<213> ORGANISM: Adeno-associated virus

<400> SEQUENCE: 36
gatgtgtacc ttcaggggcc c                                                     21

<210> SEQ ID NO 37
<211> LENGTH: 19
<212> TYPE: DNA
<213> ORGANISM: Adeno-associated virus

<400> SEQUENCE: 37
caatcctgtg gcaacagag                                                        19

<210> SEQ ID NO 38
<211> LENGTH: 21
<212> TYPE: DNA
<213> ORGANISM: Adeno-associated virus

<400> SEQUENCE: 38
gacgtgtacc ttcaaggacc t                                                     21

<210> SEQ ID NO 39
<211> LENGTH: 19
<212> TYPE: DNA
<213> ORGANISM: Adeno-associated virus

<400> SEQUENCE: 39
taaccccgtg gccaccgaa                                                        19

<210> SEQ ID NO 40
<211> LENGTH: 21
<212> TYPE: DNA
<213> ORGANISM: Adeno-associated virus

<400> SEQUENCE: 40
gacgtatacc tgcagggtcc t                                                     21

<210> SEQ ID NO 41
<211> LENGTH: 19
<212> TYPE: DNA
<213> ORGANISM: Adeno-associated virus

<400> SEQUENCE: 41
taaccctgtg gctacagag                                                        19

<210> SEQ ID NO 42
<211> LENGTH: 21
<212> TYPE: DNA
<213> ORGANISM: Adeno-associated virus

<400> SEQUENCE: 42
gacgtgtacc tgcagggtcc c                                                     21
```

<210> SEQ ID NO 43
<211> LENGTH: 19
<212> TYPE: DNA
<213> ORGANISM: Adeno-associated virus

<400> SEQUENCE: 43
taacccggta gcaacggag                                                  19

<210> SEQ ID NO 44
<211> LENGTH: 21
<212> TYPE: DNA
<213> ORGANISM: Adeno-associated virus

<400> SEQUENCE: 44
gatgtgtacc tgcaaggacc c                                               21

<210> SEQ ID NO 45
<211> LENGTH: 2211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
atggctgccg atggttatct tccagattgg ctcgaggaca acctctctga gggcattcgc      60
gagtggtggg acttgaaacc tggagccccg aagcccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac     240
cagcagctca agcgggtga caatccgtac ctgcggtata accacgccga cgccgagttt     300
caggagcgtc tgcaagaaga tacgtctttt ggggggcaacc tcgggcgagc agtcttccag     360
gccaagaagc gggttctcga acctctcggt ctggttgagg aaggcgctaa gacggctcct     420
ggaaagaaac gtccggtaga gcagtcgcca aagagccag actcctcctc gggcatcggc     480
aagacaggcc agcagcccgc taaaaagaga ctcaattttg gtcagactgg cgactcagag     540
tcagtccccg atccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgcacctg gccttgccc acctacaata accacctcta aagcaaatc     780 tccagtgctt caacgggggc cagcaacgac aaccactact cggctacag caccccctgg     840 gggtattttg atttcaacag attccactgc cacttttcac cacgtgactg gcagcgactc     900
atcaacaaca ttggggatt ccggcccaag agactcaact tcaaactctt caacatccaa     960
gtcaaggagg tcacgacgaa tgatggcgtc acaaccatcg ctaataacct taccagcacg    1020
gttcaagtct tctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg cagccaagc cgtgggacgt tcatcctttt actgcctgga atatttccct    1200
tctcagatgc tgagaacggg caacaacttt accttcagct acacctttga ggaagtgcct    1260
ttccacagca gctacgcgca cagccagagc ctggaccggc tgatgaatcc tctcatcgac    1320
cagtacctgt attacctgaa cagaactcaa aatcagtccg aagtgccca aaacaaggac    1380

| | |
|---|---|
| ttgctgttta gccgtggatc tccagctggc atgtctgttc agcccaaaaa ctggctacct | 1440 |
| ggaccctgtt accggcagca gcgcgtttct aaaacaaaaa cagacaacaa caacagcaat | 1500 |
| tttacctgga ctggtgcttc aaaatataac ctcaatgggc gtgaatccat catcaaccct | 1560 |
| ggcactgcta tggcctcaca caaagacgac gaagacaagt tctttcccat gagcggtgtc | 1620 |
| atgattttg gaaagagag cgccggagct tcaaacactg cattggacaa tgtcatgatt | 1680 |
| acagacgaag aggaaattaa agccactaac cccgtggcca ccgaaagatt tgggaccgtg | 1740 |
| gcagtcaatt tccagagcag cagcacagac cctgcgaccg gagatgtgca tgctatggga | 1800 |
| gcattacctg gcatggtgtg gcaagataga gacgtatacc tgcagggtcc tatttgggcc | 1860 |
| aaaattcctc acacagatgg acactttcac ccgtctcctc ttatgggcgg ctttggactc | 1920 |
| aagaacccgc ctcctcagat cctcatcaaa aacacgcctg ttcctgcgaa tcctccggcg | 1980 |
| gagttttcag ctacaaagtt tgcttcattc atcacccaat actccacagg acaagtgagc | 2040 |
| gtggagattg aatgggagct gcagaaagaa acagcaagc gctggaatcc gaagtgcag | 2100 |
| tacacatcca attatgcaaa atctgccaac gttgatttta ctgtggacaa caatggactt | 2160 |
| tatactgagc ctcgccccat tggcacccgt taccttaccc gtccctgta a | 2211 |

<210> SEQ ID NO 46
<211> LENGTH: 2208
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 46

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa agcctacgac | 240 |
| cggcagctcg acagcggaga caacccgtac ctcaagtaca accacgccga cgcggagttt | 300 |
| caggagcgcc ttaaagaaga tacgtctttt ggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ctcaattttg gtcagactgg cgacgcagac | 540 |
| tcagtacctg accccagcc tctcggacag ccaccagcag cccctctg tctgggaact | 600 |
| aatacgatgg ctacaggcag tggcgcacca atggcagaca taacgagggg cgccgacgga | 660 |
| gtgggtaatt cctcgggaaa ttggcattgc gattccacat ggatgggcga cagagtcatc | 720 |
| accaccagca cccgaacctg ggcctgccc acctacaaca accacctcta caaacaaatt | 780 |
| tccagccaat caggagcctc gaacgacaat cactactttg gctacagcac cccctggggg | 840 |
| tattttgatt tcaacagatt ccactgccac ttttcaccac gtgactggca agactcatc | 900 |
| aacaacaact ggggattccg acccaagaga ctcaacttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaaggc | 1080 |
| tgcctccctc cgttcccggc ggacgtcttc atggtgccac agtatggata cctcaccctg | 1140 |
| aacaacggga gtcaggcagt aggacgctct tcattttact gcctggagta ctttccttct | 1200 |

-continued

```
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acctgagcag aacaaacact ccaagtggaa ccaccacgca gtcaaggctt    1380
cagttttctc aggccggagc gagtgacatt cgggaccagt ctaggaactg gcttcctgga    1440
ccctgttacc ggcagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt ttcctcagag cggggttctc    1620
atctttggga agcaaggctc agagaaaaca aatgtgggaca ttgaaaaggt catgattaca    1680
gacgaagagg aaatcaggac aactaaccccc gtggccaccg aacagtatgg ttctgtatct    1740
accaacctcc agagaggcaa cagacaagca gctaccgcag atgtcaacac acaaggcgtt    1800
cttccaggca tggtctggca ggacagagac gtatacctgc agggtcctat ttgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagattgaat gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 47
<211> LENGTH: 2211
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
atggctgctg acggttatct tccagattgg ctcgaggaca accttctga aggcattcgt     60
gagtggtggg ctctgaaacc tggagtccct caacccaaag cgaaccaaca acaccaggac    120
aaccgtcggg gtcttgtgct tccgggttac aaatacctcg acccggtaa cggactcgac    180
aaaggagagc cggtcaacga ggcggacgcg gcagccctcg aacacgacaa agcctacgac    240
cagcagctca aggccggtga caacccgtac ctcaagtaca ccacgccga cgccgagttt    300
caggagcgtc ttcaagaaga tacgtctttt gggggcaacc ttggcagagc agtcttccag    360
gccaaaaaga ggatccttga gcctcttggt ctggttgagg aagcagctaa acggctcct    420
ggaaagaaga ggcctgtaga tcagtctcct caggaaccgg actcatcatc tggtgttggc    480
aaatcgggca acagcctgc cagaaaaaga ctcaattttg gtcagactgg cgactcagag    540
tcagtcccag accctcaacc tctcggagaa ccaccagcag cccccacaag tttgggatct    600
aatacaatgg cttcaggcgg tggcgcacca atggcagaca ataacgaggg tgccgatgga    660
gtgggtaatt cctcaggaaa ttggcattgc gattcccaat ggctgggcga cagagtcatc    720
accaccagca cccgaacctg ggccctgccc acttacaaca accatctcta caagcaaatc    780
tccagccaat caggagcttc aaacgacaac cactactttg gctacagcac ccctgggggg    840
tattttgatt tcaacagatt ccactgccac ttctcaccac gtgactggca gcgactcatt    900
aacaacaact ggggattccg gcccaagaaa ctcagcttca gctcttcaa catccaagtt    960
```

```
aaagaggtca cgcagaacga tggcacgacg actattgcca ataaccttac cagcacggtt    1020
caagtgttta cggactcgga gtatcagctc ccgtacgtgc tcgggtcggc gcaccaaggc    1080
tgcctccctc cgttcccggc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtaccttt    1260 cacagcagct acgctcacag ccagagtttg gatcgcttga tgaatcctct catcgaccag    1320
tacctgtatt acctgaacag aacgcaagga acaacctctg gaacaaccaa ccaatcacgg    1380
ctgcttttta gccaggctgg gcctcagtct atgtctttgc aggccagaaa ttggctacct    1440
ggaccctgtt accggcagca gagactttca agactgctac acgacaacaa caacagtaac    1500
tttccttgga cagcgccag caaatatcat ctcaatggcc gcgactcgct ggtgaatcca    1560
ggaccagcta tggccagtca caggacgat gaagaaaaat ttttccctat gcacggcaat    1620
ctaatatttg gcaaagaagg acaacggca agtaacgcag aattagataa tgtaatgatt    1680
acggatgaag aagagattcg taccactaac cccgtggcca ccgaacagta tggaactgtg    1740
gcaaataact tgcagagctc aaatacagct cccacgacta gaactgtcaa tgatcagggg    1800
gccttacctg gcatggtgtg gcaagatcgt gacgtatacc tgcagggtcc tatttgggca    1860
aagattcctc acacggatgg acactttcat ccttctcctc tgatgggagg ctttggactg    1920
aaacatccgc ctcctcaaat catgatcaaa atactccgg taccggcaaa tcctccgacg    1980
actttcagcc cggccaagtt tgcttcattt atcactcagt actccactgg acaggtcagc    2040
gtggagattg aatgggagct gcagaaagaa acagcaaac gttggaatcc agagattcag    2100
tacacttcca actacaacaa gtctgttaat gtggacttta ctgtagacac taatggtgtt    2160
tatagtgaac ctcgccctat tggaacccgg tatctcacac gaaacttgtg a             2211
```

<210> SEQ ID NO 48
<211> LENGTH: 2175
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
atgtcttttg ttgatcaccc tccagattgg ttggaagaag ttggtgaagg tcttcgcgag     60
tttttgggcc ttgaagcggg cccaccgaaa ccaaaaccca atcagcagca tcaagatcaa    120
gcccgtggtc ttgtgctgcc tggttataac tatctcggac ccggaaacgg actcgatcga    180
ggagagcctg tcaacagggc agacgaggtc gcgcgagagc acgacatctc gtacaacgag    240
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgaagagg tgctaagac ggcccctacc    420 ggaaagcgga tagacgacca ctttccaaaa agaaagaagg ctcggaccga gaggactcc     480 aagccttcca cctcgtcaga cgccgaagct ggacccagcg atcccagca gctgcaaatc    540 ccagcccaac cagcctcaag tttgggagct gatacaatgt ctgcgggagg tggcggccca    600
ttgggcgaca ataaccaagg tgccgatgga gtggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
```

```
aacgcctact ttggatacag cacccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggggcgca ctttcaccccc   1860 tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccgac ctatcggaac ccgatacctt   2160
acccgacccc tttaa                                                    2175
```

<210> SEQ ID NO 49
<211> LENGTH: 2211
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49

```
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg acccttcaa cggactcgac    180 aagggggagc ccgtcaacgc ggcggatgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaaga gggttctcga acctttggt ctggttgagg aaggtgctaa gacggctcct    420
ggaaagaaac gtccggtaga gcagtcgcca aagagccag actcctcctc gggcattggc    480
aagacaggcc agcagcccgc taaaaagaga ctcaattttg gtcagactgg cgactcagag    540
```

-continued

| | |
|---|---|
| tcagtccccg acccacaacc tctcggagaa cctccagcaa ccccgctgc tgtgggacct | 600 |
| actacaatgg cttcaggcgg tggcgcacca atggcagaca ataacgaagg cgccgacgga | 660 |
| gtgggtaatg cctcaggaaa ttggcattgc gattccacat ggctgggcga cagagtcatc | 720 |
| accaccagca cccgaacatg gccttgccc acctataaca accacctcta caagcaaatc | 780 |
| tccagtgctt caacgggggc cagcaacgac aaccactact tcggctacag caccccctgg | 840 |
| gggtattttg atttcaacag attccactgc catttctcac cacgtgactg gcagcgactc | 900 |
| atcaacaaca attggggatt ccggcccaag agactcaact tcaagctctt caacatccaa | 960 |
| gtcaaggagg tcacgacgaa tgatggcgtc acgaccatcg ctaataacct taccagcacg | 1020 |
| gttcaagtct ctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |
| ctcaacaatg gcagccaggc agtgggacgg tcatcctttt actgcctgga atatttccca | 1200 |
| tcgcagatgc tgagaacggg caataacttt accttcagct acaccttcga ggacgtgcct | 1260 |
| ttccacagca gctacgcgca cagccagagc ctggaccggc tgatgaatcc tctcatcgac | 1320 |
| cagtacctgt attacctgaa cagaactcag aatcagtccg gaagtgccca aaacaaggac | 1380 |
| ttgctgttta gccggggctc tccagctggc atgtctgttc agcccaaaaa ctggctacct | 1440 |
| ggaccctgtt accggcagca gcgcgttcct aaaacaaaaa cagacaacaa caacagcaac | 1500 |
| tttacctgga ctggtgcttc aaaatataac cttaatgggc gtgaatctat aatcaaccct | 1560 |
| ggcactgcta tggcctcaca caaagacgac aaagacaagt tctttcccat gagcggtgtc | 1620 |
| atgattttg gaaggagag cgccggagct tcaaacactg cattggacaa tgtcatgatc | 1680 |
| acagacgaag aggaaatcaa agccactaac cccgtggcca ccgaaagatt tgggactgtg | 1740 |
| gcagtcaatc tccagagcag cagcacagac cctgcgaccg gagatgtgca tgttatggga | 1800 |
| gccttacctg gaatggtgtg gcaagacaga gacgtatacc tgcagggtcc tatttgggcc | 1860 |
| aaaattcctc acacggatgg acactttcac ccgtctcctc tcatgggcgg ctttggactt | 1920 |
| aagcacccgc ctcctcagat cctcatcaaa acacgcctg ttcctgcgaa tcctccggca | 1980 |
| gagttttcgg ctacaaagtt tgcttcattc atcacccagt attccacagg acaagtgagc | 2040 |
| gtggagattg aatgggagct gcagaaagaa aacagcaaac gctggaatcc cgaagtgcag | 2100 |
| tatacatctg actatgcaaa atctgccaac gttgatttca ctgtggacaa caatggactt | 2160 |
| tatactgagc ctcgccccat ggcacccgt tacctcaccc gtccctgta a | 2211 |

<210> SEQ ID NO 50
<211> LENGTH: 2217
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtaccctc gacccttcaa cggactcgac | 180 |
| aagggggagc ccgtcaacgc ggcggacgca gcggccctcg agcacgacaa ggcctacgac | 240 |
| cagcagctgc aggcgggtga caatccgtac ctgcggtata accacgccga cgccgagttt | 300 |
| caggagcgtc tgcaagaaga tacgtctttt ggggggcaacc tcgggcgagc agtcttccag | 360 |

```
gccaagaagc gggttctcga acctctcggt ctggttgagg aaggcgctaa gacggctcct    420
ggaaagaaga ggccggtaga gccatcaccc cagcgttctc cagactcctc tacgggcatc    480
ggcaagaaag ccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca caaccaccct ctacaagcaa    780
atctccaacg ggacatcggg aggagccacc aacgacaaca cctacttcgg ctacagcacc    840
ccctgggggt attttgattt caacagattc cactgccact tttcaccacg tgactggcag    900
cgactcatca caacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctccctcc gttcccggcg gacgtgttca tgattcccca gtacggctac   1140
ctaacactca caacggtag tcaggccgtg gacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctc   1320
atcgaccagt acctgtatta cctgtctcgg actcaaacaa caggaggcac ggcaaatacg   1380
cagactctgg gcttcagcca aggtgggcct aatacaatgg ccaatcaggc aaagaactgg   1440
ctgcctggac cctgttaccg gcagcagcgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgttttt tcccagtaac   1620 gggatcctga ttttggcaa acaaaatgct gccagagaca atgcggatta cagcgatgtc   1680
atgctcacca gcgaggaaga aatcaaaacc actaaccccg tggccaccga agaatacggt   1740
atcgtggcag ataacttgca gcagcaaaac acggctcctc aaattggaac tgtcaacagc   1800 caggggggcct tacccggtat ggtctggcag aaccgggacg tatacctgca gggtcctatt   1860
tgggccaaga ttcctcacac ggacggcaac ttccaccccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg agattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc accgttacc tcacccgtaa tctgtaa     2217
```

<210> SEQ ID NO 51
<211> LENGTH: 2211
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
atggctgccg atggttatct tccagattgg ctcgaggaca accttagtga aggaattcgc     60
gagtggtggg ctttgaaacc tggagcccct caacccaagg caaatcaaca acatcaagac    120
```

```
aacgctcgag gtcttgtgct tccgggttac aaataccttg gacccggcaa cggactcgac      180 aaggggagc cggtcaacgc agcagacgcg gcggccctcg agcacgacaa ggcctacgac       240
cagcagctca aggccggaga caacccgtac ctcaagtaca accacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaattttg gtcagactgg cgacacagag   540
tcagtcccag accctcaacc aatcggagaa cctcccgcag cccccctcagg tgtgggatct    600 cttacaatgg cttcaggtgg tggcgcacca gtggcagaca ataacgaagg tgccgatgga   660
gtgggtagtt cctcgggaaa ttggcattgc gattcccaat ggctgggcga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc  840
tgggggtatt ttgatttcaa cagattccac tgccatttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac  1080
gagggctgcc tccctccgtt cccggcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccagtacc tgtattacct gtcaaagact attaacggtt ctggacagaa tcaacaaacg  1380
ctaaaattca gtgtggccgg acccagcaac atggctgtcc agggaagaaa ctacatacct  1440
ggaccctgtt accggcagca gcgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttcctt gtctggatct    1620 ttaattttg gcaaacaagg aactggaaga gacaacgtgg atgcggacaa agtcatgata  1680
accaacgaag aagaaattaa aactactaac cccgtggcca ccgaatccta tggacaagtg  1740
gccacaaacc accagagtgc ccaagcacag gcgcagaccg gctgggttca aaaccaagga  1800
atacttccgg gtatggtttg gcaggacaga gacgtatacc tgcagggtcc tatttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagattg aatgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a             2211
```

<210> SEQ ID NO 52
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<220> FEATURE:
<221> NAME/KEY: modified_base
<222> LOCATION: (21)..(24)
<223> OTHER INFORMATION: a, c, t, g, unknown or other

<400> SEQUENCE: 52
acacgacgct cttccgatct nnnnagagtc atcaccacca gcacc                45

<210> SEQ ID NO 53
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 53
gacgtgtgct cttccgatct nnnngaaatc aaaataccccc caggg               45

<210> SEQ ID NO 54
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 54
acacgacgct cttccgatct nnnnatcgac cagtacctgt attacctg              48

<210> SEQ ID NO 55
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 55
gacgtgtgct cttccgatct nnnntgccgg taacagggtc cag                   43

<210> SEQ ID NO 56
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 56
acacgacgct cttccgatct nnnntaaccc cgtggccacc gaa         43

<210> SEQ ID NO 57
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 57
gacgtgtgct cttccgatct nnnnaggacc ctgcaggtat acgtct      46

<210> SEQ ID NO 58
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 58
acacgacgct cttccgatct nnnngtgaac cgcgtggcgt acaac       45

<210> SEQ ID NO 59
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 59
gacgtgtgct cttccgatct nnnngggtcc ttggaggtac acgtcc      46

<210> SEQ ID NO 60
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
gtactctaga gtcctgtatt agaggtcacg tga                    33

<210> SEQ ID NO 61
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
tgctgcatgc tgtaccgaat taacatgttt attggtacga tcagagagag tgtcctcgag    60
c    61

<210> SEQ ID NO 62
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
accccgccat ggtggctgcg cgtt    24

<210> SEQ ID NO 63
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
aacgcgcagc caccatggcg gggt    24

<210> SEQ ID NO 64
<211> LENGTH: 7
<212> TYPE: PRT
<213> ORGANISM: Simian virus 40

<400> SEQUENCE: 64

Pro Lys Lys Lys Arg Lys Val
1               5

<210> SEQ ID NO 65
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
ggttacaaat aaagcaatag catcac    26

<210> SEQ ID NO 66
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 66
acacgacgct cttccgatct nnnngcatca caaatttcac aaataaagc    49

```
<210> SEQ ID NO 67
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(24)
<223> OTHER INFORMATION: a, c, t, g, unknown or other

<400> SEQUENCE: 67
gacgtgtgct cttccgatct nnnngccgtg tccgagggta ctaag           45

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Ala Leu Arg Asp Ile Arg
1               5

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Pro Ala Ile Lys Thr Tyr Ser
1               5

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Thr Gly Asp Arg Ile Ser Ser Arg Thr Leu
1               5                   10

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ser Val Val Val Ser Ser Asp Ser Ser Lys Arg Pro Arg Asn Leu
1               5                   10                  15

<210> SEQ ID NO 72
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Val Gly Ala Arg Leu Ser Ala
1               5

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ile Glu Lys Pro Asn Thr Ser Thr Lys Lys
1               5                   10

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Thr Val Arg Ser Lys Asn
1               5

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Lys Glu Leu Asn Lys Ala Arg
1               5

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Pro Tyr Ala Ser Ile Thr Gly
1               5

<210> SEQ ID NO 77
<211> LENGTH: 7
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 77

Thr Gly Ala Phe Ser Ser Thr
1               5

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Glu Gln Phe Arg Asn Leu Ala
1               5

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Phe Asn Ser Pro Val Ile Gln
1               5

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Thr Asp Phe Arg Ser Pro Gln
1               5

<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Met Tyr Ser Leu Met Lys Asp
1               5

<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 82

Leu Tyr Leu Ser Ser Ala Ser
1               5

<210> SEQ ID NO 83
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Tyr Gly Ser Arg Ser Val Asp
1               5

<210> SEQ ID NO 84
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Leu Tyr Ser His Gln Val Ser
1               5

<210> SEQ ID NO 85
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Ile Ser Thr His Ser Pro Pro
1               5

<210> SEQ ID NO 86
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Arg Gln Pro Thr Thr Ile Pro
1               5

<210> SEQ ID NO 87
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg Ser Thr Ser Ser Leu Leu
1               5
```

```
<210> SEQ ID NO 88
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Phe Arg Leu Ser Ser Pro Gln
1               5

<210> SEQ ID NO 89
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Asn Ile Pro Lys Ala Tyr Gly
1               5

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Met Thr Leu Thr Arg Gln Glu
1               5

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Thr Ser Asn Ser Arg Thr Glu
1               5

<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Glu Val Arg Gly Gly Pro Ser
1               5

<210> SEQ ID NO 93
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Val Ile Ser Asp Arg Ser Ser
1               5

<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Pro Arg Asp Thr Phe Asn Gly
1               5

<210> SEQ ID NO 95
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Arg Pro Leu Thr Ala Asn Asp
1               5

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Pro Leu Arg Met Val Asn Glu
1               5

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Asp Val Gly Ile Arg Pro Ser
1               5

<210> SEQ ID NO 98
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 98

Lys Asp Ser Thr Ala Phe Gly
1               5

<210> SEQ ID NO 99
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Tyr Pro Gly Arg Asn Pro Asp
1               5

<210> SEQ ID NO 100
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Ile Ser Asp Thr Arg Ile Ser
1               5

<210> SEQ ID NO 101
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Glu Asn Phe Ser Lys Val Ala
1               5

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg Asp Ala Leu Ser Gly Leu Arg Pro Glu
1               5                   10

<210> SEQ ID NO 103
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103
```

```
Leu Gly Asn Gly Lys Met Thr Val Gln Pro
1               5                   10

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Val Ser Asn Pro Leu Asn Gln
1               5

<210> SEQ ID NO 105
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Leu Asn Glu Arg Gly Leu Gly
1               5

<210> SEQ ID NO 106
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Arg Asn Thr Val Gly Leu Ser Ser Ala
1               5                   10

<210> SEQ ID NO 107
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Val Gly His Ala Gly Asn Pro
1               5

<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ser Arg Ala Gly Thr Val Pro
1               5
```

```
<210> SEQ ID NO 109
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Leu Val Ala Lys Leu Pro
1               5

<210> SEQ ID NO 110
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ala Glu Ser Leu Arg Thr Pro
1               5

<210> SEQ ID NO 111
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
aaatcacctg ac                                                         12

<210> SEQ ID NO 112
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
tgattcttct ac                                                         12

<210> SEQ ID NO 113
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
ggccactggt tg                                                         12

<210> SEQ ID NO 114
<211> LENGTH: 12
<212> TYPE: DNA
<213> ORGANISM: Artificial Sequence
<220> FEATURE:
<221> NAME/KEY: source
```

<223> OTHER INFORMATION: /note="Description of Artificial Sequence:
        Synthetic oligonucleotide"

<400> SEQUENCE: 114
aatctatcgc ct                                                              12

<210> SEQ ID NO 115
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 115
agacgatcaa gg                                                              12

<210> SEQ ID NO 116
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 116
gtgtagtgat cg                                                              12

<210> SEQ ID NO 117
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 117
tggtagtttc ca                                                              12

<210> SEQ ID NO 118
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 118
gatcagttgc gg                                                              12

<210> SEQ ID NO 119
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 119
cttgggacac ac                                                              12

<210> SEQ ID NO 120

```
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gatgcggcct cg                                                            12

<210> SEQ ID NO 121
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
cgcatcctcg tt                                                            12

<210> SEQ ID NO 122
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
acgatgtcta cg                                                            12

<210> SEQ ID NO 123
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gtgttccacc tg                                                            12

<210> SEQ ID NO 124
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
ggagggagct gg                                                            12

<210> SEQ ID NO 125
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
```
cataactctt gc                                                    12

<210> SEQ ID NO 126
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
tgacagtctc gc                                                    12

<210> SEQ ID NO 127
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
ctaccaggat tc                                                    12

<210> SEQ ID NO 128
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
acacatgatg gc                                                    12

<210> SEQ ID NO 129
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
ggtgctcgca at                                                    12

<210> SEQ ID NO 130
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gattgcaccg ca                                                    12

<210> SEQ ID NO 131
<211> LENGTH: 12
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 131
aacggaggct gc                                                             12

<210> SEQ ID NO 132
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gggagagttc cg                                                             12

<210> SEQ ID NO 133
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
cgggtagccg aa                                                             12

<210> SEQ ID NO 134
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
tgacctaatt gg                                                             12

<210> SEQ ID NO 135
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gggtgaagga tt                                                             12

<210> SEQ ID NO 136
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
ctgtgagaga ag                                                             12
```

```
<210> SEQ ID NO 137
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
acttggttcc gc                                                          12

<210> SEQ ID NO 138
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gttggctgta cc                                                          12

<210> SEQ ID NO 139
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
tgtaagctgt ag                                                          12

<210> SEQ ID NO 140
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
agctaccctg ga                                                          12

<210> SEQ ID NO 141
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
ccaaacaagc gt                                                          12

<210> SEQ ID NO 142
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 142
gcttgcccat cc                                                    12

<210> SEQ ID NO 143
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
cattccgggt ta                                                    12

<210> SEQ ID NO 144
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
ctttgccggt ac                                                    12

<210> SEQ ID NO 145
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
catcaactgt gc                                                    12

<210> SEQ ID NO 146
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gcacagccga at                                                    12

<210> SEQ ID NO 147
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
atgcatcggt ca                                                    12

<210> SEQ ID NO 148
<211> LENGTH: 12
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 148
gaaccagaat gc                                                               12

<210> SEQ ID NO 149
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
cggacggtat gg                                                               12

<210> SEQ ID NO 150
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
tcctatgaac aa                                                               12

<210> SEQ ID NO 151
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
tgggagtaga gg                                                               12

<210> SEQ ID NO 152
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gctcaacgat cg                                                               12

<210> SEQ ID NO 153
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ggactaggat at                                                               12
```

```
<210> SEQ ID NO 154
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ccattgtggg aa                                                           12

<210> SEQ ID NO 155
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
cttgtcgata ag                                                           12

<210> SEQ ID NO 156
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
gtggtaagca cg                                                           12

<210> SEQ ID NO 157
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
aactggctcc ca                                                           12

<210> SEQ ID NO 158
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
tgcgatcgta ca                                                           12

<210> SEQ ID NO 159
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 159
cagaggatag ct                                                          12

<210> SEQ ID NO 160
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gaggagtctc at                                                          12

<210> SEQ ID NO 161
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
agttcccacg ga                                                          12

<210> SEQ ID NO 162
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
cccttcagca gt                                                          12

<210> SEQ ID NO 163
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
cgtactccgc ga                                                          12

<210> SEQ ID NO 164
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
tcaccgacgt gg                                                          12

<210> SEQ ID NO 165
<211> LENGTH: 12
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
caacggtctt cc                                                              12

<210> SEQ ID NO 166
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gtaacagtcc gg                                                              12

<210> SEQ ID NO 167
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gtcgaggata cc                                                              12

<210> SEQ ID NO 168
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
tgcgatgtga tg                                                              12

<210> SEQ ID NO 169
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
taacccgccg aa                                                              12

<210> SEQ ID NO 170
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
cgaccaacga ca                                                              12
```

```
<210> SEQ ID NO 171
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ctgctgccat ca                                                              12

<210> SEQ ID NO 172
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
ctagtacacg cg                                                              12

<210> SEQ ID NO 173
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
taggtgctag tg                                                              12

<210> SEQ ID NO 174
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
tcctcccagg at                                                              12

<210> SEQ ID NO 175
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
taggcggcat ta                                                              12

<210> SEQ ID NO 176
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 176
cttaggctag ct                                                         12

<210> SEQ ID NO 177
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
cgacgtgcga ta                                                         12

<210> SEQ ID NO 178
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
accattccat cg                                                         12

<210> SEQ ID NO 179
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
tggaaaggcc ta                                                         12

<210> SEQ ID NO 180
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gggaacattg ga                                                         12

<210> SEQ ID NO 181
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
aagtgaacgc gc                                                         12

<210> SEQ ID NO 182
<211> LENGTH: 12

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
agcaacgttg ta                                                         12

<210> SEQ ID NO 183
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
aagtgacgga cc                                                         12

<210> SEQ ID NO 184
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
agtaacgccc gt                                                         12

<210> SEQ ID NO 185
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
tgggctatga ca                                                         12

<210> SEQ ID NO 186
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
ctgcagtgaa gt                                                         12

<210> SEQ ID NO 187
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
```
attctgttcg ca                                                          12

<210> SEQ ID NO 188
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
cttcctcacc tc                                                          12

<210> SEQ ID NO 189
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gagagtcgaa ac                                                          12

<210> SEQ ID NO 190
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
agtcgtgaat cg                                                          12

<210> SEQ ID NO 191
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
ggtgacaaca at                                                          12

<210> SEQ ID NO 192
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gcctagtagc at                                                          12

<210> SEQ ID NO 193
<211> LENGTH: 12
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 193
acagaagcgc ct                                                            12

<210> SEQ ID NO 194
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
ctagttgagt tc                                                            12

<210> SEQ ID NO 195
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
aagttcagga ta                                                            12

<210> SEQ ID NO 196
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ttgcctctat tc                                                            12

<210> SEQ ID NO 197
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
tgaacgtcta ag                                                            12

<210> SEQ ID NO 198
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
cgctatcacg ca                                                            12

<210> SEQ ID NO 199
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Lys Ser Pro His Pro Ser Val
1               5

<210> SEQ ID NO 200
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Ile Lys Ser Asn Leu Thr Tyr
1               5

<210> SEQ ID NO 201
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ser Thr Ser Pro His Ala Pro Ser Lys Glu
1               5                   10

<210> SEQ ID NO 202
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

His Ala Thr Pro Gln Phe Asp Pro Ser Gln
1               5                   10

<210> SEQ ID NO 203
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Ser Ala Leu Gly Leu Gln Ala Lys Ala Tyr
1               5                   10

<210> SEQ ID NO 204
<211> LENGTH: 24
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 204
ttggtagaga tgttcgttta gagg                                            24

<210> SEQ ID NO 205
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (25)..(69)
<223> OTHER INFORMATION: a, c, t, g, unknown or other
<220> FEATURE:
<221> NAME/KEY: misc_feature
<222> LOCATION: (25)..(69)
<223> OTHER INFORMATION: /note="This region may encompass 12-45
      nucleotides"

<400> SEQUENCE: 205
cctctaaacg aacatctcta ccaannnnnn nnnnnnnnnn nnnnnnnnnn nnnnnnnnnn     60
nnnnnnnnnt actttggcta cagcacccct                                      90

<210> SEQ ID NO 206
<211> LENGTH: 735
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro

```
            180                 185                 190
Ala Thr Pro Ala Ala Val Gly Pro Thr Thr Met Ala Ser Gly Gly Gly
            195                 200                 205
Ala Pro Met Ala Asp Asn Asn Glu Gly Asp Gly Val Gly Asn Ala Ser
            210                 215                 220
Gly Asn Trp His Cys Asp Ser Thr Trp Leu Gly Asp Arg Val Ile Thr
225                 230                 235                 240
Thr Ser Thr Arg Thr Trp Ala Leu Pro Thr Tyr Asn Asn His Leu Tyr
                245                 250                 255
Lys Gln Ile Ser Ser Ala Ser Thr Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
            290                 295                 300
Gly Phe Arg Pro Lys Arg Leu Asn Phe Lys Leu Phe Asn Ile Gln Val
305                 310                 315                 320
Lys Glu Val Thr Thr Asn Asp Gly Val Thr Thr Ile Ala Asn Asn Leu
                325                 330                 335
Thr Ser Thr Val Gln Val Phe Ser Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Ile Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Glu Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
            435                 440                 445
Gln Asn Gln Ser Gly Ser Ala Gln Asn Lys Asp Leu Leu Phe Ser Arg
            450                 455                 460
Gly Ser Pro Ala Gly Met Ser Val Gln Pro Lys Asn Trp Leu Pro Gly
465                 470                 475                 480
Pro Cys Tyr Arg Gln Gln Arg Val Ser Lys Thr Lys Thr Asp Asn Asn
                485                 490                 495
Asn Ser Asn Phe Thr Trp Thr Gly Ala Ser Lys Tyr Asn Leu Asn Gly
            500                 505                 510
Arg Glu Ser Ile Ile Asn Pro Gly Thr Ala Met Ala Ser His Lys Asp
            515                 520                 525
Asp Glu Asp Lys Phe Phe Pro Met Ser Gly Val Met Ile Phe Gly Lys
            530                 535                 540
Glu Ser Ala Gly Ala Ser Asn Thr Ala Leu Asp Asn Val Met Ile Thr
545                 550                 555                 560
Asp Glu Glu Glu Ile Lys Ala Thr Asn Pro Val Ala Thr Glu Arg Phe
                565                 570                 575
Gly Thr Val Ala Val Asn Phe Gln Ser Ser Ser Thr Asp Pro Ala Thr
            580                 585                 590
Gly Asp Val His Ala Met Gly Ala Leu Pro Gly Met Val Trp Gln Asp
            595                 600                 605
```

```
Arg Asp Val Tyr Leu Gln Gly Pro Ile Trp Ala Lys Ile Pro His Thr
        610                 615                 620

Asp Gly His Phe His Pro Ser Pro Leu Met Gly Phe Gly Leu Lys
625                 630                 635                 640

Asn Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
                660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
        690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735

<210> SEQ ID NO 207
<211> LENGTH: 735
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
        20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
```

```
                    645                 650                 655
Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 208
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685
```

```
Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 209
<211> LENGTH: 724
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
```

```
            305                 310                 315                 320
        Thr Thr Ile Ala Asn Asn Leu Thr Ser Thr Val Gln Val Phe Thr Asp
                        325                 330                 335

Asp Asp Tyr Gln Leu Pro Tyr Val Val Gly Asn Gly Thr Glu Gly Cys
                        340                 345                 350

Leu Pro Ala Phe Pro Pro Gln Val Phe Thr Leu Pro Gln Tyr Gly Tyr
                        355                 360                 365

Ala Thr Leu Asn Arg Asp Asn Thr Glu Asn Pro Thr Glu Arg Ser Ser
                        370                 375                 380

Phe Phe Cys Leu Glu Tyr Phe Pro Ser Lys Met Leu Arg Thr Gly Asn
        385                 390                 395                 400

Asn Phe Glu Phe Thr Tyr Asn Phe Glu Glu Val Pro Phe His Ser Ser
                        405                 410                 415

Phe Ala Pro Ser Gln Asn Leu Phe Lys Leu Ala Asn Pro Leu Val Asp
                        420                 425                 430

Gln Tyr Leu Tyr Arg Phe Val Ser Thr Asn Asn Thr Gly Gly Val Gln
                        435                 440                 445

Phe Asn Lys Asn Leu Ala Gly Arg Tyr Ala Asn Thr Tyr Lys Asn Trp
                        450                 455                 460

Phe Pro Gly Pro Met Gly Arg Thr Gln Gly Trp Asn Leu Gly Ser Gly
        465                 470                 475                 480

Val Asn Arg Ala Ser Val Ser Ala Phe Ala Thr Thr Asn Arg Met Glu
                        485                 490                 495

Leu Glu Gly Ala Ser Tyr Gln Val Pro Pro Gln Pro Asn Gly Met Thr
                        500                 505                 510

Asn Asn Leu Gln Gly Ser Asn Thr Tyr Ala Leu Glu Asn Thr Met Ile
                        515                 520                 525

Phe Asn Ser Gln Pro Ala Asn Pro Gly Thr Thr Ala Thr Tyr Leu Glu
                        530                 535                 540

Gly Asn Met Leu Ile Thr Ser Glu Ser Glu Thr Gln Pro Val Asn Arg
        545                 550                 555                 560

Val Ala Tyr Asn Val Gly Gly Gln Met Ala Thr Asn Asn Gln Ser Ser
                        565                 570                 575

Thr Thr Ala Pro Ala Thr Gly Thr Tyr Asn Leu Gln Glu Ile Val Pro
                        580                 585                 590

Gly Ser Val Trp Met Glu Arg Asp Val Tyr Leu Gln Gly Pro Ile Trp
                        595                 600                 605

Ala Lys Ile Pro Glu Thr Gly Ala His Phe His Pro Ser Pro Ala Met
                        610                 615                 620

Gly Gly Phe Gly Leu Lys His Pro Pro Met Met Leu Ile Lys Asn
        625                 630                 635                 640

Thr Pro Val Pro Gly Asn Ile Thr Ser Phe Ser Asp Val Pro Val Ser
                        645                 650                 655

Ser Phe Ile Thr Gln Tyr Ser Thr Gly Gln Val Thr Val Glu Met Glu
                        660                 665                 670

Trp Glu Leu Lys Lys Glu Asn Ser Lys Arg Trp Asn Pro Glu Ile Gln
                        675                 680                 685

Tyr Thr Asn Asn Tyr Asn Asp Pro Gln Phe Val Asp Phe Ala Pro Asp
                        690                 695                 700

Ser Thr Gly Glu Tyr Arg Thr Thr Arg Pro Ile Gly Thr Arg Tyr Leu
        705                 710                 715                 720

Thr Arg Pro Leu
```

<210> SEQ ID NO 210
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 210

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
```

```
                355                 360                 365
Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 211
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 211

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400
```

```
Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 212
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Ala Pro Gln Pro
             20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
     50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

```
Asp Arg Leu Met Asn Pro Leu Ile Asp Gln Tyr Leu Tyr Tyr Leu Ser
        435             440             445

Lys Thr Ile Asn Gly Ser Gly Gln Asn Gln Gln Thr Leu Lys Phe Ser
        450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
            515             520             525

Glu Gly Glu Asp Arg Phe Phe Pro Leu Ser Gly Ser Leu Ile Phe Gly
        530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Ala Gln Ala Gln
            580             585             590

Thr Gly Trp Val Gln Asn Gln Gly Ile Leu Pro Gly Met Val Trp Gln
        595             600             605

Asp Arg Asp Val Tyr Leu Gln Gly Pro Ile Trp Ala Lys Ile Pro His
        610             615             620

Thr Asp Gly Asn Phe His Pro Ser Pro Leu Met Gly Gly Phe Gly Met
625             630             635             640

Lys His Pro Pro Pro Gln Ile Leu Ile Lys Asn Thr Pro Val Pro Ala
            645             650             655

Asp Pro Pro Thr Ala Phe Asn Lys Asp Lys Leu Asn Ser Phe Ile Thr
            660             665             670

Gln Tyr Ser Thr Gly Gln Val Ser Val Glu Ile Glu Trp Glu Leu Gln
        675             680             685

Lys Glu Asn Ser Lys Arg Trp Asn Pro Glu Ile Gln Tyr Thr Ser Asn
        690             695             700

Tyr Tyr Lys Ser Asn Asn Val Glu Phe Ala Val Asn Thr Glu Gly Val
705             710             715             720

Tyr Ser Glu Pro Arg Pro Ile Gly Thr Arg Tyr Leu Thr Arg Asn Leu
            725             730             735
```

ENGINEERING AAV

CROSS-REFERENCE TO RELATED APPLICATIONS

This application claims the benefit of and priority from U.S. Provisional Applications 62/839,421, filed Apr. 26, 2019; 62/915,386, filed Oct. 15, 2019 and 62/939,094, filed Nov. 22, 2019. Each of the foregoing applications is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 30, 2023, is named 91355.01200.txt and is 115,719 bytes in size

TECHNICAL FIELD

The present disclosure is in the fields of delivery of molecules associated with genome engineering and gene therapy.

BACKGROUND

Artificial nucleases, such as engineered zinc finger nucleases (ZFN), transcription-activator like effector nucleases (TALENs), the CRISPR/Cas system with an engineered crRNA/tracrRNA ('single guide RNA'), also referred to as RNA guided nucleases, and/or nucleases based on the Argonaute system are revolutionizing the fields of medicine, biotechnology and agriculture. These molecular tools are allowing the genetic manipulation (e.g. editing) of genomes in organisms to a level never-before possible. In addition, gene therapy (delivery of a transgene to a cell in the body that is maintained extra-chromosomally and expresses a product encoded by the transgene) is being studied in the clinic to deliver such needed proteins as clotting factors and proteins to treat ocular disorders. The promise of these revolutionary technologies is dependent on efficient delivery of the nuclease systems and/or transgenes to the appropriate tissue in the body.

Adeno-associated virus (AAV) is a promising in vitro and in vivo gene delivery vector for delivering nuclease systems described above as well as the vectors associated with gene therapy. There are several naturally occurring ("wild-type") serotypes and over 100 known variants of AAV, each of which differs in amino acid sequence, particularly within the hypervariable regions of the capsid proteins, and thus in their gene delivery properties. AAV has not been associated with any human disease, making recombinant AAV attractive for clinical applications. AAV also displays several additional favorable characteristics including an absence of pathogenicity, low immunogenicity, and stable episomal transgene expression. However, the use of AAV also has some issues including promiscuous viral tropism, limited ability to circumvent biological barriers, and the high prevalence of pre-existing neutralizing antibodies against AAV capsid proteins in human subjects that potentially limit their efficacy. Thus, improvements in AAV design are needed to fully exploit these new systems.

SUMMARY

The present disclosure provides methods and compositions to develop AAV capsids with a desired characteristic compared to a natural AAV serotype. These capsids are useful, for example, for the delivery of genome engineering molecules and gene therapy molecules for the treatment of a subject in need thereof. In some embodiments, the capsids are used to deliver a payload to a desired tissue, cell or organelle.

In a first aspect, the present disclosure provides a method of identifying an AAV capsid variant with a desired characteristic compared to a natural AAV serotype, comprising: (i) contacting a cell, cell line, or tissue with a library of AAV variants, wherein each member of the library comprises: a) a nucleic acid encoding an AAV variant capsid protein comprising a peptide inserted into a hypervariable and/or surface-exposed loop of the variant capsid protein; and one or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein; (ii) allowing the AAV variants in said library to transduce the cell, cell line, or tissue; (iii) recovering from the cell, cell line, or tissue the AAV variant; and (iv) identifying the AAV capsid variant with the desired characteristic.

In some embodiments, each member of the library used in the methods disclosed herein comprises a) a nucleic acid encoding an AAV variant capsid protein comprising a peptide inserted into a hypervariable and/or surface-exposed loop of the variant capsid protein and b) one or more silent mutations in the nucleic acid sequence flanking the peptide insertion site in the AAV variant capsid protein. In some embodiments, each member of the library used in the methods disclosed herein comprises a) a nucleic acid encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, and c) a nucleic acid encoding a localization signal. In some embodiments, each member of the library used in the methods disclosed herein comprises a) a nucleic acid encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, and d) a nucleic acid comprising a barcode. In some embodiments, each member of the library used in the methods disclosed herein comprises a) a nucleic acid encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, d) a nucleic acid comprising a barcode, and e) a nucleic acid encoding a reporter protein.

In some embodiments, each member of the library used in the methods disclosed herein comprises a) a nucleic acid encoding an AAV variant capsid protein comprising a peptide inserted into a hypervariable and/or surface-exposed loop of the variant capsid protein, and c) a nucleic acid encoding a localization signal. In some embodiments, each member of the library used in the methods disclosed herein comprises a) a nucleic acid encoding an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, each member of the library used in the methods disclosed herein comprises a) a nucleic acid encoding an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, each member of the library used in the methods disclosed herein comprises a) an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, each member of the library used in the methods disclosed herein comprises a) a nucleic acid encoding an AAV variant capsid protein comprising a peptide inserted into a hypervariable and/or surface-exposed loop of the variant capsid protein, and d) a nucleic acid comprising a barcode. In some embodiments, each member of the library used in the methods disclosed herein comprises a) a nucleic acid encoding an AAV variant capsid protein comprising a peptide inserted into a hypervariable and/or surface-exposed loop of the variant capsid protein, and e) a nucleic acid encoding a reporter protein. In some embodiments, each member of the library used in the methods disclosed herein comprises a) an AAV variant capsid protein comprising a peptide inserted into a hypervariable and/or surface-exposed loop of the variant capsid protein, and e) a nucleic acid encoding a reporter protein.

In a second aspect, the present disclosure provides a method of identifying an AAV capsid variant with a desired characteristic compared to a natural AAV serotype, comprising: (i) contacting a cell, cell line, or tissue with a library of AAV variants, wherein each member of the library comprises: a) an AAV variant capsid protein comprising a peptide inserted into a hypervariable and/or surface-exposed loop of the variant capsid protein; and one or more of: b) one or more silent mutations in the nucleic acid encoding the AAV variant capsid protein of a), wherein the one or more silent mutations are in the nucleic acid sequence flanking the peptide insertion site; c) a nucleic acid encoding a localization signal; d) a nucleic acid comprising a barcode; and e) a nucleic acid encoding a reporter protein; (ii) allowing the AAV variants in said library to transduce the cell, cell line, or tissue; (iii) recovering from the cell, cell line, or tissue the AAV variant; and (iv) identifying the AAV capsid variant with the desired characteristic.

In some embodiments, each member of the library used in the methods disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site. In some embodiments, each member of the library used in the methods disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, and c) a nucleic acid encoding a localization signal. In some embodiments, each member of the library used in the methods disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, and d) a nucleic acid comprising a barcode. In some embodiments, each member of the library used in the methods disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, d) a nucleic acid comprising a barcode, and e) a nucleic acid encoding a reporter protein.

In some embodiments, each member of the library used in the methods disclosed herein comprises a) an AAV variant capsid protein comprising a peptide inserted into a hypervariable and/or surface-exposed loop of the variant capsid protein, and c) a nucleic acid encoding a localization signal. In some embodiments, each member of the library used in the methods disclosed herein comprises a) an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, each member of the library used in the methods disclosed herein comprises a) an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, each member of the library used in the methods disclosed herein comprises a) an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, each member of the library used in the methods disclosed herein comprises a) an AAV variant capsid protein comprising a peptide inserted into a hypervariable and/or surface-exposed loop of the variant capsid protein, and d) a nucleic acid comprising a barcode. In some embodiments, each member of the library used in the methods disclosed herein comprises a) an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, each member of the library used in the methods disclosed herein comprises a) an AAV variant capsid protein comprising a peptide inserted into a hypervariable and/or surface-exposed loop of the variant capsid protein, and e) a nucleic acid encoding a reporter protein.

In some embodiments, the nucleic acid encoding an AAV variant capsid protein, and the nucleic acid encoding a localization signal, the nucleic acid comprising a barcode, and/or the nucleic acid encoding a reporter protein, are located in separate nucleic acid molecules. In other embodiments, the nucleic acid encoding an AAV variant capsid protein, the nucleic acid encoding a localization signal, the nucleic acid comprising a barcode, and/or the nucleic acid encoding a reporter protein, are located in one nucleic acid molecule. In some embodiments, the nucleic acid encoding an AAV variant capsid protein, and the nucleic acid encoding a localization signal, the nucleic acid comprising a barcode, and/or the nucleic acid encoding a reporter protein, are linked to each other in any order. In some embodiments, each member of the library comprises: a 5'ITR sequence, the nucleic acid comprising a barcode, the nucleic acid encoding a reporter protein, the nucleic acid encoding an AAV variant capsid protein, and a 3'ITR sequence, in that order.

In some embodiments, the library of AAV variants used in the methods disclosed herein comprises AAV variant capsid proteins derived from two or more AAV serotypes. In some embodiments, the AAV serotype is selected from one or more of: AAV1, AAV2, AAV3B, AAV5, AAV6, AAV8, AAV9, AAV3, AAV4, AAV7, AAV11, AAVrh10, AAVrh39, and AAVrh74.

In some embodiments, the nucleic acid encoding the reporter protein and the nucleic acid encoding the AAV variant capsid are under the control of separate promoters. In some embodiments, the nucleic acid encoding the reporter protein and the nucleic acid encoding the AAV variant capsid are each independently operatively linked to a promoter.

In some embodiments, the desired characteristic of the AAV capsid variant identified by the methods disclosed herein is enhanced cell or tissue tropism.

In a third aspect, the disclosure provides a method of identifying an AAV capsid variant with a desired characteristic compared to a natural AAV serotype, comprising: (i) inserting a plurality of nucleic acids encoding peptides, into a population of nucleic acids encoding a hypervariable and/or surface-exposed loop of an AAV capsid protein to create a library of nucleic acids encoding AAV variant capsid proteins; (ii) linking each nucleic acid encoding an AAV variant capsid protein in said library to one or more of: (a) a nucleic acid comprising a barcode, (b) a nucleic acid encoding a reporter protein, and (c) a nucleic acid encoding a localization signal; (iii) manufacturing a library of AAV variants in producer cells by providing adenovirus helper and AAV rep functions in trans; (iv) purifying the library of AAV variants; (v) contacting a cell, cell line, or tissue with the library of AAV variants; (vi) recovering the AAV variants from the target cell, cell line, or tissue; and (vii) identifying the AAV capsid variant with the desired characteristic.

In some embodiments, each nucleic acid encoding an AAV variant capsid protein in said library used in the methods disclosed herein is linked to (a) a nucleic acid comprising a barcode. In some embodiments, each nucleic acid encoding an AAV variant capsid protein in said library used in the methods disclosed herein is linked to (a) a nucleic acid comprising a barcode, and (b) a nucleic acid encoding a reporter protein. In some embodiments, each nucleic acid encoding an AAV variant capsid protein in said library used in the methods disclosed herein is linked to (a) a nucleic acid comprising a barcode, and (c) a nucleic acid encoding a localization signal. In some embodiments, each nucleic acid encoding an AAV variant capsid protein in said library used in the methods disclosed herein is linked to (a) a nucleic acid comprising a barcode, (b) a nucleic acid encoding a reporter protein, and (c) a nucleic acid encoding a localization signal. In some embodiments, each nucleic acid encoding an AAV variant capsid protein in said library used in the methods disclosed herein is linked to (a) a nucleic acid comprising a barcode, and (d) one or more silent mutations in the nucleic acid sequence flanking the peptide insertion site. In some embodiments, each nucleic acid encoding an AAV variant capsid protein in said library used in the methods disclosed herein is linked to (a) a nucleic acid comprising a barcode, (b) a nucleic acid encoding a reporter protein, and (d) one or more silent mutations in the nucleic acid sequence flanking the peptide insertion site. In some embodiments, each nucleic acid encoding an AAV variant capsid protein in said library used in the methods disclosed herein is linked to (a) a nucleic acid comprising a barcode, (b) a nucleic acid encoding a reporter protein, (c) a nucleic acid encoding a localization signal and (d) one or more silent mutations in the nucleic acid sequence flanking the peptide insertion site.

In some embodiments, each nucleic acid encoding an AAV variant capsid protein in said library used in the methods disclosed herein is linked to (b) a nucleic acid encoding a reporter protein. In some embodiments, each nucleic acid encoding an AAV variant capsid protein in said library used in the methods disclosed herein is linked to (b) a nucleic acid encoding a reporter protein, and (c) a nucleic acid encoding a localization signal. In some embodiments, each nucleic acid encoding an AAV variant capsid protein in said library used in the methods disclosed herein is linked to (c) a nucleic acid encoding a localization signal. In some embodiments, each nucleic acid encoding a AAV variant capsid protein further comprises one or more silent mutations in the nucleic acid sequence flanking the peptide insertion site. In some embodiments, each nucleic acid encoding an AAV variant capsid protein in said library used in the methods disclosed herein is linked to (b) a nucleic acid encoding a reporter protein, and (d) one or more silent mutations in the nucleic acid sequence flanking the peptide insertion site. In some embodiments, each nucleic acid encoding an AAV variant capsid protein in said library used in the methods disclosed herein is linked to (c) a nucleic acid encoding a localization signal and (d) one or more silent mutations in the nucleic acid sequence flanking the peptide insertion site. In some embodiments, each nucleic acid encoding an AAV variant capsid protein in said library used in the methods disclosed herein is linked to (d) one or more silent mutations in the nucleic acid sequence flanking the peptide insertion site.

In some embodiments, step (iv) further comprises combining libraries of variant AAVs based on two or more AAV serotypes to generate a single pool. In some embodiments, the population of nucleic acid sequences encoding a hypervariable and/or surface-exposed loop of an AAV capsid protein used in the methods disclosed herein comprises sequences derived from two or more AAV serotypes. In some embodiments, the AAV serotype is selected from one or more of: AAV1, AAV2, AAV3B, AAV5, AAV6, AAV8, AAV9, AAV3, AAV4, AAV7, AAV11, AAVrh10, AAVrh39, and AAVrh74.

In some embodiments, the adenovirus helper functions used in the methods disclosed herein comprise one or more of E2A, E4, VA, E1A, and E1B. In some embodiments, the AAV rep function comprises rep78, rep 68, rep 52 and rep40 genes. In some embodiments the start codon of the rep78 and/or rep68 gene used in the methods disclosed herein is modified from ACG to ATG. In some embodiments, the producer cells used in the methods disclosed herein are HEK293 cells.

In some embodiments, the nucleic acid encoding an AAV variant capsid protein, the nucleic acid comprising a barcode, the nucleic acid encoding a reporter protein, and/or a nucleic acid encoding a localization signal used in the methods disclosed herein are linked to each other in any order. In some embodiments, each member of the library comprises: a 5'ITR sequence, the nucleic acid comprising a barcode, the nucleic acid encoding a reporter protein, the nucleic acid encoding an AAV variant capsid protein, and a 3'ITR sequence, in that order.

In some embodiments, the nucleic acid encoding a reporter protein and the nucleic acid encoding the AAV variant capsid used in the methods disclosed herein are under the control of separate promoters. In some embodiments, the nucleic acid encoding a reporter protein and the nuclei acid encoding the AAV variant capsid used in the methods disclosed herein are each independently operatively linked to a promoter.

In some embodiments, the desired characteristic of the AAV capsid variant is enhanced cell or tissue tropism.

In some embodiments of the methods disclosed herein, the AAV capsid variant with the desired characteristic is identified through sequencing of the associated barcode. In some embodiments of the methods disclosed herein, the AAV capsid variant with the desired characteristic is identified through sequencing of the associated one or more barcode. In some embodiments, a first barcode operatively linked to a promoter identifies barcoded transcripts in a target cell population, for example neurons or hepatocytes, because the promoter is only expressed in a specific cell population. In some embodiments, a second barcode identifies expression in all cell types, because it is operatively linked to a promoter which drives ubiquitous expression.

In some embodiments of the methods disclosed herein, the AAV capsid variant with the desired characteristic is identified by purification and sequencing of the AAV genome.

In some embodiments of the methods disclosed herein, the cell or tissue includes but is not limited to a cell or tissue from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa.

In some embodiments of the methods disclosed herein, the cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

In some embodiments of the methods disclosed herein, one or more of (i) the nucleic acid encoding a localization signal; (ii) the nucleic acid comprising a barcode; and (iii) the nucleic acid encoding a reporter protein are provided in trans with respect to the nucleic acid encoding the AAV variant capsid protein comprising the inserted peptide. In some embodiments of the methods disclosed herein, i) the nucleic acid encoding a localization signal; (ii) the nucleic acid comprising a barcode; and (iii) the nucleic acid encoding a reporter protein are all provided in trans with respect to the nucleic acid encoding the AAV variant capsid protein comprising the inserted peptide. In some embodiments of the methods disclosed herein, one or more of (i) the nucleic acid encoding a localization signal; (ii) the nucleic acid comprising a barcode; and (iii) the nucleic acid encoding a reporter protein are provided in cis with respect to the nucleic acid encoding the AAV variant capsid protein comprising the inserted peptide. In some embodiments of the methods disclosed herein, i) the nucleic acid encoding a localization signal; (ii) the nucleic acid comprising a barcode; and (iii) the nucleic acid encoding a reporter protein are all provided in cis with respect to the nucleic acid encoding the AAV variant capsid protein comprising the inserted peptide.

In a fourth aspect, the present disclosure provides a library of AAV variants, wherein each member of said library comprises: a) a nucleic acid sequence encoding an AAV variant capsid protein comprising a peptide inserted into a hypervariable and/or surface-exposed loop of the variant capsid protein; and one or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, each member of the library disclosed herein comprises a) a nucleic acid sequence encoding an AAV variant capsid protein comprising a peptide inserted into a hypervariable and/or surface-exposed loop of the variant capsid protein and b) one or more silent mutations in the nucleic acid sequence flanking the peptide insertion site in the AAV variant capsid protein. In some embodiments, each member of the library disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, and c) a nucleic acid encoding a localization signal. In some embodiments, each member of the library disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, and d) a nucleic acid comprising a barcode. In some embodiments, each member of the library disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, d) a nucleic acid comprising a barcode, and e) a nucleic acid encoding a reporter protein.

In some embodiments, each member of the library disclosed herein comprises a) a nucleic acid sequence encoding an AAV variant capsid protein comprising a peptide inserted into a hypervariable and/or surface-exposed loop of the variant capsid protein, and c) a nucleic acid encoding a localization signal. In some embodiments, each member of the library disclosed herein comprises a) an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, each member of the library disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, each member of the library disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, each member of the library disclosed herein comprises a) a nucleic acid sequence encoding an AAV variant capsid protein comprising a peptide inserted into a hypervariable and/or surface-exposed loop of the variant capsid protein, and d) a nucleic acid comprising a barcode. In some embodiments, each member of the library disclosed herein comprises a) a nucleic acid sequence encoding an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, each member of the library disclosed herein comprises a) a nucleic acid sequence encoding an AAV variant capsid protein comprising a peptide inserted into a hypervariable and/or surface-exposed loop of the variant capsid protein, and e) a nucleic acid encoding a reporter protein.

In a fifth aspect, the present disclosure provides a library of AAV variants, wherein each member of said library comprises: a) an AAV variant capsid protein comprising a peptide inserted into a hypervariable and/or surface-exposed loop of the variant capsid protein; and one or more of: b) one or more silent mutations in the nucleic acid encoding the AAV variant capsid protein of a), wherein the one or more silent mutations are in the nucleic acid sequence flanking the peptide insertion site; c) a nucleic acid encoding a localization signal; d) a nucleic acid comprising a barcode; and e) a nucleic acid encoding a reporter protein.

In some embodiments, each member of the library disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site. In some embodiments, each member of the library disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, and c) a nucleic acid encoding a localization signal. In some embodiments, each member of the library disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, and d) a nucleic acid comprising a barcode. In some embodiments, each member of the library disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, d) a nucleic acid comprising a barcode, and e) a nucleic acid encoding a reporter protein.

In some embodiments, each member of the library disclosed herein comprises a) an AAV variant capsid protein comprising a peptide inserted into a hypervariable and/or surface-exposed loop of the variant capsid protein, and c) a nucleic acid encoding a localization signal. In some embodiments, each member of the library disclosed herein comprises a) an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, each member of the library disclosed herein comprises a) an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, each member of the library disclosed herein comprises a) an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, each member of the library disclosed herein comprises a) an AAV variant capsid protein comprising a peptide inserted into a hypervariable and/or surface-exposed loop of the variant capsid protein, and d) a nucleic acid comprising a barcode. In some embodiments, each member of the library disclosed herein comprises a) an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, each member of the library disclosed herein comprises a) an AAV variant capsid protein comprising a peptide inserted into a hypervariable and/or surface-exposed loop of the variant capsid protein, and e) a nucleic acid encoding a reporter protein.

In some embodiments, the nucleic acid encoding an AAV variant capsid protein, and the nucleic acid encoding a localization signal, the nucleic acid comprising a barcode, and/or the nucleic acid encoding a reporter protein, are located in separate nucleic acid molecules. In other embodiments, the nucleic acid encoding an AAV variant capsid protein, the nucleic acid encoding a localization signal, the nucleic acid comprising a barcode, and/or the nucleic acid encoding a reporter protein, are located in one nucleic acid molecule. In some embodiments, the nucleic acid encoding an AAV variant capsid protein, and the nucleic acid encoding a localization signal, the nucleic acid comprising a barcode, and/or the nucleic acid encoding a reporter protein, are linked to each other in any order. In some embodiments, each member of the library disclosed herein comprises: a 5'ITR sequence, the nucleic acid comprising a barcode, the nucleic acid encoding a reporter protein, the nucleic acid encoding an AAV variant capsid protein, and a 3'ITR sequence, in that order.

In some embodiments, the library of AAV variants disclosed herein comprises AAV variant capsid proteins derived from two or more AAV serotypes. In some embodiments, the AAV serotype is selected from one or more of: AAV1, AAV2, AAV3B, AAV5, AAV6, AAV8, AAV9, AAV3, AAV4, AAV7, AAV11, AAVrh10, AAVrh39, and AAVrh74.

In some embodiments, the nucleic acid encoding the reporter protein and the nucleic acid encoding the AAV variant capsid are under the control of separate promoters. In some embodiments, the nucleic acid encoding the reporter protein and the nucleic acid encoding the AAV variant capsid are each independently operatively linked to a promoter.

In a sixth aspect, the present disclosure provides an AAV variant comprising: a) a nucleic acid sequence encoding an AAV variant capsid protein comprising a peptide inserted into a hypervariable and/or surface-exposed loop of the variant capsid protein; and one or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, an AAV variant disclosed herein comprises a) a nucleic acid sequence encoding an AAV variant capsid protein comprising a peptide inserted into a hypervariable and/or surface-exposed loop of the variant capsid protein and b) one or more silent mutations in the nucleic acid sequence flanking the peptide insertion site in the AAV variant capsid protein. In some embodiments, an AAV variant disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, and c) a nucleic acid encoding a localization signal. In some embodiments, an AAV variant disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, and d) a nucleic acid comprising a barcode. In some embodiments, an AAV variant disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, d) a nucleic acid comprising a barcode, and e) a nucleic acid encoding a reporter protein.

In some embodiments, an AAV variant disclosed herein comprises a) a nucleic acid sequence encoding an AAV variant capsid protein comprising a peptide inserted into a hypervariable and/or surface-exposed loop of the variant capsid protein, and c) a nucleic acid encoding a localization signal. In some embodiments, an AAV variant disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, an AAV variant disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, an AAV variant disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, an AAV variant disclosed herein comprises a) a nucleic acid sequence encoding an AAV variant capsid protein comprising a peptide inserted into a hypervariable and/or surface-exposed loop of the variant capsid protein, and d) a nucleic acid comprising a barcode. In some embodiments, an AAV variant disclosed herein comprises a) a nucleic acid sequence encoding an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, an AAV variant disclosed herein comprises a) a nucleic acid sequence encoding an AAV variant capsid protein comprising a peptide inserted into a hypervariable and/or surface-exposed loop of the variant capsid protein, and e) a nucleic acid encoding a reporter protein.

In a seventh aspect, the present disclosure provides an AAV variant comprising: a) an AAV variant capsid protein comprising a peptide inserted into a hypervariable and/or surface-exposed loop of the variant capsid protein; and one or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, an AAV variant disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site. In some embodiments, an AAV variant disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, and c) a nucleic acid encoding a localization signal. In some embodiments, an AAV variant disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, and d) a nucleic acid comprising a barcode. In some embodiments, an AAV variant disclosed herein comprises a) an AAV variant capsid protein comprising a peptide inserted into a hypervariable and/or surface-exposed loop of the variant capsid protein, and b) one or more silent mutations in the nucleic acid encoding the AAV variant capsid protein of a), wherein the one or more silent mutations are in the nucleic acid sequence flanking the peptide insertion site, c) a nucleic acid encoding a localization signal, d) a nucleic acid comprising a barcode, and e) a nucleic acid encoding a reporter protein.

In some embodiments, an AAV variant disclosed herein comprises a) an AAV variant capsid protein comprising a peptide inserted into a hypervariable and/or surface-exposed loop of the variant capsid protein, and c) a nucleic acid encoding a localization signal. In some embodiments, an AAV variant disclosed herein comprises a) an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, an AAV variant disclosed herein comprises a) an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, an AAV variant disclosed herein comprises a) an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, an AAV variant disclosed herein comprises a) an AAV variant capsid protein comprising a peptide inserted into a hypervariable and/or surface-exposed loop of the variant capsid protein, and d) a nucleic acid comprising a barcode. In some embodiments, an AAV variant disclosed herein comprises a) an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, an AAV variant disclosed herein comprises a) an AAV variant capsid protein comprising a peptide inserted into a hypervariable and/or surface-exposed loop of the variant capsid protein, and e) a nucleic acid encoding a reporter protein.

In some embodiments, the nucleic acid encoding an AAV variant capsid protein, and the nucleic acid encoding a localization signal, the nucleic acid comprising a barcode, and/or the nucleic acid encoding a reporter protein, are located in separate nucleic acid molecules. In other embodiments, the nucleic acid encoding an AAV variant capsid protein, the nucleic acid encoding a localization signal, the nucleic acid comprising a barcode, and/or the nucleic acid encoding a reporter protein, are located in one nucleic acid molecule. In some embodiments, the nucleic acid encoding an AAV variant capsid protein, and the nucleic acid encoding a localization signal, the nucleic acid comprising a barcode, and/or the nucleic acid encoding a reporter protein, are linked to each other in any order. In some embodiments, an AAV variant comprises: a 5'ITR sequence, the nucleic acid comprising a barcode, the nucleic acid encoding a reporter protein, the nucleic acid encoding an AAV variant capsid protein, and a 3'ITR sequence, in that order.

In some embodiments, an AAV variant disclosed herein is derived from the group consisting of: AAV1, AAV2, AAV3B, AAV5, AAV6, AAV8, AAV9, AAV3, AAV4, AAV7, AAV11, AAVrh10, AAVrh39, and AAVrh74.

In some embodiments, the nucleic acid encoding the reporter protein and the nucleic acid encoding the AAV variant capsid are under the control of separate promoters. In some embodiments, the nucleic acid encoding the reporter protein and the nucleic acid encoding the AAV variant capsid are each independently operatively linked to a promoter.

In an eighth aspect, the present disclosure provides a nucleic acid molecule comprising a) a nucleic acid sequence encoding an AAV variant capsid protein comprising a peptide inserted into a hypervariable and/or surface-exposed loop of the variant capsid protein; and one or more of: b) a nucleic acid sequence encoding a variant capsid protein comprising one or more silent mutations in the nucleotide sequence flanking the peptide insertion site in the hypervariable and/or surface-exposed loop of the variant capsid protein; c) a nucleic acid sequence encoding a localization signal; d) a nucleic acid sequence comprising a barcode; and e) a nucleic acid sequence encoding a reporter protein.

In some embodiments, a nucleic acid disclosed herein comprises a) a nucleic acid sequence encoding an AAV variant capsid protein comprising a peptide inserted into a hypervariable and/or surface-exposed loop of the variant capsid protein and b) one or more silent mutations in the nucleic acid sequence flanking the peptide insertion site in the AAV variant capsid protein. In some embodiments, a nucleic acid disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, and c) a nucleic acid encoding a localization signal. In some embodiments, a nucleic acid disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, and d) a nucleic acid comprising a barcode. In some embodiments, a nucleic acid disclosed herein comprises a) a nucleic acid sequence encoding an AAV variant capsid protein comprising a peptide inserted into a hypervariable and/or surface-exposed loop of the variant capsid protein, b) one or more silent mutations in the nucleic acid sequence flanking the peptide insertion site in the AAV variant capsid protein, c) a nucleic acid encoding a localization signal, d) a nucleic acid comprising a barcode, and e) a nucleic acid encoding a reporter protein.

In some embodiments, a nucleic acid disclosed herein comprises a) a nucleic acid sequence encoding an AAV variant capsid protein comprising a peptide inserted into a hypervariable and/or surface-exposed loop of the variant capsid protein, and c) a nucleic acid encoding a localization signal. In some embodiments, a nucleic acid disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, and d) a nucleic acid comprising a barcode. In some embodiments, a nucleic acid disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, and e) a nucleic acid encoding a reporter protein. In some embodiments, a nucleic acid disclosed herein comprises a) a nucleic acid sequence encoding an AAV variant capsid protein comprising a peptide inserted into a hypervariable and/or surface-exposed loop of the variant capsid protein, c) a nucleic acid encoding a localization signal, d) a nucleic acid comprising a barcode, and e) a nucleic acid encoding a reporter protein.

In some embodiments, a nucleic acid disclosed herein comprises a) a nucleic acid sequence encoding an AAV variant capsid protein comprising a peptide inserted into a hypervariable and/or surface-exposed loop of the variant capsid protein, and d) a nucleic acid comprising a barcode. In some embodiments, a nucleic acid disclosed herein comprises a) a nucleic acid sequence encoding an AAV variant capsid protein comprising a peptide inserted into a hypervariable and/or surface-exposed loop of the variant capsid protein, d) a nucleic acid comprising a barcode, and e) a nucleic acid encoding a reporter protein. In some embodiments, a nucleic acid disclosed herein comprises a) a nucleic acid sequence encoding an AAV variant capsid protein comprising a peptide inserted into a hypervariable and/or surface-exposed loop of the variant capsid protein, and e) a nucleic acid encoding a reporter protein.

In some embodiments of a method, library, AAV variant, or nucleic acid disclosed herein, the peptide inserted into a variant capsid protein has a length of 4-15 amino acids. In some embodiments, the peptide has a length of 6-15 amino acids. In some embodiments, the peptide has a length of 7, 10, or 15 amino acids. In some embodiments, the peptide has a length of 7 amino acids. In some embodiments, the inserted peptide comprises at least 4 contiguous amino acids of an amino acid sequence set forth in any one of SEQ ID NO: 1-32. In some embodiments, the inserted peptide comprises at least 4 contiguous amino acids of an amino acid sequence set forth in any one of SEQ ID NO: 68-110. In some embodiments, the peptide comprises an amino acid sequence set forth in any one of SEQ ID NO: 1-32. In some embodiments, the peptide comprises an amino acid sequence set forth in any one of SEQ ID NO: 68-110.

In some embodiments, the peptide is inserted into the VR-I, VR-II, VR-III, VR-IV, VR-V, VR-VI, VR-VII, VR-VIII or VR-IX region of the capsid protein. In some embodiments, the peptide is inserted into the VR-I of the capsid protein. In some embodiments, the peptide is inserted into the VR-IV of the capsid protein. In some embodiments, the peptide is inserted into the VR-VIII of the capsid protein. In some embodiments, the peptide is inserted into the capsid protein VP1, VP2, or VP3. It is well recognized that VP2 and VP3 proteins are truncated forms of VP1 protein.

In some embodiments, the peptide is inserted at a location between amino acid residues 450 and 600 of the capsid protein. In some embodiments, (i) the AAV serotype is AAV1 and the peptide is inserted at amino acid position 590 of the capsid protein, (ii) the AAV serotype is AAV6 and the peptide is inserted at amino acid position 454 or 590 of the capsid protein, (iii) the AAV serotype is AAV2 and the peptide is inserted at amino acid position 588 of the capsid protein, (iv) the AAV serotype is AAV3B and the peptide is inserted at amino acid position 589 of the capsid protein, (v) the AAV serotype is AAV5 and the peptide is inserted at amino acid position 578 of the capsid protein, (vi) the AAV serotype is AAV8 and the peptide is inserted at amino acid position 591 of the capsid protein, or (vii) the AAV serotype is AAV9 and the peptide is inserted at amino acid position 266, 455, or 589 of the capsid protein, wherein the positions correspond to the numbering of VP1 in the AAV serotype.

In some embodiments of a method, library, AAV variant, or nucleic acid disclosed herein, the nucleic acid encoding an AAV variant capsid protein is under the control of the p40 promoter. In some embodiments of a method, library, AAV variant, or nucleic acid disclosed herein, the nucleic acid encoding an AAV variant capsid protein is operatively linked to the p40 promoter.

In some embodiments of a method, library, AAV variant, or nucleic acid disclosed herein, the nucleic acid encoding the reporter protein the encodes a fluorescent protein. In some embodiments, the reporter protein is selected from the group consisting of: EGFP, mCherry, mClover3, mRuby3, mApple, iRFP, tdTomato, mVenus, YFP, RFP, firefly luciferase, and nanoluciferase.

In some embodiments, the nucleic acid encoding a reporter protein is under the control of a cell type and/or tissue specific promoter. In some embodiments, the nucleic acid encoding a reporter protein is operatively linked to a cell type and/or tissue specific promoter. In some embodiments, the nucleic acid encoding a reporter protein is operatively linked to a cell-type specific RNA polymerase II promoter (e.g. transthyretin or hSynapsin1). In some embodiments, the cell type and/or tissue specific promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter. In some embodiments, the cell type and/or tissue specific promoter is the hSyn1 promoter. In some embodiments, the cell type and/or tissue specific promoter is the TTR promoter.

In some embodiments of a method, library, AAV variant, or nucleic acid disclosed herein, the reporter protein is fused to the localization signal. In some embodiments, the localization signal is fused N-terminally, C-terminally or both N-terminally and C-terminally to the reporter protein. In some embodiments, the localization signal is a nuclear localization signal (NLS), a nuclear envelope binding domain or a histone binding domain. In some embodiments, the NLS is the SV40 NLS. In some embodiments, the nuclear envelope binding domain is a KASH domain. In some embodiments, the histone binding domain is H2B.

In some embodiments of a method, library, AAV variant, or nucleic acid disclosed herein, the barcode is 5-18 nucleotides long.

In some embodiments of a method, library, AAV variant, or nucleic acid disclosed herein, the nucleic acid comprising the barcode comprises a sequence selected from any one of sequences SEQ ID NO: 111-154 or 155-198. In some embodiments, the nucleic acid comprising the barcode comprises a sequence selected from any one of sequences SEQ ID NO: 111-154. In some embodiments, the nucleic acid comprising the barcode comprises a sequence selected from any one of sequences SEQ ID NO: 155-198. In some embodiments of a method, library, AAV variant, or nucleic acid disclosed herein, the nucleic acid comprising the barcode is selected from any one of sequences SEQ ID NO: 111-154 or 155-198. In some embodiments, the nucleic acid comprising the barcode is selected from any one of sequences SEQ ID NO: 111-154. In some embodiments, the nucleic acid comprising the barcode is selected from any one of sequences SEQ ID NO: 155-198.

In some embodiments of a method, library of AAV variants, AAV variant, or nucleic acid disclosed herein, each member of the library comprises a first nucleic acid comprising a first barcode and a second nucleic acid comprising a second barcode. In some embodiments, the first nucleic acid comprising the first barcode and the second nucleic acid comprising the second barcode are different. In some embodiments, the first nucleic acid comprising the first barcode comprises a sequence selected from any one of sequences SEQ ID NO: 111-154 or is selected from any one of sequences SEQ ID NO: 111-154. In some embodiments of the method, library of AAV variants, AAV variant, or nucleic acid disclosed herein, the second nucleic acid comprising the second barcode comprises a sequence selected from any one of sequences SEQ ID NO: 155-198 or is selected from any one of sequences SEQ ID NO: 155-198. In some embodiments, the first nucleic acid comprising the first barcode comprises a sequence selected from any one of sequences SEQ ID NO: 111-154 or is selected from any one of sequences SEQ ID NO: 111-154 and the second nucleic acid comprising the second barcode comprises a sequence selected from any one of sequences SEQ ID NO: 155-198 or is selected from any one of sequences SEQ ID NO: 155-198. In some embodiments, each of the first nucleic acid comprising the first barcode and the second nucleic acid comprising the second barcode is independently operatively linked to a promoter. In some embodiments, said promoter is different for each of the first barcode and the second barcode. In some embodiments, each of the first nucleic acid comprising the first barcode and the second nucleic acid are independently controlled under a different promoter. In some embodiments, the promoter operatively linked to the first nucleic acid comprising the first barcode and the promoter operatively linked to the second nucleic acid comprising the second barcode is each independently an RNA Pol II promoter (e.g., human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, or methyl CpG-binding protein 2 (Mecp2) promoter). In some embodiments, the promoter operatively linked to the first nucleic acid comprising the first barcode and the promoter operatively linked to the second nucleic acid comprising the second barcode is each independently an RNA Pol III promoter (e.g., U6 promoter, H1 promoter or 7SK promoter). In some embodiments, the promoter operatively linked to the first nucleic acid comprising the first barcode is an RNA Pol II promoter and the promoter operatively linked to the second nucleic acid comprising the second barcode is an RNA Pol III promoter. In some embodiments, the nucleic acid comprising the barcode further comprises a reporter gene, a nuclear localization signal and a polyadenylation signal.

In some embodiments, of a method, library, AAV variant, or nucleic acid disclosed herein, each inserted peptide coding sequence is synthesized with multiple different nucleic acid sequences, all encoding the same peptide. Each nucleic acid sequence is linked to a unique bar code such that performance (e.g. enrichment) of an inserted peptide can be verified when two or more variants are identified with the same inserted peptide sequence but wherein different nucleic acid sequences encode that inserted peptide.

In some embodiments, of a method, library, AAV variant or nucleic acid disclosed herein, one or more of (i) the nucleic acid encoding a localization signal; (i) the nucleic acid comprising a barcode; and (iii) the nucleic acid encoding a reporter protein are provided in trans with respect to the nucleic acid encoding the AAV variant capsid protein comprising the inserted peptide. In some embodiments of a method, library, AAV variant or nucleic acid disclosed herein, (i) the nucleic acid encoding a localization signal, (ii) the nucleic acid comprising a barcode; and (iii) the nucleic acid encoding a reporter protein are all provided in trans with respect to the nucleic acid encoding the AAV variant capsid protein comprising the inserted peptide. In some embodiments of a method, library, AAV variant or nucleic acid disclosed herein, one or more of (i) the nucleic acid encoding a localization signal; (ii) the nucleic acid comprising a barcode; and (iii) the nucleic acid encoding a reporter protein are provided in cis with respect to the nucleic acid encoding the AAV variant capsid protein comprising the inserted peptide. In some embodiments of a method, library, AAV variant or nucleic acid disclosed herein, (i) the nucleic acid encoding a localization signal; (ii) the nucleic acid comprising a barcode; and (iii) the nucleic acid encoding a reporter protein are all provided in cis with respect to the nucleic acid encoding the AAV variant capsid protein comprising the inserted peptide.

In a ninth aspect, an AAV variant disclosed herein is used to deliver a transgene to a target cell or tissue. In some embodiments, the transgene is useful in gene therapy. In some embodiments, the transgene is useful in genome editing.

In a tenth aspect, the present disclosure provides an AAV vector comprising a nucleic acid encoding a peptide that comprises at least 4 contiguous amino acids of an amino acid sequence set forth in SEQ ID Nos. 1-32 or 68-110. In some embodiments, the AAV vector comprises a nucleic acid encoding a peptide that comprises at least 4 contiguous amino acids of an amino acid sequence set forth in SEQ ID Nos. 1-32. In other embodiments, the AAV vector comprises a nucleic acid encoding a peptide that comprises at least 4 contiguous amino acids of an amino acid sequence set forth in SEQ ID Nos. 68-110. In some embodiments, the nucleic acid encodes an amino acid sequence of any one of SEQ ID Nos. 1-32 or SEQ ID Nos. 68-110. In some embodiments, the nucleic acid encodes the amino acid sequence is any one of SEQ ID Nos. 1-32. In some embodiments, the nucleic acid encodes the amino acid sequence of any one of SEQ ID Nos. 68-110. In some embodiments, the inserted amino acid sequence is a part of a capsid protein. In some embodiments, the capsid protein is VP1, VP2, or VP3. In some embodiments, the amino acid sequence is inserted at a location between amino acid residues 450 and 600 of the capsid protein. In some embodiments, amino acid sequence is inserted at (i) amino acid position 590 of an AAV1 capsid protein, (ii) amino acid position 454 or 590 of an AAV6 capsid protein, (iii) amino acid position 588 of an AAV2 capsid protein, (iv) amino acid position 589 of an AAV3B capsid protein, (v) amino acid position 578 of an AAV5 capsid protein, (vi) amino acid position 591 of the an AAV8 capsid protein, or (vi) amino acid position 266, 455, or 589 of an AAV9 capsid protein, wherein the positions correspond to the numbering of VP1 in the AAV serotype.

In an eleventh aspect, the present disclosure provides a pharmaceutical composition comprising an AAV vector disclosed herein and a pharmaceutically acceptable carrier.

In a twelfth aspect, the present disclosure provides a peptide comprising an amino acid sequence set forth in any one of SEQ ID Nos. 1-32 or 68-110. In some embodiments, the peptide comprises an amino acid sequence set forth in any one of SEQ ID Nos. 1-32. In some embodiments, the peptide comprises an amino acid sequence set forth in any one of SEQ ID Nos. 68-110. In some embodiments, the peptide is any of the sequences set forth in SEQ ID Nos. 1-32. In some embodiments, the peptide is any of the sequences set forth in SEQ ID Nos. 68-110. In some embodiments, the peptide is part of an AAV vector. In some embodiments, the peptide is part of a capsid protein of the AAV vector.

In a thirteenth aspect, the present disclosure provides a capsid protein comprising a peptide comprising at least 4 contiguous amino acids of an amino acid sequence set forth in SEQ ID Nos. 1-32 or 68-110. In some embodiments, the capsid protein comprises an inserted peptide comprising at least 4 contiguous amino acids of an amino acid sequence set forth in SEQ ID Nos. 1-32. In some embodiments, the capsid protein comprises the amino acid sequence set forth in any one of SEQ ID Nos. 1-32. In some embodiments, the capsid protein comprises an inserted peptide comprising at least 4 contiguous amino acids of an amino acid sequence set forth in SEQ ID Nos. 68-110. In some embodiments, the capsid protein comprises the amino acid sequence set forth in any one of SEQ ID Nos. 68-110.

In a fourteenth aspect, the present disclosure provides a nucleic acid sequence encoding the peptides or capsid proteins disclosed herein.

In a fifteenth aspect, the present disclosure provides a method of delivering a nucleic acid to a target cell or tissue of a subject, comprising: administering a composition comprising an AAV vector comprising the nucleic acid, and wherein the AAV vector further comprises a capsid protein comprising an inserted peptide comprising at least 4 contiguous amino acids of an amino acid sequence set forth in SEQ ID Nos. 1-32 or 68-110. In some embodiments, the capsid protein comprises an inserted peptide comprising at least 4 contiguous amino acids of an amino acid sequence set forth in SEQ ID Nos. 1-32. In other embodiments, the capsid protein comprises an inserted peptide comprising at least 4 contiguous amino acids of an amino acid sequence set forth in SEQ ID Nos. 68-110. In some embodiments, the capsid protein comprises an amino acid sequence set forth in any one of SEQ ID Nos. 1-32. In other embodiments, the capsid protein comprises an amino acid sequence set forth in any one of SEQ ID Nos. 68-110.

In some embodiments, the target cell or tissue includes, but is not limited to, a cell or tissue from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa. In some embodiments, the target cell or tissue includes, but is not limited to CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa. In some embodiments, the target cell or tissue is CNS cell or tissue. In other embodiments, the target cell or tissue is liver cell or tissue.

In some embodiments, the target cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

In some embodiments, the target cell or tissue is from liver.

In some embodiments, the target cell or tissue is from CNS.

These and other aspects will be readily apparent to the skilled artisan in light of the disclosure as a whole.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4C and FIG. 4D illustrate an alternate approach to Method 1 for bioinformatically linking each variant capsid sequence with a randomly generated barcode. In step 1 two DNA fragments are synthesized. Fragment A comprises Gibson assembly region #1, a BsaI site, the variable capsid region, and a region homologous to the capsid gene that is used as a PCR primer. Fragment B comprises Gibson assembly region #2, a random barcode, a BsaI site, and Gibson assembly region #1. Next, a PCR procedure is performed where the 3' sequence of capsid gene is amplified using fragment A synthesized in step 1 as a PCR primer. Next, an intermediate AAV construct is generated by Gibson assembly where the construct comprises in a 5' to 3' order the 5' ITR, the SV40 poly A signal, the barcode, the two restriction endonuclease sites, the variant capsid sequences, the 3' region of the capsid protein, the polyA sequence for the capsid expression construct and the 3' ITR (step 3). Step 4 comprises performing ILLUMINA® sequencing across the barcode and the variant capsid sequences. Step 5 comprises digestion with the BsaI restriction enzyme. Step 6 is a PCR amplification step where the H2B, EGFP, hSyn1 and p40 promoters, and the 5' end of the capsid gene are prepared. Alternatively, the fragment comprising the H2B, EGFP, hSyn1, p40 promoter, and 5' end of the capsid gene may be pre-assembled in a donor plasmid, digested with BsaI, and gel purified. Step 7 is the final golden gate cloning step to create the final construct.

In FIG. 7A, wild type AAV1, lacking any inserted peptide in the capsid sequence, is labeled. The data demonstrates that many of the inserted peptide sequences caused an enrichment of the variants as compared to the wild type AAV1. In FIG. 7B, wild type AAV2, lacking any inserted peptide in the capsid sequence, is labeled. The data demonstrates that many of the inserted peptide sequences caused an enrichment of the variants in nuclei as compared to the wild type AAV2.

FIG. 9 shows micrographs of HEK293 cells transduced with the different reporter gene constructs. Panel A shows HEK293 cells transduced with AAV variants comprising the EGFP reporter alone, while Panel B shows the results when HEK293 cells are transduced with constructs comprising the SV40 nuclear localization sequence (NLS) fused to the EGFP gene, causing accumulation of the reporter in the nucleus. Panel C shows the results of HEK293 cells transduced with the AAV construct comprising the KASH-linked EGFP sequence and Panel D shows HEK293 cells transduced with the AAV construct comprising the mCherry reporter. Panel E shows the results when the AAV construct comprised the mCherry fused to the SV40 NLS, and Panel F shows the results when mCherry is fused to KASH.

FIG. 10A and FIG. 10B are immunohistochemistry micrographs from mouse brain tissues depicting nuclear localized neuronal reporter expression (cortex, hippocampus, thalamus) of the AAV variant library comprising the EGFP-H2B fusion (Panels A and B) following injection. Panel C shows mouse brain tissue depicting nuclear localized neuronal reporter expression (cortex, hippocampus, thalamus) of the AAV variant library comprising the mClover3-H2B fusion following injection. Panels D and E show mouse brain tissue depicting nuclear envelope localized neuronal reporter expression (cortex, hippocampus, thalamus) of the AAV variant library comprising the EGFP-KASH fusion following injection. Panel F shows mouse brain tissue depicting nuclear localized neuronal reporter expression (cortex, hippocampus, thalamus) of the AAV variant library comprising the mRuby3-H2B fusion following injection. Images in Panel F are native fluorescence in fixed brain sections.

FIG. 11 depicts FACS analysis of nuclei isolated from neuronal tissue in mice treated with AAV variants comprising the EGFP-H2B reporter. In mice injected with formulation buffer alone (Formulation) examined brain tissues did not exhibit any EGFP fluorescence (depicted in graph is the cortex tissue). In comparison, for nuclei isolated from mice treated with the AAV variants, reporter signaling could be detected in the thoracic spinal cord (7.68% of total events), the thalamus (16.53% of total events) and the cortex (6.54% of total events).

FIG. 15A, FIG. 15B and FIG. 15C depict a series of graphs supporting a clear dose response of EGFP reporter signal when the AAV variant library comprising the EGFP-H2B construct driven by the liver-specific TTR promoter are introduced into HepG2 cells in vitro at different doses ($3\times10^3$ (Panel B); $1\times10^4$ (Panel C); $3\times10^4$ (Panel D); $1\times10^5$ (Panel E); $3\times10^5$ (Panel F) and $1\times10^6$ (Panel G) compared to mock (Panel A)).

FIG. 17A and FIG. 17B show the distribution of the top 2500 fold enriched AAV variants according to which parent serotype the peptide insertion was made in. Data were obtained from sorting and sequencing. EGFP positive nuclei isolated from HepG2 (Panel A) and primary human hepatocytes in vitro (Panel B) in comparison with mouse (Panel C) and NHP liver tissue in vivo (Panel D). As can be seen in the figure, there are significant differences in the parent serotypes of AAV variants that are successful when challenged with different selective pressures.

FIG. 29A, FIG. 29B, FIG. 29C and FIG. 29D show highly enriched AAV variants and the sequences of peptides inserted ("Peptide", SEQ ID NOs 68-110) identified from the second round of screening from NHP CNS tissue. The variants are based on insertions into AAV1, AAV2, AAV3B, and AAV9 serotypes, where the peptide sequences were inserted into the following amino acid positions in each serotype indicated: AAV1 (590), AAV2 (588), AAV3B (589), AAV9 (589). The number to the left of each variant (1 through 43 (SEQ ID NO: 68-110)) corresponds to the numbers used for plotting in FIGS. 19 through 28. The data shows the enrichment of the individual variants through a second screening round in multiple cell lines or species as measured by quantification of AAV library barcoded mRNA transcripts or vector genomic DNA isolated from cells or CNS tissues. The degree of enrichment of each individual variant when isolated from the cells or tissue as compared to its percentage in the library prior to injection is indicated by the size of the circle. The darkness of the color of the circles also relates to the scale shown in the bottom right of FIG. 29D showing the relative variability in performance across multiple replicates, animals and/or tissue punches for a particular variant.

FIG. 41 shows a summary of serotype performance across different species. Data presented are for the hSyn1 barcode RNA analysis and serotypes are ordered according to performance in the non-human primate CNS.

FIG. 42 shows a summary of serotype performance across different species. Data presented are for the hU6 barcode RNA analysis and serotypes are ordered according to performance in the non-human primate CNS.

DETAILED DESCRIPTION

Figure 1:
FIG. 1 depicts information relating to the assembly of the capsid libraries. Panel A is an illustration of an AAV capsid protein where arrows indicate the exposed loops into which the peptides are inserted. Panel 1B is a diagram of the AAV serotype backbones that the peptides were inserted into. Silent mutations were made in the regions surrounding the peptide insertion sites (shown as grey boxes adjacent to the inserted peptide region, "peptide") to enable the use of the same universal Next-Generation Sequencing (NGS) primers to amplify the diversified region and quantify variant performance in a head to head comparison. A single insertion region is depicted (VR-VIII) as a representative example, but the same strategy is generalizable to other capsid regions targeted for diversification.

The present disclosure provides methods and compositions to develop AAV capsids with a desired characteristic compared to a natural AAV serotype. These capsids are useful, for example, for the delivery of genome engineering molecules and gene therapy molecules to a target cell, cell line, or tissue (e.g., in vitro or in vivo) for the treatment of a subject in need thereof.

Many tissues are highly heterogeneous and contain biological barriers that limit adeno-associated virus (AAV) transduction. A functional selection strategy enables selection of AAV variants from a library that are capable of transducing specific cell types within a tissue. Moreover, the selective pressure is designed to identify variants that excel in mediating post-entry steps and driving transgene expression. In order to establish a functional selection strategy that is applicable to all species and tissues, several modifications were introduced in the AAV viral genome. Herein we describe methods for the generation of AAV variant libraries and methods of functional selection of variants capable of transducing desired tissues, cells and/or organelles. These methods are applicable to the development of AAV variants suitable for all species, cell types and target organelles.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The term "herein" means the entire application.

Unless otherwise defined herein, scientific and technical terms used in this application shall have the meanings that are commonly understood by those of ordinary skill in the art to which this invention belongs. Generally, nomenclature used in connection with the compounds, composition and methods described herein, are those well-known and commonly used in the art.

It should be understood that any of the embodiments described herein, including those described under different aspects of the disclosure and different parts of the specification (including embodiments described only in the Examples) can be combined with one or more other embodiments of the invention, unless explicitly disclaimed or improper. Combination of embodiments are not limited to those specific combinations claimed via the multiple dependent claims.

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the specification, where compositions are described as having, including, or comprising (or variations thereof), specific components, it is contemplated that compositions also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "including" is used to mean "including but not limited to." "Including" and "including but not limited to" are used interchangeably.

As used herein, "about" or "approximately" means within an acceptable error range for the particular value as determined by one of ordinary skill in the art, which will depend in part on how the value is measured or determined, i.e., the limitations of the measurement system.

The use of the terms "a" and "an" and "the" and similar referents in the context of describing the elements (especially in the context of the following claims) are to be construed to cover both the singular and the plural, unless otherwise indicated herein or clearly contradicted by context.

The term "or" as used herein should be understood to mean "and/or," unless the context clearly indicates otherwise.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on-target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity.

For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cpf1).

A "DNA binding protein" (or binding domain) is a protein, or a domain within a larger protein, that binds DNA in a sequence-specific manner, for example through one or more zinc fingers or through interaction with one or more RVDs in a zinc finger protein or TALE, respectively. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526, incorporated by reference herein in its entirety.

"TtAgo" is a prokaryotic Argonaute protein thought to be involved in gene silencing. TtAgo is derived from the bacteria *Thermus thermophilus*. See, e.g. Swarts, et al., ibid; G. Sheng, et al. (2013) *Proc. Natl. Acad. Sci. U.S.A.* 111, 652). A "TtAgo system" is all the components required including e.g. guide DNAs for cleavage by a TtAgo enzyme.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

The term "editing" as used herein refers to a process wherein a nucleotide base is modified such that point mutations are introduced into a DNA strand. Introduction of the point mutation in the DNA will necessarily reproduce the change in any mRNA that is transcribed from the edited DNA. Adenine and cytidine deaminases remove an amino group from their respective nucleotide targets, converting them into inosine and uridine respectively. During DNA repair or replication, inosine is recognized as guanine and uridine is recognized as thymine by polymerase enzymes, resulting in conversion of an A:T base pair into a G:C base pair, or C:G base pair into a T:A base pair in the double stranded DNA that has been edited.

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), between about 100 and 100,000 nucleotides in length (or any integer therebetween), between about 2000 and 20,000 nucleotides in length (or any value therebetween) or between about 5 and 15 kb (or any value therebetween).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be episomally maintained or, alternatively, may be stably integrated into the cell.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

The term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid sequence encoding a heterologous gene product is an rAAV that includes a polynucleotide not normally included in a naturally-occurring, wild-type AAV, and the encoded heterologous gene product is a gene product not normally encoded by a naturally-occurring, wild type AAV.

The terms "fusion," "fused" molecule or variations thereof refer to is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristoylation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "reporter gene" or "reporter sequence" refers to any sequence that produces a protein product (a "reporter protein") that is easily measured, in an assay. The assay may be, but is not necessarily, routine. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

"Eukaryotic" cells include, but are not limited to, fungal cells (such as yeast), plant cells, animal cells, mammalian cells and human cells (e.g., T-cells), including stem cells (pluripotent and multipotent).

The term "barcode", as used herein, refers to a unique oligonucleotide sequence (e.g., 5, 6, 7, 8, 9, 10, 12, 15, 20, 25, 30, 50, 75, 100 nucleotides) having a particular sequence, that is used as a means of identifying a nucleic acid sequence in which it is incorporated. The barcode is used as a means of distinguishing or identifying individual members (e.g., variants) in a library.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid or protein (e.g., coding function, ability to hybridize to another nucleic acid, enzymatic activity assays) are well-known in the art.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals including, but not limited to, human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer, monogenic diseases and graft versus host disease are non-limiting examples of conditions that may be treated using the compositions and methods described herein.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., a muscle disease). Accordingly, an effective amount of an infectious rAAV virion is an amount of the infectious rAAV virion that is able to effectively deliver a heterologous nucleic acid to a target cell (or target cells) of the individual. Effective amounts may be determined preclinically by, e.g., detecting in the cell or tissue the gene product (RNA, protein) that is encoded by the heterologous nucleic acid sequence using techniques that are well understood in the art, e.g. RT-PCR, western blotting, ELISA, fluorescence or other reporter readouts, and the like. Effective amounts may be determined clinically by, e.g. detecting a change in the onset or progression of disease using methods known in the art, e.g. 6-minute walk test, left ventricular ejection fraction, hand-held dynamometry, Vignos Scale and the like as described herein and as known in the art.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

The term "virus genome" refers to a nucleic acid sequence that is flanked by cis acting nucleic acid sequences that mediate the packaging of the nucleic acid into a viral capsid. For AAVs and parvoviruses, for example it is known that the "inverted terminal repeats" (ITRs) that are located at the 5' and 3' end of the viral genome have this function and that the ITRs can mediate the packaging of heterologous, for example, non-wild type virus genomes, into a viral capsid.

The term "element" refers to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "variant" refers to a polynucleotide or polypeptide having a sequence substantially similar to a reference polynucleotide or polypeptide. In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans. In some instances, the term "variant" may also be used to describe an AAV comprising a variant capsid sequence.

The term "AAV" or "adeno-associated virus" refers to a Dependoparvovirus within the Parvoviridae genus of viruses. For example, the AAV can be an AAV derived from a naturally occurring "wild-type" virus, an AAV derived from a rAAV genome packaged into a capsid derived from capsid proteins encoded by a naturally occurring cap gene and/or a rAAV genome packaged into a capsid derived from capsid proteins encoded by a non-natural capsid cap gene. For the purposes of the disclosure herein, the term "AAV" is an abbreviation for adeno-associated virus, including, without limitation, the virus itself and derivatives thereof. Except where otherwise indicated, the term refers to all subtypes or serotypes and both replication-competent and recombinant forms. The term "AAV" includes, without limitation, AAV type 1 (AAV-1 or AAV1), AAV type 2 (AAV-2 or AAV2), AAV type 3A (AAV-3A or AAV3A), AAV type 3B (AAV-3B or AAV3B), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), AAV type 10 (AAV-10 or AAV10 or AAVrhl0), avian AAV, bovine AAV, canine AAV, caprine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV1), AF063497.1 (AAV1), NC 001401.2 (AAV2), AF043303.1 (AAV2), J01901.1 (AAV2), U48704.1 (AAV3A), NC_001729.1 (AAV3A), AF028705.1 (AAV3B), NC_001829.1 (AAV4), U89790.1 (AAV4), NC_006152.1 (AA5), AF085716.1 (AAV-5), AF028704.1 (AAV6), NC_006260.1 (AAV7), AF513851.1 (AAV7), AF513852.1 (AAV8) NC 006261.1 (AAV-8), AY530579.1 (AAV9), AAT46337 (AAV10) and AA088208 (AAVrhl0); the disclosures of which are incorporated by reference herein for teaching AAV nucleic acid and amino acid sequences. See also, e.g., Srivistava et al. (1983) *J. Virology* 45:555; Morini et al. (1998) *J. Virology* 71:6823; Chiorini et al. (1999) *J. Virology* 73: 1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J Virol.* 58:921; Gao et al. (2002) *Proc. Nat. Acad. Sci. USA* 99: 11854; Moris et al. (2004) *Virology* 33:375-383; international patent publications WO 00/28061, WO 99/61601, WO 98/11244; and U.S. Pat. No. 6,156,303.

The term "rAAV" refers to a "recombinant AAV". In some embodiments, a recombinant AAV has an AAV genome in which part or all of the rep and cap genes have been replaced with heterologous sequences. If an AAV virion comprises a heterologous polynucleotide (i.e. a polynucleotide other than a wild-type AAV genome, e.g., a transgene to be delivered to a target cell, a nuclease system, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "cap gene" or "capsid gene" refers to the nucleic acid sequences that encode capsid proteins that form, or contribute to the formation of, the capsid, or protein shell, of the virus. In the case of AAV, the capsid protein may be VP1, VP2, or VP3. For other parvoviruses, the names and numbers of the capsid proteins can differ.

The term "rep gene" refers to the nucleic acid sequences that encode the non-structural proteins (rep78, rep68, rep52 and rep40) required for the replication and production of virus.

The term "packaging" refers to a series of intracellular events that result in the assembly and encapsidation of an AAV particle. AAV "rep" and "cap" genes refer to polynucleotide sequences encoding replication and encapsidation proteins of adeno-associated virus. AAV rep and cap are referred to herein as AAV "packaging genes."

The term "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

The term "helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

The term "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11: S337 (describing a TCID50 infectious titer assay); and Zolotukhin et al. (1999) *Gene Ther.* 6:973.

The term "tropism" as used herein refers to the preferential targeting by a virus (e.g., an AAV) of cells of a particular host species or of particular cell types within a host species. For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

The term "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per 10 rAAV particles, less than about 1 rcAAV per $10^{12}$ rAAV particles, or no rcAAV).

A "library" may be in the form of a multiplicity of linear nucleic acids, plasmids, viral particles or viral vectors, etc. A library will include at least two nucleic acids, plasmids, viral particles, viral vectors, etc.

Libraries of AAV Variants

In one aspect, the subject matter disclosed herein relates to the development of libraries encoding AAV capsid proteins with a desired characteristic compared to a natural AAV serotype. Thus, described herein are libraries of AAV variants used to develop AAV capsids with a desired characteristic compared to a natural AAV serotype. In some embodiments, the desired characteristic is enhanced cell or tissue tropism as compared to the natural AAV serotype. In some embodiments, the desired characteristic is the evasion of a pre-existing host antibody response. In some embodiments, the desired characteristic is reduced immunogenicity so as to not provoke a host response.

In some embodiments, each member of a library of the disclosure comprises a) a nucleic acid sequence encoding an AAV variant capsid protein comprising a peptide inserted into a hypervariable and/or surface-exposed loop of the variant capsid protein; and one or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, each member of a library of the disclosure comprises a) a nucleic acid sequence encoding an AAV variant capsid protein comprising a peptide inserted into a hypervariable and/or surface-exposed loop of the variant capsid protein; and two or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, each member of a library of the disclosure comprises a) a nucleic acid sequence encoding an AAV variant capsid protein comprising a peptide inserted into a hypervariable and/or surface-exposed loop of the variant capsid protein; and three or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, each member of a library of the disclosure comprises a) a nucleic acid sequence encoding an AAV variant capsid protein comprising a peptide inserted into a hypervariable and/or surface-exposed loop of the variant capsid protein; and b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, each member of a library of the disclosure comprises a) an AAV variant capsid protein comprising a peptide inserted into a hypervariable and/or surface-exposed loop of the variant capsid protein; and one or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, each member of a library of the disclosure comprises a) an AAV variant capsid protein comprising a peptide inserted into a hypervariable and/or surface-exposed loop of the variant capsid protein; and two or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, each member of a library of the disclosure comprises a) an AAV variant capsid protein comprising a peptide inserted into a hypervariable and/or surface-exposed loop of the variant capsid protein; and three or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, each member of a library of the disclosure comprises a) an AAV variant capsid protein comprising a peptide inserted into a hypervariable and/or surface-exposed loop of the variant capsid protein; b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, each member of the library comprises a nucleic acid encoding a localization signal. In some embodiments, each member of the library comprises a nucleic acid encoding a localization signal. In some embodiments, each member of the library comprises a nucleic acid comprising a barcode. In some embodiments, each member of the library comprises a nucleic acid comprising two or more barcodes. In some embodiments, each member of the library comprises a nucleic acid encoding a reporter protein.

In any of the above embodiments, the nucleic acid encoding an AAV variant capsid protein, the nucleic acid encoding a localization signal, the nucleic acid comprising a barcode, and/or the nucleic acid encoding a reporter protein, are present on separate nucleic acid molecules. In some embodiments, the nucleic acid encoding an AAV variant capsid protein, the nucleic acid encoding a localization signal, the nucleic acid comprising a barcode, and/or the nucleic acid encoding a reporter protein, are present on a single nucleic acid molecule. In some embodiments, the nucleic acid encoding an AAV variant capsid protein, and the nucleic acid encoding a localization signal, the nucleic acid comprising a barcode, and/or the nucleic acid encoding a reporter protein, are linked to each other in any order. In some embodiments, each member of the library comprises a 5'ITR sequence, the nucleic acid comprising a barcode, the nucleic acid encoding a reporter protein, the nucleic acid encoding an AAV variant capsid protein, and a 3'ITR sequence, in that order.

In some embodiments, the AAV variant capsid proteins are derived from AAV1, AAV2, AAV3B, AAV5, AAV6, AAV8 and AAV9. In some embodiments, the AAV variant capsid proteins are derived from less well characterized AAV serotypes, including but not limited to AAV3, AAV4, AAV7, AAV11, AAVrh10, AAVrh39, and AAVrh74.

In some embodiments, a library of AAV variants comprises AAV variant capsid proteins derived from a single AAV serotype. In some embodiments, a library of AAV variants comprises AAV variant capsid proteins derived from 2, 3, 4, 5, 6, 7, 8, 9, 10, 11, 12, 13, 14, 15, or more AAV serotypes. In some embodiments, the AAV variant capsid proteins derived from 2, 3, 4, 5, 6, 7, 8, 9, 10, 11, 12, 13, 14, 15, or more AAV serotypes are combined once individual serotype libraries are developed. In some embodiments, combinatorial libraries are generated by modifying nucleic acids encoding AAV capsid proteins from 2, 3, 4, 5, 6, 7, 8, 9, 10, 11, 12, 13, 14, 15, or more serotypes in the same pool.

In some embodiments, mutations (e.g., insertions, deletions and/or substitutions) are introduced into a DNA sequence encoding an exposed loop in the capsid protein. In some embodiments, a peptide is inserted into exposed loops (e.g. hypervariable regions) in the AAV capsid. In some embodiments, the peptide comprises 6, 7, 8, 9, 10, 11, 12, 13, 14, 15 or more amino acids. In some embodiments, the HI loop is targeted (mutated) while in others, the DE loop is targeted (mutated). In some embodiments, mutations (e.g., insertions, deletions and/or substitutions) are made in both loops. In further embodiments, mutations (e.g., insertions, deletions and/or substitutions) are introduced into the VR region of a surface loop, including into VR-I, VR-II, VR-III, VR-IV, VR-V, VR-VI, VR-VII, VR-VIII and or VR-IX. In yet other embodiments, mutations (e.g., insertions, deletions and/or substitutions) are made in VR-I, VR-VIII and or VR-IV. In some embodiments, the mutations (e.g., insertions, deletions and/or substitutions) are introduced into the AAV capsid proteins VP1, VP2 or VP3, or in two of the capsid proteins in any combination, or in all three. In some embodiments, the mutations are introduced into VP1. In some embodiments, the mutations are introduced into VP2. In some embodiments, the mutations are introduced into VP3. In some embodiments, the mutations are introduced into VP1 and VP2. In some embodiments, the mutations are introduced into VP1 and VP3. In some embodiments, the mutations are introduced into VP2 and VP3. In some embodiments, the mutations are introduced into VP1, VP2, and VP3. In some embodiments, a single mutation (e.g., an insertion, a deletion and/or a substitution) is introduced at a single site in a gene encoding a capsid protein, while in other embodiments, more than 1, 2, 3, 4, 5, 6, 7, 10, 20, 30, 40, 50, 100 or more (including any number between 1 and 100 or more) mutations (e.g., insertions, deletions and/or substitutions) are introduced in a gene encoding a capsid protein.

In some exemplary embodiments, a peptide is introduced into the variable regions VR-I, VR-IV, or VR-VIII of the capsid protein. In some embodiments, the peptide is introduced at a location between positions 450 and 600 of the capsid protein. In some embodiments, the peptide is introduced at position 590 if the capsid protein corresponds to AAV1. In some embodiments, the peptide is introduced into position 454 or 590 if an AAV6 capsid is being modified. In some embodiments, the peptide introduced at position 588 if an AAV2 capsid is being modified. In some embodiments, the peptide is introduced into position 589 if an AAV3B capsid is used. In some embodiments, the peptide is introduced into position 578 if an AAV5 capsid is used. In some embodiments, the peptide is introduced into position 591 if an AAV8 capsid is used. In some embodiments the peptide is introduced into position 266, 455, and/or 589 if an AAV9 capsid is used. It is understood that other sites in the capsid proteins may be selected for insertion.

In some embodiments of the AAV libraries disclosed herein, a peptide comprising the amino acid sequence of any one of SEQ ID NO:1-32 is inserted at amino acid position 590 of the capsid protein of an AAV1 serotype. In some embodiments of the AAV libraries disclosed herein, a peptide comprising the amino acid sequence of any one of SEQ ID NO:68-110 is inserted at amino acid position 590 of the capsid protein of an AAV1 serotype. In some embodiments of the AAV libraries disclosed herein, the peptide inserted at position 590 of the capsid protein of an AAV1 serotype comprises an amino acid sequence selected from the group consisting of any one of SEQ ID NO: 68 to SEQ ID NO: 75. In some embodiments of the AAV libraries disclosed herein, the peptide inserted at position 590 of the capsid protein of an AAV1 serotype comprises the amino acid sequence SEQ ID NO: 71. In some embodiments of the AAV libraries disclosed herein, the peptide inserted at position 590 of the capsid protein of an AAV1 serotype comprises an amino acid sequence selected from the group consisting of any one of SEQ ID NO: 1, SEQ ID NO: 2 and SEQ ID NO: 3.

In some embodiments of the AAV libraries disclosed herein, a peptide comprising the amino acid sequence of any one of SEQ ID NO:1-32 is inserted at amino acid position 454 of the capsid protein of an AAV6 serotype. In some embodiments of the AAV libraries disclosed herein, a peptide comprising the amino acid sequence of any one of SEQ ID NO:68-110 is inserted at amino acid position 454 of the capsid protein of an AAV6 serotype. In some embodiments of the AAV libraries disclosed herein, a peptide comprising the amino acid sequence of any one of SEQ ID NO:1-32 is inserted at amino acid position 590 of the capsid protein of an AAV6 serotype. In some embodiments of the AAV libraries disclosed herein, a peptide comprising the amino acid sequence of any one of SEQ ID NO:68-110 is inserted at amino acid position 590 of the capsid protein of an AAV6 serotype. In some embodiments of the AAV libraries disclosed here, the peptide inserted at position 454 of the capsid protein of an AAV6 serotype comprises an amino acid sequence selected from the group consisting of any one of SEQ ID NO: 19 to SEQ ID NO: 27. In some embodiments of the AAV libraries disclosed here, the peptide inserted at position 590 of the capsid protein of an AAV6 serotype comprises an amino acid sequence selected from the group consisting of any one of SEQ ID NO: 19 to SEQ ID NO: 27.

In some embodiments of the AAV libraries disclosed herein, a peptide comprising the amino acid sequence of any one of SEQ ID NO:1-32 is inserted at amino acid position 588 of the capsid protein of an AAV2 serotype. In some embodiments of the AAV libraries disclosed herein, a peptide comprising the amino acid sequence of any one of SEQ ID NO:68-110 is inserted at amino acid position 588 of the capsid protein of an AAV2 serotype. In some embodiments of the AAV libraries disclosed here, the peptide inserted at position 588 of the capsid protein of an AAV2 serotype comprises an amino acid sequence selected from the group consisting of any one of SEQ ID NO: 90 to SEQ ID NO: 110. In some embodiments of the AAV libraries disclosed here, the peptide inserted at position 588 of the capsid protein of an AAV2 serotype comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102. In some embodiments of the AAV libraries disclosed here, the peptide inserted at position 588 of the capsid protein of an AAV2 serotype comprises an amino acid sequence selected from the group consisting of any one of SEQ ID NO: 4-7.

In some embodiments of the AAV libraries disclosed herein, a peptide comprising the amino acid sequence of any one of SEQ ID NO:1-32 is inserted at amino acid position 589 of the capsid protein of an AAV3B serotype. In some embodiments of the AAV libraries disclosed herein, a peptide comprising the amino acid sequence of any one of SEQ ID NO:68-110 is inserted at amino acid position 589 of the capsid protein of an AAV3B serotype. In some embodiments of the AAV libraries disclosed here, the peptide inserted at position 589 of the capsid protein of an AAV3B serotype comprises an amino acid sequence selected from the group consisting of any one of SEQ ID NO: 76-85. In some embodiments of the AAV libraries disclosed here, the peptide inserted at position 589 of the capsid protein of an AAV3B serotype comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83. In some embodiments of the AAV libraries disclosed here, the peptide inserted at position 589 of the capsid protein of an AAV3B serotype comprises an amino acid sequence selected from the group consisting of any one of SEQ ID NO: 8 to SEQ ID NO: 11.

In some embodiments of the AAV libraries disclosed herein, a peptide comprising the amino acid sequence of any one of SEQ ID NO:1-32 is inserted at amino acid position 578 of the capsid protein of an AAV5 serotype. In some embodiments of the AAV libraries disclosed herein, a peptide comprising the amino acid sequence of any one of SEQ ID NO:68-110 is inserted at amino acid position 578 of the capsid protein of an AAV5 serotype. In some embodiments of the AAV libraries disclosed here, the peptide inserted at position 578 of the capsid protein of an AAV5 serotype comprises an amino acid sequence selected from the group consisting of any one of SEQ ID NO: 28 to SEQ ID NO: 32.

In some embodiments of the AAV libraries disclosed herein, a peptide comprising the amino acid sequence of any one of SEQ ID NO:1-32 is inserted at amino acid position 591 of the capsid protein of an AAV8 serotype. In some embodiments of the AAV libraries disclosed herein, a peptide comprising the amino acid sequence of any one of SEQ ID NO:68-110 is inserted at amino acid position 591 of the capsid protein of an AAV8 serotype.

In some embodiments of the AAV libraries disclosed herein, a peptide comprising the amino acid sequence of any one of SEQ ID NO:1-32 is inserted at amino acid position 266 of the capsid protein of an AAV9 serotype. In some embodiments of the AAV libraries disclosed herein, a peptide comprising the amino acid sequence of any one of SEQ ID NO:68-110 is inserted at amino acid position 266 of the capsid protein of an AAV9 serotype. In some embodiments of the AAV libraries disclosed herein, a peptide comprising the amino acid sequence of any one of SEQ ID NO:1-32 is inserted at amino acid position 455 of the capsid protein of an AAV9 serotype. In some embodiments of the AAV libraries disclosed herein, a peptide comprising the amino acid sequence of any one of SEQ ID NO:68-110 is inserted at amino acid position 455 of the capsid protein of an AAV9 serotype. In some embodiments of the AAV libraries disclosed herein, a peptide comprising the amino acid sequence of any one of SEQ ID NO:1-32 is inserted at amino acid position 589 of the capsid protein of an AAV9 serotype. In some embodiments of the AAV libraries disclosed herein, a peptide comprising the amino acid sequence of any one of SEQ ID NO:68-110 is inserted at amino acid position 589 of the capsid protein of an AAV9 serotype. In some embodiments of the AAV libraries disclosed here, the peptide inserted at position 266 of the capsid protein of an AAV9 serotype comprises an amino acid sequence selected from the group consisting of any one of SEQ ID NO: 12 to SEQ ID NO: 18. In some embodiments of the AAV libraries disclosed here, the peptide inserted at position 266 of the capsid protein of an AAV9 serotype comprises an amino acid sequence selected from the group consisting of any one of SEQ ID NO: 86 to SEQ ID NO: 89. In some embodiments of the AAV libraries disclosed here, the peptide inserted at position 266 of the capsid protein of an AAV9 serotype comprises an amino acid sequence of SEQ ID NO: 89. In some embodiments of the AAV libraries disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the AAV libraries disclosed here, the peptide inserted at position 455 of the capsid protein of an AAV9 serotype comprises an amino acid sequence selected from the group consisting of any one of SEQ ID NO: 86 to SEQ ID NO: 89. In some embodiments of the AAV libraries disclosed here, the peptide inserted at position 455 of the capsid protein of an AAV9 serotype comprises an amino acid sequence of SEQ ID NO: 89. In some embodiments of the AAV libraries disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the AAV libraries disclosed here, the peptide inserted at position 589 of the capsid protein of an AAV9 serotype comprises an amino acid sequence selected from the group consisting of any one of SEQ ID NO: 86 to SEQ ID NO: 89. In some embodiments of the AAV libraries disclosed here, the peptide inserted at position 589 of the capsid protein of an AAV9 serotype comprises an amino acid sequence of SEQ ID NO: 89.

In some embodiments, the inserted peptide is 1, 2, 3, 4, 5, 6, 7, 8, 9, 10, 11, 12, 13, 14, 15 or more amino acids long. In some embodiments, the peptide is 7 amino acids long. In some embodiments, the peptide is 10 amino acids long. In some embodiments, the peptide is 15 amino acids long. In some embodiments, the peptides are introduced during amplification of the fragment of the capsid gene that is 3' of the insertion site by PCR. Thus, in some embodiments, the capsid gene is diversified using PCR. In some embodiments, the introduced sequences are introduced during amplification of the fragment of the capsid gene that is 3' of the insertion site.

In some embodiments, silent mutations are introduced into regions of the capsid gene flanking the region into which the peptides are introduced so that all capsid serotype genes have the same nucleotide sequence in these flanking regions. The flanking region may include 10 or more, 20 or more, 30 or more, 40 or more, 50 or more, 100 or more, 150 or more, or 200 or more nucleotides on either side of the peptide insertion site. In this way the same primer sequences can be used for PCR amplification and next-generation sequencing (NGS) for all serotype libraries. This allows for faster screening of libraries based on 2, 3, 4, 5, 6, 7, 8, 9, 10, 11, 12, 13, 14, 15, or more serotypes. In some embodiments, 2, 3, 4, 5, 6, 7, 8, 9, 10, 11, 12, 13, 14, 15 or more silent mutations are introduced to bring the flanking sequences into alignment with two common sequences (one at the 5' end of the diversified region and one at the 3' end of the diversified region). In some embodiments, the silent mutations are introduced at one or more of position 571, 612, and 617 if the capsid protein corresponds to AAV1. In some embodiments, the silent mutations are introduced at one or more of position 568, 569, 572, 573, 574, 610, 611, 613, 615, 616, and 617 if the capsid protein corresponds to AAV2. In some embodiments, the silent mutations are introduced at one or more of position 569, 570, 571, 573, 574, 575, 612, 614, 615, and 616 if the capsid protein corresponds to AAV3B. In some embodiments, the silent mutations are introduced at one or more of position 573, 575, 576, 577, 614, and 619 if the capsid protein corresponds to AAV8. In some embodiments, the silent mutations are introduced at one or more of position 571, 572, 573, 574, 575, 611, 612, 615, 616, and 617 if the capsid protein corresponds to AAV9. It is understood that other sites in the capsid proteins may be selected for insertion.

In some embodiments, the payload or genome of each AAV variant in a library further comprises a reporter gene. In some embodiments, the protein encoded by the reporter is fluorescent. Exemplary, non-limiting reporter genes include EGFP, mCherry, mClover3 and mRuby3. Other exemplary non-limiting reporter genes include mApple, iRFP, tdTomato, mVenus, YFP, RFP, firefly luciferase, and nanoluciferase.

In some embodiments, the capsid gene and the reporter gene are under the control of separate promoters. In some embodiments, the capsid gene and the reporter gene are each independently operatively linked to a promoter.

In some embodiments, the reporter gene is controlled by a cell type and/or tissue specific promoter. In some embodiments, the reporter gene is operatively linked to a cell type and/or tissue specific promoter. In some embodiments, the reporter gene is operatively linked to a cell-type specific RNA polymerase II promoter. Exemplary cell type and/or tissue specific promoters include the human synapsin promoter (hSyn1), only expressed in neurons, or the transthyretin promoter (TTR), expressed in hepatocytes. Other non-limiting cell type and/or tissue specific promoters for use in the methods and compositions of the invention include cytokeratin 18 and 19 (epithelial cell specific, Zheng and Baum (2008) *Methods Mol Biol* 434:205-219), unc45b or unc-45 myosin chaperon B (muscle specific, Rudeck et al (2016) *Genesis* 54(8):431-8), cardiac troponin T (cTnT) (cardiomyocyte specific, Ma et al (2004) *Am J Physiol Cell Physiol* 286(3):556-64), glial fibrillary acidic protein (GFAP) (astrocyte specific, Lee et al (2008) *Glia* 56(5):481-93), myelin basic protein (MBP) (oligodendrocyte specific, Wei et al (2003) *Gene* 313:161-7), methyl CpG-binding protein 2 (Mecp2) (neuron specific, Adachi et al (2005) *Hum Mol Genetics* 14(23):3709-22), and other brain or eye specific rAAV-compatible MiniPromoters (Leeuw et al (2016) *Molecular Brain* 9(1):52).

In some embodiments, the payload or genome of each AAV variant in a library further comprise a nucleic acid encoding a localization signal. In some embodiments, the reporter gene is fused to the nucleic acid encoding a localization signal. In some embodiments, the reporter genes are fused to domains to increase movement of the reporter into organelles. In some embodiments, the reporter genes are fused to domains to increase movement of the reporter into the nucleus. In some embodiments, the reporter genes are fused to a nucleic acid encoding a nuclear localization signal (NLS) (for example the SV40 large T-antigen nuclear localization signal). Non-limiting examples of NLSs include an NLS sequence derived from: the NLS of the SV40 virus large T-antigen; the NLS from nucleoplasmin; a c-myc NLS; the hRNPA1 M9 NLS; the IBB domain from importin-alpha; the myoma T protein NLS; human p53 NLS; mouse c-abl IV NLS; influenza virus NS1 NLS; Hepatitis virus delta antigen NLS; the mouse Mx1 protein NLS; the human poly(ADP-ribose) polymerase NLS; and steroid hormone receptors (human) glucocorticoid NLS. Other NLSs are known in the art. In some embodiments, the reporter proteins are fused to a protein that localizes to the nuclear envelope (for example KASH domains). In some embodiments, the reporter proteins are fused to a histone binding domain (for example histone 2B binding domain, H2B). Other non-limiting histones include those in the H1, H2A, H3, and H4 families. It is understood that both N and C terminal fusions to a reporter gene support nuclear localization. In some embodiments, the reporter protein is fused to more than one localization signal. In some embodiments, the multiple localization signals are in tandem. In some embodiments, the reporter protein is fused to one or more localization signals at its N-terminus and one or more localization signals at its C-terminus.

In some embodiments, a nucleic acid comprising a barcode is added to the payload or genome of each AAV variant in a library. In some embodiments, the barcode is bioinformatically linked to the peptide introduced into the variant capsid protein. In some embodiments, the DNA sequences comprising the variant DNA sequences encoding the inserted peptide are synthesized to further comprise a random or specified barcode. The barcode may comprise 5, 6, 7, 8, 9, 10, 11, 12, 13, 14, 15, 16, 17, 18 or more nucleotides. In some embodiments, the nucleic acid comprising a barcode is selected from any one of sequences SEQ ID NO: 111-154 or 155-198. In some embodiments, the nucleic acid comprising a barcode is selected from SEQ ID NO: 111-154.

In some embodiments, the nucleic acid comprising a barcode is selected from SEQ ID NO: 155-198. In some embodiments, the nucleic acid comprising the barcode comprises a sequence selected from any one of sequences SEQ ID NO: 111-154. In some embodiments, the nucleic acid comprising the barcode comprises a sequence selected from any one of sequences SEQ ID NO: 155-198. The synthesized DNA may also comprise restriction sites and or nucleic acid sequences used for molecular cloning by Gibson assembly. In some embodiments an intron is included in the expression cassette to confirm that sequenced transcripts are derived from mRNA and not vector genomic DNA. In further embodiments, the AAV payload or genome is assembled via Gibson assembly where the 3' end of the capsid gene is linked to the random or specified insertion sequences at the insertion site, and the barcode is linked to a polyA sequence and 5'ITR. In some embodiments, ILLUMINA® sequencing (or any other sequencing technique) is performed across the barcode and the inserted variable region in the capsid gene to bioinformatically link the two random sequences. In further embodiments, the reporter construct, reporter-specific promoter, capsid-specific promoter and 5' end of the capsid gene are assembled to create the final payload construct. In some embodiments, the expression cassette relative to the cap gene is in the sense orientation.

In some embodiments, each member of the library comprises a nucleic acid comprising more than one barcode sequences. In some embodiments, each member of the library comprises two or more nucleic acids each comprising a barcode sequence. In some embodiments, each member of the library comprises a first nucleic acid comprising a first barcode and a second nucleic acid comprising a second barcode. In some embodiments, the first nucleic acid comprising the first barcode and the second nucleic acid comprising the second barcode are different. In some embodiments, the first nucleic acid comprising the first barcode sequence comprises a sequence selected from any one of sequences SEQ ID NO: 111-154. In some embodiments, the first barcode sequence is selected from any one of sequences SEQ ID NO: 111-154. In some embodiments, the second nucleic acid comprising the second barcode sequence comprises a sequence selected from any one of sequences SEQ ID NO: 155-198. In some embodiments, the second nucleic acid comprising the second barcode sequence is selected from any one of sequences SEQ ID NO: 155-198. In some embodiments, each of the first nucleic acid comprising the first barcode and the second nucleic acid comprising the second barcode is independently operatively linked to a promoter. In some embodiments, the promoter operatively linked to the first nucleic acid comprising the first barcode and the promoter operatively linked to the second nucleic acid comprising the second barcode is each independently an RNA Pol II promoter. In some embodiments, the promoter operatively linked to the first nucleic acid comprising the first barcode and the promoter operatively linked to the second nucleic acid comprising the second barcode is each independently an RNA Pol III promoter (e.g., a promoter selected from the group of U6 promoter, H1 promoter and 7SK promoter). In some embodiments, the promoter operatively linked to the first nucleic acid comprising the first barcode is operatively linked to an RNA Pol II promoter and the promoter operatively linked to the second nucleic acid comprising the second barcode is an RNA Pol III promoter (e.g., a promoter selected from the group of human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

In some embodiments, a short piece of DNA is synthesized comprising a randomly generated or specified barcode and a randomly generated or specified capsid variant region, as well as two regions used for Gibson assembly. Next, capsid sequence 3' of the diversified region are amplified. In further embodiments, a Gibson assembly reaction where the 5'ITR and polyadenylation sequences are fused to the barcode on the 5' end, and a second Gibson assembly region is fused to the 3' end of the capsid gene and the polyA signal for the capsid gene and the 3'ITR are performed. In further embodiments, ILLUMINA® sequencing is performed across the barcode and the variant capsid sequences. In further embodiments, digestion with a restriction enzyme is carried out. In further embodiments, a PCR amplification step where the reporter, localization signal, promoter(s), and the 5' end of the capsid gene are prepared. Alternatively, the fragment comprising the reporter, the localization signal, the promoter(s), and 5' end of the capsid gene may be pre-assembled in a donor plasmid, digested with BsaI, and gel purified. In further embodiments, golden gate cloning step is performed to create the final construct.

In some embodiments, two DNA fragments are synthesized. Fragment A comprises Gibson assembly region #1, a restriction enzyme site, the variable capsid region, and a region homologous to the capsid gene that is used as a PCR primer. Fragment B comprises Gibson assembly region #2, a random barcode, a restriction enzyme site, and Gibson assembly region #1. Next, a PCR procedure is performed where the 3' sequence of capsid gene is amplified using fragment A synthesized in step 1 as a PCR primer. In further embodiments, an intermediate AAV construct is generated by Gibson assembly where the construct comprises in a 5' to 3' order the 5' ITR, the SV40 poly A signal, the barcode, the two restriction endonuclease sites, the variant capsid sequences, the 3' region of the capsid protein, the polyA sequence for the capsid expression construct and the 3' ITR. In further embodiments, ILLUMINA® sequencing is performed across the barcode and the variant capsid sequences. In further embodiments, digestion with a restriction enzyme is carried out. In further embodiments, a PCR amplification step where the reporter, localization signal, promoter(s), and the 5' end of the capsid gene are prepared is performed. Alternatively, the fragment comprising the reporter, localization signal, promoter(s), and 5' end of the capsid gene may be pre-assembled in a donor plasmid, digested with BsaI, and gel purified. In further embodiments, a golden gate cloning step is performed to create the final construct.

In some embodiments, each inserted peptide may be encoded by multiple nucleic acid molecules, each having a different sequence (due to codon degeneracy). Each nucleic acid sequence is linked to a unique bar code such that performance (e.g. enrichment) of an inserted peptide can be verified when two or more variants are identified having the same inserted peptide sequence, but wherein the inserted peptides are encoded by different nucleic acid sequences.

In some embodiments, the barcode is linked to the reporter gene, the polyA sequence and the 5'ITR through standard cloning techniques. In further embodiments, the variant sequences encoding the peptide are inserted into the capsid gene through standard techniques, and then specific promoter(s) are added, and the 5'end of the capsid gene is added. ILLUMINA® sequencing (or any other highly reliable sequencing technique) is then performed in two separate reactions where the barcode and the inserted nucleotide sequences are sequenced. Finally, OXFORD NANOPORE® sequencing (or any other long read sequencing technique, for example PACBIO®SMRT sequencing) is performed such that the long-read length sequence comprises both the barcode and inserted nucleotide sequences.

In some embodiments, a 'look up' table is created linking each barcode to each nucleotide sequence that has been inserted into the capsid gene.

A library of the disclosure may comprise $10^2$, $10^3$, $10^4$, $10^5$, $10^6$, $10^7$, or $10^8$ or more unique AAV variants. In some embodiments, a library may comprise $10^2$-$10^3$, $10^3$-$10^4$, $10^4$-$10^5$, $10^5$-$10^6$, $10^6$-$10^7$, or $10^7$-$10^8$ unique AAV variants.

Any of the foregoing libraries of AAV variants may be used in the methods disclosed herein.

Methods of Identifying AAV Capsid Variants

The present disclosure provides methods and compositions to develop AAV capsids with a desired characteristic compared to a natural AAV serotype. These capsids are useful, for example, for the delivery of genome engineering molecules and gene therapy molecules to a target cell, cell line, or tissue (e.g., in vitro or in vivo) for the treatment of a subject in need thereof. In some embodiments, the capsids are used to deliver a payload to a desired tissue, cell or organelle.

In another aspect, disclosed herein are methods for directed evolution of AAV capsid proteins and identification of an AAV capsid variant with a desired characteristic compared to a natural AAV serotype.

In some embodiments, the method of identifying an AAV capsid variant with a desired characteristic compared to a natural AAV serotype comprises: (i) contacting a cell, cell line, or tissue in vitro or in vivo with any one of the libraries of AAV variants disclosed herein, (ii) allowing the AAV variants in said library to transduce the cell, cell line, or tissue; (iii) recovering from the cell, cell line, or tissue the AAV variant; and (iv) identifying the AAV capsid variant with the desired characteristic.

In some embodiments, the method of identifying an AAV capsid variant with a desired characteristic compared to a natural AAV serotype, comprises: (i) inserting a plurality of nucleic acids encoding peptides, into a population of nucleic acids encoding a hypervariable and/or surface-exposed loop of an AAV capsid protein to create a library of nucleic acids encoding AAV variant capsid proteins; (ii) linking each nucleic acid encoding an AAV variant capsid protein in said library to one or more of: (a) a nucleic acid comprising a barcode, (b) a nucleic acid encoding a reporter protein, and (c) a nucleic acid encoding a localization signal, to form a payload construct; (iii) manufacturing a library of AAV variants in producer cells by providing adenovirus helper and AAV rep functions in trans; (iv) purifying the library of AAV variants; (v) contacting a cell, cell line, or tissue in vitro or in vivo with the library of AAV variants; (vi) recovering the AAV variants from the target cell, cell line, or tissue; and (vii) identifying the AAV capsid variant with the desired characteristic.

In some embodiments, the method of identifying an AAV capsid variant with a desired characteristic compared to a natural AAV serotype, comprises: (i) inserting a plurality of nucleic acids encoding peptides, into a population of nucleic acids encoding a hypervariable and/or surface-exposed loop of an AAV capsid protein to create a library of nucleic acids encoding AAV variant capsid proteins; (ii) linking each nucleic acid encoding an AAV variant capsid protein in said library to two or more of: (a) a nucleic acid comprising a barcode, (b) a nucleic acid encoding a reporter protein, and (c) a nucleic acid encoding a localization signal, to form a payload construct; (iii) manufacturing a library of AAV variants in producer cells by providing adenovirus helper and AAV rep functions in trans; (iv) purifying the library of AAV variants; (v) contacting a cell, cell line, or tissue in vitro or in vivo with the library of AAV variants; (vi) recovering the AAV variants from the target cell, cell line, or tissue; and (vii) identifying the AAV capsid variant with the desired characteristic.

In some embodiments, the method of identifying an AAV capsid variant with a desired characteristic compared to a natural AAV serotype, comprises: (i) inserting a plurality of nucleic acids encoding peptides, into a population of nucleic acids encoding a hypervariable and/or surface-exposed loop of an AAV capsid protein to create a library of nucleic acids encoding AAV variant capsid proteins; (ii) linking each nucleic acid encoding an AAV variant capsid protein in said library to (a) a nucleic acid comprising a barcode, (b) a nucleic acid encoding a reporter protein, and (c) a nucleic acid encoding a localization signal, to form a payload construct; (iii) manufacturing a library of AAV variants in producer cells by providing adenovirus helper and AAV rep functions in trans; (iv) purifying the library of AAV variants; (v) contacting a cell, cell line, or tissue in vitro or in vivo with the library of AAV variants; (vi) recovering the AAV variants from the target cell, cell line, or tissue; and (vii) identifying the AAV capsid variant with the desired characteristic.

In some embodiments, the steps for directed evolution of AAV capsid proteins to identify AAV capsid variants with a desired characteristic compared to a natural AAV serotype comprise (i) insertion of peptides into hypervariable and/or surface-exposed loops in capsid proteins from one or more AAV serotypes creating libraries of modified variant capsids for each AAV serotype; (ii) packaging of the variant AAVs in producer cells wherein adenovirus helper and AAV rep functions are supplied in trans; (iii) purification of viral capsid library pools; (iv) administration of the pools in vitro or in vivo; (v) recovery of AAV variants from target tissues or cell lines; (vi) next-generation sequencing to determine the identity of the engineered variant capsid sequences; (vii) repeated rounds of in vitro or in vivo selection where variants are isolated from a target tissue or cell line; and (viii) full evaluation of enriched variants.

In some embodiments, the desired characteristic is enhanced cell or tissue tropism as compared to the natural AAV serotype. These methods may also be adapted for selecting AAV capsid variants that evade a pre-existing host antibody response and/or the development of AAV variants that will not provoke a host response.

In some embodiments, capsid proteins, for example from AAV1, AAV2, AAV3B, AAV5, AAV6, AAV8 and AAV9 are chosen for starting points. In some embodiments, capsid proteins from less well characterized AAV serotypes are chosen, including but not limited to AAV3, AAV4, AAV7, AAV11, AAVrh10, AAVrh39, and AAVrh74. In some embodiments, a library of AAV variants comprises AAV variant capsid proteins derived from a single AAV serotype. In some embodiments, a library of AAV variants comprises AAV variant capsid proteins derived from 2, 3, 4, 5, 6, 7, 8, 9, 10, 11, 12, 13, 14, 15, or more AAV serotypes. In some embodiments, the AAV variant capsid proteins derived from 2, 3, 4, 5, 6, 7, 8, 9, 10, 11, 12, 13, 14, 15, or more AAV serotypes are combined once individual serotype libraries are developed. In some embodiments, combinatorial libraries are generated by modifying nucleic acids encoding AAV capsid proteins from 2, 3, 4, 5, 6, 7, 8, 9, 10, 11, 12, 13, 14, 15, or more serotypes in the same pool.

In some embodiments, directed evolution comprises mutating the AAV capsid (e.g., insertions, deletions and/or substitutions). In some embodiments, the mutations (e.g., insertions, deletions and/or substitutions) are introduced into a DNA sequence encoding an exposed loop in the capsid protein. In some embodiments, directed evolution comprises insertion of peptides into exposed loops (e.g. hypervariable regions) in the AAV capsid.

In some embodiments, the libraries are packaged in HEK293 cells where the helper functions (e.g. E2A, E4, VA, E1A and E1B) are supplied in trans. In some embodiments, the AAV rep function comprises rep78, rep 68, rep 52, and rep40 genes. In some embodiments, the rep genes are supplied in trans. In some embodiments, the start codon of the rep78 and/or the rep68 gene is altered from ACG to ATG to increase replication of the capsid library construct containing inverted terminal repeats (ITRs), thereby improving AAV library manufacturing yield. In some embodiments, the cap genes are supplied as payload to the manufactured AAVs. In some embodiments, the capsid gene is controlled by the p40 promoter such that it is only expressed during manufacturing in HEK293 cells in the presence of helper virus functions.

In some embodiments, the libraries are selected in cells. In some embodiments, the individual serotype libraries are combined to generate a single library comprising 2, 3, 4, 5, 6, 7, 8, 9, 10, 11, 12, 13, 14, 15, or more serotypes where each AAV variant also comprises the peptide inserted into the AAV variant capsid. In some embodiments, single serotype libraries are used wherein each AAV in that serotype library comprises a peptide inserted into the AAV variant capsid. In some embodiments, the cells are treated with the libraries and then monitored for the expression of the reporter gene in the cytoplasm of the cell or in the organelle of interest. In some embodiments, the organelle of interest is the nucleus. In some embodiments, the organelles comprising the AAV payload or genome as evidenced by the expression of the reporter gene are isolated from the cells. In some embodiments, the organelle is the nucleus. In some embodiments, the nucleic acid is extracted from the organelle (e.g. nucleus). In some embodiments, the nucleic acid extracted is RNA, while in some embodiments, the nucleic acid extracted is DNA. In some embodiments, the extracted RNA is subject to reverse transcription to generate cDNA which is then amplified using primers specific to the barcoded region and sequenced. In some embodiments, the extracted DNA is amplified and sequenced using the primers specific for the introduced variable sequence. In some embodiments, enrichment of specific AAV variants is observed following selection in cells.

The cell used includes, but is not limited to, a cell from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa.

In some embodiments, the cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

In some embodiments, the libraries are selected in animals. In some embodiments, the individual serotype libraries are combined to generate a single library comprising 2, 3, 4, 5, 6, 7, 8, 9, 10, 11, 12, 13, 14, 15, or more serotypes where each AAV also comprises the peptide inserted into the AAV variant capsid. In some embodiments, single serotype libraries are used wherein each AAV in that serotype library comprises a peptide inserted into the AAV variant capsid. In some embodiments, the animals are treated with the libraries via intravenous, intracranial, or intrathecal injection, or by injection by some other route (e.g. nasal, hepatic, intracerebroventricular, intracisternal, intravitreal, intracochlear, etc.). Following a sufficient time for the AAV to traffic to the desired tissue or organ (for example, 7, 10, 14, 18, 21, 24, 28, 30 days or more), the animal is sacrificed, and the tissue/organ of interest is harvested. In some embodiments, the cells in the tissues are monitored for the expression of the reporter gene in the cytoplasm of the cell or in the organelle of interest. In some embodiments, the organelle of interest is the nucleus. In some embodiments, the organelles comprising the AAV payload as evidenced by the expression of the reporter gene are isolated from the tissue. In some embodiments, the organelle is the nucleus. In some embodiments, the nucleic acid is extracted from the organelle (e.g. nucleus). In some embodiments, the nucleic acid extracted is RNA, while in some embodiments, the nucleic acid extracted is DNA. In some embodiments, the extracted RNA is subject to reverse transcription to generate cDNA which is then amplified using primers specific to the barcoded region and sequenced. In some embodiments, the extracted DNA is amplified and sequenced using the primers specific for the introduced variable sequence. In some embodiments, enrichment of specific AAV variants is observed following selection in vivo.

In either of these embodiments, the selection of AAV variants through cells or in vivo may be performed in 1, 2, 3, 4, 5 or more rounds, in each case pooling the AAV variants obtained from the previous round or synthesizing a subset of variants that were enriched and re-selecting in the cells or in vivo.

In some embodiments, following the desired number of selection rounds, the variants are analyzed. In some embodiments, the individual variants are used to deliver a transgene to a desired cell or organ in vivo. After analysis of the delivery capability of the variants, the best candidates are selected for future use.

In some embodiments, each member of the library comprises a nucleic acid comprising two barcode sequences. In some embodiments, each member of the library comprises a first nucleic acid comprising a first barcode and a second nucleic acid comprising a second barcode. In some embodiments, the first nucleic acid comprising the first barcode and the second nucleic acid comprising the second barcode are different. In some embodiments, the first nucleic acid comprising the first barcode comprises a sequence selected from any one of sequences SEQ ID NO: 111-154 or is selected from any one of sequences SEQ ID NO: 111-154. In some embodiments of the method, library of AAV variants, AAV variant, or nucleic acid disclosed herein, the second nucleic acid comprising the second barcode comprises a sequence selected from any one of sequences SEQ ID NO: 155-198 or is selected from any one of sequences SEQ ID NO: 155-198. In some embodiments, the first nucleic acid comprising the first barcode comprises a sequence selected from any one of sequences SEQ ID NO: 111-154 or is selected from any one of sequences SEQ ID NO: 111-154 and the second nucleic acid comprising the second barcode comprises a sequence selected from any one of sequences SEQ ID NO: 155-198 or is selected from any one of sequences SEQ ID NO: 155-198. In some embodiments, each of the first nucleic acid comprising the first barcode and the second nucleic acid comprising the second barcode is independently operatively linked to a promoter. In some embodiments, said promoter is different for each of the first barcode and the second barcode. In some embodiments, each of the first nucleic acid comprising the first barcode and the second nucleic acid are independently controlled under a different promoter. In some embodiments, the promoter operatively linked to the first nucleic acid comprising the first barcode and the promoter operatively linked to the second nucleic acid comprising the second barcode is each independently an RNA Pol II promoter (e.g., human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, or methyl CpG-binding protein 2 (Mecp2) promoter). In some embodiments, the promoter operatively linked to the first nucleic acid comprising the first barcode and the promoter operatively linked to the second nucleic acid comprising the second barcode is each independently an RNA Pol III promoter (e.g., U6 promoter, H1 promoter or 7SK promoter). In some embodiments, the promoter operatively linked to the first nucleic acid comprising the first barcode is an RNA Pol II promoter and the promoter operatively linked to the second nucleic acid comprising the second barcode is an RNA Pol III promoter. In some embodiments, the nucleic acid comprising the barcode further comprises a reporter gene, a nuclear localization signal and a polyadenylation signal.

AAV Variants

Described herein are AAV variants used to develop AAV capsids with a desired characteristic compared to a natural AAV serotype. In some embodiments, the desired characteristic is enhanced cell or tissue tropism as compared to the natural AAV serotype. In some embodiments, the desired characteristic is the evasion of a pre-existing host antibody response. In some embodiments, the desired characteristic is reduced immunogenicity so as to not provoke a host response.

In some embodiments, an AAV variant of the disclosure comprises: a) a nucleic acid sequence encoding an AAV variant capsid protein comprising a peptide inserted into a hypervariable and/or surface-exposed loop of the variant capsid protein; and one or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, an AAV variant of the disclosure comprises: a) a nucleic acid sequence encoding an AAV variant capsid protein comprising a peptide inserted into a hypervariable and/or surface-exposed loop of the variant capsid protein; and two or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, an AAV variant of the disclosure comprises: a) a nucleic acid sequence encoding an AAV variant capsid protein comprising a peptide inserted into a hypervariable and/or surface-exposed loop of the variant capsid protein; and three or more of: b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, an AAV variant of the disclosure comprises: a) a nucleic acid sequence encoding an AAV variant capsid protein comprising a peptide inserted into a hypervariable and/or surface-exposed loop of the variant capsid protein; b) one or more silent mutations in the nucleic acid sequence flanking the peptide insertion site in the AAV variant capsid protein of a); c) a nucleic acid encoding a localization signal; d) a nucleic acid comprising a barcode; and e) a nucleic acid encoding a reporter protein.

In some embodiments, an AAV variant of the disclosure comprises: a) an AAV variant capsid protein comprising a peptide inserted into a hypervariable and/or surface-exposed loop of the variant capsid protein; and one or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, an AAV variant of the disclosure comprises: a) an AAV variant capsid protein comprising a peptide inserted into a hypervariable and/or surface-exposed loop of the variant capsid protein; and two or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, an AAV variant of the disclosure comprises: a) an AAV variant capsid protein comprising a peptide inserted into a hypervariable and/or surface-exposed loop of the variant capsid protein; and three or more of: b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In some embodiments, an AAV variant of the disclosure comprises: a) an AAV variant capsid protein comprising a peptide inserted into a hypervariable and/or surface-exposed loop of the variant capsid protein; b) one or more silent mutations in the nucleic acid encoding the AAV variant capsid protein of a) in the nucleic acid sequence flanking the peptide insertion site; c) a nucleic acid encoding a localization signal; d) a nucleic acid comprising a barcode; and e) a nucleic acid encoding a reporter protein.

In any of the above embodiments, the nucleic acid encoding an AAV variant capsid protein, the nucleic acid encoding a localization signal, the nucleic acid comprising a barcode, and/or the nucleic acid encoding a reporter protein, are present on separate nucleic acid molecules. In some embodiments, the nucleic acid encoding an AAV variant capsid protein, the nucleic acid encoding a localization signal, the nucleic acid comprising a barcode, and/or the nucleic acid encoding a reporter protein, are present on a single nucleic acid molecule. In some embodiments, the nucleic acid encoding an AAV variant capsid protein, and the nucleic acid encoding a localization signal, the nucleic acid comprising a barcode, and/or the nucleic acid encoding a reporter protein, are linked to each other in any order. In some embodiments, each member of the library comprises a 5'ITR sequence, the nucleic acid comprising a barcode, the nucleic acid encoding a reporter protein, the nucleic acid encoding an AAV variant capsid protein, and a 3'ITR sequence, in that order.

The various components of the AAV variants (e.g., AAV variant capsid protein, inserted peptides, silent mutations flanking the peptide insertion site, localization signal, barcode, reporter protein, promoter(s) or related nucleic acid sequences, etc.) are disclosed elsewhere herein.

In another aspect, the present disclosure provides a nucleic acid molecule encoding an AAV variant disclosed herein. In some embodiments, the nucleic acid molecule comprises a) a nucleic acid sequence encoding an AAV variant capsid protein comprising a peptide inserted into a hypervariable and/or surface-exposed loop of the variant capsid protein; and one or more of: b) a nucleic acid sequence encoding a variant capsid protein comprising one or more silent mutations in the nucleotide sequence flanking the peptide insertion site in the hypervariable and/or surface-exposed loop of the variant capsid protein; c) a nucleic acid sequence encoding a localization signal; d) a nucleic acid sequence comprising a barcode; and e) a nucleic acid sequence encoding a reporter protein.

In some embodiments, the present disclosure provides a nucleic acid molecule comprising two or more of: a) a nucleic acid sequence encoding an AAV variant capsid protein comprising a peptide inserted into a hypervariable and/or surface-exposed loop of the variant capsid protein; and two or more of: b) a nucleic acid sequence encoding a variant capsid protein comprising one or more silent mutations in the nucleotide sequence flanking the peptide insertion site in the hypervariable and/or surface-exposed loop of the variant capsid protein; c) a nucleic acid sequence encoding a localization signal; d) a nucleic acid sequence comprising a barcode; and e) a nucleic acid sequence encoding a reporter protein.

In some embodiments, the present disclosure provides a nucleic acid molecule comprising a) a nucleic acid sequence encoding an AAV variant capsid protein comprising a peptide inserted into a hypervariable and/or surface-exposed loop of the variant capsid protein; and three or more of: b) a nucleic acid sequence encoding a variant capsid protein comprising one or more silent mutations in the nucleotide sequence flanking the peptide insertion site in the hypervariable and/or surface-exposed loop of the variant capsid protein; c) a nucleic acid sequence encoding a localization signal; d) a nucleic acid sequence comprising a barcode; and e) a nucleic acid sequence encoding a reporter protein.

In some embodiments, the present disclosure provides a nucleic acid molecule comprising a) a nucleic acid sequence encoding an AAV variant capsid protein comprising a peptide inserted into a hypervariable and/or surface-exposed loop of the variant capsid protein; b) a nucleic acid sequence encoding a variant capsid protein comprising one or more silent mutations in the nucleotide sequence flanking the peptide insertion site in the hypervariable and/or surface-exposed loop of the variant capsid protein; c) a nucleic acid sequence encoding a localization signal; d) a nucleic acid sequence comprising a barcode; and e) a nucleic acid sequence encoding a reporter protein.

In some embodiments, the barcode nucleic acid sequence comprises more than one barcode sequences. In some embodiments, the barcode nucleic acid sequence comprises two or more barcode sequences. In some embodiments, the barcode nucleic acid sequence comprises a first nucleic acid comprising a first barcode and a second nucleic acid comprising a second barcode. In some embodiments, the first nucleic acid comprising the first barcode and the second nucleic acid comprising the second barcode are different.

In some embodiments, the first nucleic acid comprising the first barcode sequence comprises a sequence selected from any one of sequences SEQ ID NO: 111-154. In some embodiments, the first barcode sequence is selected from any one of sequences SEQ ID NO: 111-154. In some embodiments, the second nucleic acid comprising the second barcode sequence comprises a sequence selected from any one of sequences SEQ ID NO: 155-198. In some embodiments, the second nucleic acid comprising the second barcode sequence is selected from any one of sequences SEQ ID NO: 155-198. In some embodiments, each of the first nucleic acid comprising the first barcode and the second nucleic acid comprising the second barcode is independently operatively linked to a promoter. In some embodiments, the promoter operatively linked to the first nucleic acid comprising the first barcode and the promoter operatively linked to the second nucleic acid comprising the second barcode is each independently an RNA Pol II promoter. In some embodiments, the promoter operatively linked to the first nucleic acid comprising the first barcode and the promoter operatively linked to the second nucleic acid comprising the second barcode is each independently an RNA Pol III promoter (e.g., a promoter selected from the group of U6 promoter, H1 promoter and 7SK promoter). In some embodiments, the promoter operatively linked to the first nucleic acid comprising the first barcode is operatively linked to an RNA Pol II promoter and the promoter operatively linked to the second nucleic acid comprising the second barcode is an RNA Pol III promoter (e.g., a promoter selected from the group of human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

In some embodiments, the AAV variant is selected from any one the following: (i) the AAV serotype is AAV1 and the peptide is inserted at amino acid position 590 of the capsid protein, (ii) the AAV serotype is AAV6 and the peptide is inserted at amino acid position 454 or 590 of the capsid protein, (iii) the AAV serotype is AAV2 and the peptide is inserted at amino acid position 588 of the capsid protein, (iv) the AAV serotype is AAV3B and the peptide is inserted at amino acid position 589 of the capsid protein, (v) the AAV serotype is AAV5 and the peptide is inserted at amino acid position 578 of the capsid protein, (vi) the AAV serotype is AAV8 and the peptide is inserted at amino acid position 591 of the capsid protein, or (vii) the AAV serotype is AAV9 and the peptide is inserted at amino acid position 266, 455, or 589 of the capsid protein, wherein the positions correspond to the numbering of VP1 in the AAV serotype.

In some embodiments of the AAV variants disclosed herein, a peptide comprising the amino acid sequence of any one of SEQ ID NO. 1-32 is inserted at amino acid position 590 of the capsid protein of an AAV1 serotype. In some embodiments of the AAV variants disclosed herein, a peptide comprising the amino acid sequence of any one of SEQ ID NO. 68-110 is inserted at amino acid position 590 of the capsid protein of an AAV1 serotype. In some embodiments of the AAV variants disclosed herein, the peptide inserted at position 590 of the capsid protein of an AAV1 serotype comprises an amino acid sequence selected from the group consisting of any one of SEQ ID NO: 68 to SEQ ID NO: 75. In some embodiments of the AAV variants disclosed herein, the peptide inserted at position 590 of the capsid protein of an AAV1 serotype comprises the amino acid sequence SEQ ID NO: 71. In some embodiments of the AAV variants disclosed herein, the peptide inserted at position 590 of the capsid protein of an AAV1 serotype comprises an amino acid sequence selected from the group consisting of any one of SEQ ID NO: 1, SEQ ID NO: 2 and SEQ ID NO: 3.

In some embodiments of the AAV variants disclosed herein, a peptide comprising the amino acid sequence of any one of SEQ ID NO. 1-32 is inserted at amino acid position 454 of the capsid protein of an AAV6 serotype. In some embodiments of the AAV variants disclosed herein, a peptide comprising the amino acid sequence of any one of SEQ ID NO. 68-110 is inserted at amino acid position 454 of the capsid protein of an AAV6 serotype.

In some embodiments of the AAV variants disclosed herein, a peptide comprising the amino acid sequence of any one of SEQ ID NO. 1-32 is inserted at amino acid position 590 of the capsid protein of an AAV6 serotype. In some embodiments of the AAV variants disclosed herein, a peptide comprising the amino acid sequence of any one of SEQ ID NO. 68-110 is inserted at amino acid position 590 of the capsid protein of an AAV6 serotype. In some embodiments of the AAV variants disclosed here, the peptide inserted at position 454 of the capsid protein of an AAV6 serotype comprises an amino acid sequence selected from the group consisting of any one of SEQ ID NO: 19 to SEQ ID NO: 27. In some embodiments of the AAV variants disclosed here, the peptide inserted at position 590 of the capsid protein of an AAV6 serotype comprises an amino acid sequence selected from the group consisting of any one of SEQ ID NO: 19 to SEQ ID NO: 27.

In some embodiments of the AAV variants disclosed herein, a peptide comprising the amino acid sequence of any one of SEQ ID NO. 1-32 is inserted at amino acid position 588 of the capsid protein of an AAV2 serotype. In some embodiments of the AAV variants disclosed herein, a peptide comprising the amino acid sequence of any one of SEQ ID NO. 68-110 is inserted at amino acid position 588 of the capsid protein of an AAV2 serotype. In some embodiments of the AAV variants disclosed here, the peptide inserted at position 588 of the capsid protein of an AAV2 serotype comprises an amino acid sequence selected from the group consisting of any one of SEQ ID NO: 90 to SEQ ID NO: 110. In some embodiments of the AAV variants disclosed here, the peptide inserted at position 588 of the capsid protein of an AAV2 serotype comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102. In some embodiments of the AAV variants disclosed here, the peptide inserted at position 588 of the capsid protein of an AAV2 serotype comprises an amino acid sequence selected from the group consisting of any one of SEQ ID NO: 4-7.

In some embodiments of the AAV variants disclosed herein, a peptide comprising the amino acid sequence of any one of SEQ ID NO. 1-32 is inserted at amino acid position 589 of the capsid protein of an AAV3B serotype. In some embodiments of the AAV variants disclosed herein, a peptide comprising the amino acid sequence of any one of SEQ ID NO. 68-110 is inserted at amino acid position 589 of the capsid protein of an AAV3B serotype. In some embodiments of the AAV variants disclosed here, the peptide inserted at position 589 of the capsid protein of an AAV3B serotype comprises an amino acid sequence selected from the group consisting of any one of SEQ ID NO: 76-85. In some embodiments of the AAV variants disclosed here, the peptide inserted at position 589 of the capsid protein of an AAV3B serotype comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83. In some embodiments of the AAV variants disclosed here, the peptide inserted at position 589 of the capsid protein of an AAV3B serotype comprises an amino acid sequence selected from the group consisting of any one of SEQ ID NO: 8 to SEQ ID NO: 11.

In some embodiments of the AAV variants disclosed herein, a peptide comprising the amino acid sequence of any one of SEQ ID NO. 1-32 is inserted at amino acid position 578 of the capsid protein of an AAV5 serotype. In some embodiments of the AAV variants disclosed herein, a peptide comprising the amino acid sequence of any one of SEQ ID NO. 68-110 is inserted at amino acid position 578 of the capsid protein of an AAV5 serotype. In some embodiments of the AAV variants disclosed here, the peptide inserted at position 578 of the capsid protein of an AAV5 serotype comprises an amino acid sequence selected from the group consisting of any one of SEQ ID NO: 28 to SEQ ID NO: 32.

In some embodiments of the AAV variants disclosed herein, a peptide comprising the amino acid sequence of any one of SEQ ID NO. 1-32 is inserted at amino acid position 591 of the capsid protein of an AAV8 serotype. In some embodiments of the AAV variants disclosed herein, a peptide comprising the amino acid sequence of any one of SEQ ID NO. 68-110 is inserted at amino acid position 591 of the capsid protein of an AAV8 serotype.

In some embodiments of the AAV variants disclosed herein, a peptide comprising the amino acid sequence of any one of SEQ ID NO. 1-32 is inserted at amino acid position 266 of the capsid protein of an AAV9 serotype. In some embodiments of the AAV variants disclosed herein, a peptide comprising the amino acid sequence of any one of SEQ ID NO. 68-110 is inserted at amino acid position 266 of the capsid protein of an AAV9 serotype. In some embodiments of the AAV variants disclosed herein, a peptide comprising the amino acid sequence of any one of SEQ ID NO. 1-32 is inserted at amino acid position 455 of the capsid protein of an AAV9 serotype. In some embodiments of the AAV variants disclosed herein, a peptide comprising the amino acid sequence of any one of SEQ ID NO. 68-110 is inserted at amino acid position 455 of the capsid protein of an AAV9 serotype. In some embodiments of the AAV variants disclosed herein, a peptide comprising the amino acid sequence of any one of SEQ ID NO. 1-32 is inserted at amino acid position 589 of the capsid protein of an AAV9 serotype. In some embodiments of the AAV variants disclosed herein, a peptide comprising the amino acid sequence of any one of SEQ ID NO. 68-110 is inserted at amino acid position 589 of the capsid protein of an AAV9 serotype. In some embodiments of the AAV variants disclosed here, the peptide inserted at position 266 of the capsid protein of an AAV9 serotype comprises an amino acid sequence selected from the group consisting of any one of SEQ ID NO: 12 to SEQ ID NO: 18. In some embodiments of the AAV variants disclosed here, the peptide inserted at position 266 of the capsid protein of an AAV9 serotype comprises an amino acid sequence selected from the group consisting of any one of SEQ ID NO: 86 to SEQ ID NO: 89. In some embodiments of the AAV variants disclosed here, the peptide inserted at position 266 of the capsid protein of an AAV9 serotype comprises an amino acid sequence of SEQ ID NO: 89. In some embodiments of the AAV variants disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the AAV variants disclosed here, the peptide inserted at position 455 of the capsid protein of an AAV9 serotype comprises an amino acid sequence selected from the group consisting of any one of SEQ ID NO: 86 to SEQ ID NO: 89. In some embodiments of the AAV variants disclosed here, the peptide inserted at position 455 of the capsid protein of an AAV9 serotype comprises an amino acid sequence of SEQ ID NO: 89. In some embodiments of the AAV variants disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the AAV variants disclosed here, the peptide inserted at position 589 of the capsid protein of an AAV9 serotype comprises an amino acid sequence selected from the group consisting of any one of SEQ ID NO: 86 to SEQ ID NO: 89. In some embodiments of the AAV variants disclosed here, the peptide inserted at position 589 of the capsid protein of an AAV9 serotype comprises an amino acid sequence of SEQ ID NO: 89.

In some embodiments, an AAV3B variant comprises a peptide comprising any one of the sequences selected from the group consisting of EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76) and YGSRSVD (SEQ ID NO: 83). In some embodiments, an AAV3B variant comprises a peptide sequence selected from the group consisting of sequences EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76) and YGSRSVD (SEQ ID NO: 83).

In some embodiments, an AAV1 variant comprises a peptide comprising the sequence SVVVSSDSSKRPNL (SEQ ID NO: 71). In some embodiments, an AAV1 variant comprises the peptide sequence SVVVSSDSSKRPNL (SEQ ID NO: 71).

In some embodiments, an AAV2 variant comprises a peptide comprising any one of the sequences selected from the group consisting of RPLTAND (SEQ ID NO: 95), PRDTFNG (SEQ ID NO: 94), PLRMVNE (SEQ ID NO: 96), ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102). In some embodiments, an AAV2 variant comprises a peptide sequence selected from the group consisting of RPLTAND (SEQ ID NO: 95), PRDTFNG (SEQ ID NO: 94), PLRMVNE (SEQ ID NO: 96), ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102). In some embodiments, an AAV2 variant comprises a peptide comprising any one of the sequences selected from the group consisting of RPLTAND (SEQ ID NO: 95), PRDTFNG (SEQ ID NO: 94), and PLRMVNE (SEQ ID NO: 96). In some embodiments, an AAV2 variant comprises a peptide comprising any one of the sequences selected from the group consisting of ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102). In some embodiments, an AAV2 variant comprises a peptide sequence selected from the group consisting of RPLTAND (SEQ ID NO: 95), PRDTFNG (SEQ ID NO: 94), and PLRMVNE (SEQ ID NO: 96). In some embodiments, an AAV2 variant comprises a peptide sequence selected from the group consisting of ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102).

In some embodiments, an AAV9 variant comprises a peptide comprising the sequence NIPKAYG (SEQ ID NO: 89). In some embodiments, an AAV9 variant comprises the peptide sequence NIPKAYG (SEQ ID NO: 89).

In some embodiments, an AAV3B variant comprises a peptide comprising the amino acid sequence EQFRNLA (SEQ ID NO: 78). In some embodiments, an AAV3B variant comprises a peptide comprising the amino acid sequence TDFRSPQ (SEQ ID NO: 80). In some embodiments, an AAV3B variant comprises a peptide comprising the amino acid sequence TGAFSST (SEQ ID NO: 77). In some embodiments, an AAV3B variant comprises a peptide comprising the amino acid sequence FNSPVIQ (SEQ ID NO: 79). In some embodiments, an AAV3B variant comprises a peptide comprising the amino acid sequence PYASITG (SEQ ID NO: 76). In some embodiments, an AAV3B variant comprises a peptide comprising an amino acid sequence YGSRSVD (SEQ ID NO: 83).

In some embodiments, an AAV2 variant comprises a peptide comprising the amino acid sequence RPLTAND (SEQ ID NO: 95). In some embodiments, an AAV2 variant comprises a peptide comprising the amino acid sequence PRDTFNG (SEQ ID NO: 94). In some embodiments, the peptide comprises amino acid sequence PLRMVNE (SEQ ID NO: 96). In some embodiments, an AAV2 variant comprises a peptide comprising the amino acid sequence ENFSKVA (SEQ ID NO: 101). In some embodiments, an AAV2 variant comprises a peptide comprising the amino acid sequence LGNGKMTVQP (SEQ ID NO: 103). In some embodiments, an AAV2 variant comprises a peptide comprising the amino acid sequence GRNTVGLSSA (SEQ ID NO: 106). In some embodiments, an AAV2 variant comprises a peptide comprising the amino acid sequence TSNSRTE (SEQ ID NO: 91). In some embodiments, an AAV2 variant comprises a peptide comprising an amino acid sequence RDALSGLRPE (SEQ ID NO: 102).

In some embodiments, an AAV1 variant comprises a peptide comprising an amino acid sequence selected from the group consisting of KSPQSKV (SEQ ID NO:1), SDLRSKV (SEQ ID NO:2) and TTTVRKV (SEQ ID NO:3). In some embodiments, an AAV1 variant comprises a peptide selected from the group consisting of KSPQSKV (SEQ ID NO:1), SDLRSKV (SEQ ID NO:2) and TTTVRKV (SEQ ID NO:3).

In some embodiments, an AAV1 variant comprises a peptide comprising an amino acid sequence selected from the group consisting of AALRDIR (SEQ ID NO:68), PAIKTYS (SEQ ID NO: 69), TGDRISSRTL (SEQ ID NO: 70), SVVVSSDSSKRPRNL (SEQ ID NO: 71), VGARLSA (SEQ ID NO: 72), IEKPNTSTKK (SEQ ID NO: 73), DTVRSKN (SEQ ID NO: 74), and KELNKAR (SEQ ID NO: 75). In some embodiments, an AAV1 variant comprises a peptide selected from the group consisting of AALRDIR (SEQ ID NO:68), PAIKTYS (SEQ ID NO: 69), TGDRISSRTL (SEQ ID NO: 70), SVVVSSDSSKRPRNL (SEQ ID NO: 71), VGARLSA (SEQ ID NO: 72), IEKPNTSTKK (SEQ ID NO: 73), DTVRSKN (SEQ ID NO: 74), and KELNKAR (SEQ ID NO: 75).

In some embodiments, an AAV2 variant comprises a peptide comprising an amino acid sequence selected from the group consisting of GRSDMAG (SEQ ID NO: 4), LLSSERS (SEQ ID NO: 5), EQRPNVS (SEQ ID NO: 6) and TRQISSD (SEQ ID NO: 7). In some embodiments, an AAV2 variant comprises a peptide selected from the group consisting of GRSDMAG (SEQ ID NO: 4), LLSSERS (SEQ ID NO: 5), EQRPNVS (SEQ ID NO: 6) and TRQISSD (SEQ ID NO: 7).

In some embodiments, an AAV2 variant comprises a peptide comprising an amino acid sequence selected from the group consisting of MTLTRQE (SEQ ID NO: 90), TSNSRTE (SEQ ID NO: 91), EVRGGPS (SEQ ID NO: 92), VISDRSS (SEQ ID NO: 93), PRDTFNG (SEQ ID NO: 94), RPLTAND (SEQ ID NO: 95), PLRMVNE (SEQ ID NO: 96), DVGIRPS (SEQ ID NO: 97), KDSTAFG (SEQ ID NO: 98), YPGRNPD (SEQ ID NO: 99), ISDTRIS (SEQ ID NO: 100), ENFSKVA (SEQ ID NO: 101), RDALSGLRPE (SEQ ID NO: 102), LGNGKMTVQP (SEQ ID NO: 103), VSNPLNQ (SEQ ID NO: 104), LNERGLG (SEQ ID NO: 105), GRNTVGLSSA (SEQ ID NO: 106), VGHAGNP (SEQ ID NO: 107), SRAGTVP (SEQ ID NO: 108), GLVAKLP (SEQ ID NO: 109), and AESLRTP (SEQ ID NO: 110). In some embodiments, an AAV2 variant comprises a peptide selected from the group consisting of MTLTRQE (SEQ ID NO: 90), TSNSRTE (SEQ ID NO: 91), EVRGGPS (SEQ ID NO: 92), VISDRSS (SEQ ID NO: 93), PRDTFNG (SEQ ID NO: 94), RPLTAND (SEQ ID NO: 95), PLRMVNE (SEQ ID NO: 96), DVGIRPS (SEQ ID NO: 97), KDSTAFG (SEQ ID NO: 98), YPGRNPD (SEQ ID NO: 99), ISDTRIS (SEQ ID NO: 100), ENFSKVA (SEQ ID NO: 101), RDALSGLRPE (SEQ ID NO: 102), LGNGKMTVQP (SEQ ID NO: 103), VSNPLNQ (SEQ ID NO: 104), LNERGLG (SEQ ID NO: 105), GRNTVGLSSA (SEQ ID NO: 106), VGHAGNP (SEQ ID NO: 107), SRAGTVP (SEQ ID NO: 108), GLVAKLP (SEQ ID NO: 109), and AESLRTP (SEQ ID NO: 110).

In some embodiments, an AAV3B variant comprises a peptide comprising an amino acid sequence selected from the group consisting of QGALAQV (SEQ ID NO: 8), YPSSNTP (SEQ ID NO: 9), MLNPRTE (SEQ ID NO: 10) and QMRTRDE (SEQ ID NO: 11). In some embodiments, an AAV3B variant comprises a peptide selected from the group consisting of QGALAQV (SEQ ID NO: 8), YPSSNTP (SEQ ID NO: 9), MLNPRTE (SEQ ID NO: 10) and QMRTRDE (SEQ ID NO: 11).

In some embodiments, an AAV3B variant comprises a peptide comprising an amino acid sequence selected from the group consisting of PYASITG (SEQ ID NO: 76), TGAFSST (SEQ ID NO: 77), EQFRNLA (SEQ ID NO: 78), FNSPVIQ (SEQ ID NO: 79), TDFRSPQ (SEQ ID NO:80), MYSLMKD (SEQ ID NO:81), LYLSSAS (SEQ ID NO: 82), YGSRSVD (SEQ ID NO:83), LYSHQVS (SEQ ID NO: 84), and ISTHSPP (SEQ ID NO: 85). In some embodiments, an AAV3B variant comprises a peptide selected from the group consisting of PYASITG (SEQ ID NO: 76), TGAFSST (SEQ ID NO: 77), EQFRNLA (SEQ ID NO: 78), FNSPVIQ (SEQ ID NO: 79), TDFRSPQ (SEQ ID NO:80), MYSLMKD (SEQ ID NO:81), LYLSSAS (SEQ ID NO: 82), YGSRSVD (SEQ ID NO:83), LYSHQVS (SEQ ID NO: 84), and ISTHSPP (SEQ ID NO: 85).

In some embodiments, an AAV9 variant comprises a peptide comprising an amino acid sequence selected from the group consisting of MPGRAPI (SEQ ID NO: 12), LGRLTAN (SEQ ID NO: 13), SYSTSRS (SEQ ID NO: 14), TRPSSTN (SEQ ID NO: 15), VPQSSSR (SEQ ID NO: 16), VSRSYPA (SEQ ID NO: 17) and QRARPDT (SEQ ID NO: 18). In some embodiments, an AAV9 variant comprises a peptide selected from the group consisting of MPGRAPI (SEQ ID NO: 12), LGRLTAN (SEQ ID NO: 13), SYSTSRS (SEQ ID NO: 14), TRPSSTN (SEQ ID NO: 15), VPQSSSR (SEQ ID NO: 16), VSRSYPA (SEQ ID NO: 17) and QRARPDT (SEQ ID NO: 18).

In some embodiments, an AAV9 variant comprises a peptide comprising an amino acid sequence selected from the group consisting of RQPTTIP (SEQ ID NO: 86), RSTSSLL (SEQ ID NO: 87), FRLSSPQ (SEQ ID NO: 88), and NIPKAYG (SEQ ID NO: 89). In some embodiments, an AAV9 variant comprises a peptide selected from the group consisting of RQPTTIP (SEQ ID NO: 86), RSTSSLL (SEQ ID NO: 87), FRLSSPQ (SEQ ID NO: 88), and NIPKAYG (SEQ ID NO: 89).

In some embodiments, an AAV6 variant comprises a peptide comprising an amino acid sequence selected from the group consisting of SQLTPHS (SEQ ID NO: 19), LGSHLPS (SEQ ID NO: 20), YTLSSGQ (SEQ ID NO: 21), SSRIPPD (SEQ ID NO: 22), WTETIPR (SEQ ID NO: 23), HGLQGVA (SEQ ID NO: 24), TMRVSDQ (SEQ ID NO: 25), GSSKVVM (SEQ ID NO: 26), and SALDRGV (SEQ ID NO: 27). In some embodiments, an AAV6 variant comprises a peptide selected from the group consisting of SQLTPHS (SEQ ID NO: 19), LGSHLPS (SEQ ID NO: 20), YTLSSGQ (SEQ ID NO: 21), SSRIPPD (SEQ ID NO: 22), WTETIPR (SEQ ID NO: 23), HGLQGVA (SEQ ID NO: 24), TMRVSDQ (SEQ ID NO: 25), GSSKVVM (SEQ ID NO: 26), and SALDRGV (SEQ ID NO: 27).

In some embodiments, an AAV5 variant comprises a peptide comprising an amino acid sequence selected from the group consisting of KELGTQR (SEQ ID NO: 28), RSSDVQR (SEQ ID NO: 29), PSAPKTF (SEQ ID NO: 30), HTKRSEY (SEQ ID NO: 31), and IKGSNLP (SEQ ID NO: 32). In some embodiments, an AAV5 variant comprises a peptide selected from the group consisting of KELGTQR (SEQ ID NO: 28), RSSDVQR (SEQ ID NO: 29), PSAPKTF (SEQ ID NO: 30), HTKRSEY (SEQ ID NO: 31), and IKGSNLP (SEQ ID NO: 32).

Peptides

Described herein are inserted peptides identified using the methods of the present disclosure that confer a desired characteristic to an AAV variant compared to a natural AAV serotype. In some embodiments, the desired characteristic is enhanced cell or tissue tropism as compared to the natural AAV serotype. In some embodiments, an inserted peptide of the disclosure allows an AAV variant to evade a pre-existing host antibody response. In some embodiments, an inserted peptide of the disclosure renders an AAV variant less immunogenic such that it will not provoke a host response. In some embodiments, the inserted peptides are capable of directing an AAV vector to a particular target cell or tissue.

An inserted peptide can be 4, 5, 6, 7, 8, 9, 10, 11, 12, 13, 14, 15, 20, 25, 30, or more amino acids in length or a range between any two of these values. In some embodiments, the peptide is 7 amino acids long. In some embodiments, the peptide is 10 amino acids long. In some embodiments, the peptide is 15 amino acids long.

In some embodiments, the inserted peptide comprises at least 4 contiguous amino acids of an amino acid sequence set forth in SEQ ID Nos. 1-32. In some embodiments, the peptide comprises at least 5 contiguous amino acids of an amino acid sequence set forth in SEQ ID Nos. 1-32. In some embodiments, the peptide comprises at least 6 contiguous amino acids of an amino acid sequence set forth in SEQ ID Nos. 1-32. In some embodiments, the peptide comprises an amino acid sequence set forth in SEQ ID Nos. 1-32. In some embodiments, the peptide comprises an amino acid sequence with at least about 60%, about 65%, about 70%, about 75%, about 80%, about 85%, about 90%, about 91%, about 92%, about 93%, about 94%, about 95%, about 96%, about 97%, about 98%, about 99% or more sequence identity to an amino acid sequence set forth in SEQ ID Nos. 1-32. In some embodiments, the inserted peptide comprises at least 4 contiguous amino acids of an amino acid sequence set forth in SEQ ID Nos. 68-110. In some embodiments, the peptide comprises at least 5 contiguous amino acids of an amino acid sequence set forth in SEQ ID Nos. 68-110. In some embodiments, the peptide comprises at least 6 contiguous amino acids of an amino acid sequence set forth in SEQ ID Nos. 68-110. In some embodiments, the peptide comprises an amino acid sequence set forth in SEQ ID Nos. 68-110. In some embodiments, the peptide comprises an amino acid sequence with at least about 60%, about 65%, about 70%, about 75%, about 80%, about 85%, about 90%, about 91%, about 92%, about 93%, about 94%, about 95%, about 96%, about 97%, about 98%, about 99% or more sequence identity to an amino acid sequence set forth in SEQ ID Nos. 68-110.

In some embodiments, the peptide comprises any one of the sequences selected from the group consisting of EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76) and YGSRSVD (SEQ ID NO: 83). In some embodiments, the peptide sequence is selected from the group consisting of sequences EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76) and YGSRSVD (SEQ ID NO: 83). In some embodiments, the peptide comprises sequence SVVVSSDSSKRPNL (SEQ ID NO: 71). In some embodiments, the peptide sequence is SVVVSSDSSKRPNL (SEQ ID NO: 71). In some embodiments, the peptide comprises any one of the sequences selected from the group consisting of RPLTAND (SEQ ID NO: 95), PRDTFNG (SEQ ID NO: 94), PLRMVNE (SEQ ID NO: 96), ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102). In some embodiments, the peptide sequence is selected from the group consisting of sequences RPLTAND (SEQ ID NO: 95), PRDTFNG (SEQ ID NO: 94), PLRMVNE (SEQ ID NO: 96), ENFSKVA (SEQ ID NO: 101), LGNGKMTVQP (SEQ ID NO: 103), GRNTVGLSSA (SEQ ID NO: 106), TSNSRTE (SEQ ID NO: 91) and RDALSGLRPE (SEQ ID NO: 102). In some embodiments, the peptide comprises sequence NIPKAYG (SEQ ID NO: 89). In some embodiments, the peptide sequence is NIPKAYG (SEQ ID NO: 89).

In some embodiments, the peptide comprises an amino acid sequence selected from the group consisting of EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76), YGSRSVD (SEQ ID NO: 83), SVVVSSDSSKRPNL (SEQ ID NO: 71), RPLTAND (SEQ ID NO: 95), PRDTFNG (SEQ ID NO: 94) and PLRMVNE (SEQ ID NO: 96). In some embodiments, the peptide sequence is selected from the group consisting of EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76), YGSRSVD (SEQ ID NO: 83), SVVVSSDSSKRPNL (SEQ ID NO: 71), RPLTAND (SEQ ID NO: 95), PRDTFNG (SEQ ID NO: 94) and PLRMVNE (SEQ ID NO: 96).

In some embodiments, the peptide comprises an amino acid sequence selected from the group consisting of ENFSKVA (SEQ ID NO: 101), LGNGKMTVQP, GRNTVGLSSA (SEQ ID NO: 103), TSNSRTE (SEQ ID NO: 91), RDALSGLRPE (SEQ ID NO: 102) and NIPKAYG (SEQ ID NO: 89). In some embodiments, the peptide sequence is selected from the group consisting of EQFRNLA (SEQ ID NO: 78), TDFRSPQ (SEQ ID NO: 80), TGAFSST (SEQ ID NO: 77), FNSPVIQ (SEQ ID NO: 79), PYASITG (SEQ ID NO: 76), YGSRSVD (SEQ ID NO: 83), SVVVSSDSSKRPNL (SEQ ID NO: 71), RPLTAND (SEQ ID NO: 95), PRDTFNG (SEQ ID NO: 94) and PLRMVNE (SEQ ID NO: 96).

In some embodiments, the peptide comprises amino acid sequence EQFRNLA (SEQ ID NO: 78). In some embodiments, the peptide comprises amino acid sequence TDFRSPQ (SEQ ID NO: 80). In some embodiments, the peptide comprises amino acid sequence TGAFSST (SEQ ID NO: 77). In some embodiments, the peptide comprises amino acid sequence FNSPVIQ (SEQ ID NO: 79). In some embodiments, the peptide comprises amino acid sequence PYASITG (SEQ ID NO: 76). In some embodiments, the peptide comprises amino acid sequence YGSRSVD (SEQ ID NO: 83). In some embodiments, the peptide comprises amino acid sequence RPLTAND (SEQ ID NO: 95). In some embodiments, the peptide comprises amino acid sequence PRDTFNG (SEQ ID NO: 94). In some embodiments, the peptide comprises amino acid sequence PLRMVNE (SEQ ID NO: 96). In some embodiments, the peptide comprises amino acid sequence ENFSKVA (SEQ ID NO: 101). In some embodiments, the peptide comprises amino acid sequence LGNGKMTVQP (SEQ ID NO: 103). In some embodiments, the peptide comprises amino acid sequence GRNTVGLSSA (SEQ ID NO: 106). In some embodiments, the peptide comprises amino acid sequence TSNSRTE (SEQ ID NO: 91). In some embodiments, the peptide comprises amino acid sequence RDALSGLRPE (SEQ ID NO: 102).

In some embodiments, the peptide comprises an amino acid sequence selected from the group consisting of KSPQSKV (SEQ ID NO:1), SDLRSKV (SEQ ID NO:2) and TTTVRKV (SEQ ID NO:3). In some embodiments, the peptide is selected from the group consisting of KSPQSKV (SEQ ID NO:1), SDLRSKV (SEQ ID NO:2) and TTTVRKV (SEQ ID NO:3).

In some embodiments, the peptide comprises an amino acid sequence selected from the group consisting of AALRDIR (SEQ ID NO:68), PAIKTYS (SEQ ID NO: 69), TGDRISSRTL (SEQ ID NO: 70), SVVVSSDSSKRPRNL (SEQ ID NO: 71), VGARLSA (SEQ ID NO: 72), IEKPNTSTKK (SEQ ID NO: 73), DTVRSKN (SEQ ID NO: 74), and KELNKAR (SEQ ID NO: 75). In some embodiments, the peptide is selected from the group consisting of AALRDIR (SEQ ID NO:68), PAIKTYS (SEQ ID NO: 69), TGDRISSRTL (SEQ ID NO: 70), SVVVSSDSSKRPRNL (SEQ ID NO: 71), VGARLSA (SEQ ID NO: 72), IEKPNTSTKK (SEQ ID NO: 73), DTVRSKN (SEQ ID NO: 74), and KELNKAR (SEQ ID NO: 75).

In some embodiments, the peptide comprises an amino acid sequence selected from the group consisting of GRSDMAG (SEQ ID NO: 4), LLSSERS (SEQ ID NO: 5), EQRPNVS (SEQ ID NO: 6) and TRQISSD (SEQ ID NO: 7). In some embodiments, the peptide is selected from the group consisting of GRSDMAG (SEQ ID NO: 4), LLSSERS (SEQ ID NO: 5), EQRPNVS (SEQ ID NO: 6) and TRQISSD (SEQ ID NO: 7).

In some embodiments, the peptide comprises an amino acid sequence selected from the group consisting of MTLTRQE (SEQ ID NO: 90), TSNSRTE (SEQ ID NO: 91), EVRGGPS (SEQ ID NO: 92), VISDRSS (SEQ ID NO: 93), PRDTFNG (SEQ ID NO: 94), RPLTAND (SEQ ID NO: 95), PLRMVNE (SEQ ID NO: 96), DVGIRPS (SEQ ID NO: 97), KDSTAFG (SEQ ID NO: 98), YPGRNPD (SEQ ID NO: 99), ISDTRIS (SEQ ID NO: 100), ENFSKVA (SEQ ID NO: 101), RDALSGLRPE (SEQ ID NO: 102), LGNGKMTVQP (SEQ ID NO: 103), VSNPLNQ (SEQ ID NO: 104), LNERGLG (SEQ ID NO: 105), GRNTVGLSSA (SEQ ID NO: 106), VGHAGNP (SEQ ID NO: 107), SRAGTVP (SEQ ID NO: 108), GLVAKLP (SEQ ID NO: 109), and AESLRTP (SEQ ID NO: 110). In some embodiments, the peptide is selected from the group consisting of MTLTRQE (SEQ ID NO: 90), TSNSRTE (SEQ ID NO: 91), EVRGGPS (SEQ ID NO: 92), VISDRSS (SEQ ID NO: 93), PRDTFNG (SEQ ID NO: 94), RPLTAND (SEQ ID NO: 95), PLRMVNE (SEQ ID NO: 96), DVGIRPS (SEQ ID NO: 97), KDSTAFG (SEQ ID NO: 98), YPGRNPD (SEQ ID NO: 99), ISDTRIS (SEQ ID NO: 100), ENFSKVA (SEQ ID NO: 101), RDALSGLRPE (SEQ ID NO: 102), LGNGKMTVQP (SEQ ID NO: 103), VSNPLNQ (SEQ ID NO: 104), LNERGLG (SEQ ID NO: 105), GRNTVGLSSA (SEQ ID NO: 106), VGHAGNP (SEQ ID NO: 107), SRAGTVP (SEQ ID NO: 108), GLVAKLP (SEQ ID NO: 109), and AESLRTP (SEQ ID NO: 110).

In some embodiments, the peptide comprises an amino acid sequence selected from the group consisting of QGALAQV (SEQ ID NO: 8), YPSSNTP (SEQ ID NO: 9), MLNPRTE (SEQ ID NO: 10) and QMRTRDE (SEQ ID NO: 11). In some embodiments, the peptide is selected from the group consisting of QGALAQV (SEQ ID NO: 8), YPSSNTP (SEQ ID NO: 9), MLNPRTE (SEQ ID NO: 10) and QMRTRDE (SEQ ID NO: 11).

In some embodiments, the peptide comprises an amino acid sequence selected from the group consisting of PYASITG (SEQ ID NO: 76), TGAFSST (SEQ ID NO: 77), EQFRNLA (SEQ ID NO: 78), FNSPVIQ (SEQ ID NO: 79), TDFRSPQ (SEQ ID NO:80), MYSLMKD (SEQ ID NO:81), LYLSSAS (SEQ ID NO: 82), YGSRSVD (SEQ ID NO:83), LYSHQVS (SEQ ID NO: 84), and ISTHSPP (SEQ ID NO: 85). In some embodiments, the peptide is selected from the group consisting of PYASITG (SEQ ID NO: 76), TGAFSST (SEQ ID NO: 77), EQFRNLA (SEQ ID NO: 78), FNSPVIQ (SEQ ID NO: 79), TDFRSPQ (SEQ ID NO:80), MYSLMKD (SEQ ID NO:81), LYLSSAS (SEQ ID NO: 82), YGSRSVD (SEQ ID NO:83), LYSHQVS (SEQ ID NO: 84), and ISTHSPP (SEQ ID NO: 85).

In some embodiments, the peptide comprises an amino acid sequence selected from the group consisting of MPGRAPI (SEQ ID NO: 12), LGRLTAN (SEQ ID NO: 13), SYSTSRS (SEQ ID NO: 14), TRPSSTN (SEQ ID NO: 15), VPQSSSR (SEQ ID NO: 16), VSRSYPA (SEQ ID NO: 17) and QRARPDT (SEQ ID NO: 18). In some embodiments, the peptide is selected from the group consisting of MPGRAPI (SEQ ID NO: 12), LGRLTAN (SEQ ID NO: 13), SYSTSRS (SEQ ID NO: 14), TRPSSTN (SEQ ID NO: 15), VPQSSSR (SEQ ID NO: 16), VSRSYPA (SEQ ID NO: 17) and QRARPDT (SEQ ID NO: 18).

In some embodiments, the peptide comprises an amino acid sequence selected from the group consisting of RQPTTIP (SEQ ID NO: 86), RSTSSLL (SEQ ID NO: 87), FRLSSPQ (SEQ ID NO: 88), and NIPKAYG (SEQ ID NO: 89). In some embodiments, the peptide is selected from the group consisting of RQPTTIP (SEQ ID NO: 86), RSTSSLL (SEQ ID NO: 87), FRLSSPQ (SEQ ID NO: 88), and NIPKAYG (SEQ ID NO: 89).

In some embodiments, the peptide comprises an amino acid sequence selected from the group consisting of SQLTPHS (SEQ ID NO: 19), LGSHLPS (SEQ ID NO: 20), YTLSSGQ (SEQ ID NO: 21), SSRIPPD (SEQ ID NO: 22), WTETIPR (SEQ ID NO: 23), HGLQGVA (SEQ ID NO: 24), TMRVSDQ (SEQ ID NO: 25), GSSKVVM (SEQ ID NO: 26), and SALDRGV (SEQ ID NO: 27). In some embodiments, the peptide is selected from the group consisting of SQLTPHS (SEQ ID NO: 19), LGSHLPS (SEQ ID NO: 20), YTLSSGQ (SEQ ID NO: 21), SSRIPPD (SEQ ID NO: 22), WTETIPR (SEQ ID NO: 23), HGLQGVA (SEQ ID NO: 24), TMRVSDQ (SEQ ID NO: 25), GSSKVVM (SEQ ID NO: 26), and SALDRGV (SEQ ID NO: 27).

In some embodiments, the peptide comprises an amino acid sequence selected from the group consisting of KELGTQR (SEQ ID NO: 28), RSSDVQR (SEQ ID NO: 29), PSAPKTF (SEQ ID NO: 30), HTKRSEY (SEQ ID NO: 31), and IKGSNLP (SEQ ID NO: 32). In some embodiments, the peptide is selected from the group consisting of KELGTQR (SEQ ID NO: 28), RSSDVQR (SEQ ID NO: 29), PSAPKTF (SEQ ID NO: 30), HTKRSEY (SEQ ID NO: 31), and IKGSNLP (SEQ ID NO: 32).

In some embodiments, the disclosure provides a capsid protein comprising an inserted peptide, wherein the peptide is inserted at i) amino acid position 590 of an AAV1 capsid protein, (ii) amino acid position 454 or 590 of an AAV6 capsid protein, (iii) amino acid position 588 of an AAV2 capsid protein, (iv) amino acid position 589 of an AAV3B capsid protein, (v) amino acid position 578 of an AAV5 capsid protein, (vi) amino acid position 591 of the an AAV8 capsid protein, or (vi) amino acid position 266, 455, or 589 of an AAV9 capsid protein, wherein the positions correspond to the numbering of VP1 in the AAV serotype.

In some embodiments of the capsid proteins disclosed herein, a peptide comprising the amino acid sequence of any one of SEQ ID NO. 1-32 is inserted at amino acid position 590 of the capsid protein of an AAV1 serotype. In some embodiments of the capsid proteins disclosed herein, a peptide comprising the amino acid sequence of any one of SEQ ID NO. 68-110 is inserted at amino acid position 590 of the capsid protein of an AAV1 serotype. In some embodiments of the capsid proteins disclosed herein, the peptide inserted at position 590 of the capsid protein of an AAV1 serotype comprises an amino acid sequence selected from the group consisting of any one of SEQ ID NO: 68 to SEQ ID NO: 75. In some embodiments of the capsid proteins disclosed herein, the peptide inserted at position 590 of the capsid protein of an AAV1 serotype comprises the amino acid sequence SEQ ID NO: 71. In some embodiments of the capsid proteins disclosed herein, the peptide inserted at position 590 of the capsid protein of an AAV1 serotype comprises an amino acid sequence selected from the group consisting of any one of SEQ ID NO: 1, SEQ ID NO: 2 and SEQ ID NO: 3.

In some embodiments of the capsid proteins disclosed herein, a peptide comprising the amino acid sequence of any one of SEQ ID NO. 1-32 is inserted at amino acid position 454 of the capsid protein of an AAV6 serotype. In some embodiments of the capsid proteins disclosed herein, a peptide comprising the amino acid sequence of any one of SEQ ID NO. 68-110 is inserted at amino acid position 454 of the capsid protein of an AAV6 serotype. In some embodiments of the capsid proteins disclosed herein, a peptide comprising the amino acid sequence of any one of SEQ ID NO. 1-32 is inserted at amino acid position 590 of the capsid protein of an AAV6 serotype. In some embodiments of the capsid proteins disclosed herein, a peptide comprising the amino acid sequence of any one of SEQ ID NO. 68-110 is inserted at amino acid position 590 of the capsid protein of an AAV6 serotype. In some embodiments of the capsid proteins disclosed here, the peptide inserted at position 454 of the capsid protein of an AAV6 serotype comprises an amino acid sequence selected from the group consisting of any one of SEQ ID NO: 19 to SEQ ID NO: 27. In some embodiments of the capsid proteins disclosed here, the peptide inserted at position 590 of the capsid protein of an AAV6 serotype comprises an amino acid sequence selected from the group consisting of any one of SEQ ID NO: 19 to SEQ ID NO: 27.

In some embodiments of the capsid proteins disclosed herein, a peptide comprising the amino acid sequence of any one of SEQ ID NO. 1-32 is inserted at amino acid position 588 of the capsid protein of an AAV2 serotype. In some embodiments of the capsid proteins disclosed herein, a peptide comprising the amino acid sequence of any one of SEQ ID NO. 68-110 is inserted at amino acid position 588 of the capsid protein of an AAV2 serotype. In some embodiments of the capsid proteins disclosed here, the peptide inserted at position 588 of the capsid protein of an AAV2 serotype comprises an amino acid sequence selected from the group consisting of any one of SEQ ID NO: 90 to SEQ ID NO: 110. In some embodiments of the capsid proteins disclosed here, the peptide inserted at position 588 of the capsid protein of an AAV2 serotype comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102. In some embodiments of the capsid proteins disclosed here, the peptide inserted at position 588 of the capsid protein of an AAV2 serotype comprises an amino acid sequence selected from the group consisting of any one of SEQ ID NO: 4-7.

In some embodiments of the capsid proteins disclosed herein, a peptide comprising the amino acid sequence of any one of SEQ ID NO. 1-32 is inserted at amino acid position 589 of the capsid protein of an AAV3B serotype. In some embodiments of the capsid proteins disclosed herein, a peptide comprising the amino acid sequence of any one of SEQ ID NO. 68-110 is inserted at amino acid position 589 of the capsid protein of an AAV3B serotype. In some embodiments of the capsid proteins disclosed here, the peptide inserted at position 589 of the capsid protein of an AAV3B serotype comprises an amino acid sequence selected from the group consisting of any one of SEQ ID NO: 76-85. In some embodiments of the capsid proteins disclosed here, the peptide inserted at position 589 of the capsid protein of an AAV3B serotype comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83. In some embodiments of the capsid proteins disclosed here, the peptide inserted at position 589 of the capsid protein of an AAV3B serotype comprises an amino acid sequence selected from the group consisting of any one of SEQ ID NO: 8 to SEQ ID NO: 11.

In some embodiments of the capsid proteins disclosed herein, a peptide comprising the amino acid sequence of any one of SEQ ID NO. 1-32 is inserted at amino acid position 578 of the capsid protein of an AAV5 serotype. In some embodiments of the capsid proteins disclosed herein, a peptide comprising the amino acid sequence of any one of SEQ ID NO. 68-110 is inserted at amino acid position 578 of the capsid protein of an AAV5 serotype. In some embodiments of the capsid proteins disclosed herein, the peptide inserted at position 578 of the capsid protein of an AAV5 serotype comprises an amino acid sequence selected from the group consisting of any one of SEQ ID NO: 28 to SEQ ID NO: 32.

In some embodiments of the capsid proteins disclosed herein, a peptide comprising the amino acid sequence of any one of SEQ ID NO. 1-32 is inserted at amino acid position 591 of the capsid protein of an AAV8 serotype. In some embodiments of the capsid proteins disclosed herein, a peptide comprising the amino acid sequence of any one of SEQ ID NO. 68-110 is inserted at amino acid position 591 of the capsid protein of an AAV8 serotype.

In some embodiments of the capsid proteins disclosed herein, a peptide comprising the amino acid sequence of any one of SEQ ID NO. 1-32 is inserted at amino acid position 266 of the capsid protein of an AAV9 serotype. In some embodiments of the capsid proteins disclosed herein, a peptide comprising the amino acid sequence of any one of SEQ ID NO. 68-110 is inserted at amino acid position 266 of the capsid protein of an AAV9 serotype. In some embodiments of the capsid proteins disclosed herein, a peptide comprising the amino acid sequence of any one of SEQ ID NO. 1-32 is inserted at amino acid position 455 of the capsid protein of an AAV9 serotype. In some embodiments of the capsid proteins disclosed herein, a peptide comprising the amino acid sequence of any one of SEQ ID NO. 68-110 is inserted at amino acid position 455 of the capsid protein of an AAV9 serotype. In some embodiments of the capsid proteins disclosed herein, a peptide comprising the amino acid sequence of any one of SEQ ID NO. 1-32 is inserted at amino acid position 589 of the capsid protein of an AAV9 serotype. In some embodiments of the capsid proteins disclosed herein, a peptide comprising the amino acid sequence of any one of SEQ ID NO. 68-110 is inserted at amino acid position 589 of the capsid protein of an AAV9 serotype. In some embodiments of the capsid proteins disclosed here, the peptide inserted at position 266 of the capsid protein of an AAV9 serotype comprises an amino acid sequence selected from the group consisting of any one of SEQ ID NO: 12 to SEQ ID NO: 18. In some embodiments of the capsid proteins disclosed here, the peptide inserted at position 266 of the capsid protein of an AAV9 serotype comprises an amino acid sequence selected from the group consisting of any one of SEQ ID NO: 86 to SEQ ID NO: 89. In some embodiments of the capsid proteins disclosed here, the peptide inserted at position 266 of the capsid protein of an AAV9 serotype comprises an amino acid sequence of SEQ ID NO: 89. In some embodiments of the capsid proteins disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the capsid proteins disclosed here, the peptide inserted at position 455 of the capsid protein of an AAV9 serotype comprises an amino acid sequence selected from the group consisting of any one of SEQ ID NO: 86 to SEQ ID NO: 89. In some embodiments of the capsid proteins disclosed here, the peptide inserted at position 455 of the capsid protein of an AAV9 serotype comprises an amino acid sequence of SEQ ID NO: 89. In some embodiments of the capsid proteins disclosed here, the peptide inserted at position 455 of the capsid protein of an AAV9 serotype comprises an amino acid sequence selected from the group consisting of any one of SEQ ID NO: 12 to SEQ ID NO: 18. In some embodiments of the capsid proteins disclosed here, the peptide inserted at position 589 of the capsid protein of an AAV9 serotype comprises an amino acid sequence selected from the group consisting of any one of SEQ ID NO: 86 to SEQ ID NO: 89. In some embodiments of the capsid proteins disclosed here, the peptide inserted at position 589 of the capsid protein of an AAV9 serotype comprises an amino acid sequence of SEQ ID NO: 89.

Also disclosed herein are AAV capsid proteins comprising an inserted peptide as disclosed herein. In some embodiments, the capsid protein is VP1, VP2, or VP3. In some embodiments, the peptide is inserted at a location between residues 450 and 600 of the capsid protein. In some embodiments, the peptide is inserted at (i) position 590 of an AAV1 capsid protein, (ii) position 454 or 590 of an AAV6 capsid protein, (iii) position 588 of an AAV2 capsid protein, (iv) position 589 of an AAV3B capsid protein, (v) position 578 of an AAV5 capsid protein, (vi) position 591 of an AAV8 capsid protein, or (vii) position 266, 455, or 589 of an AAV9 capsid protein, wherein the positions correspond to the numbering of VP1 in the AAV serotype. In some embodiments, the peptide is inserted at position 590 of an AAV1 capsid protein. In some embodiments, the peptide is inserted at position 454 or 590 of an AAV6 capsid protein. In some embodiments, the peptide is inserted at position 588 of an AAV2 capsid protein. In some embodiments, the peptide is inserted at position 589 of an AAV3B capsid protein. In some embodiments, the peptide is inserted at position 578 of an AAV5 capsid protein. In some embodiments, the peptide is inserted at position 591 of an AAV8 capsid protein. In some embodiments, the peptide is inserted at position 266, 455, or 589 of an AAV9 capsid protein. It is understood that other sites in the capsid proteins may be selected for insertion. It will also be understood that the amino acid sequences may be inserted at corresponding positions of VP2 or VP3.

Also disclosed herein are nucleic acid sequences encoding the peptides, capsid proteins and AAV variants disclosed herein.

Further, disclosed herein are AAV vectors comprising the inserted peptides disclosed herein. In some embodiments, the peptide is part of a capsid protein of the AAV vector.

In some embodiments, the inserted peptide of the disclosure has cell or tissue tropism for a target cell or tissue. In some embodiments, the target cell or tissue includes, but is not limited to, a cell from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa. In some embodiments, the target cell or tissue is from the liver. In some embodiments, the target cell or tissue is from the CNS. In some embodiments, the target cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

A vector comprising an inserted peptide of the disclosure may be used to deliver a nucleic acid to a target cell or tissue. In one aspect, the present disclosure provides a method of delivering a nucleic acid to a target cell or tissue comprising administering an AAV vector comprising the nucleic acid, wherein the AAV vector comprises a targeting protein of the disclosure. In some embodiments, the target cell or tissue includes, but is not limited to, a cell from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa. In some embodiments, the target cell or tissue is from the liver. In some embodiments, the target cell or tissue is from the CNS. In some embodiments, the target cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

DNA-Binding Molecules/Domains

Described herein are compositions comprising a DNA-binding molecule/domain that specifically binds to a target site in any gene or locus of interest. Any DNA-binding molecule/domain can be used in the compositions and methods disclosed herein, including but not limited to a zinc finger DNA-binding domain, a TALE DNA binding domain, the DNA-binding portion (guide or sgRNA) of a CRISPR/Cas nuclease, or a DNA-binding domain from a meganuclease. In the methods and compositions described herein, it is understood that the term "'Cas" includes both Cas9 and Cfp1 proteins. Thus, as used herein, a "CRISPR/Cas system" refers both CRISPR/Cas and/or CRISPR/Cfp1 systems, including both nuclease, nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein, et al. (2017) *Nature* 542:237-241) for example HF1/spCas9 (Kleinstiver, et al. (2016) *Nature* 529: 490-495; Cebrian-Serrano and Davies (2017) *Mamm Genome* (2017) 28(7): 247-261); split Cas9 systems (Zetsche, et al. (2015) *Nat Biotechnol* 33(2):139-142), trans-spliced Cas9 based on an intein-extein system (Troung, et al. (2015) *Nucl Acid Res* 43(13):6450-8); mini-SaCas9 (Ma, et al. (2018) *ACS Synth Biol* 7(4):978-985). Thus, in the methods and compositions described herein, it is understood that the term "'Cas" includes all Cas variant proteins, both natural and engineered. Thus, as used herein, a "CRISPR/Cas system" refers to any CRISPR/Cas system, including both nuclease, nickase and/or transcription factor systems.

Systems

The DNA-editing complexes (or component molecules thereof) described herein may be delivered to a target cell by the methods and compositions as described herein. Delivery may be to isolated cells (which in turn may be administered to a living subject for ex vivo cell therapy) or a living subject. Delivery of gene editing molecules to cells and subjects are known in the art.

Suitable cells include but not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

DNA-editing complexes as described herein may also be delivered using vectors of the invention containing sequences encoding one or more of the components (e.g., fusion molecules). Additionally, additional nucleic acids (e.g., donors) also may be delivered via these vectors. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired. Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses.

Packaging cells are used to form virus particles that are capable of infecting a host cell. Such cells include HEK293 cells, which package adenovirus or AAV. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In some embodiments, baculovirus systems are used to produce the AAV (see for example Smith et al (2009) *Mol Ther* 434:37-54).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Delivery methods for CRISPR/Cas systems can comprise those methods described above. For example, in animal models, in vitro transcribed Cas encoding mRNA or recombinant Cas protein can be directly injected into one-cell stage embryos using glass needles to genome-edited animals. To express Cas and guide RNAs in cells in vitro, typically plasmids that encode them are transfected into cells via lipofection or electroporation. Also, recombinant Cas protein can be complexed with in vitro transcribed guide RNA where the Cas-guide RNA ribonucleoprotein is taken up by the cells of interest (Kim, et al. (2014) *Genome Res* 24(6):1012). For therapeutic purposes, Cas and guide RNAs can be delivered by a combination of viral and non-viral techniques. For example, mRNA encoding Cas may be delivered via nanoparticle delivery while the guide RNAs and any desired transgene or repair template are delivered via AAV (Yin, et al. (2016) *Nat Biotechnol* 34(3):328).

Gene therapy vectors can be delivered in vivo by administration to an individual patient (subject), typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In some embodiments, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney, et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-$\gamma$ and TNF-$\alpha$ are known (see Inaba, et al. (1992) *J. Exp. Med.* 176:1693-1702).

The vectors as described herein containing therapeutic DNA-binding proteins (or nucleic acids encoding these proteins) can also be administered directly to an organism for transduction of cells in vivo. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces*. Progeny, variants and derivatives of these cell lines can also be used.

Applications

Engineered AAV capsids can be used for many different applications of in vivo and ex vivo gene therapy and genome editing. The AAV variants disclosed herein were generated through the use of directed evolution involving the use of cell and in vivo selections following administration. In some embodiments, the variant capsid proteins disclosed herein, when present in an AAV virion, confer increased transduction of a cell, tissue or organelle compared to the transduction of the cell, tissue or organelle by an AAV virion comprising the corresponding parental AAV capsid protein or wild-type AAV. For example, in some embodiments, the variant capsid proteins disclosed herein, when present in an AAV virion, confer more efficient transduction of cells, tissues or organelle than AAV virions comprising the corresponding parental AAV capsid protein or wild-type AAV capsid protein, e.g. the cells, tissues or organelles take up more AAV virions comprising the variant AAV capsid protein than AAV virions comprising the parental AAV capsid protein or wild-type AAV. In some such embodiments, the AAV variant virion or variant rAAV exhibits at least 2-fold, at least 5-fold, at least 10-fold, at least 15-fold, at least 20-fold, at least 25-fold, at least 30-fold, at least 40-fold, at least 50-fold, or more than 50-fold, increased transduction of a cell, tissue or organelle compared to the transduction of the cell, tissue or organelle by a wild-type AAV virion or rAAV comprising the corresponding parental AAV capsid protein. In some embodiments, the cell or tissue includes, but is not limited to, a cell or tissue from the CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, or oral mucosa. In some embodiments, the cell or tissue is from the liver. In some embodiments, the cell or tissue is from the CNS. In some embodiments, the target cell includes, but is not limited to, neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells. In some embodiments, the AAV variant virion or variant rAAV exhibits at least 2-fold, at least 5-fold, at least 10-fold, at least 15-fold, at least 20-fold, at least 25-fold, at least 30-fold, at least 40-fold, at least 50-fold, at least 100-fold, at least 1000-fold or more than 1000-fold, increased transduction of a cell, tissue or organelle compared to the transduction of the cell, tissue or organelle by a wild-type AAV1, AAV2, AAV3B, AAV4, AAV5, AAV6, AAV8 or AAV9 virion. In certain such embodiments, the variant capsid proteins disclosed herein, when present in an AAV virion, confer broader transduction of primate CNS cells than AAV virions comprising the corresponding parental AAV capsid protein or wild type AAV capsid protein. In some embodiments, the variant AAV virion transduces cell types not transduced by virions comprising the corresponding parental AAV capsid protein, and hence more types of cells in the CNS than the corresponding parental AAV virion. In some embodiments, the AAV variant virion preferentially transduces a CNS cell, e.g., a rAAV virion infects a CNS cell with 2-fold, 5-fold, 10-fold, 15-fold, 20-fold, 25-fold, 50-fold, or more than 50-fold, specificity than another cell. In some embodiments, the transduced CNS cell is a neuron or glial cell, including without limitation, an astrocyte, oligodendroglia, microglia, Schwann cell, or ependymal cell.

In certain such embodiments, the variant capsid proteins disclosed herein, when present in an AAV virion, confer broader transduction of primate liver cells than AAV virions comprising the corresponding parental AAV capsid protein or wild type AAV capsid protein. In some embodiments, the variant AAV virion transduces cell types not transduced by virions comprising the corresponding parental AAV capsid protein, and hence more types of cells in the liver than the corresponding parental AAV virion. In some embodiments, the AAV variant virion preferentially transduces a liver cell, e.g., a rAAV virion infects a liver cell with 2-fold, 5-fold, 10-fold, 15-fold, 20-fold, 25-fold, 50-fold, or more than 50-fold, specificity than another cell. In some embodiments, the transduced liver cell is, without limitation, a hepatocyte, stellate fat storing cell, Kupffer cell or liver endothelial cell.

An increase in transduction of a CNS or liver cell, e.g. increased efficiency of transduction, broader transduction, more preferential transduction, etc. may be readily assessed in vitro or in vivo by any number of methods in the art for measuring gene expression. For example, the AAV may be packaged with a genome comprising an expression cassette comprising a reporter gene, e.g. a fluorescent protein, under the control of or operatively linked to a ubiquitous or cell type and/or tissue specific promoter, and the extent of transduction assessed by detecting the fluorescent protein by, e.g., fluorescence microscopy. As another example, the AAV may be packaged with a genome comprising a bar-coded nucleic acid sequence, and the extent of transduction assessed by detecting the nucleic acid sequence by, e.g., PCR. As another example, the AAV may be packaged with a genome comprising an expression cassette comprising a therapeutic gene for the treatment of a disease, and the extent of transduction assessed by detecting the treatment of the disease in a subject in need of treatment that was administered the AAV.

Exemplary genetic diseases that may be treated and/or prevented by the compositions and methods described herein include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefelter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, phenylketonuria (PKU). porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA base editing include acquired immunodeficiencies, lysosomal storage diseases (e.g., Gaucher's disease, GM1, Fabry disease and Tay-Sachs disease), mucopolysaccharidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism). Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Gene products delivered by the subject AAV variants can be used to alter the level of gene products or gene product activity directly or indirectly linked to muscle diseases and trauma. Skeletal, cardiac or smooth muscle transduced with subject AAV variants can also be used as a biofactory to produce and secrete therapeutic proteins for the treatment of diseases in trans in distant organs. Genes whose gene products are directly or indirectly linked to genetic diseases include, e.g., genes encoding any of the following gene products: dystrophin including mini- and micro-dystrophins (DMD; e.g. GenBank Accession Number NP 003997.1); titin (TTN); titin cap (TCAP) cc-sarcoglycan (SGCA), β-sarcoglycan (SGCB), γ-sarcoglycan (SGCG) or δ-sarcoglycan (SGCD); alpha-1-antitrypsin (A1-AT); myosin heavy chain 6 (MYH6); myosin heavy chain 7 (MYH7); myosin heavy chain 11 (MYH11); myosin light chain 2 (ML2); myosin light chain 3 (ML3); myosin light chain kinase 2 (MYLK2); myosin binding protein C (MYBPC3); desmin (DES); dynamin 2 (DNM2); laminin cc2 (LAMA2); lamin A/C (LMNA); lamin B (LMNB); lamin B receptor (LBR); dysferlin (DYSF); emerin (EMD); insulin; blood clotting factors, including but not limited to, factor VIII and factor IX; erythropoietin (EPO); lipoprotein lipase (LPL); sarcoplasmic reticulum Ca2++-ATPase (SERCA2A), S100 calcium binding protein A1 (S100A1); myotubularin (MTM); DM1 protein kinase (DMPK; e.g. GenBank Accession Number NG_009784.1); glycogen phosphorylase L (PYGL); glycogen phosphorylase, muscle associated (PYGM; e.g. GenBank Accession Number NP 005600.1); glycogen synthase 1 (GYS1); glycogen synthase 2 (GYS2); cc-galactosidase A (GLA; e.g. GenBank Accession Number NP_000160.1; SEQ ID NO:67); a-N-acetylgalactosaminidase (NAGA); acid cc-glucosidase (GAA; e.g. GenBank Accession Number NP_000143.2; SEQ ID NO:68), sphingomyelinase phosphodiesterase 1 (SMPD1); lysosomal acid lipase (LIPA); collagen type I a1 chain (COL1 Al); collagen type I o2 chain (COL1A2); collagen type III a1 chain (COL3A1); collagen type V a1 chain (COL5A1); collagen type V a2 chain (COL5A2); collagen type VI a1 chain (COL6A1); collagen type VI o2 chain (COL6A2); collagen type VI a3 chain (COL6A3); procollagen-lysine 2-oxoglutarate 5-dioxygenase (PLOD1); lysosomal acid lipase (LIP A); frataxin (FXN; e.g. GenBank Accession Number NP_000135.2); myostatin (MSTN); β-N-acetyl hexosaminidase A (HEXA); β-N-acetylhexosaminidase B (HEXB); β-glucocerebrosidase (GBA); adenosine monophosphate deaminase 1 (AMPD1); β-globin (HBB); iduronidase (IDUA); iduronate 2-sulfate (IDS); troponin 1 (TNNI3); troponin T2 (TNNT2); troponin C (TNNC1); tropomyosin 1 (TPM1); tropomyosin 3 (TPM3); N-acetyl-a-glucosaminidase (NAGLU); N-sulfoglucosamine sulfohydrolase (SGSH); heparan-a-glucosaminide N-acetyltransferase (HGSNAT); integrin a 7 (IGTA7); integrin a 9 (IGTA9); glucosamine(N-acetyl)-6-sulfatase (GNS); galactosamine (N-acetyl)-6-sulfatase (GALNS); β-galactosidase (GLB1); β-glucuronidase (GUSB); hyaluronoglucosaminidase 1 (HYAL1); acid ceramidase (ASAHI); galactosylcermidase (GALC); cathepsin A (CTSA); cathepsin D (CTSA); cathepsin K (CTSK); GM2 ganglioside activator (GM2A); arylsulfatase A (ARSA); arylsulfatase B (ARSB); formylglycine-generating enzyme (SUMF1); neuraminidase 1 (NEU1); N-acetylglucosamine-1-phosphate transferase a (GNPTA); N-acetylglucosamine-1-phosphate transferase β (GNPTB); N-acetylglucosamine-1-phosphate transferase γ (GNPTG); mucolipin-1 (MCOLN1); NPC intracellular transporter 1 (NPC1); NPC intracellular transporter 2 (NPC2); ceroid lipofuscinosis 5 (CLN5); ceroid lipofuscinosis 6 (CLN6); ceroid lipofuscinosis 8 (CLN8); palmitoyl protein thioesterase 1 (PPT1); tripeptidyl peptidase 1 (TPP1); battenin (CLN3); DNAJ heat shock protein family 40 member C5 (DNAJC5); major facilitator superfamily domain containing 8 (MFSD8); mannosidase a class 2B member 1 (MAN2B1); mannosidase β (MANBA); aspartylglucosaminidase (AGA); cc-L-fucosidase (FUCA1); cystinosin, lysosomal cysteine transporter (CTNS); sialin; solute carrier family 2 member 10 (SLC2A10); solute carrier family 17 member 5 (SLC17A5); solute carrier family 6 member 19 (SLC6A19); solute carrier family 22 member 5 (SLC22A5); solute carrier family 37 member 4 (SLC37A4); lysosomal associated membrane protein 2 (LAMP2); sodium voltage-gated channel a subunit 4 (SCN4A); sodium voltage-gated channel β subunit 4 (SCN4B); sodium voltage-gated channel a subunit 5 (SCN5A); sodium voltage-gated channel a subunit 4 (SCN4A); calcium voltage-gated channel subunit ale (CACNAlC); calcium voltage-gated channel subunit eels (CACNAlS); phosphoglycerate kinase 1 (PGK1); phosphoglycerate mutase 2 (PGAM2); amylo-a-

1,6-glucosidase,4-cc-glucanotransferase (AGL); potassium voltage-gated channel ISK-related subfamily member 1 (KCNE1); potassium voltage-gated channel ISK-related subfamily member 2 (KCNE2); potassium voltage-gated channel subfamily J member 2 (KCNJ2); potassium voltage-gated channel subfamily J member 5 (KCNJ5); potassium voltage-gated channel subfamily H member 2 (KCNH2); potassium voltage-gated channel KQT-like subfamily member 1 (KCNQ1); hyperpolarization-activated cyclic nucleotide-gated potassium channel 4 (HCN4); chloride voltage-gated channel 1 (CLCN1); carnitine palmitoyltransferase 1 A (CPT1 A); ryanodine receptor 1 (RYR1); ryanodine receptor 2 (RYR2); bridging integrator 1 (BIN1); LARGE xylosyl- and glucuronyltransferase 1 (LARGE1); docking protein 7 (DOK7); fukutin (FKTN); fukutin related protein (FKRP); selenoprotein N (SELENON); protein O-mannosyltransferase 1 (POMT1); protein O-mannosyltransferase 2 (POMT2); protein 0-linked mannose N-acetylglucosaminyltransferase 1 (POMGNT1); protein O-linked mannose N-acetylglucosaminyltransferase 2 (POMGNT2); protein-O-mannose kinase (POMK); isoprenoid synthase domain containing (ISPD); plectin (PLEC); cholinergic receptor nicotinic epsilon subunit (CHRNE); choline O-acetyltransferase (CHAT); choline kinase β (CHKB); collagen like tail subunit of asymmetric acetylcholinesterase (COLQ); receptor associated protein of the synapse (RAPSN); four and a half LIM domains 1 (FHL1); β-1,4-glucuronyltransferase 1 (B4GAT1); β-1-N-acetylgalactosaminyltransferase 2 (B3GALNT2); dystroglycan 1 (DAG1); transmembrane protein 5 (TMEM5); transmembrane protein 43 (TMEM43); SECIS binding protein 2 (SECISBP2); glucosamine (UDP-N-acetyl)-2-epimerase/N-acetylmannosamine kinase (GNE); anoctamin 5 (AN05); structural maintenance of chromosomes flexible hinge domain containing 1 (SMCHD1); lactate dehydrogenase A (LDHA); lactate dehydrogenase B (LHDB); calpain 3 (CAPN3); caveolin 3 (CAV3); tripartite motif containing 32 (TRIM32); CCHC-type zinc finger nucleic acid binding protein (CNBP); nebulin (NEB); actin, ccl, skeletal muscle (ACTA1); actin, ccl, cardiac muscle (ACTC1); actinin cc2 (ACTN2); poly(A)-binding protein nuclear 1 (PABPNI); LEM domain-containing protein 3 (LEMD3); zinc metalloproteinase STE24 (ZMPSTE24); microsomal triglyceride transfer protein (MTTP); a cholinergic receptor nicotinic ccl subunit; a tocopherol transferase protein (TTPA); kinesin family member 21 A (KIF21 A); paired-like homeobox 2a (PHOX2A); heparan sulfate proteoglycan 2 (HSPG2); stromal interaction molecule 1 (STIM1); notch 1 (NOTCHI); notch 3 (NOTCH3); dystrobrevin a (DTNA); protein kinase AMP-activated, noncatalytic j2 (PRKAG2); cysteine- and glycine-rich protein 3 (CSRP3); viniculin (VCL); myozenin 2 (MyoZ2); myopalladin (MYPN); junctophilin 2 (JPH2); phospholamban (PLN); calreticulin 3 (CALR3); nexilin F-actin-binding protein (NEXN); LIM domain binding 3 (LDB3); eyes absent 4 (EYA4); huntingtin (HTT); androgen receptor (AR); protein tyrosine phosphate non-receptor type 11 (PTPN1 1); junction plakoglobin (JUP); desmoplakin (DSP); plakophilin 2 (PKP2); desmoglein 2 (DSG2); desmocollin 2 (DSC2); catenin cc3 (CTNNA3); NK2 homeobox 5 (NKX2-5); A-kinase anchor protein 9 (AKAP9); A-kinase anchor protein 10 (AKAP10); guanine nucleotide-binding protein a-inhibiting activity polypeptide 2 (GNAI2); ankyrin 2 (ANK2); syntropbin cc-1 (SNTA1); calmodulin 1 (CALM1); calmodulin 2 (CALM2); HTRA serine peptidase 1 (HTRA1); fibrillin 1 (FBN1); fibrillin 2 (FBN2); xylosyltransferase 1 (XYLT1); xylosyltransferase 2 (XYLT2); tafazzin (TAZ); homogentisate 1,2-dioxygenase (HGD); glucose-6-phosphatase catalytic subunit (G6PC); 1,4-alpha-glucan enzyme 1 (GBEl); phosphofructokinase, muscle (PFKM); phosphorylase kinase regulatory subunit alpha 1 (PHKA1); phosphorylase kinase regulatory subunit alpha 2 (PHKA2); phosphorylase kinase regulatory subunit beta (PHKB); phosphorylase kinase catalytic subunit gamma 2 (PHKG2); phosphoglycerate mutase 2 (PGAM2); cystathionine-beta-synthase (CBS); methylenetetrahydrofolate reductase (MTHFR); 5-methyltetrahydro folate-homocysteine methyltransferase (MTR); 5-methyl tetrahydrofolate-homocysteine methyltransferase reductase (MTRR); methylmalonic aciduria and homocystinuria, cblD type (MMADHC); mitochondrial DNA, including, but not limited to mitochondrially encoded NADH:ubiquinone oxidoreductase core subunit 1 (MT-ND1); mitochondrially encoded NADH:ubiquinone oxidoreductase core subunit 5 (MT-ND5); mitochondrially encoded tRNA glutamic acid (MT-TE); mitochondrially encoded tRNA histadine (MT-TH); mitochondrially encoded tRNA leucine 1 (MT-TLI); mitochondrially encoded tRNA lysine (MT-TK); mitochondrially encoded tRNA serine 1 (MT-TS1); mitochondrially encoded tRNA valine (MT-TV); mitogen-activated protein kinase 1 (MAP2K1); B-Raf proto-oncogene, serine/threonine kinase (BRAF); raf-1 proto-oncogene, serine/threonine kinase (RAF1); growth factors, including, but not limited to insulin growth factor 1 (IGF-1); transforming growth factor 33 (TGF 3); transforming growth factor R receptor, type I (TGF Rl); transforming growth factor R receptor, type II (TGF R2), fibroblast growth factor 2 (FGF2), fibroblast growth factor 4 (FGF4), vascular endothelial growth factor A (VEGF-A), vascular endothelial growth factor B (VEGF-B); vascular endothelial growth factor C (VEGF-C), vascular endothelial growth factor D (VEGF-D), vascular endothelial growth factor receptor 1 (VEGFR1), and vascular endothelial growth factor receptor 2 (VEGFR2); interleukins; immunoadhesins; cytokines; and antibodies. In some embodiments, genes that encode products that are immunomodulators are delivered. Exemplary immunomodulatory genes include cytokines, chemokines, and the fusion proteins or antibodies that are specific for them and/or their receptors, e.g. the anti-IL-6 fusion protein Rilonacept 1, the Complement Factor H-specific antibody lampamizumab, etc.

In some embodiments, genes encoding a site-specific endonuclease are delivered. Exemplary endonucleases include naturally occurring restriction enzymes and the like. In some embodiments, the endonucleases delivered include zinc finger nucleases, TALENs, megaTALs, meganucleases, CRISPR/Cas systems including Cas9, CasX, CasY and the like. Such site-specific nucleases can be engineered to cut specific locations within a genome, and non-homologous end joining can then repair the break while inserting or deleting several nucleotides (also referred to as "INDELs"). Such site-specific endonucleases then throw the protein out of frame and effectively knock out the gene.

In some embodiments of the variant rAAV vector disclosed herein, a nucleotide sequence encoding a gene product of interest is operably linked to a constitutive promoter. Suitable constitutive promoters include e.g. cytomegalovirus promoter (CMV) (Stinski et al. (1985) *Journal of Virology* 55(2): 431-441), CMV early enhancer/chicken β-actin (CBA) promoter/rabbit β-globin intron (CAG) (Miyazaki et al. (1989) *Gene* 79(2): 269-277, CBSB (Jacobson et al. (2006) *Molecular Therapy* 13(6): 1074-1084), human elongation factor 1a promoter (EFI a) (Kim et al. (1990) *Gene* 91 (2): 217-223), human phosphoglycerate kinase promoter (PGK) (Singer-Sam et al. (1984) *Gene* 32(3): 409-417, mitochondrial heavy-strand promoter (Loderio et al. (2012) *Proc Natl Acad Sci USA* 109(17): 6513-6518), ubiquitin promoter (Wulff et al. (1990) *FEBS Letters* 261: 101-105). In other embodiments, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a liver-specific regulatory element (e.g., a liver specific promoter), e.g., a regulatory element that confers selective expression of the operably linked gene in a liver cell. Suitable liver-specific regulatory elements include, e.g., the albumin promoter, the alpha 1-antitrypsin, and the transthyretin promoter (TTR). In some instances, a gene of interest is operably linked to a CNS specific promoter or regulatory element. Suitable CNS specific promoters include, but are not limited to, the GFAP promoter (astrocytes), SYN1 promoter (neurons) and the NSE/RU5' promoter (mature neurons). In some instances, a gene of interest is operably linked to a ligand responsive promoter or molecular switch (for example, the TetR system (Berens and Hillen (2003) *Eur J Biochem* 270: 3109-3121).

As noted above, the compositions and methods described herein can be used for gene modification, gene correction, and gene disruption.

The compositions and methods described herein can also be applied to stem cell based therapies, including but not limited to editing that results in: correction of somatic cell mutations; disruption of dominant negative alleles; disruption of genes required for the entry or productive infection of pathogens into cells; enhanced tissue engineering, for example, by editing gene activity to promote the differentiation or formation of functional tissues; and/or disrupting gene activity to promote the differentiation or formation of functional tissues; blocking or inducing differentiation, for example, by editing genes that block differentiation to promote stem cells to differentiate down a specific lineage pathway. Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy, thereby allowing production of stocks of cells that have been modified to enhance their biological properties. Such cells can be infused into a variety of patients, independent of the donor source of the cells and their histocompatibility to the recipient.

In addition to therapeutic applications, the DNA-editing complexes described herein can be used for cell line engineering and the construction of disease models.

EXAMPLES

Example 1: Library Construction

Overview: The methods and compositions disclosed herein are useful in designing and identifying AAV capsids that can be used for a variety of applications including specific delivery to tissues, cells or organelles, and to the discovery of AAV capsids that are capable of evading anti-AAV neutralizing antibodies that may be present in patients to be dosed using AAV. The methods describe insertion of random sequences (libraries) into one of the surface-exposed loops and/or hypervariable regions in the AAV capsid protein to confer new and/or improved attributes to the AAV. The methods also include the insertion of the random sequences into the capsid proteins of many naturally occurring AAV serotypes producing several AAV libraries for screening. The libraries of these AAV variants are then injected into animals or used to infect cell lines. To aid in the identification of AAV variants that are capable of enhanced transduction of desired tissues, cells or organelles, the genome of the AAV variants may comprise a fluorescent reporter protein for tracking the delivery and transgene expression of the AAV. In some embodiments, the reporter protein is linked to a barcode that is bioinformatically associated with the random sequences inserted into the capsid gene. In some embodiments, the AAV libraries are subject to in vivo selection wherein nuclei in the desired tissue and/or cells are isolated following exposure to the AAV variant libraries. The inserted sequences can be then identified through sequencing of the associated barcode, or by purification and sequencing of AAV payload nucleic acid from cells expressing the reporter gene. The selected AAV nucleic acid sequence can then be analyzed to determine the parent AAV serotype comprising the inserted sequences as well as determining the inserted amino acids themselves. The process may be repeated 2, 3 or more rounds where the AAV variants isolated from the first round are pooled or synthesized and used to inject a second set of animals or another set of cells to further bolster confidence in the specificity and performance of the isolated AAV variants.

Construction: Capsid libraries were constructed by insertion of peptides into the exposed loops of the capsid proteins. Libraries comprising insertions that encoded 7, 10 or 15 amino acid peptides were made in the capsid proteins of AAVs 1, 2, 3B, 5, 6, 8 and 9. The AAV capsid sequences were each manufactured synthetically (ATUM). Prior to insertion of the sequences encoding the peptides, silent mutations were introduced into the areas encoding the capsid proteins adjacent to the insertion site. In this way, the same set of primers (e.g. DO112_MiCap1_VRVIII_Fwd and DO113_MiCap1_VRVIII_Rev) could be used on all libraries (see FIG. 1). In addition, restriction enzyme sites needed for molecular cloning including HindIII, AgeI, and BsaI were ablated by silent mutagenesis. Table 1 below shows the wildtype sequences for each capsid gene in the region that the mutations were introduced. Mutated nucleotides are indicated in bold. The resulting sequences can be amplified with a conserved NGS primer pair.

A similar approach was used to design conserved primer binding sites flanking other variable regions or surface exposed loops in the capsid gene. The full capsid gene nucleotide sequences that were synthesized are included below:

TABLE 1

Positions of silent mutations for primer binding sites flanking the VR-VIII insertion region

| Capsid | Wildtype Forward Sequence (Nucleotides for mutation in bold) | aa positions | Wildtype Reverse Sequence (Nucleotides for mutation in bold) | aa positions |
|---|---|---|---|---|
| AAV1 | TAACCCTGTGGCCACCGAA (SEQ ID NO: 33) | 571 | GACGTGTACCTGCAGGGTCCC (SEQ ID NO: 34) | 612, 617 |
| AAV2 | CAATCCCGTGGCTACGGAG (SEQ ID NO: 35) | 568, 569, 572, 573, 574 | GATGTGTACCTTCAGGGCCCC (SEQ ID NO: 36) | 610, 611, 613, 615, 616, 617 |
| AAV3B | CAATCCTGTGGCAACAGAG (SEQ ID NO: 37) | 569, 570, 571, 573, 574, 575 | GACGTGTACCTTCAAGGACCT (SEQ ID NO: 38) | 612, 614, 615, 616 |
| AAV6 | TAACCCCGTGGCCACCGAA (SEQ ID NO: 39) | N/A | GACGTATACCTGCAGGGTCCT (SEQ ID NO: 40) | N/A |
| AAV8 | TAACCCTGTGGCTACAGAG (SEQ ID NO: 41) | 573, 575, 576, 577 | GACGTGTACCTGCAGGGTCCC (SEQ ID NO: 42) | 614, 619 |
| AAV9 | TAACCCGGTAGCAACGGAG (SEQ ID NO: 43) | 571, 572, 573, 574, 575 | GATGTGTACCTGCAAGGACCC (SEQ ID NO: 44) | 611, 612, 615, 616, 617 |

AAV1 synthesized VP1 capsid gene
(SEQ ID No: 45)
ATGGCTGCCGATGGTTATCTTCCAGATTGGCTCGAGGACAACCTCTCTGA

GGGCATTCGCGAGTGGTGGGACTTGAAACCTGGAGCCCCGAAGCCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGACGCAGCGGCCCTCGAGCACGACAAGGCCTACGACCAGCAGCTCA

AAGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAACGTCCGGTAGAGCAGTCGCCA

CAAGAGCCAGACTCCTCCTCGGGCATCGGCAAGACAGGCCAGCAGCCCGC

TAAAAAGAGACTCAATTTTGGTCAGACTGGCGACTCAGAGTCAGTCCCCG

ATCCACAACCTCTCGGAGAACCTCCAGCAACCCCCGCTGCTGTGGGACCT

ACTACAATGGCTTCAGGCGGTGGCGCACCAATGGCAGACAATAACGAAGG

CGCCGACGGAGTGGGTAATGCCTCAGGAAATTGGCATTGCGATTCCACAT

GGCTGGGCGACAGAGTCATCACCACCAGCACCCGCACCTGGGCCTTGCCC

ACCTACAATAACCACCTCTACAAGCAAATCTCCAGTGCTTCAACGGGGGC

CAGCAACGACAACCACTACTTCGGCTACAGCACCCCCTGGGGGTATTTTG

ATTTCAACAGATTCCACTGCCACTTTTCACCACGTGACTGGCAGCGACTC

ATCAACAACAATTGGGGATTCCGGCCCAAGAGACTCAACTTCAAACTCTT

CAACATCCAAGTCAAGGAGGTCACGACGAATGATGGCGTCACAACCATCG

CTAATAACCTTACCAGCACGGTTCAAGTCTTCTCGGACTCGGAGTACCAG

-continued

CTTCCGTACGTCCTCGGCTCTGCGCACCAGGGCTGCCTCCCTCCGTTCCC

GGCGGACGTGTTCATGATTCCGCAATACGGCTACCTGACGCTCAACAATG

GCAGCCAAGCCGTGGGACGTTCATCCTTTTACTGCCTGGAATATTTCCCT

TCTCAGATGCTGAGAACGGGCAACAACTTTACCTTCAGCTACACCTTTGA

GGAAGTGCCTTTCCACAGCAGCTACGCGCACAGCCAGAGCCTGGACCGGC

TGATGAATCCTCTCATCGACCAGTACCTGTATTACCTGAACAGAACTCAA

AATCAGTCCGGAAGTGCCCAAAACAAGGACTTGCTGTTTAGCCGTGGATC

TCCAGCTGGCATGTCTGTTCAGCCCAAAAACTGGCTACCTGGACCCTGTT

ACCGGCAGCAGCGCGTTTCTAAAACAAAAACAGACAACAACAACAGCAAT

TTTACCTGGACTGGTGCTTCAAAATATAACCTCAATGGGCGTGAATCCAT

CATCAACCCTGGCACTGCTATGGCCTCACACAAAGACGACGAAGACAAGT

TCTTTCCCATGAGCGGTGTCATGATTTTTGGAAAAGAGAGCGCCGGAGCT

TCAAACACTGCATTGGACAATGTCATGATTACAGACGAAGAGGAAATTAA

AGCCACTAACCCCGTGGCCACCGAAAGATTTGGGACCGTGGCAGTCAATT

TCCAGAGCAGCAGCACAGACCCTGCGACCGGAGATGTGCATGCTATGGGA

GCATTACCTGGCATGGTGTGGCAAGATAGAGACGTATACCTGCAGGGTCC

TATTTGGGCCAAAATTCCTCACACAGATGGACACTTTCACCCGTCTCCTC

TTATGGGCGGCTTTGGACTCAAGAACCCGCCTCCTCAGATCCTCATCAAA

AACACGCCTGTTCCTGCGAATCCTCCGGCGGAGTTTTCAGCTACAAAGTT

TGCTTCATTCATCACCCAATACTCCACAGGACAAGTGAGCGTGGAGATTG

AATGGGAGCTGCAGAAAGAAAACAGCAAGCGCTGGAATCCCGAAGTGCAG

TACACATCCAATTATGCAAAATCTGCCAACGTTGATTTTACTGTGGACAA

CAATGGACTTTATACTGAGCCTCGCCCCATTGGCACCCGTTACCTTACCC

GTCCCCTGTAA

AAV2 synthesized VP1 capsid gene (SEQ ID No: 46)
ATGGCTGCCGATGGTTATCTTCCAGATTGGCTCGAGGACACTCTCTGA

AGGAATAAGACAGTGGTGGAAGCTCAAACCTGGCCCACCACCACCAAAGC

CCGCAGAGCGGCATAAGGACGACAGCAGGGGTCTTGTGCTTCCTGGGTAC

AAGTACCTCGGACCCTTCAACGGACTCGACAAGGGAGAGCCGGTCAACGA

GGCAGACGCCGCGGCCCTCGAGCACGACAAAGCCTACGACCGGCAGCTCG

ACAGCGGAGACAACCCCGTACCTCAAGTACAACCACGCCGACGCGGAGTTT

CAGGAGCGCCTTAAAGAAGATACGTCTTTTGGGGGCAACCTCGGACGAGC

AGTCTTCCAGGCGAAAAAGAGGGTTCTTGAACCTCTGGGCCTGGTTGAGG

AACCTGTTAAGACGGCTCCGGGAAAAAAGAGGCCGGTAGAGCACTCTCCT

GTGGAGCCAGACTCCTCCTCGGGAACCGGAAAGGCGGGCCAGCAGCCTGC

AAGAAAAAGACTCAATTTTGGTCAGACTGGCGACGCAGACTCAGTACCTG

ACCCCCAGCCTCTCGGACAGCCACCAGCAGCCCCCTCTGGTCTGGGAACT

AATACGATGGCTACAGGCAGTGGCGCACCAATGGCAGACAATAACGAGGG

CGCCGACGGAGTGGGTAATTCCTCGGGAAATTGGCATTGCGATTCCACAT

GGATGGGCGACAGAGTCATCACCACCAGCACCCGAACCTGGGCCCTGCCC

ACCTACAACAACCACCTCTACAAACAAATTTCCAGCCAATCAGGAGCCTC

GAACGACAATCACTACTTTGGCTACAGCACCCCCTGGGGGTATTTTGATT

TCAACAGATTCCACTGCCACTTTTCACCACGTGACTGGCAAAGACTCATC

AACAACAACTGGGGATTCCGACCCAAGAGACTCAACTTCAAGCTCTTTAA

CATTCAAGTCAAAGAGGTCACGCAGAATGACGGTACGACGACGATTGCCA

ATAACCTTACCAGCACGGTTCAGGTGTTTACTGACTCGGAGTACCAGCTC

CCGTACGTCCTCGGCTCGGCGCATCAAGGCTGCCTCCCTCCGTTCCCGGC

GGACGTCTTCATGGTGCCACAGTATGGATACCTCACCCTGAACAACGGGA

GTCAGGCAGTAGGACGCTCTTCATTTTACTGCCTGGAGTACTTTCCTTCT

CAGATGCTGCGTACCGGAAACAACTTTACCTTCAGCTACACTTTTGAGGA

CGTTCCTTTCCACAGCAGCTACGCTCACAGCCAGAGTCTGGACCGTCTCA

TGAATCCTCTCATCGACCAGTACCTGTATTACCTGAGCAGAACAAACACT

CCAAGTGGAACCACCACGCAGTCAAGGCTTCAGTTTTCTCAGGCCGGAGC

GAGTGACATTCGGGACCAGTCTAGGAACTGGCTTCCTGGACCCTGTTACC

GGCAGCAGCGAGTATCAAAGACATCTGCGGATAACAACAACAGTGAATAC

TCGTGGACTGGAGCTACCAAGTACCACCTCAATGGCAGAGACTCTCTGGT

GAATCCGGGCCCGGCCATGGCAAGCCACAAGGACGATGAAGAAAGTTTT

TTCCTCAGAGCGGGGTTCTCATCTTTGGGAAGCAAGGCTCAGAGAAAACA

AATGTGGACATTGAAAAGGTCATGATTACAGACGAAGAGGAAATCAGGAC

AACTAACCCCGTGGCCACCGAACAGTATGGTTCTGTATCTACCAACCTCC

AGAGAGGCAACAGACAAGCAGCTACCGCAGATGTCAACACACAAGGCGTT

CTTCCAGGCATGGTCTGGCAGGACAGAGACGTATACCTGCAGGGTCCTAT

TTGGGCAAAGATTCCACACACGGACGGACATTTTCACCCCTCTCCCCTCA

TGGGTGGATTCGGACTTAAACACCCTCCTCCACAGATTCTCATCAAGAAC

ACCCCGGTACCTGCGAATCCTTCGACCACCTTCAGTGCGGCAAAGTTTGC

TTCCTTCATCACACAGTACTCCACGGGACAGGTCAGCGTGGAGATTGAAT

GGGAGCTGCAGAAGGAAAACAGCAAACGCTGGAATCCCGAAATTCAGTAC

ACTTCCAACTACAACAAGTCTGTTAATGTGGACTTTACTGTGGACACTAA

TGGCGTGTATTCAGAGCCTCGCCCCATTGGCACCAGATACCTGACTCGTA

ATCTGTAA

AAV3B synthesized VP1 capsid gene (SEQ ID No: 47)
ATGGCTGCTGACGGTTATCTTCCAGATTGGCTCGAGGACAACCTTTCTGA

AGGCATTCGTGAGTGGTGGGCTCTGAAACCTGGAGTCCCTCAACCCAAAG

CGAACCAACAACACCAGGACAACCGTCGGGGTCTTGTGCTTCCGGGTTAC

AAATACCTCGGACCCGGTAACGGACTCGACAAAGGAGAGCCGGTCAACGA

GGCGGACGCGGCAGCCCTCGAACACGACAAAGCCTACGACCAGCAGCTCA

AGGCCGGTGACAACCCGTACCTCAAGTACAACCACGCCGACGCCGAGTTT

CAGGAGCGTCTTCAAGAAGATACGTCTTTTGGGGGCAACCTTGGCAGAGC

AGTCTTCCAGGCCAAAAAGAGGATCCTTGAGCCTCTTGGTCTGGTTGAGG

AAGCAGCTAAAACGGCTCCTGGAAAGAAGAGGCCTGTAGATCAGTCTCCT

CAGGAACCGGACTCATCATCTGGTGTTGGCAAATCGGGCAAACAGCCTGC

CAGAAAAAGACTCAATTTTGGTCAGACTGGCGACTCAGAGTCAGTCCCAG

ACCCTCAACCTCTCGGAGAACCACCAGCAGCCCCCACAAGTTTGGGATCT

AATACAATGGCTTCAGGCGGTGGCGCACCAATGGCAGACAATAACGAGGG

TGCCGATGGAGTGGGTAATTCCTCAGGAAATTGGCATTGCGATTCCCAAT

GGCTGGGCGACAGAGTCATCACCACCAGCACCCGAACCTGGGCCCTGCCC

ACTTACAACAACCATCTCTACAAGCAAATCTCCAGCCAATCAGGAGCTTC

AAACGACAACCACTACTTTGGCTACAGCACCCCCTGGGGGTATTTTGATT

TCAACAGATTCCACTGCCACTTCTCACCACGTGACTGGCAGCGACTCATT

AACAACAACTGGGGATTCCGGCCCAAGAAACTCAGCTTCAAGCTCTTCAA

CATCCAAGTTAAAGAGGTCACGCAGAACGATGGCACGACGACTATTGCCA

ATAACCTTACCAGCACGGTTCAAGTGTTTACGGACTCGGAGTATCAGCTC

CCGTACGTGCTCGGGTCGGCGCACCAAGGCTGCCTCCCTCCGTTCCCGGC

GGACGTCTTCATGGTCCCTCAGTATGGATACCTCACCCTGAACAACGGAA

GTCAAGCGGTGGGACGCTCATCCTTTTACTGCCTGGAGTACTTCCCTTCG

CAGATGCTAAGGACTGGAAATAACTTCCAATTCAGCTATACCTTCGAGGA

TGTACCTTTTCACAGCAGCTACGCTCACAGCCAGAGTTTGGATCGCTTGA

TGAATCCTCTCATCGACCAGTACCTGTATTACCTGAACAGAACGCAAGGA

ACAACCTCTGGAACAACCAACCAATCACGGCTGCTTTTTAGCCAGGCTGG

GCCTCAGTCTATGTCTTTGCAGGCCAGAAATTGGCTACCTGGACCCTGTT

ACCGGCAGCAGAGACTTTCAAAGACTGCTAACGACAACAACAACAGTAAC

TTTCCTTGGACAGCGGCCAGCAAATATCATCTCAATGGCCGCGACTCGCT

```
GGTGAATCCAGGACCAGCTATGGCCAGTCACAAGGACGATGAAGAAAAT
TTTTCCCTATGCACGGCAATCTAATATTTGGCAAAGAAGGGACAACGGCA
AGTAACGCAGAATTAGATAATGTAATGATTACGGATGAAGAAGAGATTCG
TACCACTAACCCCGTGGCCACCGAACAGTATGGAACTGTGGCAAATAACT
TGCAGAGCTCAAATACAGCTCCCACGACTAGAACTGTCAATGATCAGGGG
GCCTTACCTGGCATGGTGTGGCAAGATCGTGACGTATACCTGCAGGGTCC
TATTTGGGCAAAGATTCCTCACACGGATGGACACTTTCATCCTTCTCCTC
TGATGGGAGGCTTTGGACTGAAACATCCGCCTCCTCAAATCATGATCAAA
AATACTCCGGTACCGGCAAATCCTCCGACGACTTTCAGCCCGGCCAAGTT
TGCTTCATTTATCACTCAGTACTCCACTGGACAGGTCAGCGTGGAGATTG
AATGGGAGCTGCAGAAAGAAAACAGCAAACGTTGGAATCCAGAGATTCAG
TACACTTCCAACTACAACAAGTCTGTTAATGTGGACTTTACTGTAGACAC
TAATGGTGTTTATAGTGAACCTCGCCCTATTGGAACCCGGTATCTCACAC
GAAACTTGTGA
```

AAV5 synthesized VP1 capsid gene
                                  (SEQ ID No: 48)
```
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAAACCCA
ATCAGCAGCATCAAGATCAAGCCCGTGGTCTTGTGCTGCCTGGTTATAAC
TATCTCGGACCCGGAAACGGACTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATACAATGTCTGCGGGAGGTGGCGGCCCA
TTGGGCGACAATAACCAAGGTGCCGATGGAGTGGGCAATGCCTCGGGAGA
TTGGCATTGCGATTCCACGTGGATGGGGGACAGAGTCGTCACCAAGTCCA
CCCGAACCTGGGTGCTGCCCAGCTACAACAACCACCAGTACCGAGAGATC
AAAAGCGGCTCCGTCGACGGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
```

CGCTCCCAGTCAGAACCTGTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTGCCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAACCACCAGACCTATCGGAAC
CCGATACCTTACCCGACCCCTTTAA

AAV6 synthesized VP1 capsid gene
                                  (SEQ ID No: 49)
ATGGCTGCCGATGGTTATCTTCCAGATTGGCTCGAGGACAACCTCTCTGA
GGGCATTCGCGAGTGGTGGGACTTGAAACCTGGAGCCCCGAAACCCAAAG
CCAACCAGCAAAAGCAGGACGACGGCCGGGGTCTGGTGCTTCCTGGCTAC
AAGTACCTCGGACCCTTCAACGGACTCGACAAGGGGGAGCCCGTCAACGC
GGCGGATGCAGCGGCCCTCGAGCACGACAAGGCCTACGACCAGCAGCTCA
AAGCGGGTGACAATCCGTACCTGCGGTATAACCACGCCGACGCCGAGTTT
CAGGAGCGTCTGCAAGAAGATACGTCTTTTGGGGGCAACCTCGGGCGAGC
AGTCTTCCAGGCCAAGAAGAGGGTTCTCGAACCTTTTGGTCTGGTTGAGG
AAGGTGCTAAGACGGCTCCTGGAAAGAAACGTCCGGTAGAGCAGTCGCCA
CAAGAGCCAGACTCCTCCTCGGGCATTGGCAAGACAGGCCAGCAGCCCGC
TAAAAAGAGACTCAATTTTGGTCAGACTGGCGACTCAGAGTCAGTCCCCG
ACCCACAACCTCTCGGAGAACCTCCAGCAACCCCCGCTGCTGTGGGACCT
ACTACAATGGCTTCAGGCGGTGGCGCACCAATGGCAGACAATAACGAAGG
CGCCGACGGAGTGGGTAATGCCTCAGGAAATTGGCATTGCGATTCCACAT
GGCTGGGCGACAGAGTCATCACCACCAGCACCCGAACATGGGCCTTGCCC
ACCTATAACAACCACCTCTACAAGCAAATCTCCAGTGCTTCAACGGGGC
CAGCAACGACAACCACTACTTCGGCTACAGCACCCCCTGGGGGTATTTTG
ATTTCAACAGATTCCACTGCCATTTCTCACCACGTGACTGGCAGCGACTC
ATCAACAACAATTGGGGATTCCGGCCCAAGAGACTCAACTTCAAGCTCTT
CAACATCCAAGTCAAGGAGGTCACGACGAATGATGGCGTCACGACCATCG
CTAATAACCTTACCAGCACGGTTCAAGTCTTCTCGGACTCGGAGTACCAG -continued

TTGCCGTACGTCCTCGGCTCTGCGCACCAGGGCTGCCTCCCTCCGTTCCC

GGCGGACGTGTTCATGATTCCGCAGTACGGCTACCTAACGCTCAACAATG

GCAGCCAGGCAGTGGGACGGTCATCCTTTTACTGCCTGGAATATTTCCCA

TCGCAGATGCTGAGAACGGGCAATAACTTTACCTTCAGCTACACCTTCGA

GGACGTGCCTTTCCACAGCAGCTACGCGCACAGCCAGAGCCTGGACCGGC

TGATGAATCCTCTCATCGACCAGTACCTGTATTACCTGAACAGAACTCAG

AATCAGTCCGGAAGTGCCCAAAACAAGGACTTGCTGTTTAGCCGGGGCTC

TCCAGCTGGCATGTCTGTTCAGCCCAAAAACTGGCTACCTGGACCCTGTT

ACCGGCAGCAGCGCGTTTCTAAAACAAAAACAGACAACAACAACAGCAAC

TTTACCTGGACTGGTGCTTCAAAATATAACCTTAATGGGCGTGAATCTAT

AATCAACCCTGGCACTGCTATGGCCTCACACAAAGACGACAAAGACAAGT

TCTTTCCCATGAGCGGTGTCATGATTTTTGGAAAGGAGAGCGCCGGAGCT

TCAAACACTGCATTGGACAATGTCATGATCACAGACGAAGAGGAAATCAA

AGCCACTAACCCCGTGGCCACCGAAAGATTTGGGACTGTGGCAGTCAATC

TCCAGAGCAGCAGCACAGACCCTGCGACCGGAGATGTGCATGTTATGGGA

GCCTTACCTGGAATGGTGTGGCAAGACAGAGACGTATACCTGCAGGGTCC

TATTTGGGCCAAAATTCCTCACACGGATGGACACTTTCACCCGTCTCCTC

TCATGGGCGGCTTTGGACTTAAGCACCCGCCTCCTCAGATCCTCATCAAA

AACACGCCTGTTCCTGCGAATCCTCCGGCAGAGTTTTCGGCTACAAAGTT

TGCTTCATTCATCACCCAGTATTCCACAGGACAAGTGAGCGTGGAGATTG

AATGGGAGCTGCAGAAAGAAAACAGCAAACGCTGGAATCCCGAAGTGCAG

TATACATCTAACTATGCAAAATCTGCCAACGTTGATTTCACTGTGGACAA

CAATGGACTTTATACTGAGCCTCGCCCCATTGGCACCCGTTACCTCACCC

GTCCCCTGTAA

AAV8 synthesized VP1 capsid gene (SEQ ID No: 50)

ATGGCTGCCGATGGTTATCTTCCAGATTGGCTCGAGGACAACCTCTCTGA

GGGCATTCGCGAGTGGTGGGCGCTGAAACCTGGAGCCCCGAAGCCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGACGCAGCGGCCCTCGAGCACGACAAGGCCTACGACCAGCAGCTGC

AGGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAGAGGCCGGTAGAGCCATCACCC

CAGCGTTCTCCAGACTCCTCTACGGGCATCGGCAAGAAAGGCCAACAGCC

CGCCAGAAAAGACTCAATTTTGGTCAGACTGGCGACTCAGAGTCAGTTC

CAGACCCTCAACCTCTCGGAGAACCTCCAGCAGCGCCCTCTGGTGTGGGA

CCTAATACAATGGCTGCAGGCGGTGGCGCACCAATGGCAGACAATAACGA

AGGCGCCGACGGAGTGGGTAGTTCCTCGGGAAATTGGCATTGCGATTCCA

CATGGCTGGGCGACAGAGTCATCACCACCAGCACCCGAACCTGGGCCCTG

CCCACCTACAACAACCACCTCTACAAGCAAATCTCCAACGGGACATCGGG

AGGAGCCACCAACGACAACACCTACTTCGGCTACAGCACCCCCTGGGGGT

ATTTTGATTTCAACAGATTCCACTGCCACTTTTCACCACGTGACTGGCAG

CGACTCATCAACAACAACTGGGGATTCCGGCCCAAGAGACTCAGCTTCAA

GCTCTTCAACATCCAGGTCAAGGAGGTCACGCAGAATGAAGGCACCAAGA

CCATCGCCAATAACCTCACCAGCACCATCCAGGTGTTTACGGACTCGGAG

TACCAGCTGCCGTACGTTCTCGGCTCTGCCCACCAGGGCTGCCTCCCTCC

GTTCCCGGCGGACGTGTTCATGATTCCCCAGTACGGCTACCTAACACTCA

ACAACGGTAGTCAGGCCGTGGGACGCTCCTCCTTCTACTGCCTGGAATAC

TTTCCTTCGCAGATGCTGAGAACCGGCAACAACTTCCAGTTTACTTACAC

CTTCGAGGACGTGCCTTTCCACAGCAGCTACGCCCACAGCCAGAGCTTGG

ACCGGCTGATGAATCCTCTCATCGACCAGTACCTGTATTACCTGTCTCGG

ACTCAAACAACAGGAGGCACGGCAAATACGCAGACTCTGGGCTTCAGCCA

AGGTGGGCCTAATACAATGGCCAATCAGGCAAAGAACTGGCTGCCTGGAC

CCTGTTACCGGCAGCAGCGCGTCTCAACGACAACGGGCAAAACAACAAT

AGCAACTTTGCCTGGACTGCTGGGACCAAATACCATCTGAATGGAAGAAA

TTCATTGGCTAATCCTGGCATCGCTATGGCAACACACAAAGACGACGAGG

AGCGTTTTTTTCCCAGTAACGGGATCCTGATTTTTGGCAAACAAAATGCT

GCCAGAGACAATGCGGATTACAGCGATGTCATGCTCACCAGCGAGGAAGA

AATCAAAACCACTAACCCCGTGGCCACCGAAGAATACGGTATCGTGGCAG

ATAACTTGCAGCAGCAAAACACGGCTCCTCAAATTGGAACTGTCAACAGC

CAGGGGGCCTTACCCGGTATGGTCTGGCAGAACCGGGACGTATACCTGCA

GGGTCCTATTTGGGCCAAGATTCCTCACACGGACGGCAACTTCCACCCGT

CTCCGCTGATGGGCGGCTTTGGCCTGAAACATCCTCCGCCTCAGATCCTG

ATCAAGAACACGCCTGTACCTGCGGATCCTCCGACCACCTTCAACCAGTC

AAAGCTGAACTCTTTCATCACGCAATACAGCACCGGACAGGTCAGCGTGG

AGATTGAATGGGAGCTGCAGAAGGAAAACAGCAAGCGCTGGAACCCCGAG

ATCCAGTACACCTCCAACTACTACAAATCTACAAGTGTGGACTTTGCTGT

TAATACAGAAGGCGTGTACTCTGAACCCCGCCCCATTGGCACCCGTTACC

TCACCCGTAATCTGTAA

AAV9 synthesized VP1 capsid gene (SEQ ID No: 51)

ATGGCTGCCGATGGTTATCTTCCAGATTGGCTCGAGGACAACCTTAGTGA

AGGAATTCGCGAGTGGTGGGCTTTGAAACCTGGAGCCCCTCAACCCAAGG

CAAATCAACAACATCAAGACAACGCTCGAGGTCTTGTGCTTCCGGGTTAC

AAATACCTTGGACCCGGCAACGGACTCGACAAGGGGGAGCCGGTCAACGC

AGCAGACGCGGCGGCCCTCGAGCACGACAAGGCCTACGACCAGCAGCTCA

AGGCCGGAGACAACCCGTACCTCAAGTACAACCACGCCGACGCCGAGTTC

CAGGAGCGGCTCAAAGAAGATACGTCTTTTGGGGGCAACCTCGGGCGAGC

AGTCTTCCAGGCCAAAAAGAGGCTTCTTGAACCTCTTGGTCTGGTTGAGG

AAGCGGCTAAGACGGCTCCTGGAAAGAAGAGGCCTGTAGAGCAGTCTCCT

CAGGAACCGGACTCCTCCGCGGGTATTGGCAAATCGGGTGCACAGCCCGC

-continued

```
TAAAAAGAGACTCAATTTTGGTCAGACTGGCGACACAGAGTCAGTCCCAG
ACCCTCAACCAATCGGAGAACCTCCCGCAGCCCCCTCAGGTGTGGGATCT
CTTACAATGGCTTCAGGTGGTGGCGCACCAGTGGCAGACAATAACGAAGG
TGCCGATGGAGTGGGTAGTTCCTCGGGAAATTGGCATTGCGATTCCCAAT
GGCTGGGCGACAGAGTCATCACCACCAGCACCCGAACCTGGGCCCTGCCC
ACCTACAACAATCACCTCTACAAGCAAATCTCCAACAGCACATCTGGAGG
ATCTTCAAATGACAACGCCTACTTCGGCTACAGCACCCCCTGGGGGTATT
TTGATTTCAACAGATTCCACTGCCATTTCTCACCACGTGACTGGCAGCGA
CTCATCAACAACAACTGGGGATTCCGGCCTAAGCGACTCAACTTCAAGCT
CTTCAACATTCAGGTCAAAGAGGTTACGGACAACAATGGAGTCAAGACCA
TCGCCAATAACCTTACCAGCACGGTCCAGGTCTTCACGGACTCAGACTAT
CAGCTCCCGTACGTGCTCGGGTCGGCTCACGAGGGCTGCCTCCCTCCGTT
CCCGGCGGACGTTTTCATGATTCCTCAGTACGGGTATCTGACGCTTAATG
ATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTT
TGAGAACGTACCTTTCCATAGCAGCTACGCTCACAGCCAAAGCCTGGACC
GACTAATGAATCCACTCATCGACCAGTACCTGTATTACCTGTCAAAGACT
ATTAACGGTTCTGGACAGAATCAACAAACGCTAAAATTCAGTGTGGCCGG
ACCCAGCAACATGGCTGTCCAGGGAAGAAACTACATACCTGGACCCTGTT
ACCGGCAGCAGCGTGTCTCAACCACTGTGACTCAAAACAACAACAGCGAA
TTTGCTTGGCCTGGAGCTTCTTCTTGGGCTCTCAATGGACGTAATAGCTT
GATGAATCCTGGACCTGCTATGGCCAGCCACAAAGAAGGAGAGGACCGTT
TCTTTCCTTTGTCTGGATCTTTAATTTTTGGCAAACAAGGAACTGGAAGA
GACAACGTGGATCGGACAAAGTCATGATAACCAACGAAGAAGAAATTAA
AACTACTAACCCCGTGGCCACCGAATCCTATGGACAAGTGGCCACAAACC
ACCAGAGTGCCCAAGCACAGGCGCAGACCGGCTGGGTTCAAAACCAAGGA
ATACTTCCGGGTATGGTTTGGCAGGACAGAGACGTATACCTGCAGGGTCC
TATTTGGGCCAAAATTCCTCACACGGACGGCAACTTTCACCCTTCTCCGC
TGATGGGAGGGTTTGGAATGAAGCACCCGCCTCCTCAGATCCTCATCAAA
AACACACCTGTACCTGCGGATCCTCCAACGGCCTTCAACAAGGACAAGCT
GAACTCTTTCATCACCCAGTATTCTACTGGCCAAGTCAGCGTGGAGATTG
AATGGGAGCTGCAGAAGGAAAACAGCAAGCGCTGGAACCCGGAGATCCAG
TACACTTCCAACTATTACAAGTCTAATAATGTTGAATTTGCTGTTAATAC
TGAAGGTGTATATAGTGAACCCCGCCCCATTGGCACCAGATACCTGACTC
GTAATCTGTAA
```

AAV1 VP1 capsid protein
(SEQ ID No: 206)
MAADGYLPDWLEDNLSEGIREWWDLKPGAPKPKANQQKQDDGRG
LVLPGYKYLGPFNGLDKGEPVNAADAAALEHDKAYDQQLKAGDNPYLRYN
HADAEFQERLQEDTSFGGNLGRAVFQAKKRVLEPLGLVEEGAKTAPGKKR
PVEQSPQEPDSSSGIGKTGQQPAKKRLNFGQTGDSESVPDPQPLGEPPAT
PAAVGPTTMASGGGAPMADNNEGDGVGNASGNWHCDSTWLGDRVITTSTR
TWALPTYNNHLYKQISSASTGASNDNHYFGYSTPWGYFDFNRFHCHFSPR
DWQRLINNNWGFRPKRLNFKLFNIQVKEVTTNDGVTTIANNLTSTVQVFS
DSEYQLPYVLGSAHQGCLPPFPADVFMIPQYGYLTLNNGSQAVGRSSFYC
LEYFPSQMLRTGNNFTFSYTFEEVPFHSSYAHSQSLDRLMNPLIDQYLYY
LNRTQNQSGSAQNKDLLFSRGSPAGMSVQPKNWLPGPCYRQQRVSKTKTD
NNNSNFTWTGASKYNLNGRESIINPGTAMASHKDDEDKFFPMSGVMIFGK
ESAGASNTALDNVMITDEEEIKATNPVATERFGTVAVNFQSSSTDPATGD
VHAMGALPGMVWQDRDVYLQGPIWAKIPHTDGHFHPSPLMGGFGLKNPPP
QILIKNTPVPANPPAEFSATKFASFITQYSTGQVSVEIEWELQKENSKRW
NPEVQYTSNYAKSANVDFTVDNNGLYTEPRPIGTRYLTRPL AAV2 VP1 capsid protein
(SEQ ID No: 207)
MAADGYLPDWLEDTLSEGIRQWWKLKPGPPPPKPAERHKDDSRG
LVLPGYKYLGPFNGLDKGEPVNEADAAALEHDKAYDRQLDSGDNPYLKYN
HADAEFQERLKEDTSFGGNLGRAVFQAKKRVLEPLGLVEEPVKTAPGKKR
PVEHSPVEPDSSSGTGKAGQQPARKRLNFGQTGDADSVPDPQPLGQPPAA
PSGLGTNTMATGSGAPMADNNEGADGVGNSSGNWHCDSTWMGDRVITTST
RTWALPTYNNHLYKQISSQSGASNDNHYFGYSTPWGYFDFNRFHCHFSPR
DWQRLINNNWGFRPKRLNFKLFNIQVKEVTQNDGTTTIANNLTSTVQVFT
DSEYQLPYVLGSAHQGCLPPFPADVFMVPQYGYLTLNNGSQAVGRSSFYC
LEYFPSQMLRTGNNFTFSYTFEDVPFHSSYAHSQSLDRLMNPLIDQYLYY
LSRTNTPSGTTTQSRLQFSQAGASDIRDQSRNWLPGPCYRQQRVSKTSAD
NNNSEYSWTGATKYHLNGRDSLVNPGPAMASHKDDEEKFFPQSGVLIFGK
QGSEKTNVDIEKVMITDEEEIRTTNPVATEQYGSVSTNLQRGNRQAATAD
VNTQGVLPGMVWQDRDVYLQGPIWAKIPHTDGHFHPSPLMGGFGLKHPPP
QILIKNTPVPANPSTTFSAAKFASFITQYSTGQVSVEIEWELQKENSKRW
NPEIQYTSNYNKSVNVDFTVDTNGVYSEPRPIGTRYLTRNL AAV3B VP1 capsid protein
(SEQ ID No: 208)
MAADGYLPDWLEDNLSEGIREWWALKPGVPQPKANQQHQDNRRG
LVLPGYKYLGPGNGLDKGEPVNEADAAALEHDKAYDQQLKAGDNPYLKYN
HADAEFQERLQEDTSFGGNLGRAVFQAKKRILEPLGLVEEAAKTAPGKKR
PVDQSPQEPDSSSGVGKSGKQPARKRLNFGQTGDSESVPDPQPLGEPPAA
PTSLGSNTMASGGGAPMADNNEGADGVGNSSGNWHCDSQWLGDRVITTST
RTWALPTYNNHLYKQISSQSGASNDNHYFGYSTPWGYFDFNRFHCHFSPR
DWQRLINNNWGFRPKKLSFKLFNIQVKEVTQNDGTTTIANNLTSTVQVFT
DSEYQLPYVLGSAHQGCLPPFPADVFMVPQYGYLTLNNGSQAVGRSSFYC
LEYFPSQMLRTGNNFQFSYTFEDVPFHSSYAHSQSLDRLMNPLIDQYLYY
LNRTQGTTSGTTNQSRLLFSQAGPQSMSLQARNWLPGPCYRQQRLSKTAN
DNNNSNFPWTAASKYHLNGRDSLVNPGPAMASHKDDEEKFFPMHGNLIFG
KEGTTASNAELDNVMITDEEEIRTTNPVATEQYGTVANNLQSSNTAPTTR
TVNDQGALPGMVWQDRDVYLQGPIWAKIPHTDGHFHPSPLMGGFGLKHPP AAV5 VP1 capsid protein
(SEQ ID No: 209)
MSFVDHPPDWLEEVGEGLREFLGLEAGPPKPKPNQQHQDQARGLVLPGYN
YLGPGNGLDRGEPVNRADEVAREHDISYNEQLEAGDNPYLKYNHADAEFQ
EKLADDTSFGGNLGKAVFQAKKRVLEPFGLVEEGAKTAPTGKRIDDHFPK
RKKARTEEDSKPSTSSDAEAGPSGSQQLQIPAQPASSLGADTMSAGGGGP
LGDNNQGADGVGNASGDWHCDSTWMGDRVVTKSTRTWVLPSYNNHQYREI
KSGSVDGSNANAYFGYSTPWGYFDFNRFHSHWSPRDWQRLINNYWGFRPR
SLRVKIFNIQVKEVTVQDSTTTIANNLTSTVQVFTDDDYQLPYVVGNGTE
GCLPAFPPQVFTLPQYGYATLNRDNTENPTERSSFFCLEYFPSKMLRTGN
NFEFTYNFEEVPFHSSFAPSQNLFKLANPLVDQYLYRFVSTNNTGGVQFN
KNLAGRYANTYKNWFPGPMGRTQGWNLGSGVNRASVSAFATTNRMELEGA
SYQVPPQPNGMTNNLQGSNTYALENTMIFNSQPANPGTTATYLEGNMLIT
SESETQPVNRVAYNVGGQMATNNQSSTTAPATGTYNLQEIVPGSVWMERD
VYLQGPIWAKIPETGAHFHPSPAMGGFGLKHPPPMMLIKNTPVPGNITSF
SDVPVSSFITQYSTGQVTVEMEWELKKENSKRWNPEIQYTNNYNDPQFVD
FAPDSTGEYRTTRPIGTRYLTRPL AAV6 VP1 capsid protein
(SEQ ID No: 210)
MAADGYLPDWLEDNLSEGIREWWDLKPGAPKPKANQQKQDDGRGLVLPGY
KYLGPFNGLDKGEPVNAADAAALEHDKAYDQQLKAGDNPYLRYNHADAEF
QERLQEDTSFGGNLGRAVFQAKKRVLEPFGLVEEGAKTAPGKKRPVEQSP
QEPDSSSGIGKTGQQPAKKRLNFGQTGDSESVPDPQPLGEPPATPAAVGP
TTMASGGGAPMADNNEGADGVGNASGNWHCDSTWLGDRVITTSTRTWALP
TYNNHLYKQISSASTGASNDNHYFGYSTPWGYFDFNRFHCHFSPRDWQRL
INNNWGFRPKRLNFKLFNIQVKEVTTNDGVTTIANNLTSTVQVFSDSEYQ
LPYVLGSAHQGCLPPFPADVFMIPQYGYLTLNNGSQAVGRSSFYCLEYFP
SQMLRTGNNFTFSYTFEDVPFHSSYAHSQSLDRLMNPLIDQYLYYLNRTQ
NQSGSAQNKDLLFSRGSPAGMSVQPKNWLPGPCYRQQRVSKTKTDNNNSN
FTWTGASKYNLNGRESIINPGTAMASHKDDKDKFFPMSGVMIFGKESAGA
SNTALDNVMITDEEEIKATNPVATERFGTVAVNLQSSSTDPATGDVHVMG
ALPGMVWQDRDVYLQGPIWAKIPHTDGHFHPSPLMGGFGLKHPPPQILIK
NTPVPANPPAEFSATKFASFITQYSTGQVSVEIEWELQKENSKRWNPEVQ
YTSNYAKSANVDFTVDNNGLYTEPRPIGTRYLTRPL AAV8 VP1 capsid protein
(SEQ ID No: 211)
MAADGYLPDWLEDNLSEGIREWWALKPGAPKPKANQQKQDDGRGLVLPGY
KYLGPFNGLDKGEPVNAADAAALEHDKAYDQQLQAGDNPYLRYNHADAEF
QERLQEDTSFGGNLGRAVFQAKKRVLEPLGLVEEGAKTAPGKKRPVEPSP
QRSPDSSTGIGKKGQQPARKRLNFGQTGDSESVPDPQPLGEPPAAPSGVG
PNTMAAGGGAPMADNNEGADGVGSSSGNWHCDSTWLGDRVITTSTRTWAL
PTYNNHLYKQISNGTSGGATNDNTYFGYSTPWGYFDFNRFHCHFSPRDWQ
RLINNNWGFRPKRLSFKLFNIQVKEVTQNEGTKTIANNLTSTIQVFTDSE
YQLPYVLGSAHQGCLPPFPADVFMIPQYGYLTLNNGSQAVGRSSFYCLEY
FPSQMLRTGNNFQFTYTFEDVPFHSSYAHSQSLDRLMNPLIDQYLYYLSR
TQTTGGTANTQTLGFSQGGPNTMANQAKNWLPGPCYRQQRVSTTTGQNNN
SNFAWTAGTKYHLNGRNSLANPGIAMATHKDDEERFFPSNGILIFGKQNA
ARDNADYSDVMLTSEEEIKTTNPVATEEYGIVADNLQQQNTAPQIGTVNS
QGALPGMVWQNRDVYLQGPIWAKIPHTDGNFHPSPLMGGFGLKEIPPPQI
LIKNTPVPADPPTTFNQSKLNSFITQYSTGQVSVEIEWELQKENSKRWNP
EIQYTSNYYKSTSVDFAVNTEGVYSEPRPIGTRYLTRNL AAV9 VP1 capsid protein
(SEQ ID No: 212)
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASHKEGEDRFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL An exemplary selection of the NGS primers are depicted in the table below, wherein the variable region is indicated in the primer name.

TABLE 2

Primers used for next-generation sequencing analysis

| Primer name | Primer nucleotide sequence (5'-3') | SEQ ID NO: |
|---|---|---|
| DO106_MiCap1_VRI_Fwd | ACACGACGCTCTTCCGATCTNNNNAGAGTCATCACCACCAGCACC | 52 |
| DO107_MiCap1_VRI_Rev | GACGTGTGCTCTTCCGATCTNNNNGAAATCAAAATACCCCCAGGG | 53 |
| DO108_MiCap1_VRIV_Fwd | ACACGACGCTCTTCCGATCTNNNNATCGACCAGTACCTGTATTACCTG | 54 |
| DO109_MiCap1_VRIV_Rev | GACGTGTGCTCTTCCGATCTNNNNTGCCGGTAACAGGGTCCAG | 55 |
| DO112_MiCap1_VRVIII_Fwd | ACACGACGCTCTTCCGATCTNNNNTAACCCCGTGGCCACCGAA | 56 |
| DO113_MiCap1_VRVIII_Rev | GACGTGTGCTCTTCCGATCTNNNNAGGACCCTGCAGGTATACGTCT | 57 |
| DO319_AAV5_MiCap1_VRVIII_Fwd | ACACGACGCTCTTCCGATCTNNNNGTGAACCGCGTGGCGTACAAC | 58 |
| DO320_AAV5_MiCap1_VRVIII_Rev | GACGTGTGCTCTTCCGATCTNNNNGGGTCCTTGGAGGTACACGTCC | 59 |

Figure 2:
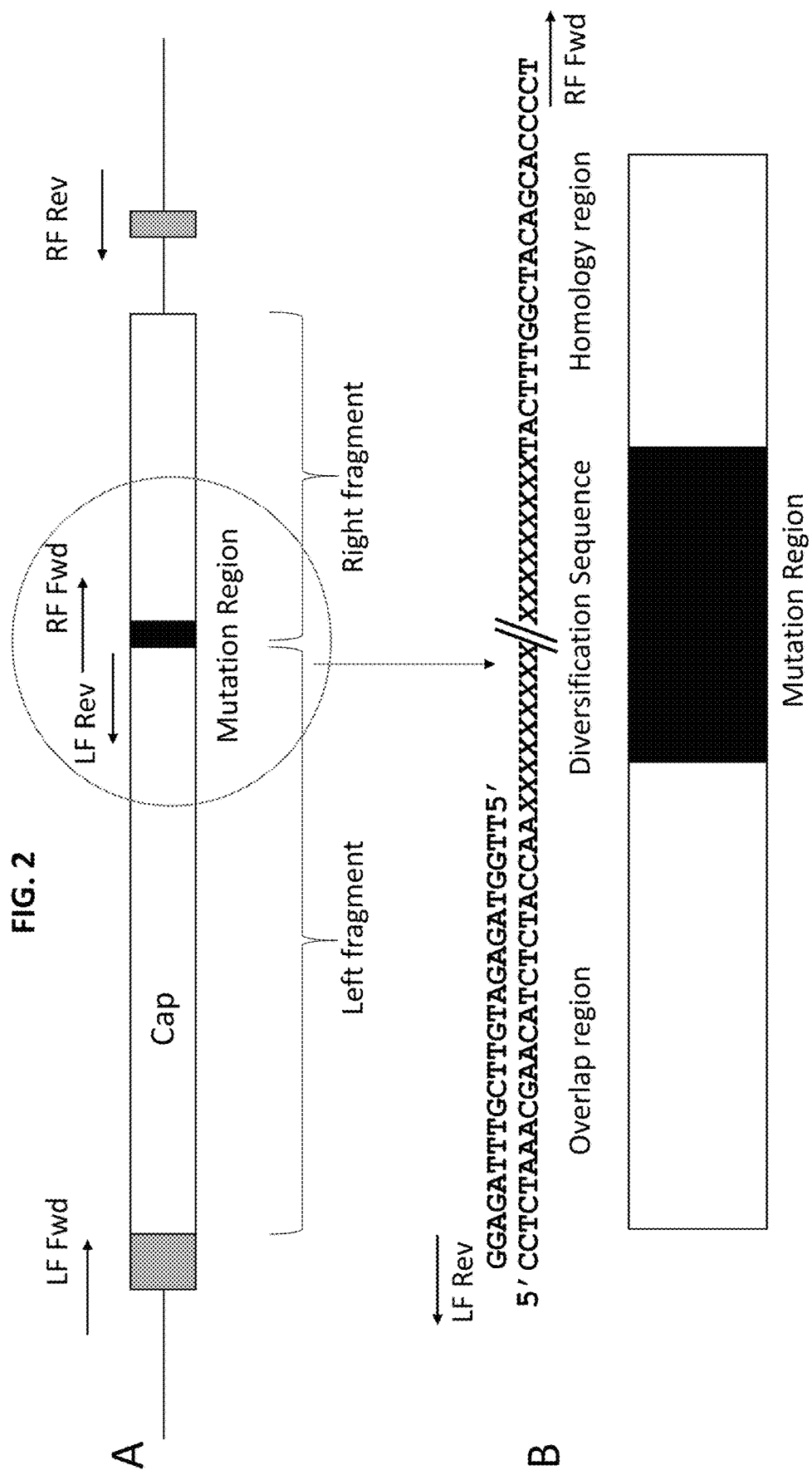
FIG. 2 illustrates an example of the method used to generate capsid libraries with high diversity. Panel A shows the fragments used to build the capsid encoding genes, where two fragments, left and right, were joined by Gibson assembly of two PCR amplification products and a pre-digested plasmid backbone. Panel B is a blow up of a primer pair (Reverse: SEQ ID NO: 204 and Forward: SEQ ID NO: 205) used to join the two fragments by Gibson assembly and also depicts the diversified sequence included in the RF Fwd primer, where X can be between 12 and 45 nucleotides in length.

Gibson assembly was used to generate the capsid libraries where the introduced peptides were encoded by the primers used to amplify the right fragment (see FIG. 2). Two PCR products from the capsid gene sequence ("Cap") were amplified (left and right fragments) that had an overlap region to facilitate assembly using the Gibson assembly procedure into a plasmid backbone (see e.g. Gibson et al (2009) Nat Meth 6(5):343-345). Specifically, the primer for the right fragment ("RF Fwd") comprises random nucleotide sequences encoding the inserted peptide built into the primer. This primer also comprises sequences encoding the overlap region so this right fragment amplified product will overlap with the amplified left fragment. Finally, the RF Fwd primer comprises a homology region which has homology to the right fragment of the sequence encoding the capsid.

The insertion position for the peptides differed for each AAV serotype (numbering begins at VP1 start codon). Table 2 below shows the amino acid position within the capsid protein where the peptide insertion occurred. Note that two libraries in the AAV6 capsid were constructed where the fragments were inserted into either position 454 or 590. Also note that three libraries based on the AAV9 capsid were constructed where the fragments were inserted into either position 266, 455, or 589.

TABLE 3

Insertion sites of peptides

| Serotype | Insertion site (aa position) |
|---|---|
| AAV1 | 590 |
| AAV2 | 588 |

TABLE 3-continued

Insertion sites of peptides

| Serotype | Insertion site (aa position) |
|---|---|
| AAV3B | 589 |
| AAV5 | 578 |
| AAV6 | 454 |
| AAV6 | 590 |
| AAV8 | 591 |
| AAV9 | 266 |
| AAV9 | 455 |
| AAV9 | 589 |

The Gibson assembly reactions were transformed into electrocompetent E. coli and the resulting plasmid library purified. The plasmid DNA library was transfected into HEK293 cells at low multiplicity of transfection to preserve the linkage between capsid genotype and phenotype.

The libraries were then manufactured to generate a library of viral capsids for testing. Wild type AAV comprises gene sequences that encode the "Rep" proteins Rep78, Rep68, Rep52, and Rep40 necessary for replication of the viral nucleic acid and for packing it into a viral particle in the presence of adenovirus helper functions. The AAV libraries described herein do not contain "Rep" in cis with viral ITRs and "Cap", therefore, to achieve efficient packaging of the libraries into viral capsids, the replication gene ("rep") and the adenovirus helper functions (for example E2A, E4, VA, E1A and E1B) are supplied in trans during viral manufacturing. For example, a helper plasmid that supplies Rep in trans during viral manufacturing was constructed. The Rep gene (NC_001401, nucleotides 191-2252) was amplified from a standard AAV helper plasmid using the following primers:

TABLE 4

Primers for amplifying a Rep gene

| Primer name | Primer nucleotide sequence (5'-3') | SEQ ID NO: |
|---|---|---|
| DO7_Rep_Fwd | GTACTCTAGAGTCCTGTATTAGA GGTCACGTGA | 60 |
| DO8_Rep_Rev | TGCTGCATGCTGTACCGAATTAA CATGTTTATTGGTACGATCAGAG AGAGTGTCCTCGAGC | 61 |

These primers add XbaI and SphI sites respectively and amplify the entire Rep gene. The amplified Rep fragment was then cloned by restriction digest and ligation into the XbaI and SphI sites in the multiple cloning site of pUC19 to generate pRepInTrans.

An additional modification was introduced by site-directed mutagenesis using the following primers to convert the VP1 ACG start codon to ATG generating pRepInTrans-ATG.

TABLE 5

Primers for modification of Rep gene

| Primer name | Primer nucleotide sequence (5'-3') | SEQ ID NO: |
|---|---|---|
| DO444_QCRep78_Fwd | ACCCCGCCATGGTGGCTGCGCGTT | 62 |
| DO445_QCRep78_Rev | AACGCGCAGCCACCATGGCGGGGT | 63 |

The ACG to ATG modification was introduced in order to increase replication of the capsid construct through greater Rep78/68 expression and thereby improve AAV library manufacturing yield. Removal of Rep renders AAV replication-deficient, an important feature for selections in non-human primates that frequently harbor AAV helper viruses including herpes simplex virus (see Morton et al (2008) ILAR J 49(2):137-44). In addition, removal of Rep is superior to a simple genetic knockout that still invites the possibility of recombination with a Rep plasmid supplied in trans that could reconstitute replication competent AAV.

The AAV libraries are then packaged in an HEK293 production system by transient transfection and purified using cesium chloride density gradient ultracentrifugation (for an exemplary process, see Xiao and Samulski (1998) J Virol 40:241-247).

The goal of this technique is to develop methods that can be used in all species, tissues, cell types and tissue processing conditions. Thus, AAVs are designed to carry the capsid libraries described above and some type of identifying marker that links the sequence of the variant capsid gene in a single AAV to a unique barcode identifier also carried by the AAV such that subsequent independent sequencing of the barcode will identify the linked capsid mutations. Further, the single AAV will also carry a reporter gene of some type such that the successful delivery of the AAV particle to its intended target (for example an organ (e.g. liver or CNS), and or specific cell types within an organ (e.g. hepatocytes or neurons)) can be monitored and selected for.

In addition, in this example, the reporter gene included a localization signal to cause the reporter to be localized to the cell nucleus once the cell had been transduced by the variant AAV capsid. Initially, an SV40 large T-antigen (PKKKRKV, SEQ ID NO:64) was introduced at the N-terminus of EGFP or mCherry. A second method used a KASH domain fused to the C-terminus of the EGFP or mCherry. KASH domains localize proteins to the nuclear envelope, in effect tethering the reporter to the nucleus and preventing diffusion out of the nuclear pore complex. A third method fused a histone H2B gene to the C-terminus of the EGFP, mClover3 or mRuby3 reporter (see FIGS. 3A and B). The hSyn1 (synapsin) promoter used to drive expression of the fluorescent reporter was selected to be specific for expression in neurons. Other promoters may be used for other targeted tissues or cells including the liver-specific transthyretin promoter. The underlying concept is to have the sequence comprising the variant AAV capsid linked physically to the reporter in the target tissue, cell or organelle. In this way, the target tissue, cell or organelle could be isolated using the fluorescent protein once successfully transduced with the AAV particle such that the user could then determine what capsid variant allowed transduction of the AAV particle into the target tissue, cell or organelle.

In some examples, a barcode is inserted into each AAV genome comprising a variant capsid protein to allow the user to identify the mutation in the capsid protein by independent sequencing analysis of the barcode once the library had been through in vivo selection (see below). The underlying concept is to have the sequence comprising the variant AAV capsid linked physically to the reporter in the target tissue, cell or organelle. In this way, the target tissue, cell or organelle could be isolated using the fluorescent protein once successfully transduced with the AAV particle such that the user could then determine what capsid variant allowed transduction of the AAV particle into the target tissue, cell or organelle. In some examples, each peptide coding sequence is synthesized with multiple different nucleic acid sequences, all encoding the same peptide. Each nucleic acid sequence is linked to a unique bar code such that performance (e.g. enrichment) of a peptide variant can be verified when two or more variants are identified with the same peptide sequence, but the variants comprise different nucleic acid sequences encoding that peptide.

For libraries generated by DNA synthesis and subsequent molecular cloning steps, all barcode and peptide encoding sequences were designed computationally. Importantly, sequences comprising restriction enzyme recognition sites that would be used for later cloning were omitted. The sequences were designed to have 40-60% GC content, no homopolymers greater than 3 in length, and minimal similarity (edit distance) between sequences.

To bioinformatically link each barcode with each mutated capsid sequence, two approaches were performed.

Figure 4A:
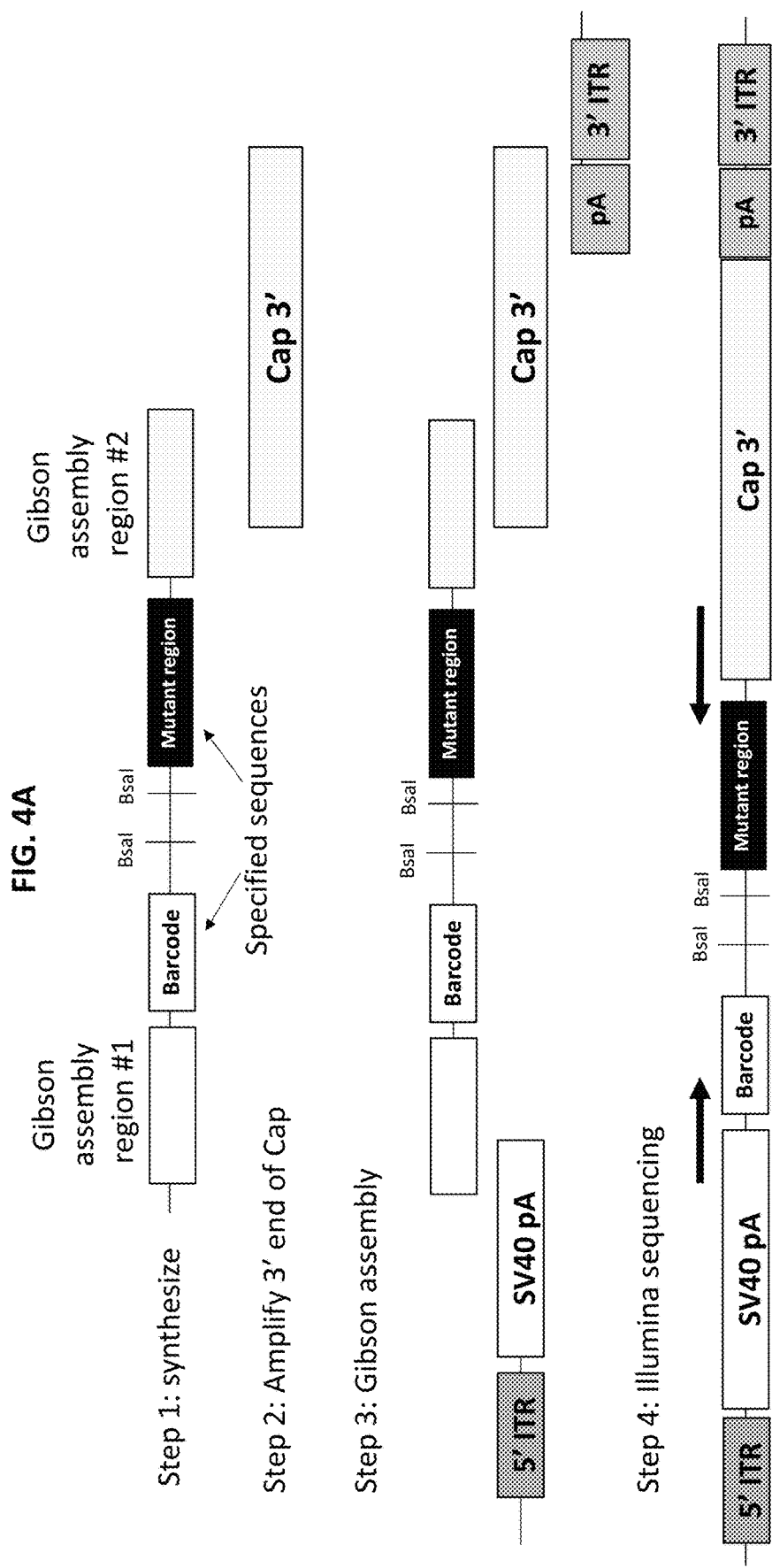
FIG. 4A and FIG. 4B illustrate the steps for Method 1 for bioinformatically linking each variant capsid sequence with a randomly generated or specified barcode. In step 1, a short piece of DNA is synthesized comprising a randomly generated or specified barcode and a randomly generated or specified capsid variant region, as well as two regions used for Gibson assembly. Step 2 comprises amplification of capsid sequence 3' of the diversified region. Step 3 is the Gibson assembly reaction where the 5'ITR and SV40 polyadenylation sequences are fused to the barcode on the 5' end, and the second Gibson assembly region is fused to the 3' end of the capsid gene and the polyA signal for the capsid gene and the 3'ITR. Step 4 comprises performing ILLUMINA® sequencing across the barcode and the variant capsid sequences. Step 5 comprises digestion with the BsaI restriction enzyme. Step 6 is a PCR amplification step where the H2B, EGFP, hSyn1 and p40 promoters, and the 5' end of the capsid gene are prepared. Alternatively, the fragment comprising the H2B, EGFP, hSyn1, p40 promoter, and 5' end of the capsid gene may be pre-assembled in a donor plasmid, digested with BsaI, and gel purified. Step 7 is the final golden gate cloning step to create the final construct.
Figure 4B:
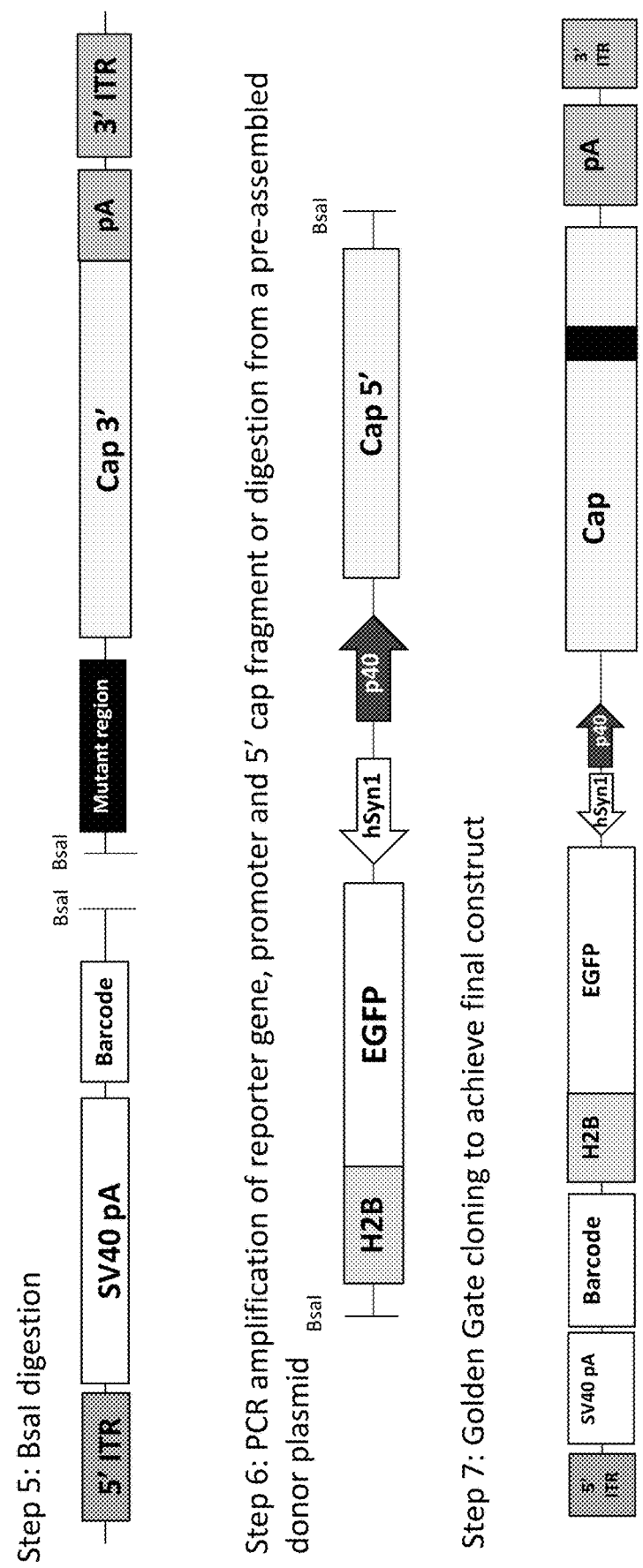
Figure 4D:
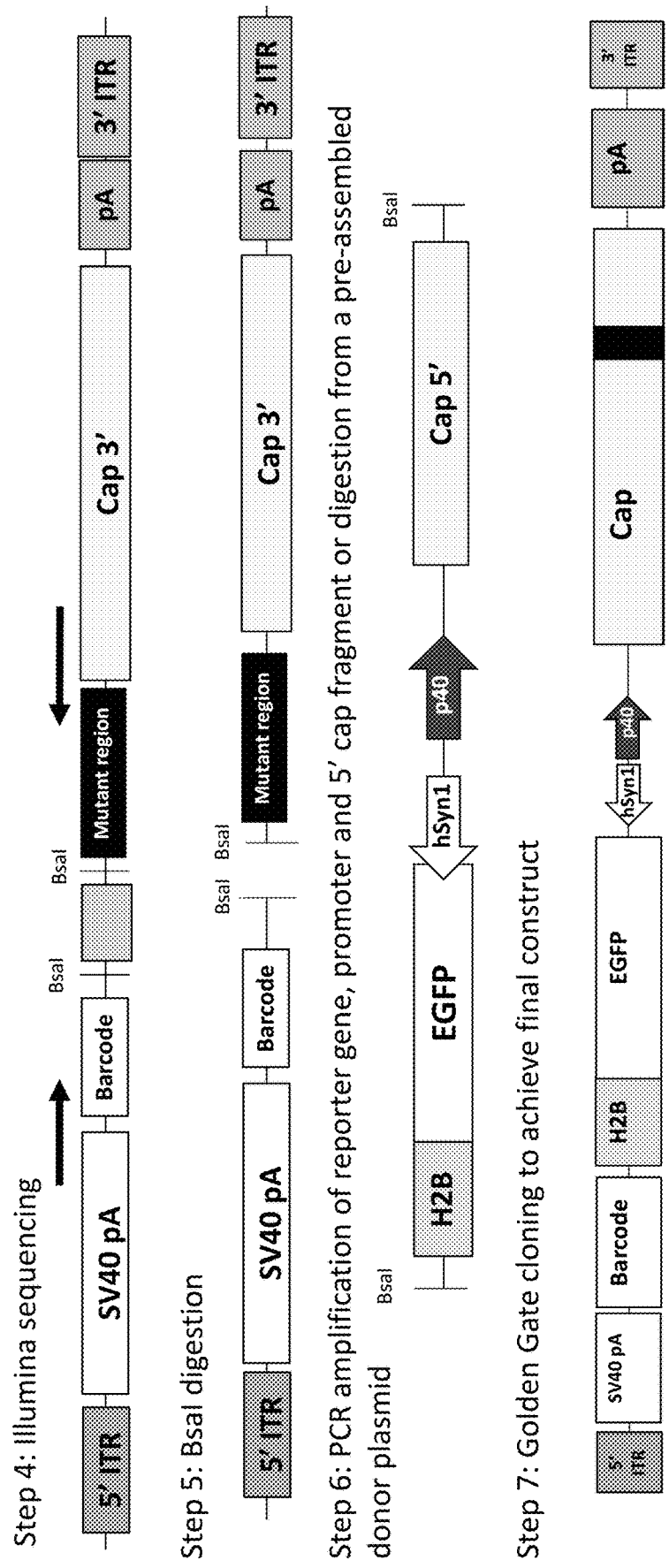

Method 1 employed ILLUMINA® sequencing. First, a barcode was inserted into the expression constructs as outlined in FIGS. 4A and B. To insert the barcode sequences, the 5' Gibson assembly region #1 was synthesized as a DNA fragment linked to the variable region in the capsid gene linked in turn to the 3' Gibson assembly region #2 (see FIG. 4A, step 1). Thus, the synthetic sequence comprises a variable barcode region and a variable capsid sequence. It also comprises two restriction nuclease sites between the barcode sequence and the variable sequence. Type IIs restriction sites BsaI were used to facilitate scarless assembly of the final construct. A separate PCR procedure was performed where the 3' sequence of the capsid gene was amplified (step 2). Next, an intermediate AAV construct was generated by Gibson assembly where the construct comprised in a 5' to 3' order the 5' ITR, the SV40 poly A signal, the barcode, the two restriction endonuclease sites, the variant capsid sequences, the 3' region of the capsid protein, the polyA sequence for the capsid expression construct and the 3' ITR (step 3). In an alternate approach (FIG. 4C) steps 1-3 are modified. In step 1, two DNA fragments are synthesized. Fragment A comprises Gibson assembly region #1, a BsaI site, the variable capsid region, and a region homologous to the capsid gene that is used as a PCR primer. Fragment B comprises Gibson assembly region #2, a random barcode, a BsaI site, and Gibson assembly region #1. Next, a PCR procedure is performed where the 3' sequence of capsid gene is amplified using fragment A synthesized in step 1 as a PCR primer. Next, an intermediate AAV construct is generated by Gibson assembly where the construct comprises in a 5' to 3' order the 5' ITR, the SV40 poly A signal, the barcode, the two restriction endonuclease sites, the variant capsid sequences, the 3' region of the capsid protein, the polyA sequence for the capsid expression construct and the 3' ITR (step 3). For both approaches described in FIGS. 4A/B and 4C/D steps 4-7 are equivalent. Paired-end ILLUMINA® sequencing is performed to span the barcode and variant capsid sequences in both directions (step 4). The sequences generated thus link specific barcode sequences to specific variant sequences in the capsid gene. ILLUMINA® sequencing at Step 4 indicated a 99.6% correct match between the barcode and variant sequence specified during synthesis. Step 5 comprised digestion with the BsaI restriction enzyme. Step 6 was a PCR amplification step where the H2B, EGFP, cell-type specific promoter (e.g. hSyn1), p40 promoter, and the 5' end of the capsid gene were prepared. Alternatively, the H2B, EGFP, cell-type specific promoter (e.g. hSyn1), p40 promoter, and the 5' end of the capsid gene can be prepared in a separate donor plasmid, digested with BsaI, and gel purified. Step 7 was the scarless golden gate cloning step to assemble the final construct. Sanger sequencing of a sample of the final library demonstrated that 88/88 individual clones showed the correct specified linkage between the barcode and the variant capsid sequences.

Figure 5:
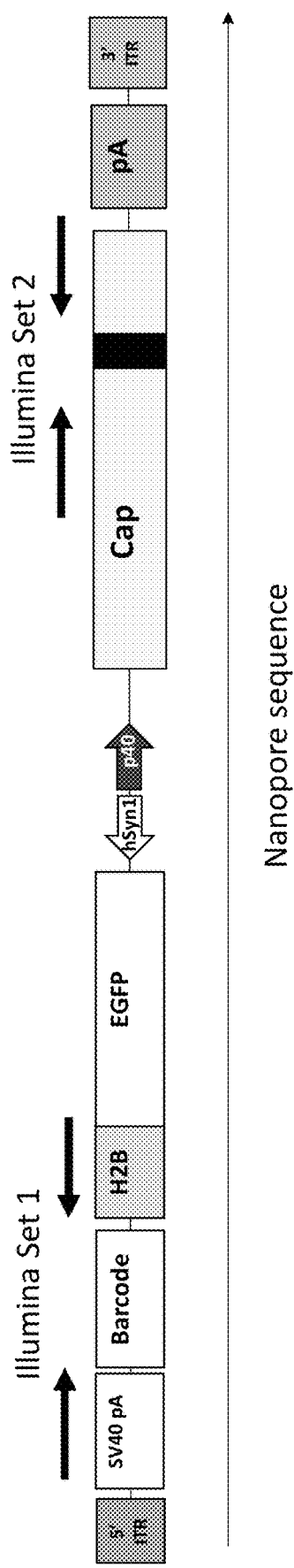
FIG. 5 illustrates the steps for Method 2 for bioinformatically linking each mutated capsid sequence with a randomly generated barcode. First, two sets of ILLUMINA® sequencing primers are used to separately sequence the random barcode and mutated capsid sequence with high fidelity. Next, OXFORD NANOPORE® sequencing is performed to sequence the entire construct. The Nanopore sequencing is less accurate than ILLUMINA® sequencing, but can be used to link the two ILLUMINA® sequences to one molecule via bioinformatic analysis.

Method 2 employed both ILLUMINA® and OXFORD NANOPORE® sequencing. First, the AAV capsid libraries were assembled through the method shown in FIG. 2 where the variable sequences were added into the capsid gene using primers. Next, the capsid gene libraries were cloned into a vector comprising the reporter gene and random barcode sequences (see FIG. 5). To link each random barcode sequence with each variant capsid sequence, two types of sequencing analyses were performed. Standard ILLUMINA® sequencing is highly accurate for short stretches of nucleic acid (approximately 300 bp), while OXFORD NANOPORE® sequencing can give much longer sequence reads. However, OXFORD NANOPORE® sequencing has an approximate 12% error rate and can generate indels in the reading sequence, so is not suitable for this purpose on its own. Thus, two sets of ILLUMINA® sequencing reactions were initially performed: one set that sequenced the barcode region and one set that sequenced the variable capsid sequence. Following that, an OXFORD NANOPORE® sequencing reaction was completed to provide long read lengths that spanned the entire AAV viral genome. Although less accurate than the ILLUMINA® sequencing, the Nanopore sequencing provides long-read length data that permits matching of known barcode sequences with known variant capsid sequences.

The result of both of these methods was that a 'lookup' table was created matching each barcode to each variant capsid sequence. Once an AAV was isolated from a target cell, tissue or organelle, only sequencing of nucleic acid barcode was necessary because through use of the lookup table, one could then know the sequence of the variant capsid.

Figure 6:
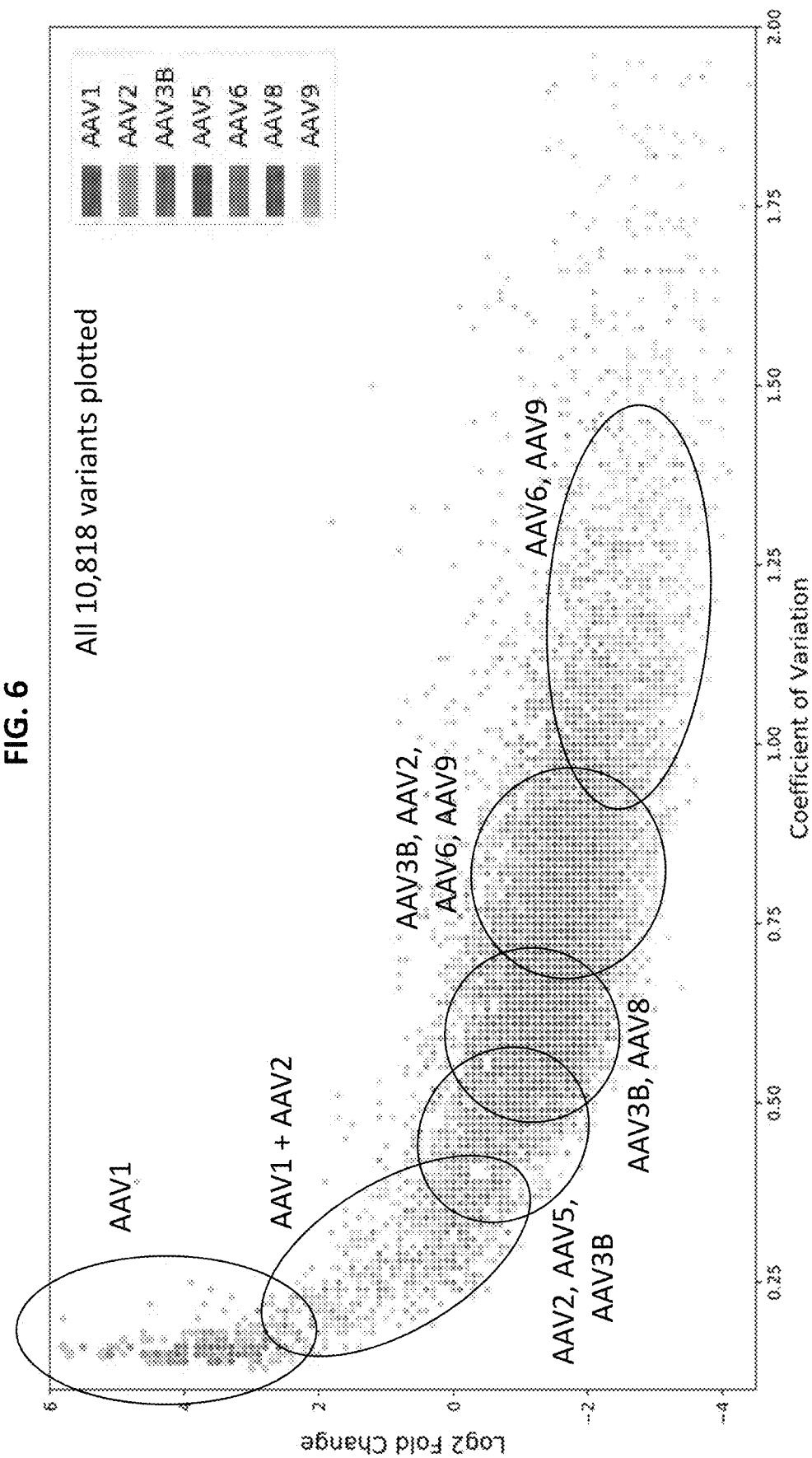
FIG. 6 is a plot of the AAV variants isolated from primary mouse cortical neurons following transduction with the AAV variant libraries. The Y axis indicates the log 2 fold change in variant frequency after selection and recovery from transduced cells as compared with the variant frequency in administered library prior to transduction. The data demonstrates that the AAV serotypes tended to cluster with variants based on AAV1 being the most enriched in the primary mouse neurons as compared with variants based on insertions into other AAV serotypes.
Figure 7A:
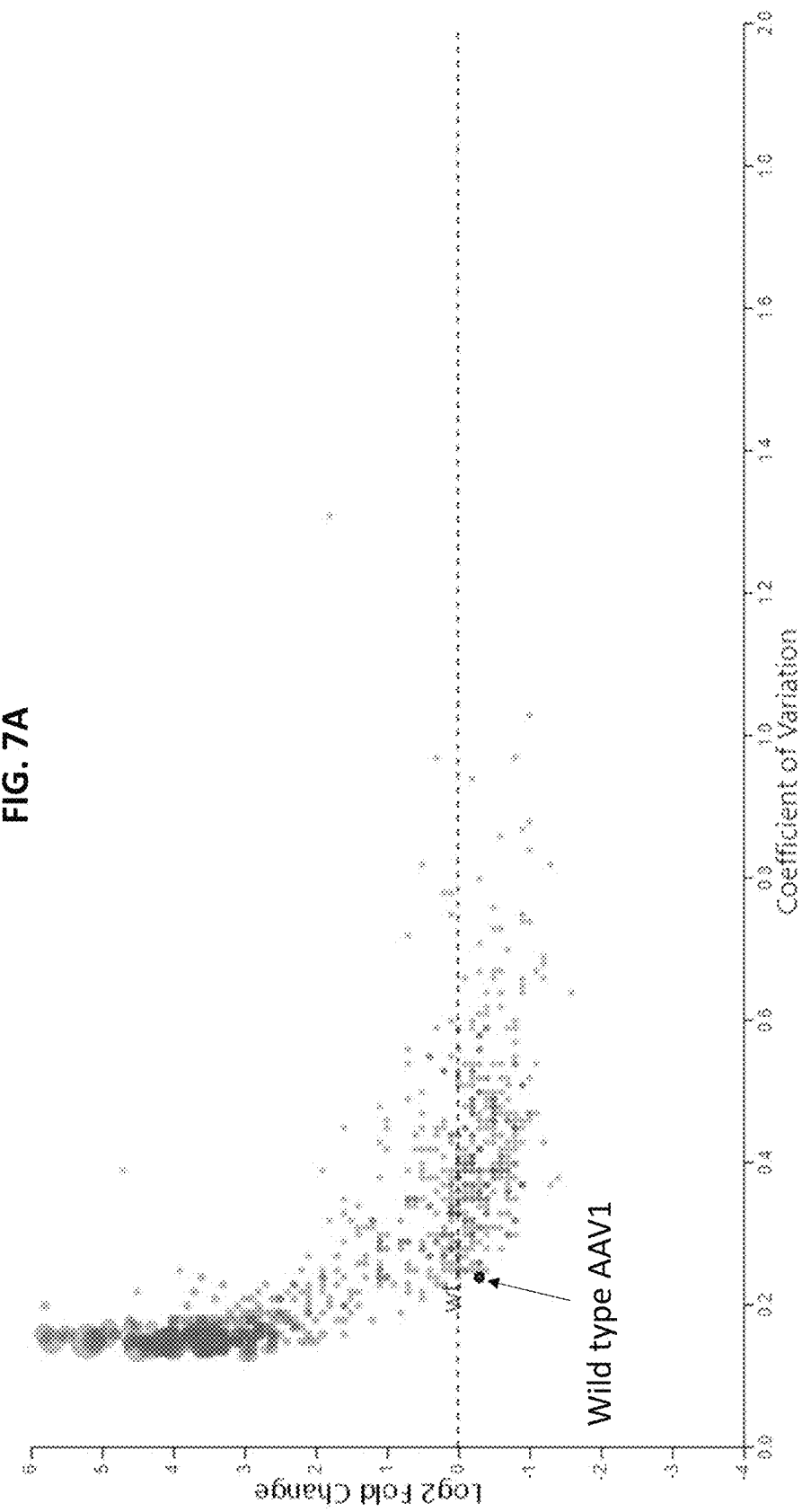
FIG. 7A and FIG. 7B are plots of either the AAV1 variants (FIG. 7A) or the AAV2 variants (FIG. 7B).
Figure 7B:
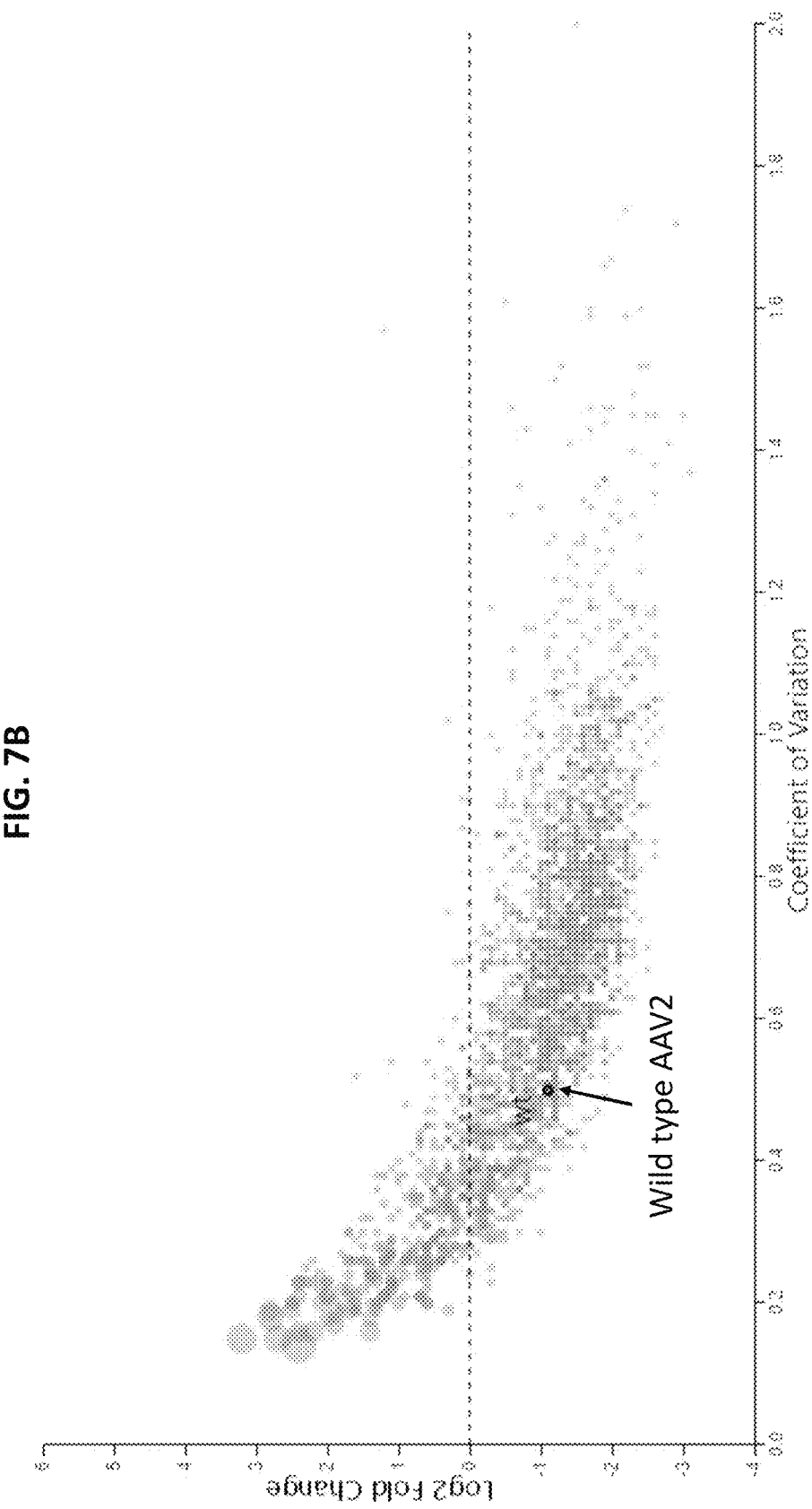
Figure 8:
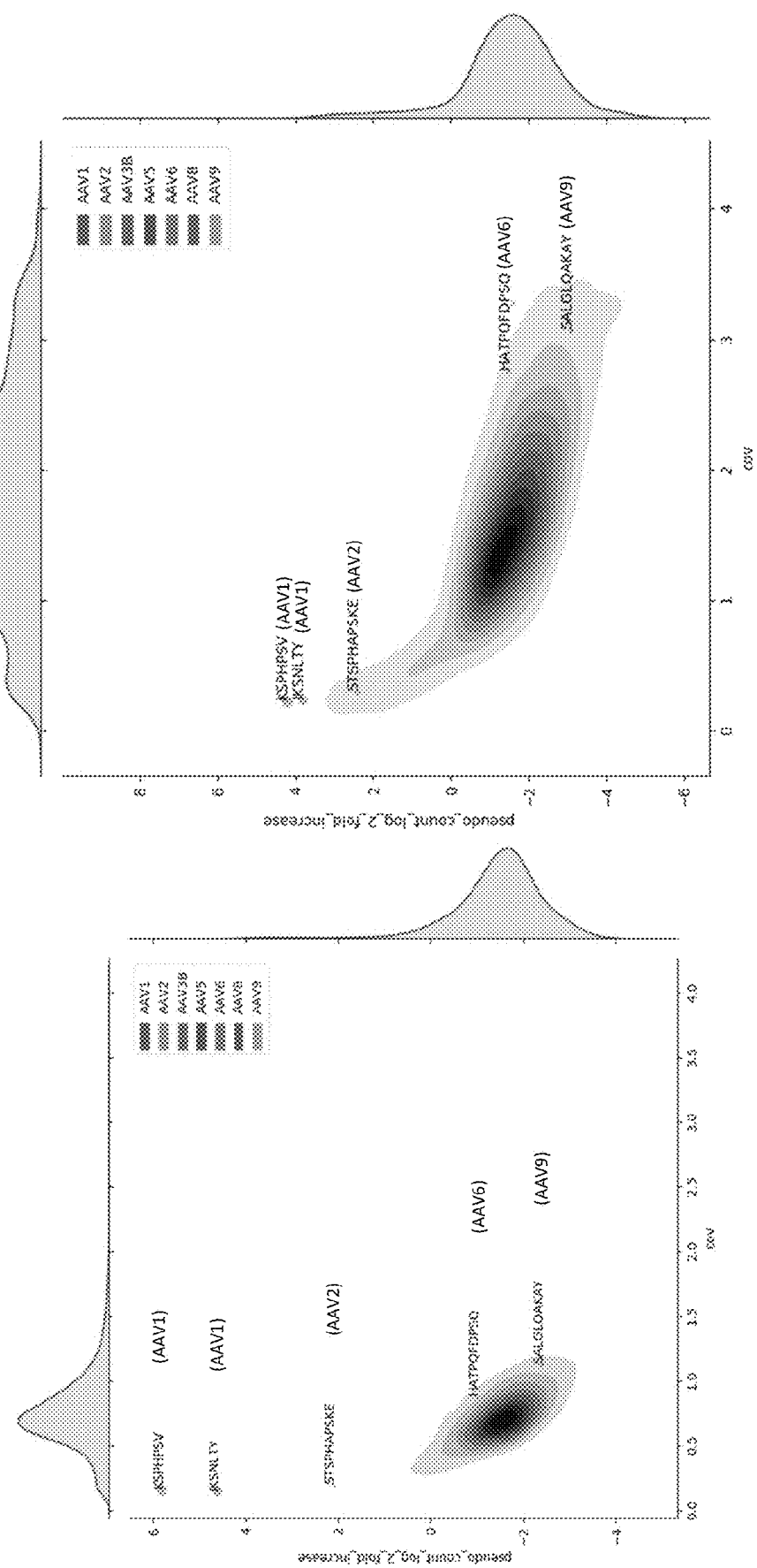
FIG. 8 depicts two plots showing the enriched AAV variants as assayed by either reverse transcription of the RNA isolated from the target cells and amplification of the barcodes (plot on left side) or by isolation of nuclei from the treated cells and sequencing of the inserted nucleotides encoding the peptides inserted into the capsid gene (plot on right side). The data demonstrates that very similar results were obtained by both analysis methods. Left and right plots each disclose SEQ ID NOS: 199-203, respectively, in order of appearance (top to bottom in each panel).

The libraries were tested in primary mouse cortical neurons (Gibco) in vitro. The libraries were a mixture of all the AAV variants in each of the serotypes. Cells were treated with the AAV variants over a dose range of $3\times10^3$, $1\times10^4$, $3\times10^4$, $1\times10^5$, and $3\times10^5$ vector genomes per cell and EGFP positive nuclei were isolated as described below. Separately, total RNA was isolated from the infected neurons and used for reverse transcription to cDNA following standard protocols and a primer specific to the AAV mRNA transcripts, DO441_AAVSpecific_RT: 5' GGTTACAAATAAAGCAATAGCATCAC (SEQ ID NO:65). The resulting cDNA barcodes were then sequenced by ILLUMINA® sequencing with NGS primers DO439_RNABarcode_Fwd: 5' ACACGACGCTCTTCCGATCTNNNNGCATCACAAATTTCACAAATAAAGC (SEQ ID NO:66) and DO440_RNABarcode_Rev: 5' GACGTGTGCTCTTCCGATCTNNNNGCCGTGTCCGAGGGTACTAAG (SEQ ID NO: 67) to quantify variant performance. The results of a sample of the AAV variants recovered are shown in FIG. 6, where the log 2 fold change represents the enrichment of the variant isolated from transduced cells as compared to its frequency in the administered library. The X axis of FIG. 6 represents the relative variability of variant performance across sample replicates. As can be seen, variant performance often clusters based on parent serotype, with variants comprising peptide insertions into AAV1 being the most enriched and least variable. FIG. 7A shows the AAV1 serotype variants plotted alone, and also indicates the performance of the wildtype AAV1 serotype (no inserted amino acids in the capsid sequence). As can be seen, there were a great deal of variants that showed an increased enrichment as compared to the wildtype AAV1 serotype. Similarly, FIG. 7B shows the variants based on peptide insertions into AAV2 plotted alone and indicates the relative performance of wildtype AAV2. The methods produced AAV2 variants that showed an enrichment in transgene expression in comparison with the wildtype sequence. A comparison was also done to see if the different methods of identifying the enriched AAV variants produced similar results. FIG. 8 shows that variant performance evaluated based on RNA isolation, cDNA synthesis, and barcode quantification was similar to performance evaluated by isolation of EGFP positive nuclei and sequencing of the variable capsid region. Additionally, library performance was evaluated in Neuro2A cells (ATCC CCL-131) and iCell neurons derived from human induced pluripotent stem cells (NCR-100-010-001, Cellular Dynamics International). Individual variant performance differed across cell lines that present different selective pressures. The methods described herein to evaluate variant performance were consistently applicable and successful. The variants were as follows:

TABLE 6

AAV variants evaluated.

| AAV variant | SEQ ID NO |
|---|---|
| KSPHPSV (AAV1) | SEQ ID NO: 199 |
| IKSNLTY (AAV1) | SEQ ID NO: 200 |
| STSPHAPSKE (AAV2) | SEQ ID NO: 201 |

TABLE 6-continued

AAV variants evaluated.

| AAV variant | SEQ ID NO |
|---|---|
| HATPQFDPSQ (AAV6) | SEQ ID NO: 202 |
| SALGLQAKAY (AAV9) | SEQ ID NO: 203 |

Example 2: In Vivo Selection of Variant AAV Libraries in Mice

The goal of the construction of these AAV libraries was to identify AAV capsid variants that would allow delivery of AAV to any tissue, cell or organelle in any species.

Figure 3A:
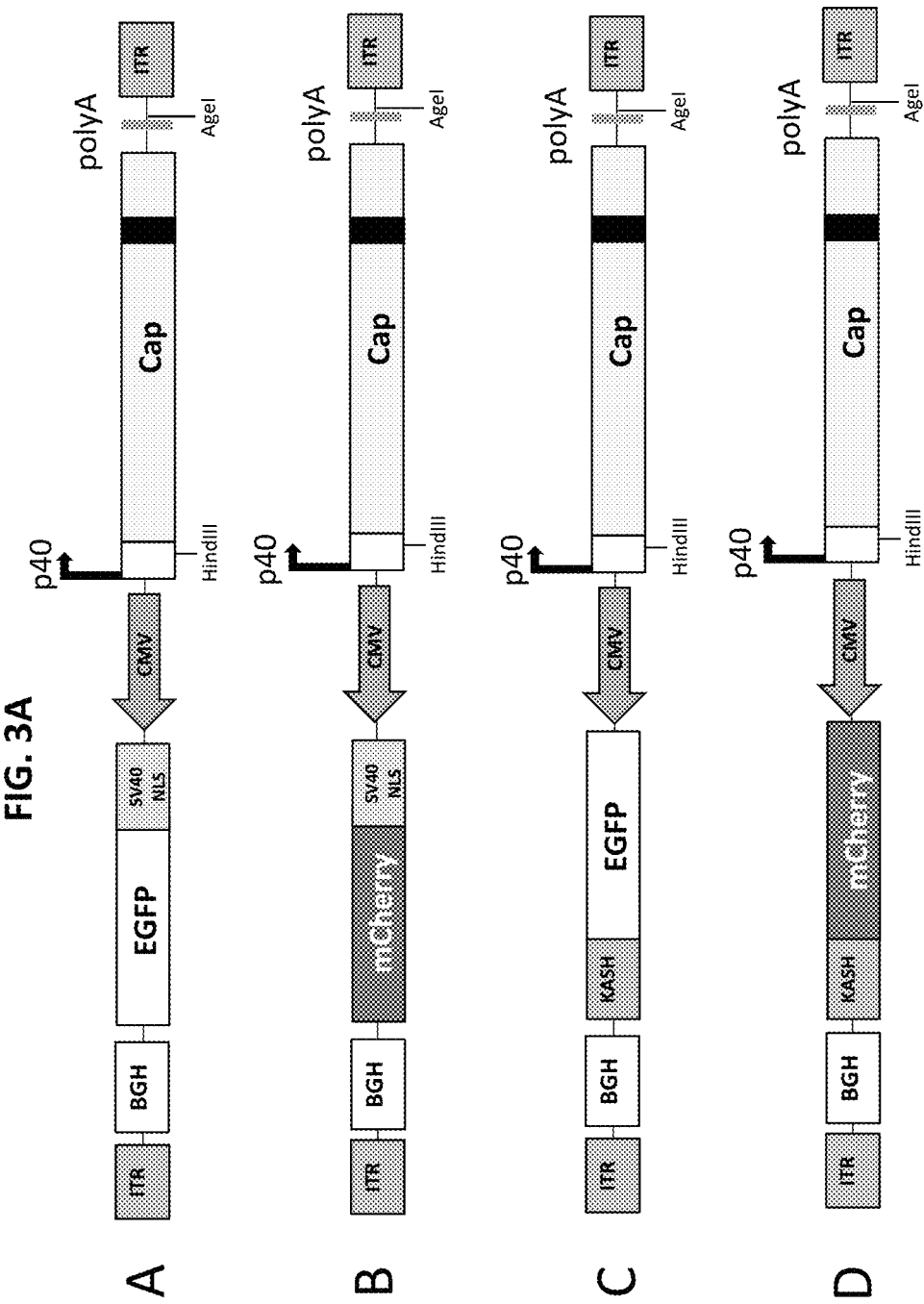
FIG. 3A and FIG. 3B are drawings of the various library constructs that contain the variant capsid library in cis with an expression cassette, both flanked by viral ITRs for encapsidation of the viral genome. Panel A is a construct where the variant capsid gene "Cap" is regulated by the p40 promoter and the transcript is terminated by a polyadenylation signal sequence ("polyA"). The construct also comprises an EGFP reporter gene regulated by the CMV promoter where the EGFP is linked to an SV40 nuclear localization sequence ("SV40 NLS") on its N-terminus. The construct also comprises a bovine growth hormone polyA signal sequence BGH and the 5' and 3' ITR sequences. Panel B is similar to that in Panel A except in that it has an mCherry reporter. Panel C shows the same design for the variant capsid gene, and further comprises an EGFP reporter gene regulated by the CMV promoter wherein the EGFP gene is fused to a KASH nuclear envelope binding domain ("KASH"). Panel D shows a construct similar to Panel C except that an mCherry reporter is used. Panel E shows a construct with the same variant capsid expression construct but has a synapsin promoter ("hSyn1") driving expression of an EGFP reporter fused to a histone 2B DNA binding domain ("H2B") on its 3' end. The construct also comprises an SV40 polyadenylation signal sequence. Panels F and G are similar to Panel E except that Panel F uses an mClover3 reporter and Panel G uses an mRuby3 reporter.
Figure 3B:
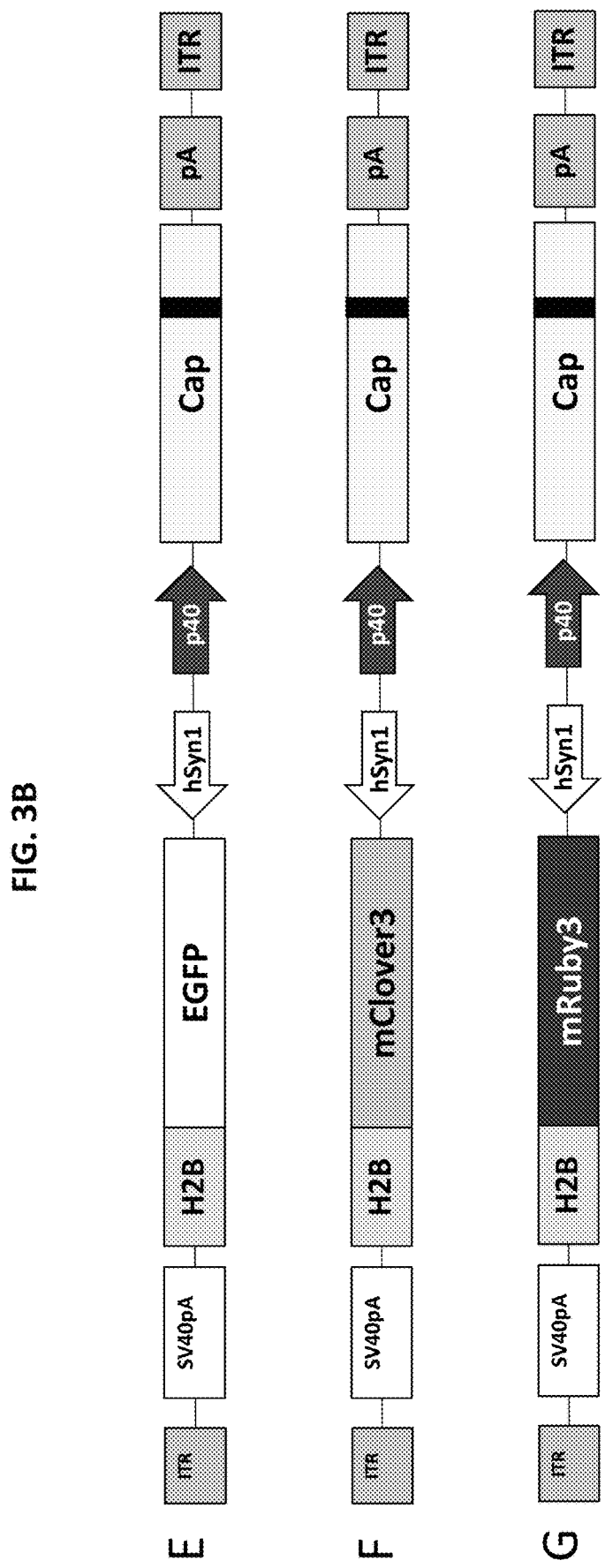

CNS delivery. One potential use of this technology is the delivery of genome editing, transgenes and regulators of gene expression to specific cell types. Thus, it was important for this particular application to identify AAV variants that would not only target particular cells within particular tissues, but would also travel to the nucleus within the cell and mediate transgene expression. In addition, isolation of nuclei from tissues is straight forward as compared to isolation of specific whole cell bodies from tissue. Nuclei have uniform morphology across tissues and are easily stained for DNA content to facilitate FACS analysis (e.g. DAPI or Hoescht dyes). For example, neurons have very extended cell bodies and are difficult to isolate intact from brain tissue. Also, some components within the brain such as lipofuscin and myelin basic protein can autofluoresce, confounding analyses that are dependent on the fluorescence signal of reporter genes (see for example Hainsworth et al (2017) *Neuropathol Appl Neurobiol* 44(4): 417-426). Thus, as shown in FIGS. 3A and 3B different approaches were taken to localize the reporter genes in the AAV genomes to the nucleus including fusing them to nuclear localization sequences (SV40 NLS), nuclear envelope binding protein domains (KASH) and histone binding domains for incorporation into nuclear chromatin (H2B).

Constructs were made to test delivery into HEK293 cells. Constructs comprising just the reporter alone with no nuclear localization sequence (EGFP and mCherry) were compared to those in which the reporters had been fused to an SV40 NLS, or to a KASH domain (see FIG. 9). All constructs showed fluorescence in the cells, while the NLS tagged constructs showed localization within the nucleus and the KASH linked constructs showed the reporter was bound to the nuclear envelope. However, upon isolation of the nuclei from the HEK293 transduced cells, only the KASH linked constructs showed retention of the signal. Signal loss after nuclei isolation is likely due to the small size of the reporter proteins (27 kDa) relative to the nuclear pore cutoff (60 kDa) in the non-tethered constructs. In the absence of a living cell the active transport mechanisms for nuclear import of the reporter are lost and the reporter can diffuse out of the nucleus. Further testing was done with fusion of the reporter to the H2B domain and robust retention of the signal in isolated nuclei was also observed. All H2B constructs drove highly efficient incorporation of the reporter into the nuclear chromatin that was stable after both nuclei isolation and freeze/thaw treatment of cells and tissue Nuclei were isolated from cultured cells and tissue essentially as described in the protocol by Krishnaswami et al. (described in Kelder et al (2016) *Nat Protoc* 11(3):499). In brief, 2-3 mm³ sections of tissue were excised with a sterile razor blade. If cultured cells were being used, the cells were collected and resuspended at approximately 1×10⁶ cells per mL in cold PBS. The tissue or cells were homogenized using a dounce homogenizer in a Tris buffer comprising sucrose, $MgCl_2$, KCL, and NuPAGE sample reducing agent (Thermo). Also included was 0.1% Triton and Hoescht 33352 (Molecular Probes). The homogenate was then filtered using a 40 or 70 micron Flowmi cell strainer (Flowmi) to remove remaining tissue fragments or high order aggregates of nuclei.

Figure 10A:
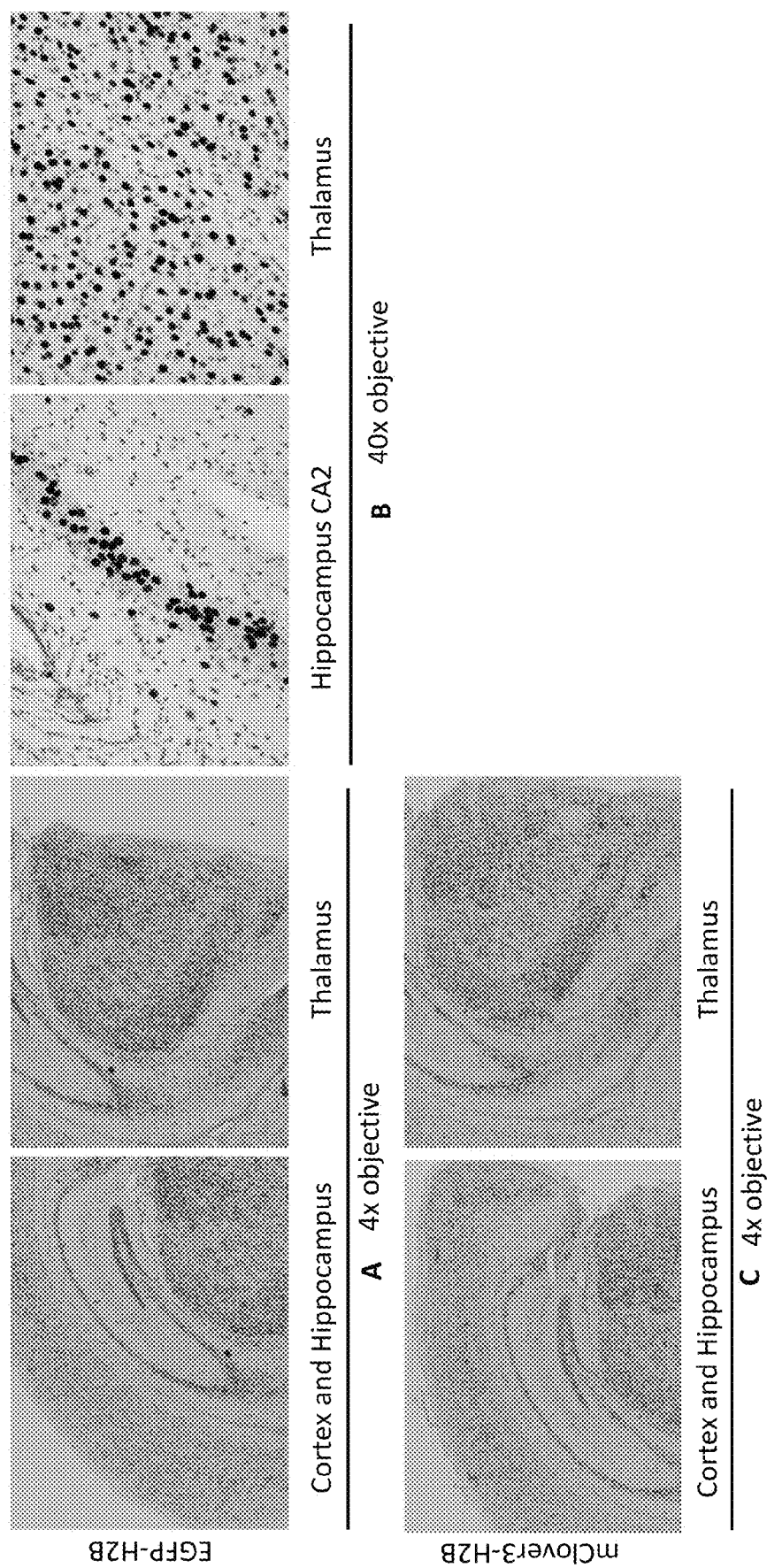

The AAV capsid library constructs comprising the EGFP-H2B, mClover3-H2B, mRuby3-H2B, and EGFP-KASH under the control of the neuron specific hSynapsin1 promoter were evaluated in C57BL/6J mice. AAV capsid libraries were manufactured by standard techniques and administered by tail vein intravenous injection at a dose of 2×10¹¹ vector genomes per mouse (n=3 per group). Two weeks after administration of the test article, mice were sacrificed, and the left hemisphere of the brain was preserved in 4% paraformaldehyde for immunohistochemistry studies targeting the expressed reporter to confirm nuclear localization by techniques know in the art. The right hemisphere was flash frozen for FACS sorting of transduced neuronal nuclei. Images from the immunohistochemistry studies verified nuclear localization for each of the constructs in the tissue (see FIGS. 10A and 10B) although for the mRuby3 constructs, direct visualization of the nuclear localized mRuby3 native fluorescence was used.

Nuclei were isolated from the frozen central nervous system mouse tissues as described above, stained with Hoescht dye during nuclei isolation, and sorted for EGFP, mClover3, mRuby3, or EGFP-KASH signal by using a Sony SH800 cell sorter according to manufacturer's instructions. For FACS sorting, the 70 micron chip was used, at sample pressure 5, in semi-purity mode. The FACS plots were gated on singlets to prevent sorting of doublets, triplets, or higher order groupings of attached nuclei. Samples were sorted into Tris buffer, pH 7.5, comprising sucrose and $MgCl_2$.

DNA was isolated from the sorted cells using a Roche High Pure Viral nucleic acid kit according to manufacturer's protocols.

Figure 12:
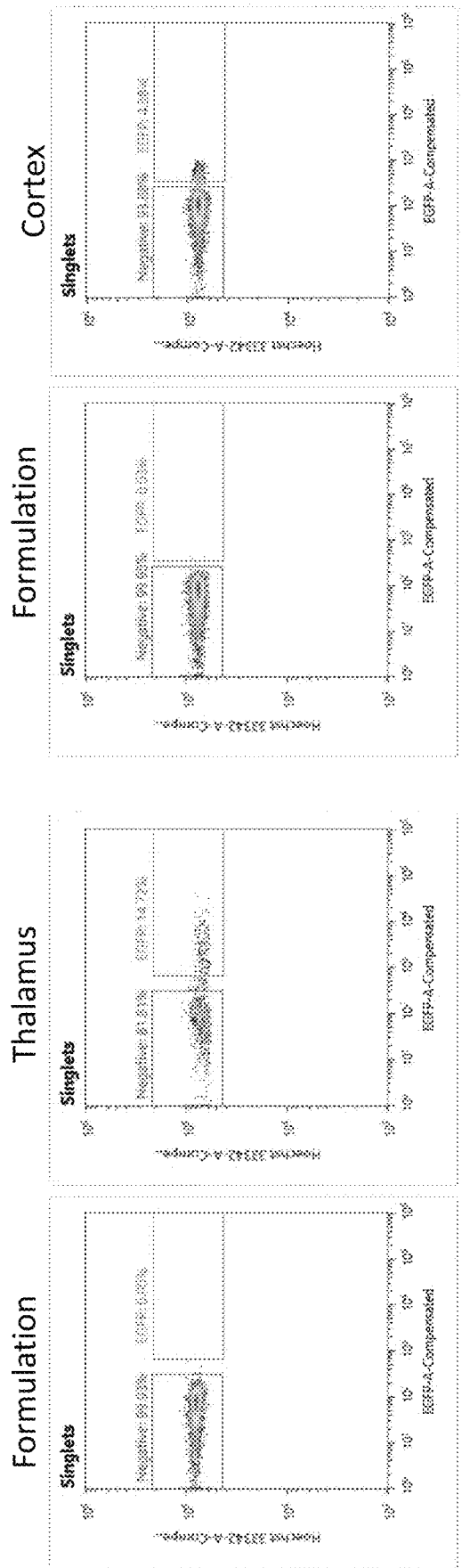
FIG. 12 depicts FACS analysis of nuclei isolated from mice treated with AAV variants comprising the mClover3 reporter construct or the EGFP-KASH reporter. With both types of AAV variants, reporter signal was seen in the thalamus for mClover3 (14.72% of total events) and in the cortex for EGFP-KASH (4.88%).
Figure 13:
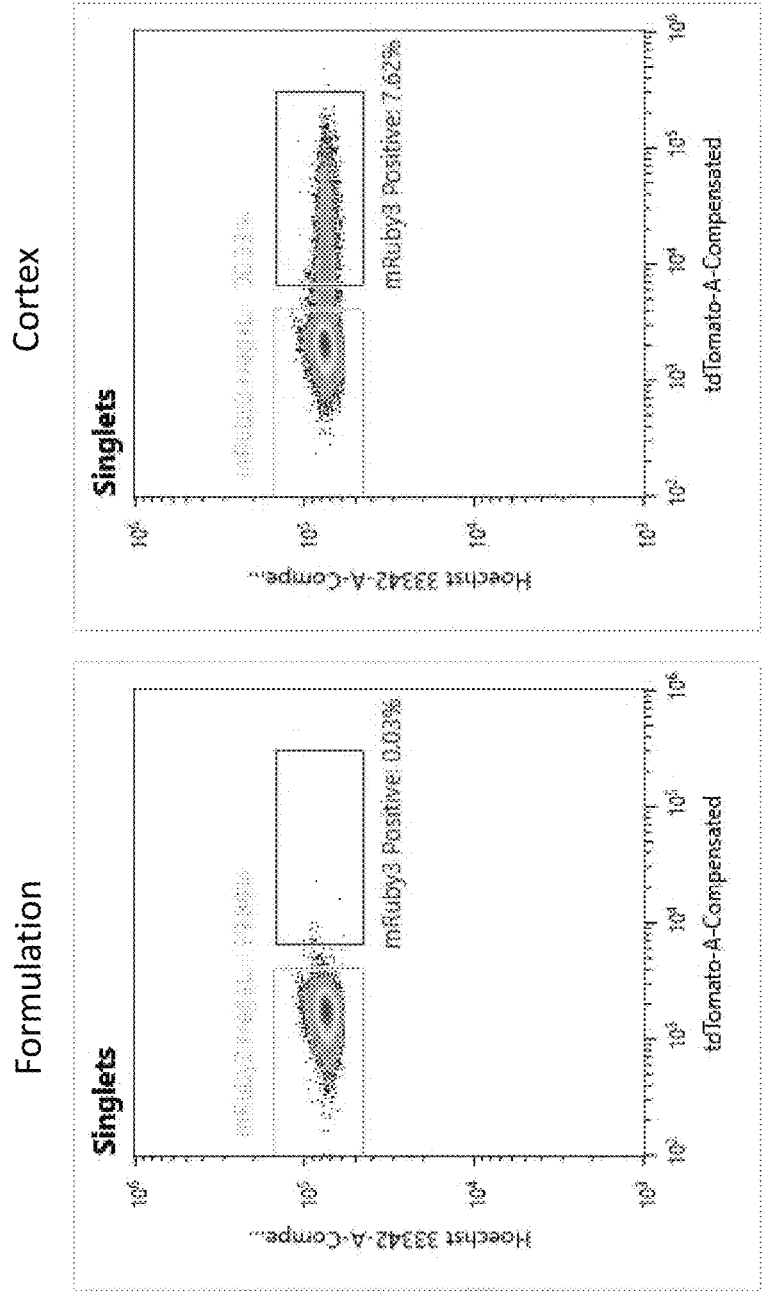
FIG. 13 depicts FACS analysis of nuclei isolated from mice treated with AAV variants comprising the mRuby3 reporter construct where reporter signal was detected in the cortex as shown (7.62% of total events).
Figure 14:
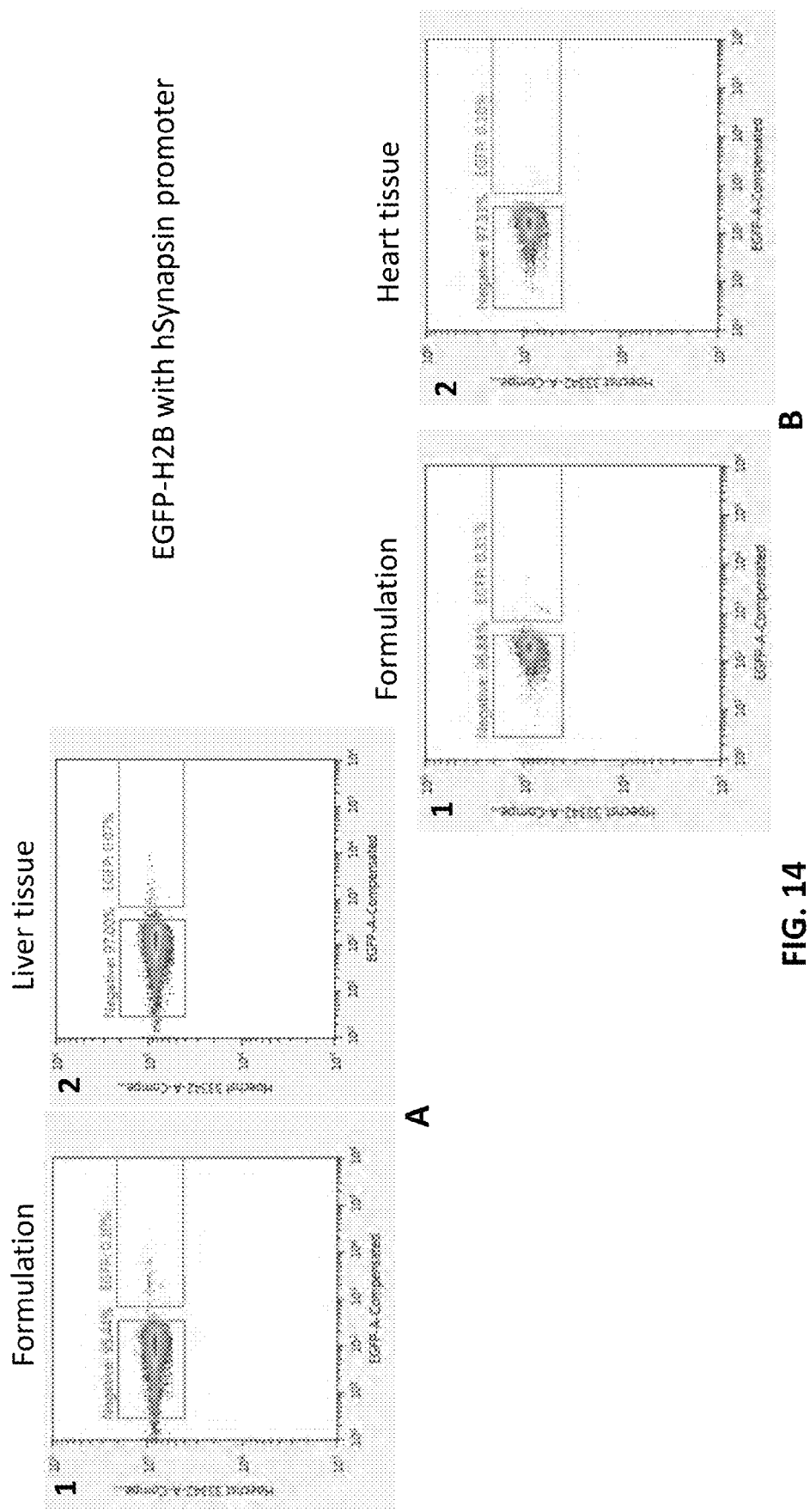
FIG. 14 depicts FACS analysis of nuclei isolated from non-CNS tissues when the reporter gene is driven by the hSyn1 promoter (neuron specific). Panel A shows the comparison in signal from liver tissue in mice treated with AAV variants comprising the EGFP-H2B construct in comparison with formulation buffer, while Panel B shows the same comparison in cardiac tissue. No off-target expression from the hSyn1 promoter was observed.

The FACS plots (FIG. 11) demonstrate that EGFP positive nuclei could be isolated from central nervous tissues in the mice injected with the libraries comprising the EGFP-H2B construct. Further, signal could be detected in the thalamus of mice treated with the mClover3 construct and in the cortex of mice treated with the EGFP-KASH libraries (FIGS. 12 and 13). Importantly, reporter signal above background could not be detected in either liver or cardiac tissue when mice were injected with the EGFP-H2B libraries (where EGFP-H2B was driven by the neuron specific hSynapsin promoter), see FIG. 14.

Example 3: In Vivo Selection in Non-Human Primates

Figure 15A:
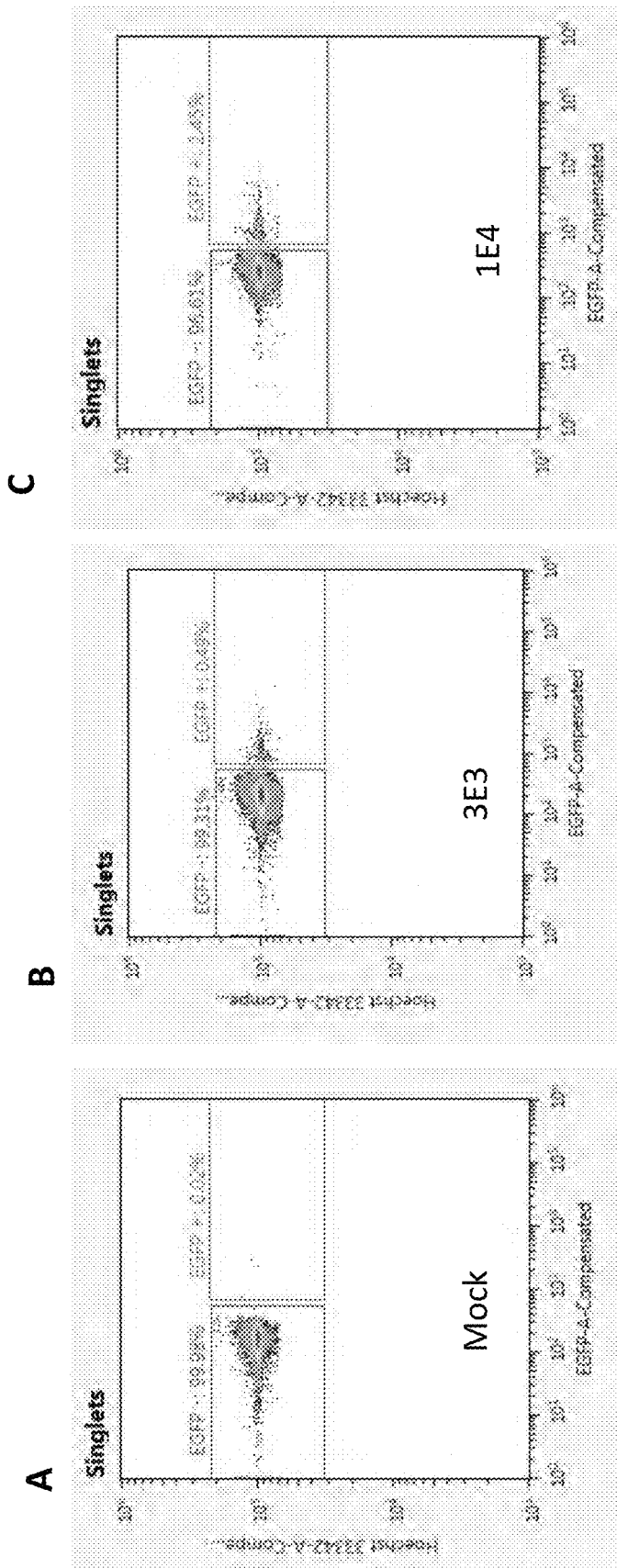
Figure 15B:
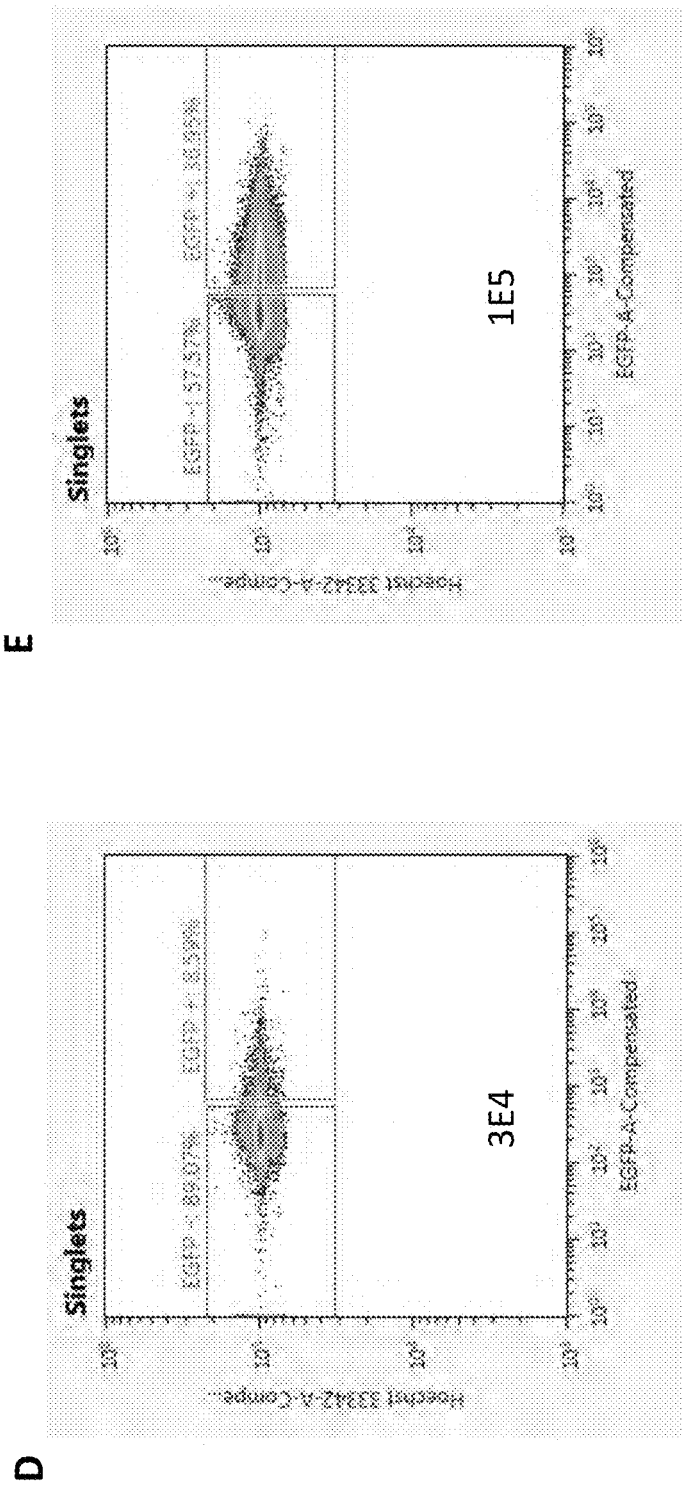

Liver delivery: The methods and compositions described herein also were used to identify liver targeting AAV variants from the libraries. In these experiments, the liver-specific promoter transthyretin (TTR) was used to express the reporter genes. The library constructs were thus modified to comprise the TTR promoter in place of the hSynapsin promoter. The libraries were first tested in cells in vitro, where a dose response was seen. HepG2 cells (ATCC HB-8065) were transduced with the AAV libraries across a range of multiplicity of infections (MOI) and then nuclei were sorted as above to measure fluorescence from the reporter gene. The results (see FIGS. 15A-C) demonstrated a dose response, which is summarized in Table 7 below:

TABLE 7

Dose response in HepG2 cells

| MOI | % EGFP positive |
|---|---|
| Mock | 0.2 |
| 3e3 | 0.5 |
| 1e4 | 2.5 |
| 3e4 | 8.6 |
| 1e5 | 36.9 |
| 3e5 | 53.3 |
| 1e6 | 64.3 |

Dose response experiments were also done in nonhuman primate hepatocytes (BioIVT) where a dose response was also observed (see Table 8 below).

TABLE 8

Dose response in NHP hepatocytes

| MOI | % EGFP Positive |
|---|---|
| Mock | 0.6 |
| 3e3 | 1.3 |
| 3e4 | 3.8 |
| 3e5 | 12.4 |

In a similar manner, the dose response was measured in primary human hepatocytes (Corning), and the data is shown below in Table 9.

TABLE 9

Dose response in primary human hepatocytes

| MOI | % EGFP Positive |
|---|---|
| Mock | 0.4 |
| 5e4 | 6.7 |
| 1e5 | 20.0 |
| 2e5 | 35.4 |
| 4e5 | 47.3 |
| 8e5 | 50.2 |

Library variant performance was also evaluated in C57BL/6J mice using the libraries where the reporter gene was driven by the TTR promoter. AAV capsid libraries were manufactured by standard techniques and administered by tail vein intravenous injection at a dose of 2E11 vector genomes per mouse (n=3 males and n=3 females). Two weeks after administration of the test article, mice were sacrificed and the liver removed to evaluate targeting of the expressed EGFP transgene.

The selections were also performed in non-human primates (cynomolgus macaques) to isolate AAV variants that would have the most relevance for transduction of human liver.

In selection round 1, a library pool comprising AAV variants from all the different serotypes was injected at a dose of 5E12 vector genomes per kilogram. In this first round, millions of unique variants were injected into one male and one female NHP. After 15 days the NHPs were sacrificed and the liver analyzed. A pool of successful AAV variants recovered from the NHP livers was generated and sequenced. The AAV variants were then used to make a single library comprising approximately 500,000 unique variants. These were then injected into a new NHP pair intravenously at a dose of 1.6E13 vector genomes per kilogram. After 28 days, the NHP were sacrificed and their livers analyzed. Endpoints analyzed were enrichment of the individual AAV variants in the liver tissue as compared with the administered library formulation, the enrichment in hepatocyte nuclei expressing EGFP encoded by the AAV variants, and sequencing of the mRNA barcodes to determine enrichment of AAV capsid variants compared to the administered library formulation.

Figure 16:
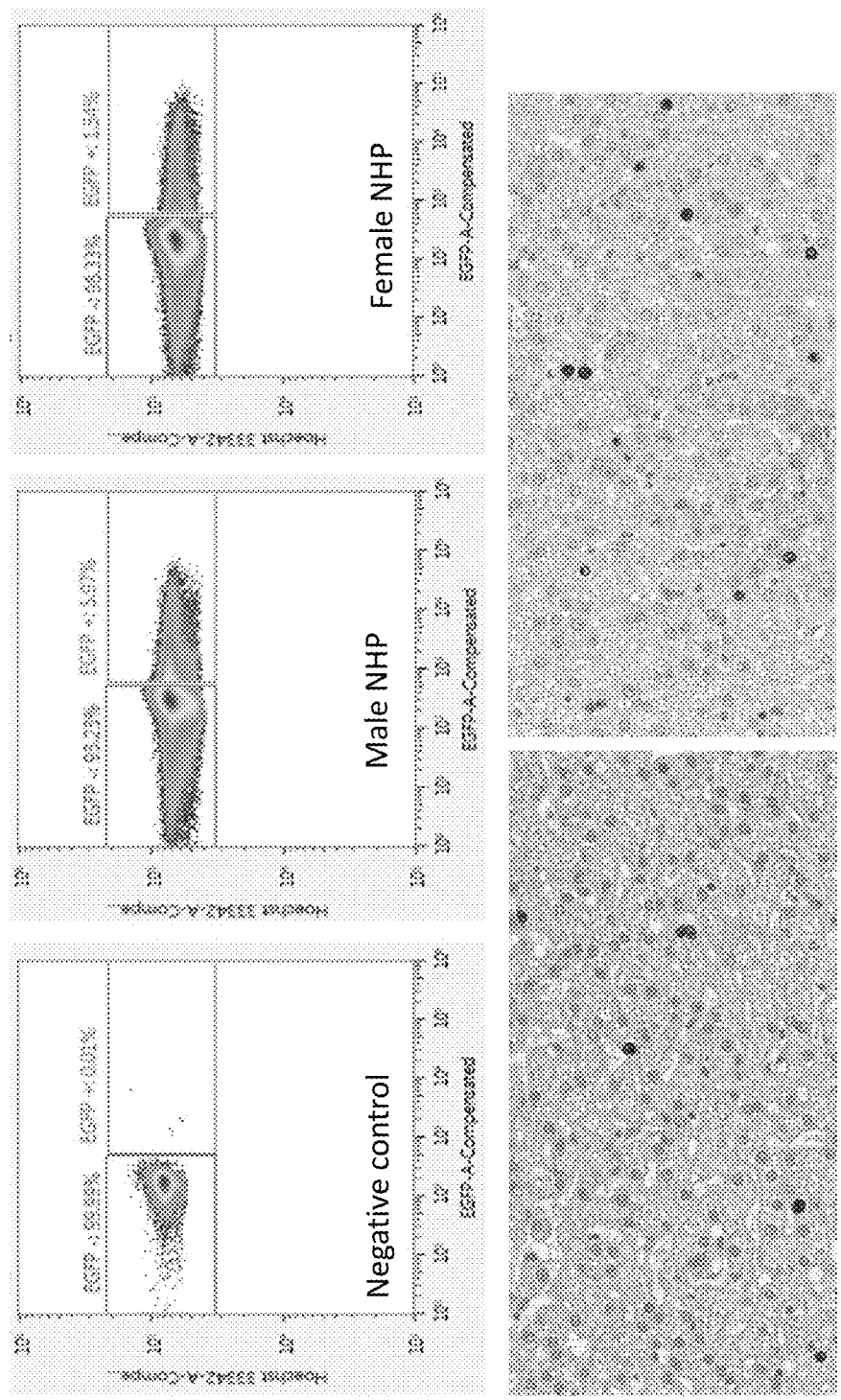
FIG. 16 depicts the reporter signal detected in NHP (Non-Human Primate) nuclei isolated from liver tissue following injection of the animals with the AAV variant library (Panel A). Panel B shows immunohistochemical analysis of the liver tissue and demonstrates that nuclear localized reporter signal (brown staining of nuclei) is detected in the liver in both the male and female NHP.

Nuclei were isolated from the livers as described above and EGFP positive hepatocyte nuclei were sorted by FACS. The results (FIG. 16, Panel A) showed that the EGFP signal was readily detectable above background. The numbers of EGFP positive nuclei isolated from three samples of each individual liver lobe for each NHP are shown below in Table 10. In addition, immunohistochemistry detection of EGFP was performed (FIG. 16, Panel B) to demonstrate nuclear localization of the reporter gene.

TABLE 10

Number of AAV variants isolated from male and female NHP liver tissue.

| | NHP 1001 (Male) | | NHP 1501 (Female) | |
|---|---|---|---|---|
| Tissue Region | GFP + Nuclei (%) | Sorted Count | GFP + Nuclei (%) | Sorted Count |
| Left lateral lobe 1 | 6.0 | 133,043 | 1.5 | 28,746 |
| Left lateral lobe 2 | 4.4 | 44,044 | 1.2 | 24,641 |
| Left lateral lobe 3 | 4.1 | 71,123 | 1.2 | 18,762 |
| Right lateral lobe 1 | 2.4 | 31,872 | 1.9 | 31,814 |
| Right lateral lobe 2 | 4.5 | 76,013 | 1.6 | 34,736 |
| Right lateral lobe 3 | 4.6 | 54,185 | 1.5 | 24,675 |
| Left medial lobe 1 | 3.2 | 66,751 | 1.7 | 18,433 |
| Left medial lobe 2 | 3.6 | 45,289 | 1.6 | 17,613 |
| Left medial lobe 3 | 2.9 | 40,757 | 1.7 | 17,961 |
| Right medial lobe 1 | 3.8 | 51,326 | 1.2 | 21,438 |
| Right medial lobe 2 | 3.7 | 58,040 | 0.9 | 12,986 |
| Right medial lobe 3 | 3.2 | 52,832 | 1.5 | 16,695 |
| Quadrate lobe 1 | 4.0 | 57,774 | 0.8 | 10,325 |
| Quadrate lobe 2 | 2.7 | 44,248 | 1.1 | 13,333 |
| Quadrate lobe 3 | 3.5 | 58,053 | 1.3 | 15,150 |

Figure 17A:
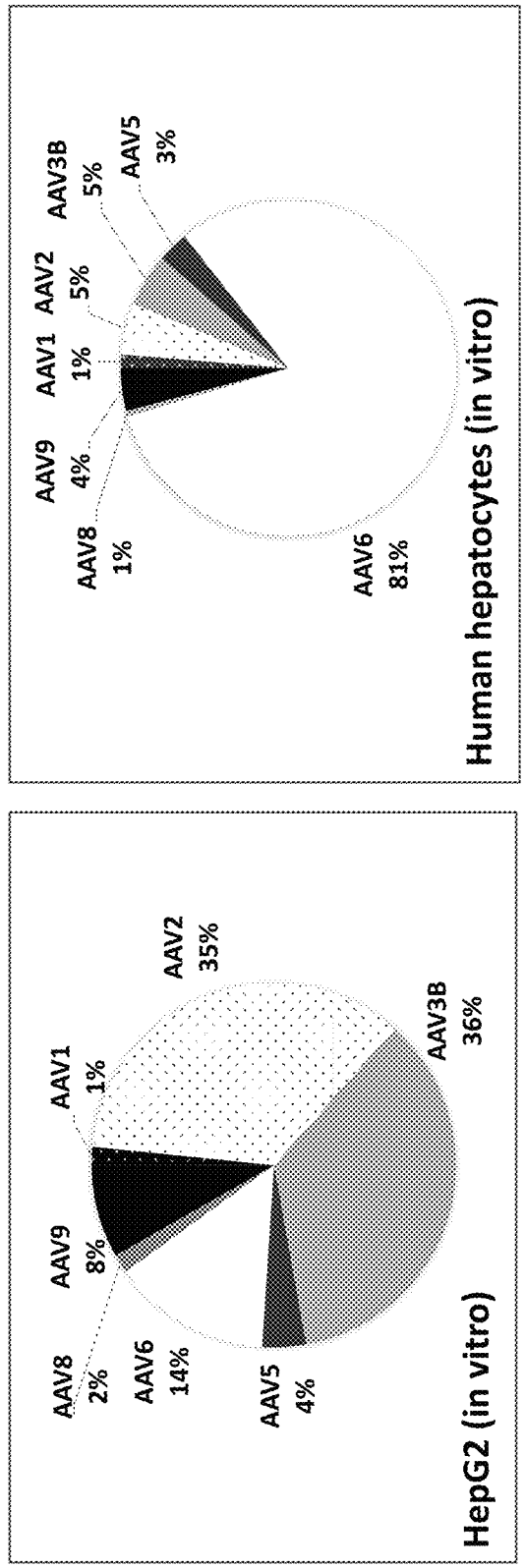

Interestingly, a comparison of the top 2500 AAV variants isolated after application of distinct selective pressures indicates striking differences in the parent serotypes of AAV variants that were most heavily enriched (FIGS. 17A and B). HepG2 and primary human hepatocytes were evaluated in vitro while mice and NHP were evaluated in vivo. These significant species-specific differences support AAV selections in animal models that are closer to human, for example NHP.

Approximately 100 AAV variants were selected for in-depth analysis based on their consistent fold enrichment in NHP mRNA, NHP EGFP positive hepatic nuclei, and NHP liver total genomic DNA. Variants excluded included those with low yield in HEK293 AAV manufacturing and a low confidence of the mapping of the barcode by Nanopore sequencing. Clustering analysis was also performed to select AAV variants that comprise unique physicochemical properties (for example, recurrent amino acid motifs or strong hydrophobicity) in response to the selective pressure.

Figure 18:
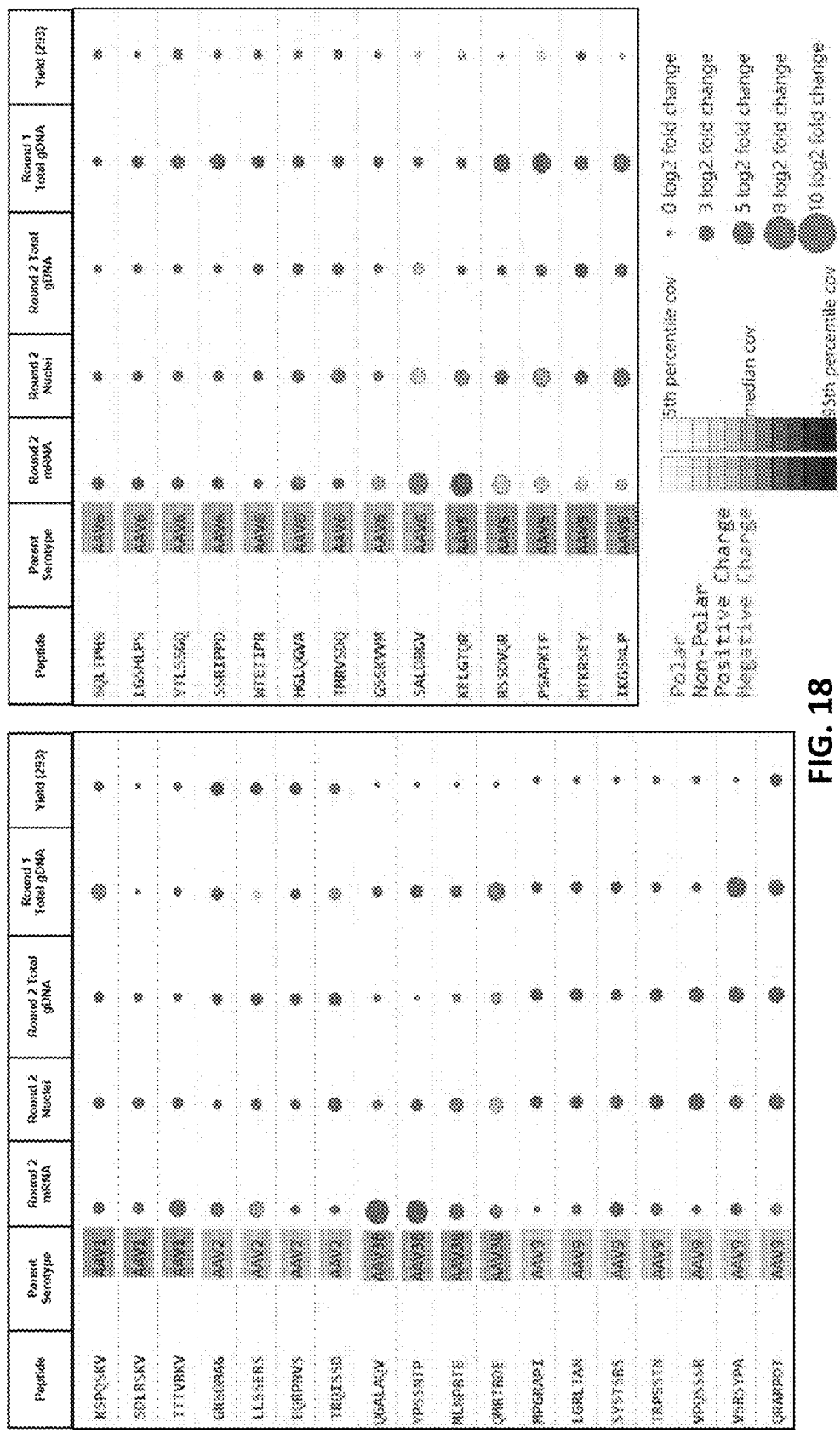
FIG. 18 shows a sampling of highly enriched AAV variants and the sequences of peptides inserted ("Peptide", SEQ ID NOs 1 to 32) identified from the second round of screening from NHP liver tissue. As can be seen, the variants are based on insertions into AAV1, AAV2, AAV3B, AAV9, AAV6 and AAV5 serotypes, where the peptide sequences were inserted into the following amino acid positions in each serotype indicated: AAV1 (590), AAV2 (588), AAV3B (589), AAV5 (578), AAV6 (454), AAV8 (591), AAV9 (589). The data shows the enrichment of the individual variants through a second screening round as measured by analysis of AAV library derived barcoded mRNA transcripts isolated from liver tissue ("Round 2 mRNA), viral genomic DNA sequenced from nuclei isolated on the basis of EGFP-H2B reporter signal using FACS ("Round 2 nuclei"), viral genomic DNA sequenced from total liver genomic DNA in round 2 ("Round 2 Total gDNA"), and viral genomic DNA sequenced from total liver genomic DNA in round 1 ("Round 1 Total gDNA"). Also shown is the relative yield of the AAV variant when produced by transient transfection into HEK293 cells. The degree of enrichment of the individual variant when isolated from the tissue as compared to its percentage in the library prior to injection is indicated by the size of the circle. For example, the AAV3B serotype variant with the inserted peptide sequence QGALAQV (SEQ ID NO: 8) has a log 2 fold enrichment of 6.1 in mRNA barcode frequency when isolated from the NHP tissue as compared with the starting library. The darkness of the color of the circles also relates to the scale shown in the bottom right showing the relative variability in performance across multiple animals and tissue punches for a particular variant.

The top 32 sequences from this initial analysis are shown in FIG. 18 and Table 11. The analysis shows the parent serotype as well as the fold enrichment in liver observed after selection in non-human primate. Also shown is the sequence of the peptide inserted into the capsid loop. Importantly, the ability to produce each AAV variant in a HEK293 AAV production system was tracked to insure any AAV identified by the methods described herein could be produced efficiently. Thus, in some embodiments, the inserted peptide sequence and AAV parent serotype may be any one of those set forth in Table 11.

TABLE 11

| Inserted Peptide Sequence | AAV parent serotype | SEQ ID NO |
|---|---|---|
| KSPQSKV | AAV1 | 1 |
| SDLRSKV | AAV1 | 2 |
| TTTVRKV | AAV1 | 3 |
| GRSDMAG | AAV2 | 4 |
| LLSSERS | AAV2 | 5 |
| EQRPNVS | AAV2 | 6 |
| TRQISSD | AAV2 | 7 |
| QGALAQV | AAV3B | 8 |
| YPSSNTP | AAV3B | 9 |
| MLNPRTE | AAV3B | 10 |
| QMRTRDE | AAV3B | 11 |
| MPGRAPI | AAV9 | 12 |
| LGRLTAN | AAV9 | 13 |
| SYSTSRS | AAV9 | 14 |
| TRPSSTN | AAV9 | 15 |
| VPQSSSR | AAV9 | 16 |
| VSRSYPA | AAV9 | 17 |
| QRARPDT | AAV9 | 18 |
| SQLTPHS | AAV6 | 19 |
| LGSHLPS | AAV6 | 20 |
| YTLSSGQ | AAV6 | 21 |
| SSRIPPD | AAV6 | 22 |
| WTETIPR | AAV6 | 23 |
| HGLQGVA | AAV6 | 24 |
| TMRVSDQ | AAV6 | 25 |
| GSSKVVM | AAV6 | 26 |
| SALDRGV | AAV6 | 27 |
| KELGTQR | AAV5 | 28 |
| RSSDVQR | AAV5 | 29 |
| PSAPKTF | AAV5 | 30 |
| HTKRSEY | AAV5 | 31 |
| IKGSNLP | AAV5 | 32 |

CNS delivery: Additional experiments were conducted to identify AAV variants with improved transduction of the CNS using the methods described herein. For these experiments the hSynapsin promoter (hSyn1) was used to express the reporter gene and mRNA barcode. The selections were performed in non-human primates (cynomolgus macaques) to isolate AAV variants that would have the most relevance for transduction of the human CNS.

In non-human primate selection round 1 a library pool comprising AAV variants based on serotypes AAV1, AAV2, AAV3B, AAV6, AAV8, and AAV9 was injected by lumbar intrathecal puncture at a total dose of 1E13 vector genomes. In this first round, millions of unique variants were injected into one male and one female NHP. After 15 days the NHPs were sacrificed and the CNS tissues were analyzed to assess AAV variant performance.

A subset of the AAV variants with high fold enrichment in the round 1 CNS non-human primate selection were synthesized using Method 1 described above to generate the library for round 2 selection. The total size of the round 2 library was 10,818 variants. Each AAV variant was synthesized using three different nucleotide sequences that code for the same peptide. Each nucleotide sequence was linked to a unique mRNA barcode driven by the hSyn1 promoter in order to rank transgene expression in neurons. The inclusion of three replicate sequences enables increased confidence in assessing variant performance since each of the three sequences can be treated independently during bioinformatic analysis.

The library prepared for round 2 selection to target the CNS was first evaluated in vitro in Neuro2A cells (ATCC CCL-131) (FIG. 19), primary mouse cortical neurons (Gibco) (FIG. 20), and iCell human neurons derived from human induced pluripotent stem cells (NCR-100-010-001, Cellular Dynamics International) (FIG. 21) as described in Example 1.

Figure 22:
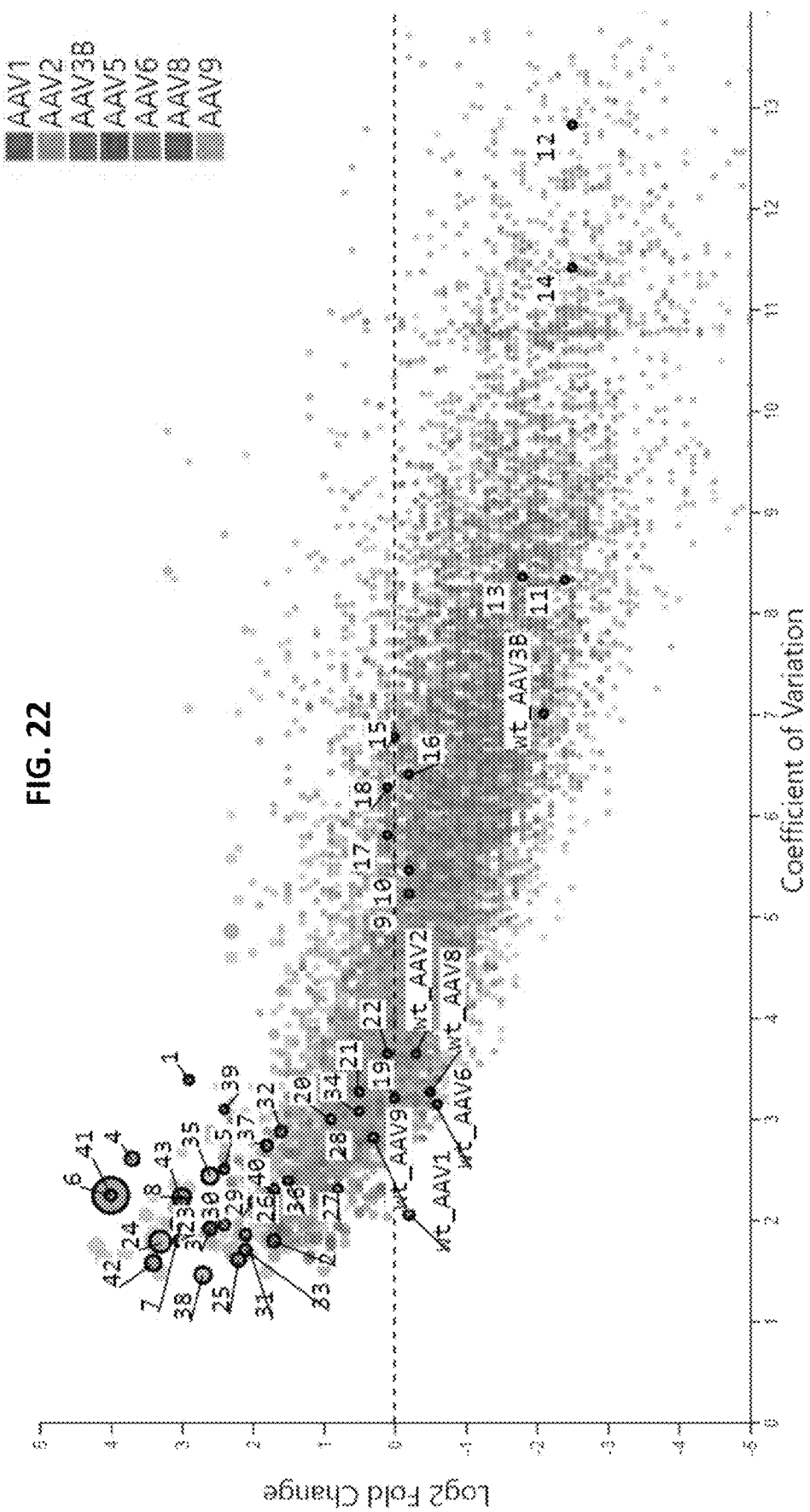
FIG. 22 is a bubble plot of the AAV library variants recovered from C57BL/6J mouse CNS tissues after intracerebroventricular administration of the AAV variant library. Tissue regions included in the analysis were striatum, hippocampus, cerebellum, thalamus, hypothalamus, midbrain, brain stem, motor cortex, somatosensory cortex, rest of cortex, cervical spinal cord, thoracic spinal cord, and lumbar spinal cord. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29A-D.

The round 2 library was next evaluated in C57BL/6J mice by unilateral intracerebroventricular injection at a dose of 1.59E11 vector genomes per mouse in a volume of 10 microliters (n=3 males and n=3 females). 28 days after administration of the test article, mice were sacrificed, and CNS tissues removed to evaluate library performance (FIG. 22). Analysis was completed on brain regions contralateral to the injected hemisphere to avoid confounding transduction associated with the injection tract.

Finally, the round 2 library was administered intrathecally into two male and one female cynomolgus macaques at a dose of 4.37E13 vg per animal. After 28 days, the NHPs were sacrificed and CNS tissues were analyzed. The brain was sliced at a 3 mm coronal slice thickness. Each slice was hemisected along the mid-sagittal plane. Punch samples (3 mm) were obtained from the brain slices from the left hemisphere for analysis of vector genome DNA. The right hemisphere was placed in RNAlater and refrigerated for approximately 24 hours to preserve RNA integrity. After storage, 3 mm punches were collected sampling various brain regions. The spinal cord was divided into cervical, thoracic, and lumbar segments for analysis.

Figure 23:
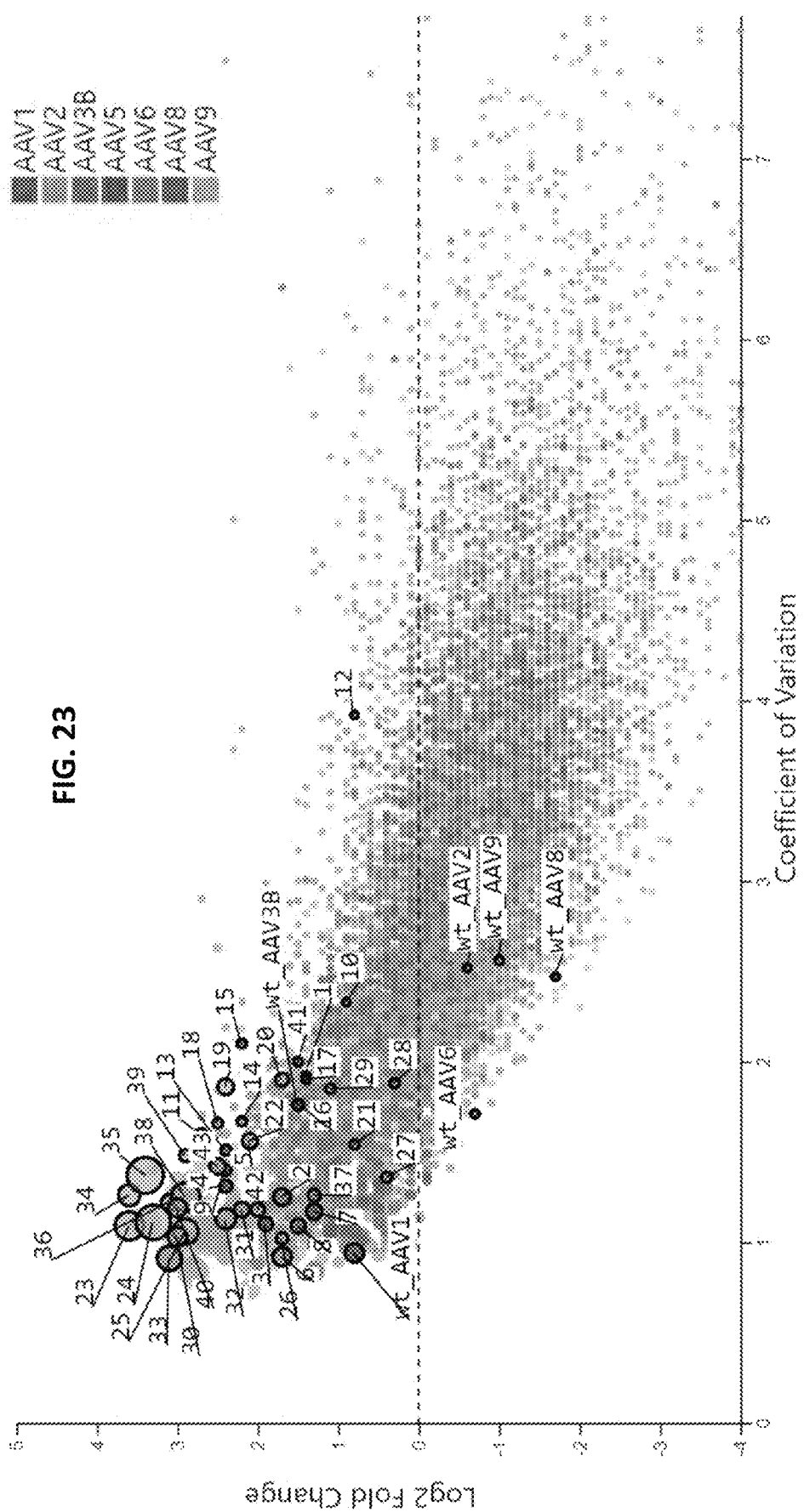
FIG. 23 is a bubble plot of the AAV library variants recovered from non-human primate CNS tissues after intrathecal administration of the AAV variant library. Tissue regions included in this analysis were hippocampus, entorhinal cortex, temporal cortex, frontal cortex, and parietal cortex. The log 2 fold change represents the change in variant frequency after infection and recovery of viral genomic DNA from tissue as compared with the variant frequency in the administered library. The performance of wild type serotypes is indicated as well as that of variants 1-43 (SEQ ID NO: 68-110) listed in FIG. 29A-D.
Figure 24:
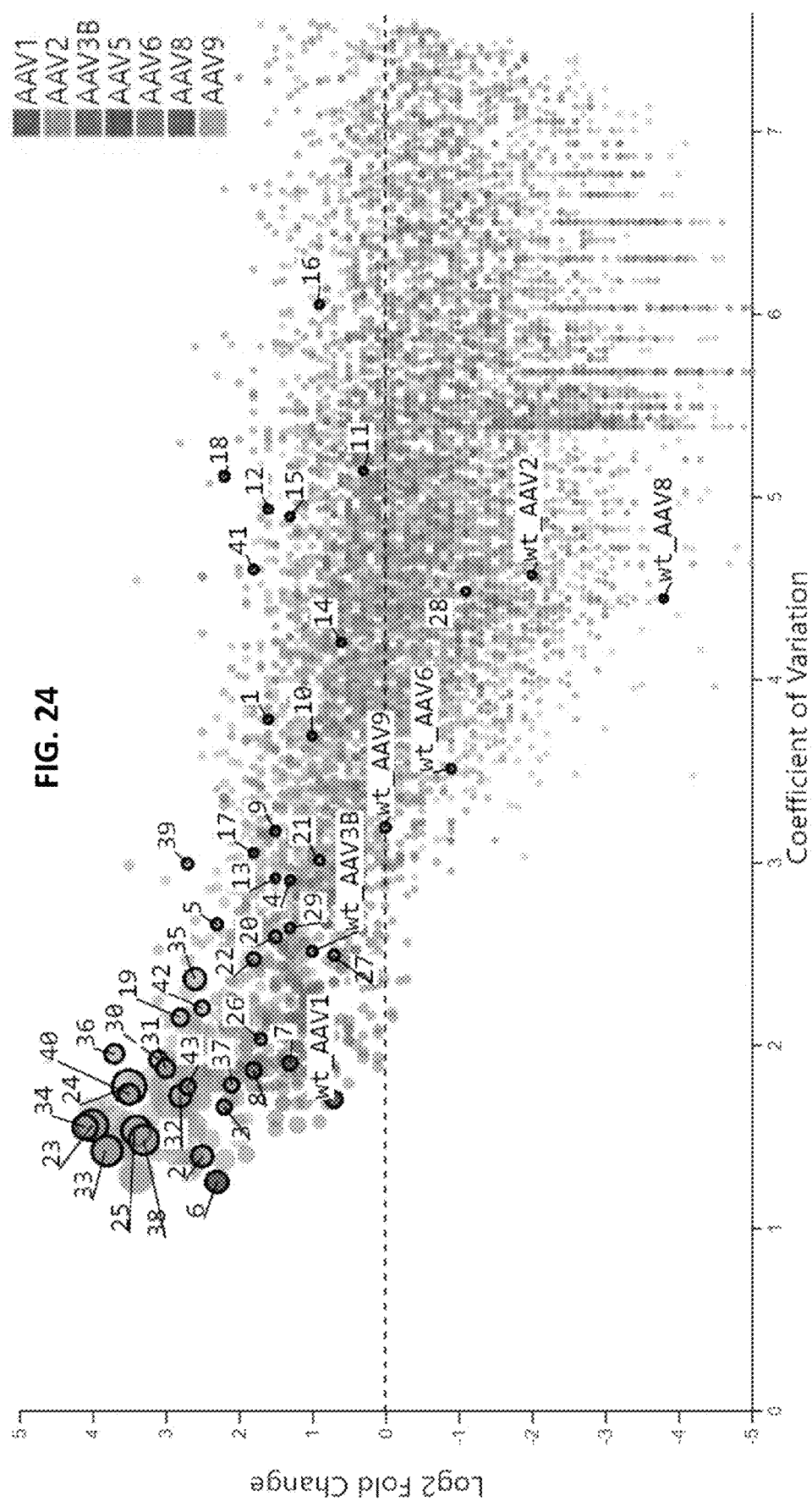
FIG. 24 is a bubble plot of the AAV library variants recovered from non-human primate CNS tissues after intrathecal administration of the AAV variant library. Tissue regions included in this analysis were pons, medulla, cerebellum, and motor cortex. The log 2 fold change represents the change in variant frequency after infection and recovery of viral genomic DNA from tissue as compared with the variant frequency in the administered library. The performance of wild type serotypes is indicated as well as that of variants 1-43 (SEQ ID NO: 68-110) listed in FIG. 29A-D.
Figure 25:
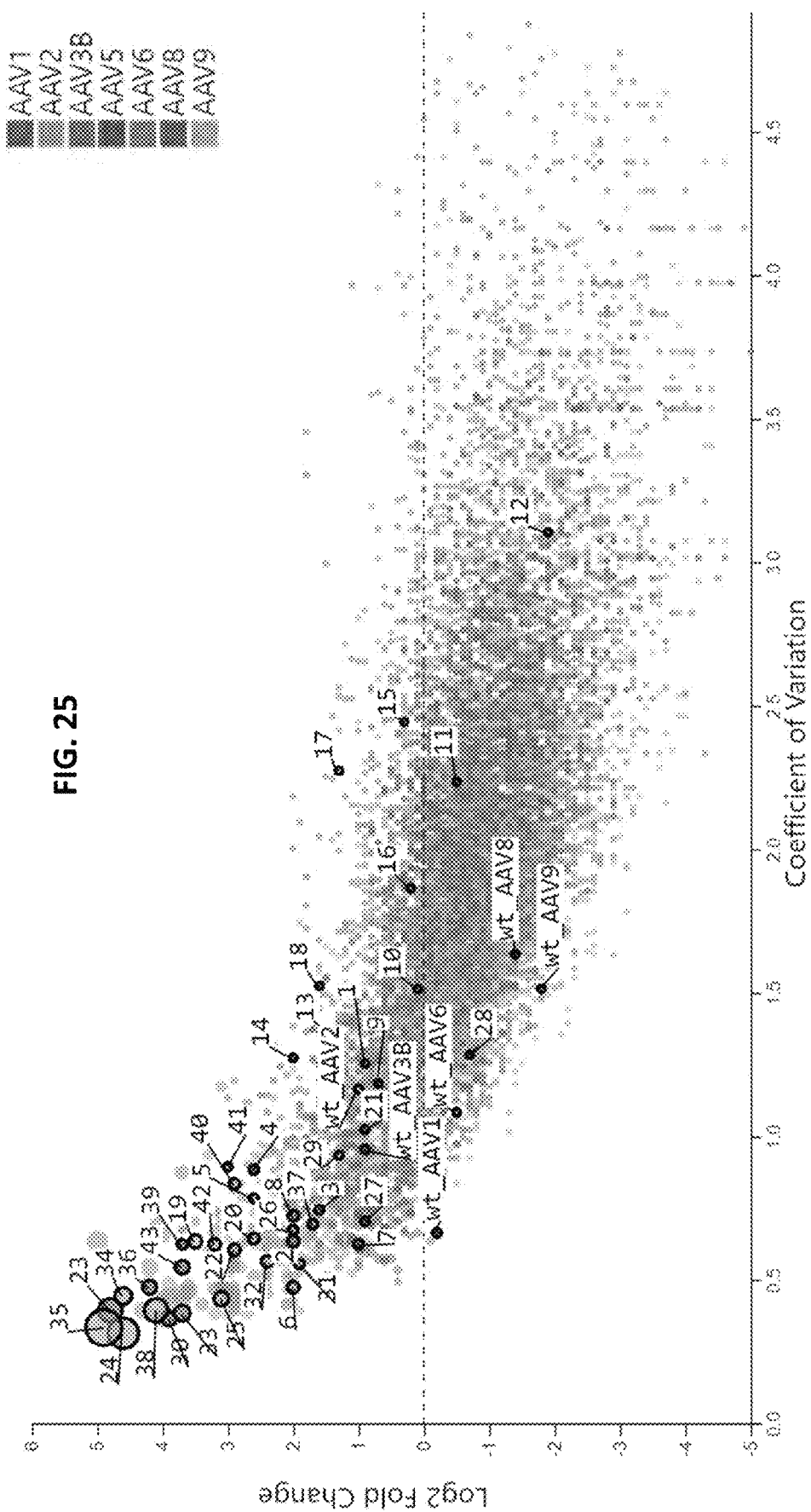
FIG. 25 is a bubble plot of the AAV library variants recovered from non-human primate spinal cord after intrathecal administration of the AAV variant library. The log 2 fold change represents the change in variant frequency after infection and recovery of viral genomic DNA from tissue as compared with the variant frequency in the administered library. The performance of wild type serotypes is indicated as well as that of variants 1-43 (SEQ ID NO: 68-110) listed in FIG. 29A-D.
Figure 26:
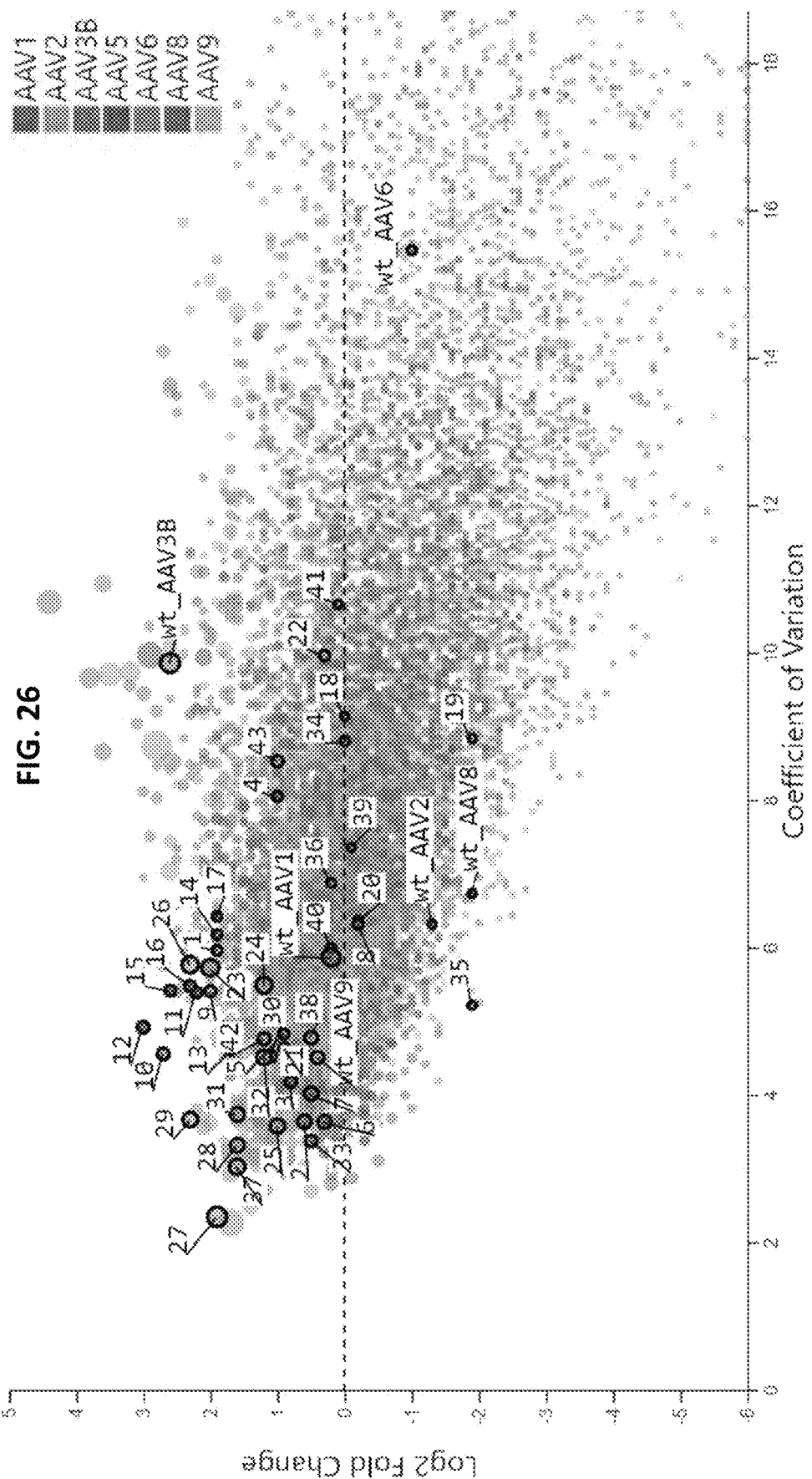
FIG. 26 is a bubble plot of the AAV library variants recovered from non-human primate CNS tissues after intrathecal administration of the AAV variant library. Tissue regions included in this analysis were hippocampus, entorhinal cortex, temporal cortex, frontal cortex, and parietal cortex. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29A-D.
Figure 27:
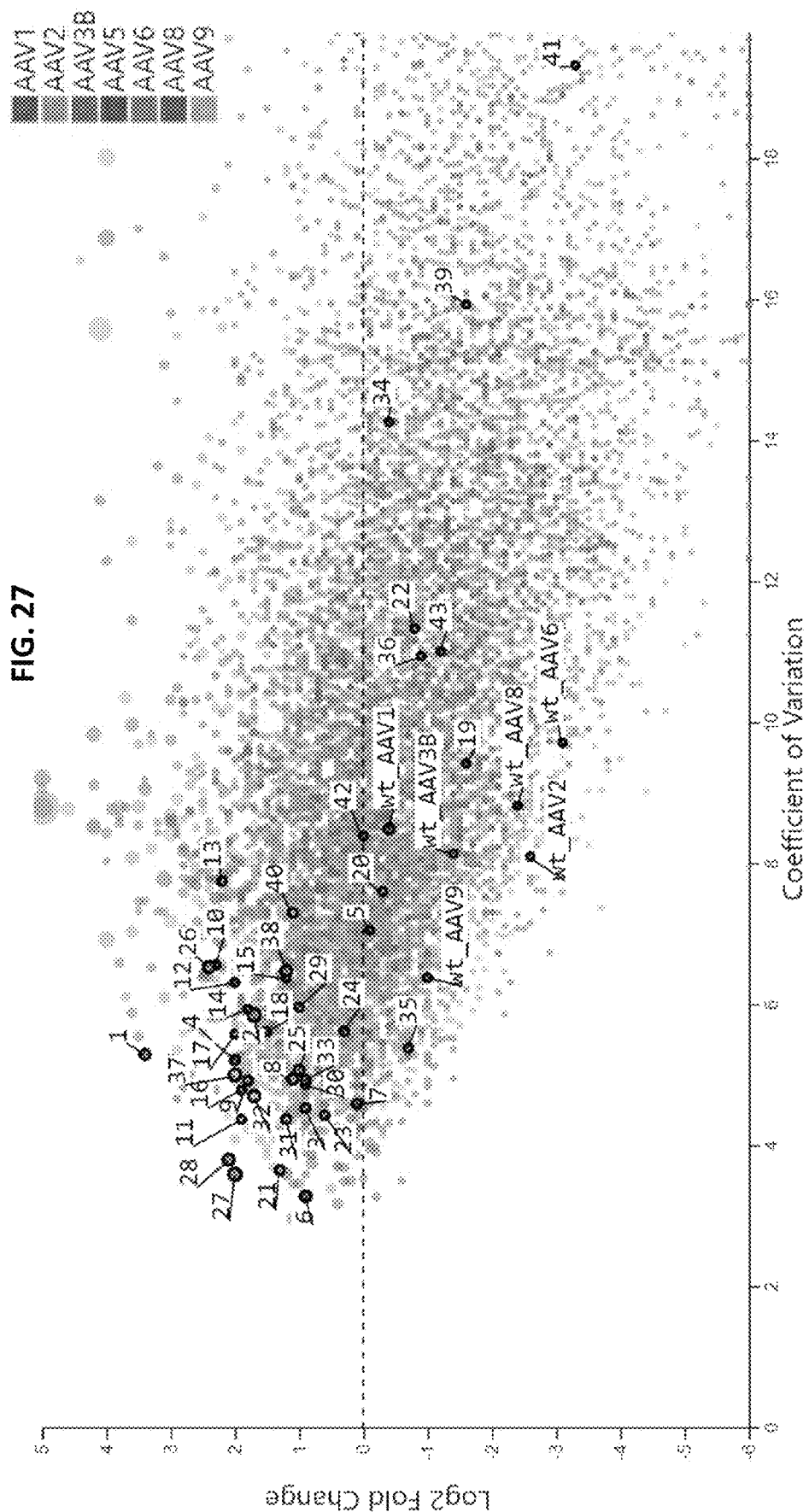
FIG. 27 is a bubble plot of the AAV library variants recovered from non-human primate CNS tissues after intrathecal administration of the AAV variant library. Tissue regions included in this analysis were pons, medulla, cerebellum, substantia nigra, and motor cortex. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29.
Figure 28:
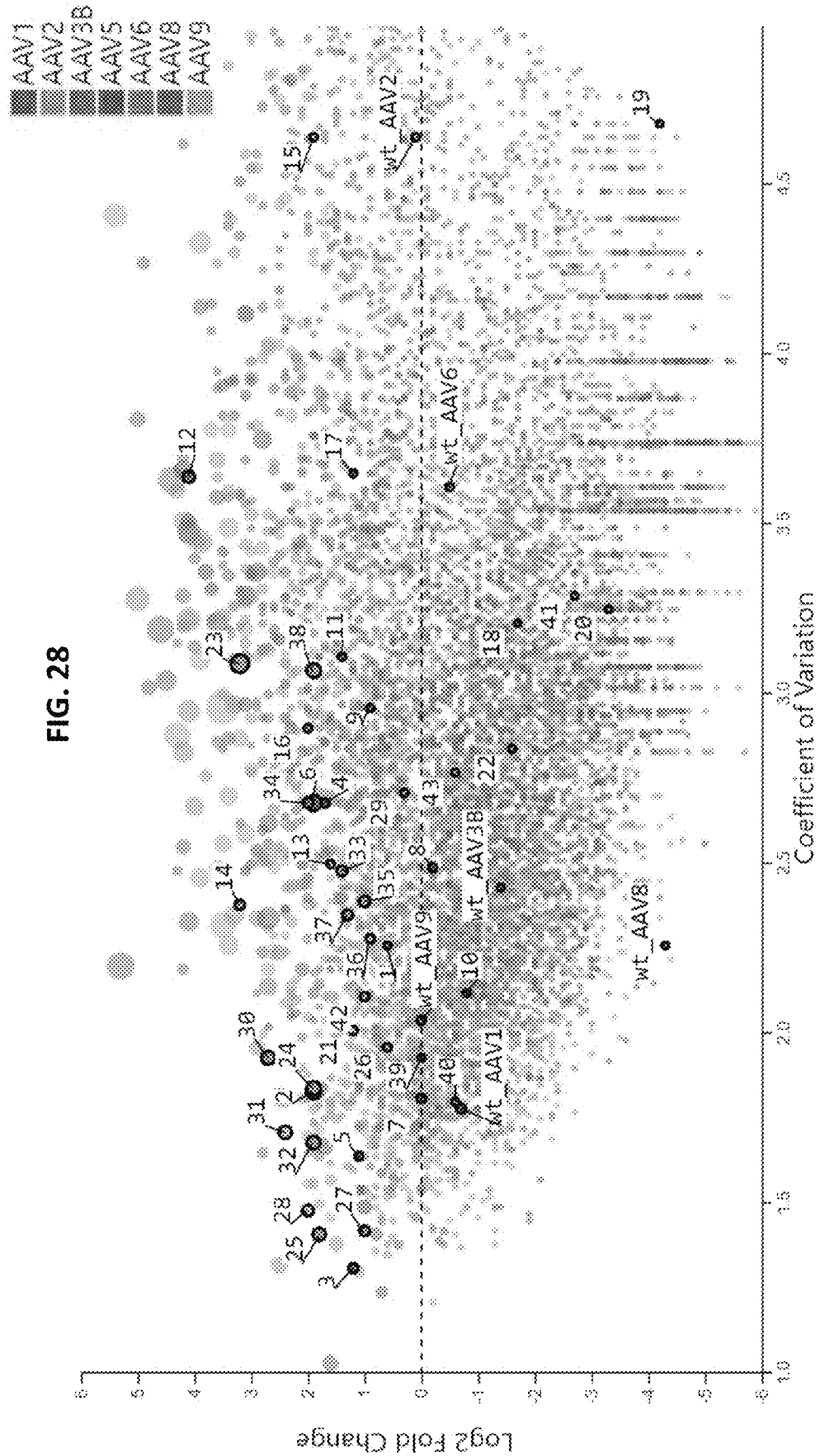
FIG. 28 is a bubble plot of the AAV library variants recovered from non-human primate spinal cord after intrathecal administration of the AAV variant library. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29.
Figure 29D:
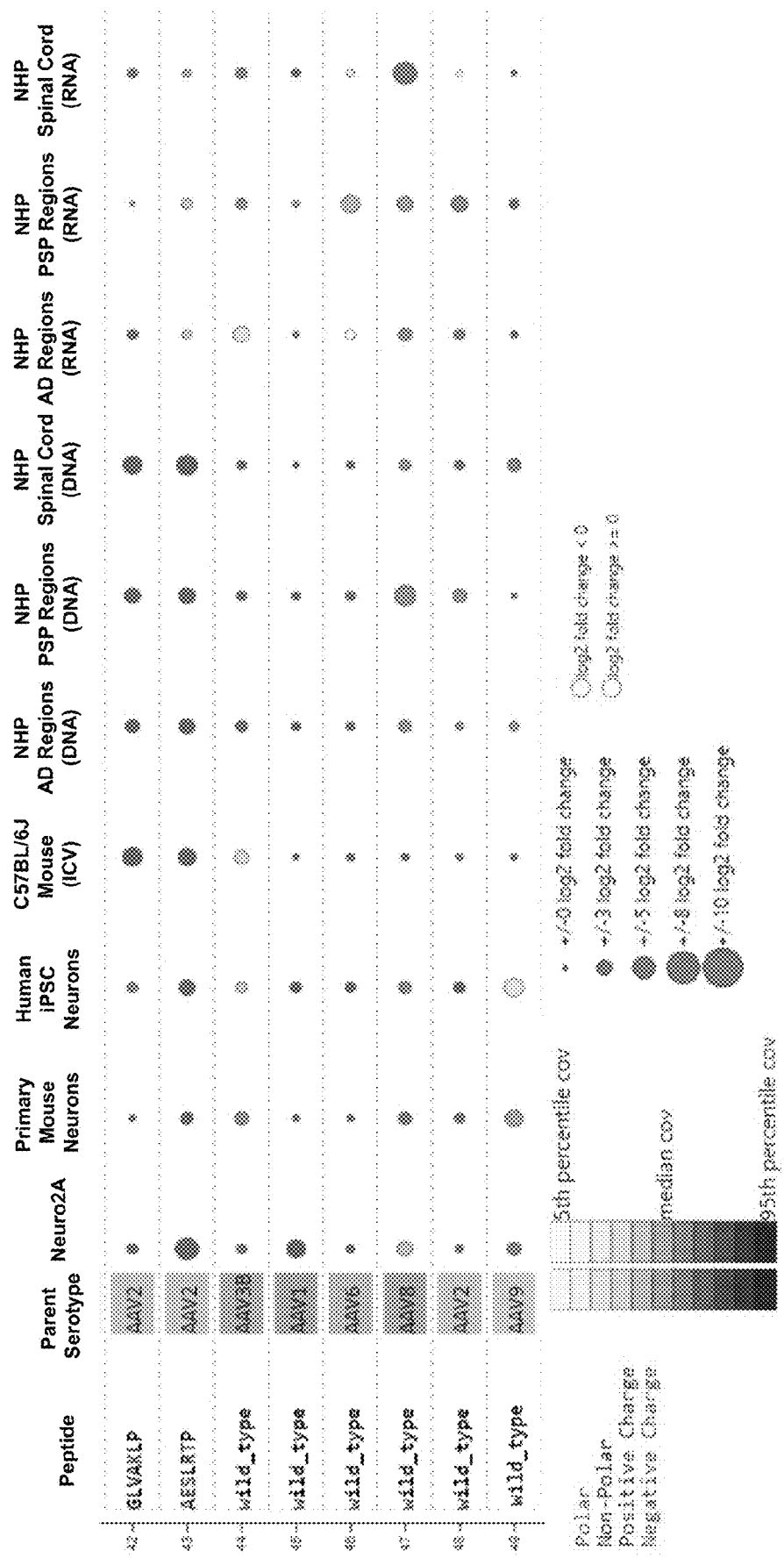

Library AAV variant performance was assessed by analysis of vector genome DNA frequency (FIGS. 23-25) as well as by quantification of cDNA reverse-transcribed from library mRNA transcript expressed specifically in neurons (FIGS. 26-28). These two data sets are referred to as DNA analysis and RNA analysis respectively. Next-generation sequencing analysis of non-human primate CNS tissues identified high performing AAV variants exhibiting transduction superior to parental wild type serotypes. A subset of these top performing variants was selected for further evaluation based on their performance across different metrics, including enrichment in both DNA and RNA analyses. A summary of the variant performance for this subset is shown in FIGS. 29A-29D. The analysis shows the parent serotype as well as the fold enrichment in tissue observed after selection in non-human primate. Also shown is the peptide sequence of the peptide inserted into the capsid loop. The variants are numbered 1-43 (SEQ ID Nos.: 68-110, see Table 12) and this numbering is used to annotate their performance relative to the rest of the library in the bubble plots in FIGS. 19 through 28. In some embodiments, the inserted peptide and AAV parent serotype may be any one of those set forth in Table 12.

apsin1) driving expression of the EGFP-H2B transgene and a unique barcode nucleotide sequence. A second RNA polymerase III promoter (e.g. hU6) was also included to provide an independent assessment of vector performance. The hU6 promoter is ubiquitously expressed in all cell types and therefore enables assessment of expression in all cell and tissue types. Moreover, the hU6 transcript is restricted to the nucleus, an advantage for single nuclei sequencing

TABLE 12

| No. | Inserted Peptide Sequence | AAV parent serotype | SEQ ID NO | No | Inserted Peptide Sequence | AAV parent serotype | SEQ ID NO |
|---|---|---|---|---|---|---|---|
| 1 | AALRDIR | AAV1 | 68 | 23 | MTLTRQE | AAV2 | 90 |
| 2 | PAIKTYS | AAV1 | 69 | 24 | TSNSRTE | AAV2 | 91 |
| 3 | TGDRISSRTL | AAV1 | 70 | 25 | EVRGGPS | AAV2 | 92 |
| 4 | SVVVSSDSSKRPRNL | AAV1 | 71 | 26 | VISDRSS | AAV2 | 93 |
| 5 | VGARLSA | AAV1 | 72 | 27 | PRDTFNG | AAV2 | 94 |
| 6 | IEKPNTSTKK | AAV1 | 73 | 28 | RPLTAND | AAV2 | 95 |
| 7 | DTVRSKN | AAV1 | 74 | 29 | PLRMVNE | AAV2 | 96 |
| 8 | KELNKAR | AAV1 | 75 | 30 | DVGIRPS | AAV2 | 97 |
| 9 | PYASITG | AAV3B | 76 | 31 | KDSTAFG | AAV2 | 98 |
| 10 | TGAFSST | AAV3B | 77 | 32 | YPGRNPD | AAV2 | 99 |
| 11 | EQFRNLA | AAV3B | 78 | 33 | ISDTRIS | AAV2 | 100 |
| 12 | FNSPVIQ | AAV3B | 79 | 34 | ENFSKVA | AAV2 | 101 |
| 13 | TDFRSPQ | AAV3B | 80 | 35 | RDALSGLRPE | AAV2 | 102 |
| 14 | MYSLMKD | AAV3B | 81 | 36 | LGNGKMTVQP | AAV2 | 103 |
| 15 | LYLSSAS | AAV3B | 82 | 37 | VSNPLNQ | AAV2 | 104 |
| 16 | YGSRSVD | AAV3B | 83 | 38 | LNERGLG | AAV2 | 105 |
| 17 | LYSHQVS | AAV3B | 84 | 39 | GRNTVGLSSA | AAV2 | 106 |
| 18 | ISTHSPP | AAV3B | 85 | 40 | VGHAGNP | AAV2 | 107 |
| 19 | RQPTTIP | AAV9 | 86 | 41 | SRAGTVP | AAV2 | 108 |
| 20 | RSTSSLL | AAV9 | 87 | 42 | GLVAKLP | AAV2 | 109 |
| 21 | FRLSSPQ | AAV9 | 88 | 43 | AESLRTP | AAV2 | 110 |
| 22 | NIPKAYG | AAV9 | 89 | | | | |

Figure 30:
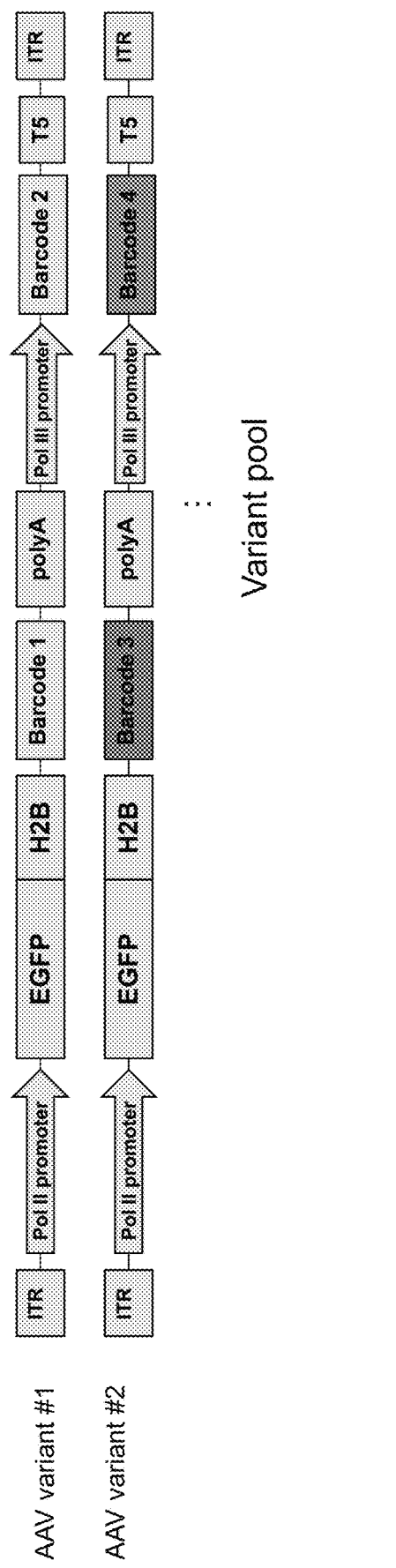
FIG. 30 is a schematic of the vector genome cassette employed for pooled evaluation of barcoded AAV variants. The cassette contains an RNA polymerase II promoter to quantify expression of barcoded transcripts in a target cell population, for example neurons or hepatocytes. In addition, there is an RNA polymerase III promoter (e.g. hU6) which drives ubiquitous expression in all cell types. The combination of these promoters enables ranking of AAV variant transduction in both an individual targeted cell type and bulk tissue.

Example 4: Evaluation of Top Performing AAV Variants Identified in Library Screens After two rounds of selection in non-human primate a subset of highly enriched variants was identified in liver and CNS tissues (FIGS. 18 and 29 respectively). Rather than proceeding directly to individual evaluation of just one or two variants, we instead generated a barcoded expression cassette to enable head-to-head comparison of dozens of the top performing variants in liver and CNS. In this approach the barcodes linked to each AAV are known with certainty because each AAV variant is manufactured and titered separately prior to pooling. Each AAV is manufactured with a vector genome (FIG. 30) containing a cell-type specific RNA polymerase II promoter (e.g. transthyretin or hSyn-approaches. All barcodes listed in Table 13 were designed computationally to minimize the potential for transcriptional bias.

TABLE 13

Unique barcodes used for pooled AAV variant evaluation

| Cassette No. | RNA polymerase II barcode | SEQ ID NO: | RNA polymerase III barcode | SEQ ID NO: |
|---|---|---|---|---|
| 1 | AAATCACCTGAC | 111 | CTTGTCGATAAG | 155 |
| 2 | TGATTCTTCTAC | 112 | GTGGTAAGCACG | 156 |

TABLE 13-continued

Unique barcodes used for pooled AAV variant evaluation

| Cassette No. | RNA polymerase II barcode | SEQ ID NO: | RNA polymerase III barcode | SEQ ID NO: |
|---|---|---|---|---|
| 3 | GGCCACTGGTTG | 113 | AACTGGCTCCCA | 157 |
| 4 | AATCTATCGCCT | 114 | TGCGATCGTACA | 158 |
| 5 | AGACGATCAAGG | 115 | CAGAGGATAGCT | 159 |
| 6 | GTGTAGTGATCG | 116 | GAGGAGTCTCAT | 160 |
| 7 | TGGTAGTTTCCA | 117 | AGTTCCCACGGA | 161 |
| 8 | GATCAGTTGCGG | 118 | CCCTTCAGCAGT | 162 |
| 9 | CTTGGGACACAC | 119 | CGTACTCCGCGA | 163 |
| 10 | GATGCGGCCTCG | 120 | TCACCGACGTGG | 164 |
| 11 | CGCATCCTCGTT | 121 | CAACGGTCTTCC | 165 |
| 12 | ACGATGTCTACG | 122 | GTAACAGTCCGG | 166 |
| 13 | GTGTTCCACCTG | 123 | GTCGAGGATACC | 167 |
| 14 | GGAGGGAGCTGG | 124 | TGCGATGTGATG | 168 |
| 15 | CATAACTCTTGC | 125 | TAACCCGCCGAA | 169 |
| 16 | TGACAGTCTCGC | 126 | CGACCAACGACA | 170 |
| 17 | CTACCAGGATTC | 127 | CTGCTGCCATCA | 171 |
| 18 | ACACATGATGGC | 128 | CTAGTACACGCG | 172 |
| 19 | GGTGCTCGCAAT | 129 | TAGGTGCTAGTG | 173 |
| 20 | GATTGCACCGCA | 130 | TCCTCCCAGGAT | 174 |
| 21 | AACGGAGGCTGC | 131 | TAGGCGGCATTA | 175 |
| 22 | GGGAGAGTTCCG | 132 | CTTAGGCTAGCT | 176 |
| 23 | CGGGTAGCCGAA | 133 | CGACGTGCGATA | 177 |
| 24 | TGACCTAATTGG | 134 | ACCATTCCATCG | 178 |
| 25 | GGGTGAAGGATT | 135 | TGGAAAGGCCTA | 179 |
| 26 | CTGTGAGAGAAG | 136 | GGGAACATTGGA | 180 |
| 27 | ACTTGGTTCCGC | 137 | AAGTGAACGCGC | 181 |
| 28 | GTTGGCTGTACC | 138 | AGCAACGTTGTA | 182 |
| 29 | TGTAAGCTGTAG | 139 | AAGTGACGGACC | 183 |
| 30 | AGCTACCCTGGA | 140 | AGTAACGCCCGT | 184 |
| 31 | CCAAACAAGCGT | 141 | TGGGCTATGACA | 185 |
| 32 | GCTTGCCCATCC | 142 | CTGCAGTGAAGT | 186 |
| 33 | CATTCCGGGTTA | 143 | ATTCTGTTCGCA | 187 |
| 34 | CTTTGCCGGTAC | 144 | CTTCCTCACCTC | 188 |
| 35 | CATCAACTGTGC | 145 | GAGAGTCGAAAC | 189 |
| 36 | GCACAGCCGAAT | 146 | AGTCGTGAATCG | 190 |
| 37 | ATGCATCGGTCA | 147 | GGTGACAACAAT | 191 |
| 38 | GAACCAGAATGC | 148 | GCCTAGTAGCAT | 192 |
| 39 | CGGACGGTATGG | 149 | ACAGAAGCGCCT | 193 |
| 40 | TCCTATGAACAA | 150 | CTAGTTGAGTTC | 194 |
| 41 | TGGGAGTAGAGG | 151 | AAGTTCAGGATA | 195 |
| 42 | GCTCAACGATCG | 152 | TTGCCTCTATTC | 196 |
| 43 | GGACTAGGATAT | 153 | TGAACGTCTAAG | 197 |
| 44 | CCATTGTGGGAA | 154 | CGCTATCACGCA | 198 |

Figure 19:
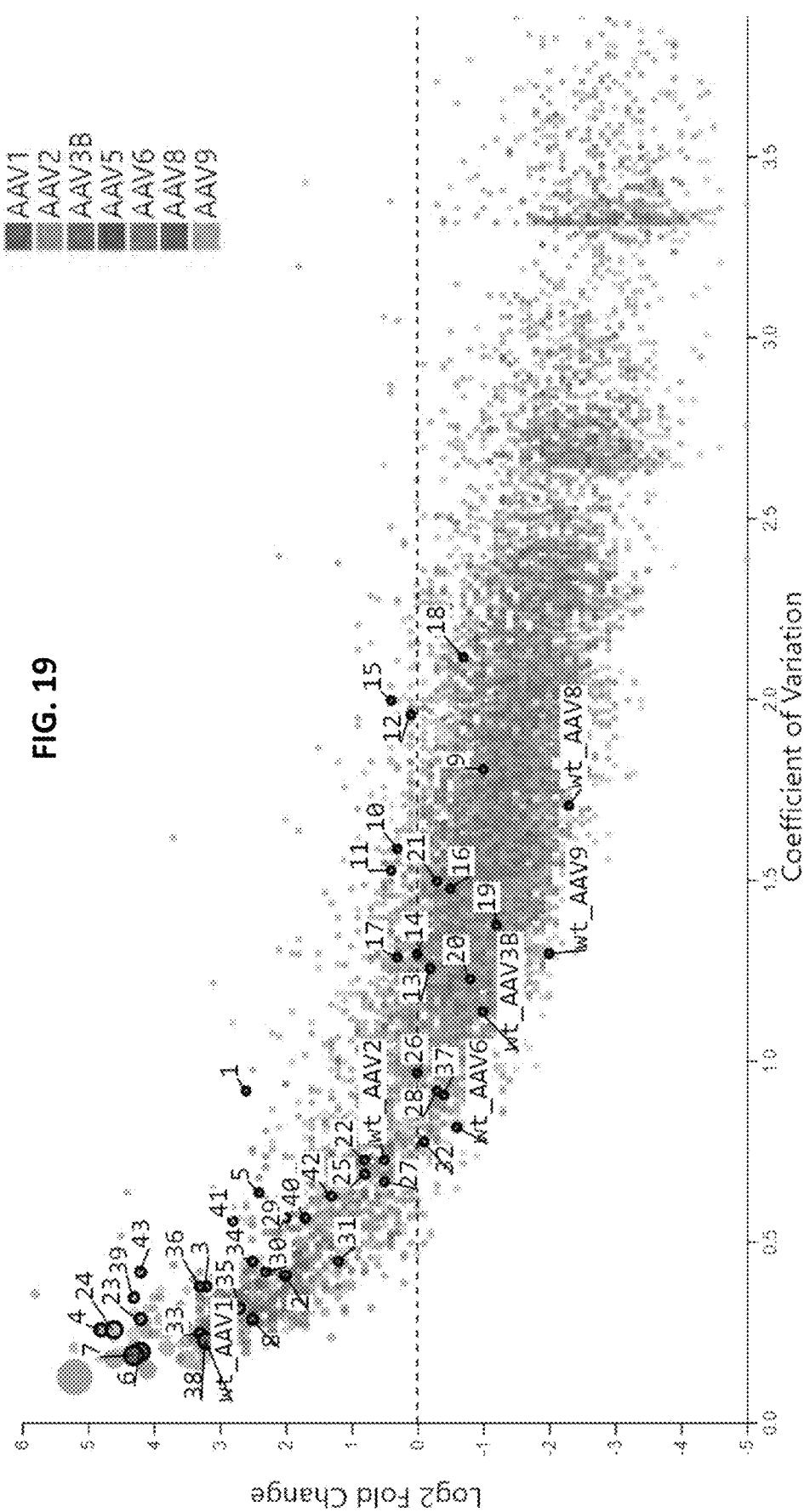
FIG. 19 is a bubble plot of the AAV library variants recovered after infection of Neuro2A cells. The log 2 fold change represents the change in variant frequency after infection and recovery of transcripts expressed in transduced Neuro2A cells as compared with the variant frequency in the administered library. The performance of wild type serotypes is indicated as well as that for variants 1-43 (SEQ ID NO: 68-110) listed in FIGS. 29A-D.
Figure 20:
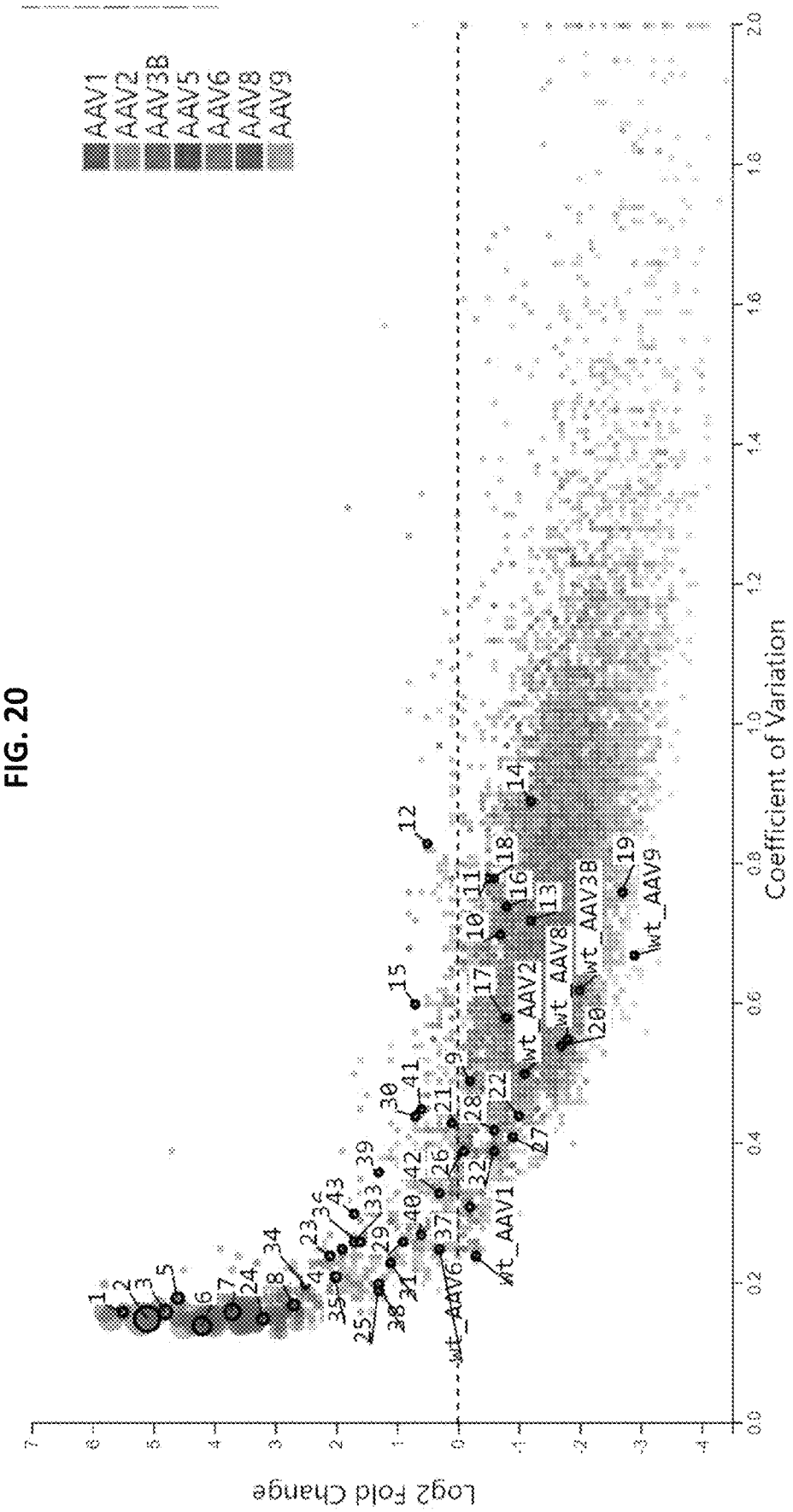
FIG. 20 is a bubble plot of the AAV library variants recovered after infection of primary mouse cortical neurons. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29A-D.
Figure 21:
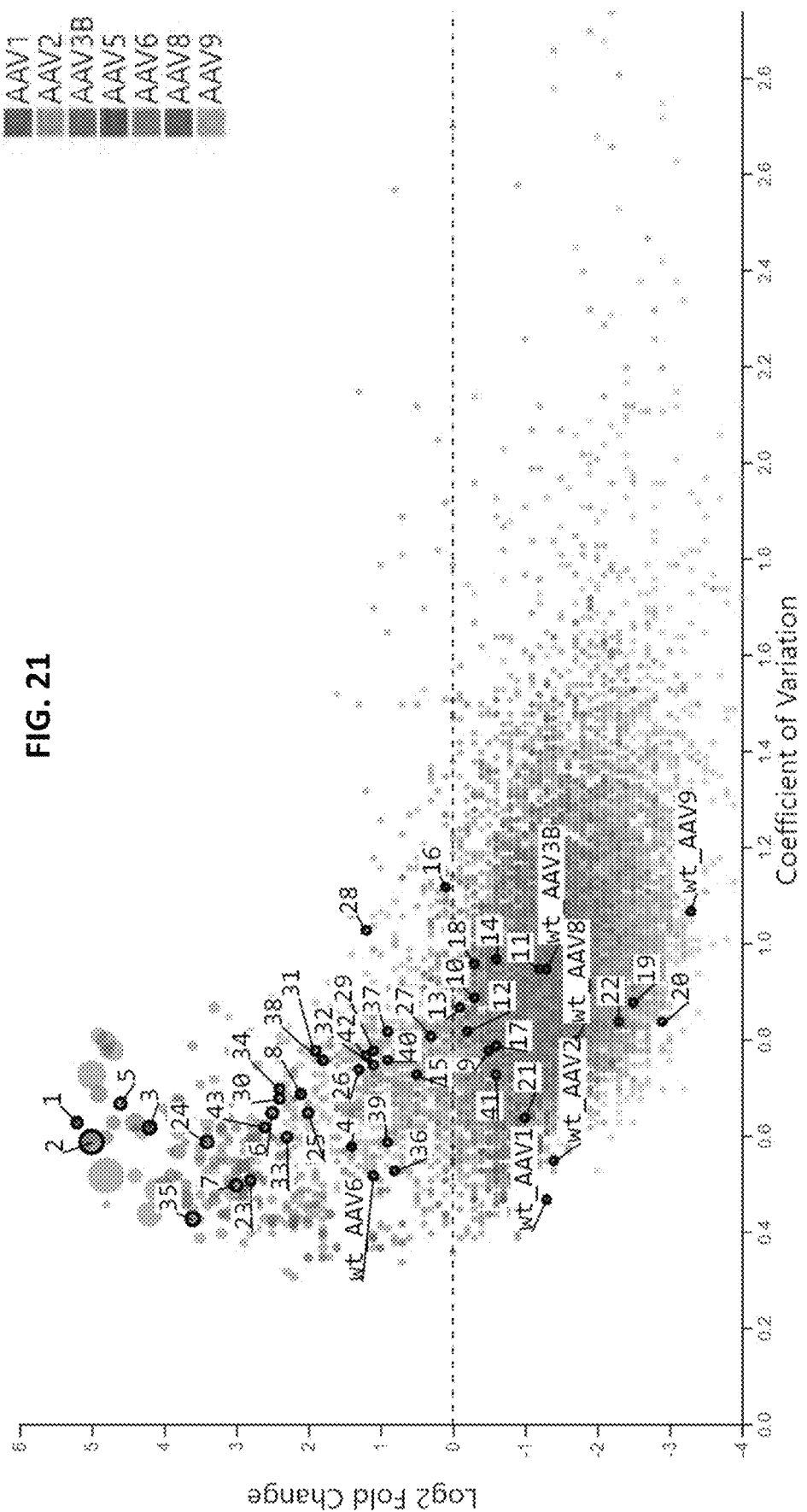
FIG. 21 is a bubble plot of the AAV library variants recovered after infection of iCell human neurons derived from human induced pluripotent stem cells. The log 2 fold change represents the change in variant frequency after infection and recovery of transcripts expressed in transduced neurons as compared with the variant frequency in the administered library. The performance of wild type serotypes is indicated as well as that of variants 1-43 (SEQ ID NO: 68-110) listed in FIG. 29A-D.
Figure 31:
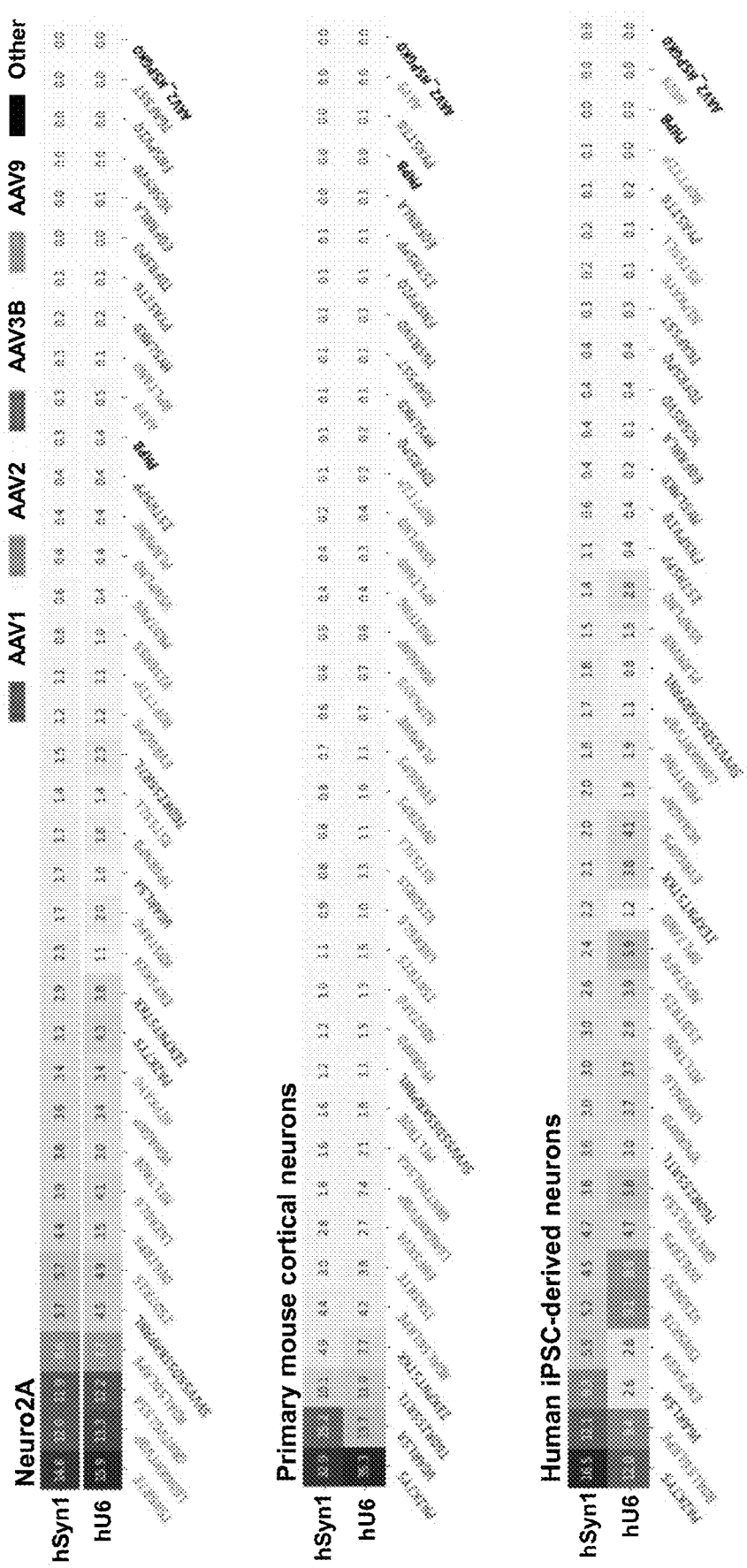
FIG. 31 shows the results of a pooled evaluation of a subset of the AAV variants in FIGS. 29A-D (variants 2, 3, 4, 5, 6, 9, 10, 11, 12, 13, 14, 16, 18, 19, 20, 22, 23, 24, 25, 26, 27, 28, 29, 30, 31, 32, 33, 34, 35, 36, 37, 38, 39, 40, 49). Control serotypes include wild-type AAV9, PHP.B, and AAV2_HSPGKO. The barcoded AAV variants were evaluated in vitro in Neuro2A cells (ATCC CCL-131), primary mouse cortical neurons (Gibco), and iCell human neurons derived from human induced pluripotent stem cells. The AAV expression cassette described in FIG. 30 was employed for the pooled evaluation and the distinct barcode quantifications from the pol II neuron-specific hSyn1 promoter and the pol III hU6 ubiquitous promoter were labeled. The values in the heat maps represent the percentage of NGS reads derived from each AAV variant and are rounded to the nearest tenth of a percent. These results were normalized by the frequency of each AAV variant in the pool that was used for infection. The parental serotype of each AAV variant is colored according to the accompanying figure legend.

An example of the application of this expression cassette to evaluate a subset of high performing CNS-tropic AAV variants (listed in FIG. 29A-D) identified from library screening is shown in FIG. 31. In addition to the engineered serotypes developed in this work several control serotypes were included: AAV9, PHP.B, and AAV2_HSPGKO. AAV9 has been evaluated extensively in the field for its CNS transduction properties including in human clinical trials (Lowes et al. Pediatr Neurol. 2019; 98:39-45), accordingly it is the primary benchmark for performance. PHP.B is an engineered AAV9 serotype that was previously shown to exhibit high potency in C57BL/6J mice (Deverman et al. Nat Biotechnol. 2016; 34(2):204-9), these properties do not extend to non-human primates (Hordeaux et al. Mol Ther. 2018 March; 26(3):664-668). AAV2_HSPGKO is a variant of AAV2 with two mutations (R585A and R588A) that abolish binding to heparan sulfate proteoglycan (HSPG) (Opie et al. Virol. 2003 June; 77(12):6995-7006). This serotype has also been previously evaluated in non-human primates (Naidoo et al. Mol Ther. 2018 Oct. 3; 26(10):2418-2430). In this experiment, barcoded AAV variants were evaluated in vitro in Neuro2A cells, primary mouse cortical neurons, and iCell human neurons derived from human induced pluripotent stem cells. Virus was produced in HEK293T cells, purified using a CsCl density-gradient, and titered by real time qPCR according to methods known in the art. Each individually manufactured and barcoded virus was then mixed together to form a single pool for downstream evaluation and the frequency of each variant in this pool was assessed by next-generation sequencing (NGS). The vector genome cassette described in FIG. 30 was employed for the pooled evaluation to enable distinct barcoded transcript quantifications from the hSyn1 pol II promoter and the hU6 pol III promoter. The barcoded virus pool was used to infect cells at $3 \times 10^5$, $1 \times 10^5$, $3 \times 10^4$, $1 \times 10^4$, $3 \times 10^3$, and $1 \times 10^3$ vector genome copies per cell. After either 72 hours (Neuro2A), 48 hours (primary mouse cortical neurons), or 96 hours (hiPSC derived human neurons) total RNA was extracted and AAV transcripts were reverse transcribed using gene specific primers targeting the hSyn1 and hU6 transcripts respectively. Next-generation sequencing was then applied to quantify the percentage of NGS reads derived from each AAV variant. These percentages were normalized by the frequency of each AAV variant in the pool that was used for infection. The results show a distribution of performance with several AAV variants based on AAV1 and AAV2 exhibiting high performance across all three cell types. Generally, the performance of AAV variants based on AAV3B was lower. The observed trends in variant performance were successfully predicted by the round 2 library data obtained in the same cell types (FIGS. 19, 20, 21). In addition, these data show the successful application of the dual pol II hSyn1 and pol III hU6 barcode measurement approach. In homogeneous cell lines like Neuro2A, the agreement between the hSyn1 and hU6 measurements is high. In primary mouse cortical neurons and hiPSC derived neurons there is a greater heterogeneity of neuronal subtypes, leading to a greater divergence in the two measurements. However, generally the two measurements are still correlated.

Figure 32:
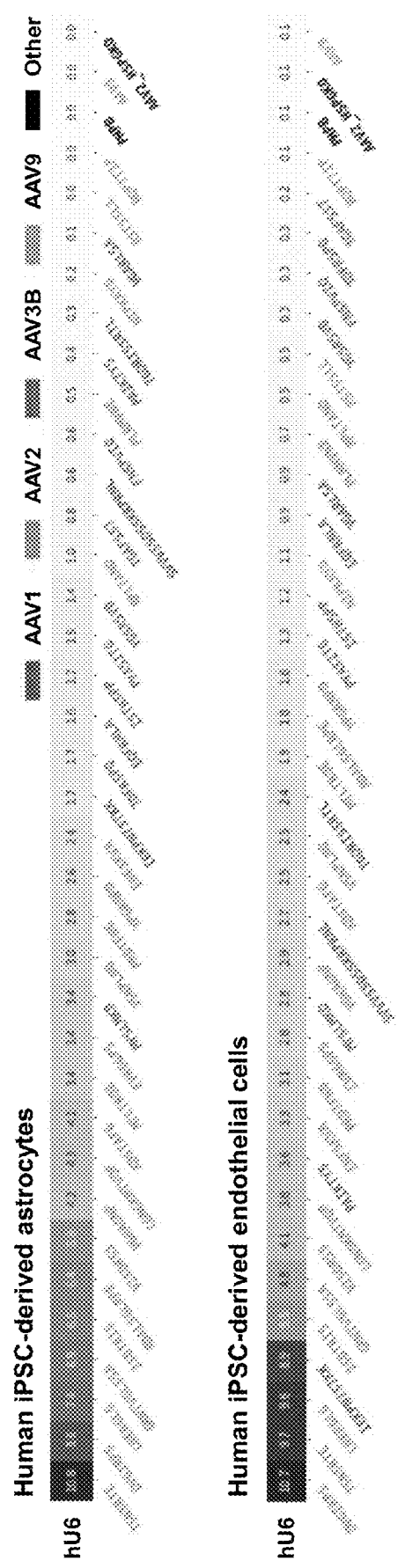
FIG. 32 shows the evaluation of the barcoded AAV variants (variants 2, 3, 4, 5, 6, 9, 10, 11, 12, 13, 14, 16, 18, 19, 20, 22, 23, 24, 25, 26, 27, 28, 29, 30, 31, 32, 33, 34, 35, 36, 37, 38, 39, 40, 49) and control serotypes wild-type AAV9, PHP.B, and AAV2_HSPGKO in vitro in iCell human astrocytes and endothelial cells derived from human induced pluripotent stem cells. The vector genome expression cassette described in FIG. 30 was employed for the pooled evaluation, data are presented for the pol III hU6 ubiquitous promoter, hSyn1 barcode measurements were not performed because the promoter has minimal activity in non-neuronal cell types. The values in the heat maps represent the percentage of NGS reads derived from each AAV variant and are rounded to the nearest tenth of a percent. These results were normalized by the frequency of each AAV variant in the pool that was used for infection. The parental serotype of each AAV variant is colored according to the accompanying figure legend.

Example 5: In Vitro Evaluation of CNS-Tropic Variants for Transduction of Non-Neuronal Cells The same subset of CNS-tropic AAV variants and controls were evaluated for transduction of non-neuronal cell types in vitro (FIG. 32). In this experiment, barcoded AAV variants were evaluated for transduction of iCell human astrocytes derived from human induced pluripotent stem cells and iCell human endothelial cells derived from human induced pluripotent stem cells. The identical AAV barcoded pool test article and methodology described above in Example 4 was used with the following specifications. For evaluation in hiPSC-derived astrocytes $3\times10^5$, $1\times10^5$, $3\times10^4$, $1\times10^4$, $3\times10^3$, and $1\times10^3$ vector genome copies per cell were used for infection. For evaluation in hiPSC-derived endothelial cells $3\times10^5$, $1\times10^5$, and $3\times10^4$ vector genome copies per cell were used for infection. Both the astrocytes and endothelial cells were harvested 72 hours post-infection. Total RNA was extracted and AAV transcripts were reverse transcribed using gene specific primers targeting the hU6 transcript, the hSyn1 transcript was not probed because the hSyn1 promoter has minimal activity in non-neuronal cell types. Next-generation sequencing was then applied to quantify the percentage of NGS reads derived from each AAV variant. These percentages were normalized by the frequency of each AAV variant in the pool that was used for infection. In hiPSC-derived astrocytes the results show a distribution of performance with several AAV variants based on AAV2 exhibiting high performance. Generally, the performance of AAV variants based on AAV1 and AAV9 was lower. In hiPSC-derived endothelial cells the results show a distribution of performance with several AAV variants based on AAV1 and AAV2 exhibiting high performance. Generally, the performance of AAV variants based on AAV3B and AAV9 was lower.

Example 6: In Vivo Evaluation of CNS-Tropic AAV Variants in Mice and Rats

Figure 33:
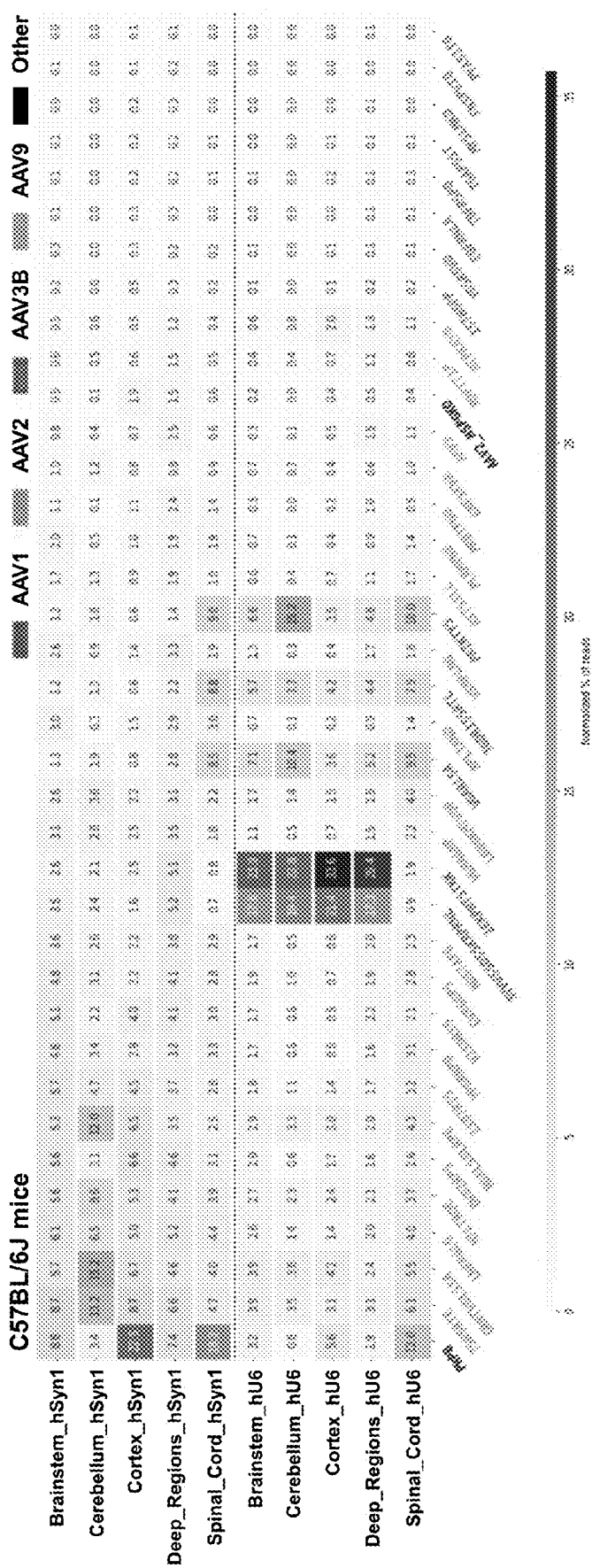
FIG. 33 shows the evaluation of the barcoded AAV variants (variants 2, 3, 4, 5, 6, 9, 10, 11, 12, 13, 14, 16, 18, 19, 20, 22, 23, 24, 25, 26, 27, 28, 29, 30, 31, 32, 33, 34, 35, 36, 37, 38, 39, 40, 49) and control serotypes wild-type AAV9, PHP.B, and AAV2_HSPGKO in vivo after unilateral intracerebroventricular administration in C57BL/6J mice. Data are aggregated according to the following CNS regions: brainstem (brainstem, midbrain), cerebellum, cortex (motor cortex, sensory cortex, rest of cortex), deep brain regions (hippocampus, hypothalamus, striatum, thalamus) and spinal cord (cervical, thoracic, and lumbar). The AAV expression cassette described in FIG. 30 was employed for the pooled evaluation and the distinct barcode quantifications from the pol II neuron-specific hSyn1 promoter and the pol III hU6 ubiquitous promoter are labeled. The values in the heat maps represent the percentage of NGS reads derived from each AAV variant and are rounded to the nearest tenth of a percent. These results were normalized by the frequency of each AAV variant in the pool that was administered. The parental serotype of each AAV variant is colored according to the accompanying figure legend.
Figure 34:
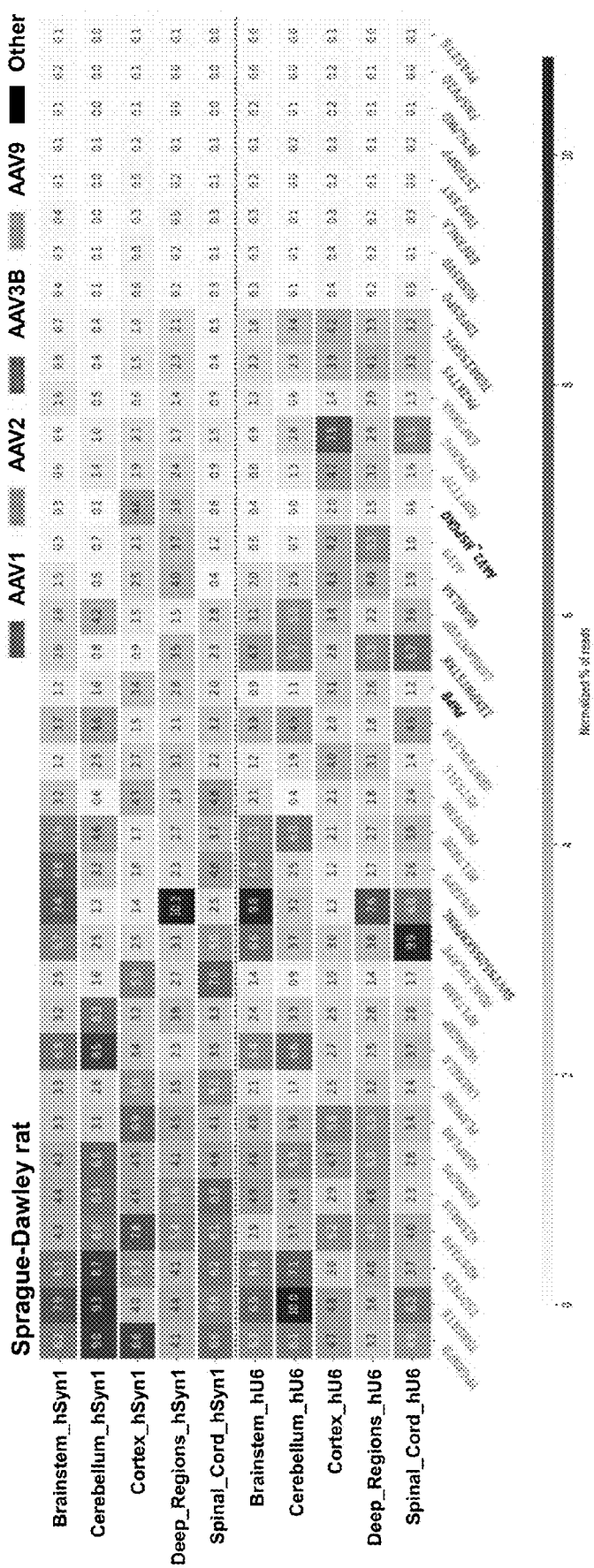
FIG. 34 shows the evaluation of the barcoded AAV variants (variants 2, 3, 4, 5, 6, 9, 10, 11, 12, 13, 14, 16, 18, 19, 20, 22, 23, 24, 25, 26, 27, 28, 29, 30, 31, 32, 33, 34, 35, 36, 37, 38, 39, 40, 49) and control serotypes wild-type AAV9, PHP.B, and AAV2_HSPGKO in vivo after unilateral intracerebroventricular administration in Sprague-Dawley rats. Data are aggregated according to the following CNS regions: brainstem (brainstem, midbrain), cerebellum, cortex (motor cortex, sensory cortex, rest of cortex), deep brain regions (hippocampus, hypothalamus, striatum, thalamus) and spinal cord (cervical, thoracic, and lumbar). The AAV expression cassette described in FIG. 30 was employed for the pooled evaluation and the distinct barcode quantifications from the pol II neuron-specific hSyn1 promoter and the pol III hU6 ubiquitous promoter are labeled. The values in the heat maps represent the percentage of NGS reads derived from each AAV variant and are rounded to the nearest tenth of a percent. These results were normalized by the frequency of each AAV variant in the pool that was administered. The parental serotype of each AAV variant is colored according to the accompanying figure legend.

The same subset of CNS-tropic AAV variants was further evaluated for transduction of the central nervous system in C57BL/6J mice and Sprague-Dawley rats in vivo (FIGS. 33 and 34). Transduction in rodents was assessed in order to complete a thorough evaluation of AAV performance across species that are commonly used for the development of therapeutics. For evaluation in C57BL/6J mice 1E11 vector genomes in a volume of 10 microliters was administered by unilateral intracerebroventricular injection into the left lateral ventricle (n=3 males and n=3 females). For evaluation in Sprague-Dawley rats 2E11 vector genomes in a volume of 20 microliters was administered by unilateral intracerebroventricular injection into the left lateral ventricle (n=3 males and n=3 females). Animals were sacrificed 32 days after administration of the test article and CNS tissues were dissected. Analysis was completed on brain regions contralateral to the injected hemisphere to avoid confounding from transduction associated with the injection tract. Total RNA was extracted from CNS tissues and AAV transcripts were reverse transcribed using gene specific primers targeting the hSyn1 and hU6 transcripts respectively. Next-generation sequencing was then applied to quantify the percentage of NGS reads derived from each AAV variant. These percentages were normalized by the frequency of each AAV variant in the pool that was administered.

In C57BL/6J mice the hSyn1 barcode measurements of transcripts expressed in neuronal cells show a distribution of performance with many AAV variants based on peptide insertions into AAV1 and AAV2 disclosed herein exhibiting high performance relative to the AAV9 benchmark. As expected, the PHP.B control serotype is high performing in C57BL/6J mice. Generally, the performance of AAV variants based on AAV9 and AAV3B was lower. In C57BL/6J mice, the hU6 barcode measurements of transcripts expressed in all cell types show a distribution of performance with many AAV variants based on peptide insertions into AAV2 and especially AAV1 disclosed herein exhibiting high performance relative to the AAV9 benchmark. Generally, the performance of AAV variants based on AAV9 and AAV3B was lower. FIG. 33.

In Sprague-Dawley rats the hSyn1 barcode measurements of transcripts expressed in neuronal cells show a distribution of performance with many AAV variants based on peptide insertions into AAV1 and AAV2 disclosed herein exhibiting high performance relative to the AAV9 benchmark. As expected, the PHP.B control serotype performs worse in Sprague-Dawley rats than it does in C57BL/6J mice. Generally, the performance of AAV variants based on AAV9 and AAV3B was lower. In Sprague-Dawley rats the hU6 barcode measurements of transcripts expressed in all cell types shows a distribution of performance with many AAV variants based on peptide insertions into AAV1 and AAV2 disclosed herein exhibiting high performance relative to the AAV9 benchmark. Generally, the performance of AAV variants based on AAV9 and AAV3B was lower. FIG. 34.

Example 7: In Vivo Evaluation of CNS-Tropic AAV Variants in Non-Human Primates

We next further evaluated the same subset of CNS-tropic AAV variants for transduction of the central nervous system in non-human primates (cynomolgus macaques) in vivo. Among the various evaluations described above, assessment of transduction in cynomolgus macaques is of particular importance for clinical translation to humans since non-human primates best exemplify the genetics and physiology of the human CNS. The pool of AAV variants was administered intrathecally into one male and one female cynomolgus macaque at a dose of $5.2\times10^{13}$ vector genomes (vg) per animal. For intrathecal administration a threaded catheter was employed to deposit the test article closer to the brain at the cervical and thoracic levels. Animals were sacrificed 57 days after administration of the test article. The brain was sliced at a 3 mm coronal slice thickness. Each slice was hemisected along the mid-sagittal plane. Punch samples (3 mm) were obtained from the brain slices from the left hemisphere for analysis of AAV genomic DNA. The right hemisphere was placed in RNAlater and refrigerated for approximately 24 hours to preserve RNA integrity. After storage, 3 mm punches were collected sampling various brain regions. The spinal cord was divided into cervical, thoracic, and lumbar segments for analysis. Genomic DNA and total RNA were extracted separately from the CNS tissues and subsequent analyses are referred to as DNA analysis and RNA analysis respectively. For DNA analysis, each of the unique barcodes, hSyn1 and hU6, was amplified separately by PCR. Next-generation sequencing was applied to quantify the percentage of NGS reads derived from each AAV variant. Note that for DNA analysis there is no cellular restriction provided by the promoters, therefore, the hSyn1 and hU6 barcodes are expected to amplify with equal likelihood. For RNA analysis, AAV transcripts were reverse transcribed using gene specific primers targeting the hSyn1 (neuronal) and hU6 (all cell types) transcripts respectively. Next-generation sequencing was then applied to quantify the percentage of NGS reads derived from each AAV variant. For both DNA and RNA analyses, these percentages were normalized by the frequency of each AAV variant in the pool that was administered.

Figure 35:
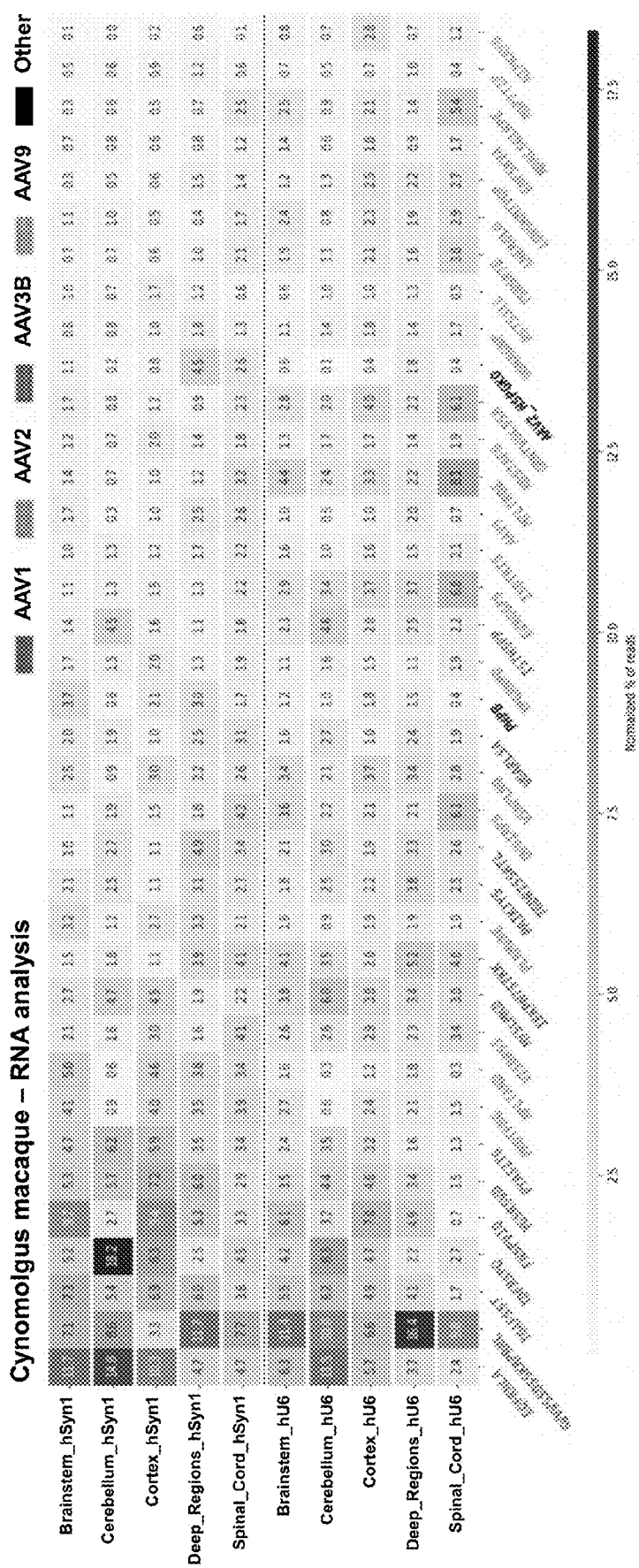
FIG. 35 shows the evaluation of the barcoded AAV variants (variants 2, 3, 4, 5, 6, 9, 10, 11, 12, 13, 14, 16, 18, 19, 20, 22, 23, 24, 25, 26, 27, 28, 29, 30, 31, 32, 33, 34, 35, 36, 37, 38, 39, 40, 49) and control serotypes wild-type AAV9, PHP.B, and AAV2_HSPGKO in vivo after intrathecal administration in non-human primates (cynomolgus macaques). Data shown are from analysis of total RNA isolated from NHP tissues. The data are aggregated according to the following CNS regions: brainstem (medulla, midbrain, pons, substantia nigra), cerebellum (cerebellum, cerebellar vermis), cortex (entorhinal cortex, frontal cortex, fronto-orbital gyrus, fusiform gyrus, lateral orbital gyrus, medial orbital gyrus, motor cortex, parahippocampal gyrus, parietal cortex, parietal-visual cortex, posterior cingulate gyrus, sensory cortex, somatosensory cortex, temporal cortex, visual cortex), deep brain regions (amygdala, caudate nucleus, hippocampus, hypothalamus, putamen, thalamus) and spinal cord (cervical, thoracic, and lumbar). The AAV expression cassette described in FIG. 30 was employed for the pooled evaluation and the distinct barcode quantifications from the pol II neuron-specific hSyn1 promoter and the pol III hU6 ubiquitous promoter are labeled. The values in the heat maps represent the percentage of NGS reads derived from each AAV variant and are rounded to the nearest tenth of a percent. These results were normalized by the frequency of each AAV variant in the pool that was administered. The parental serotype of each AAV variant is colored according to the accompanying figure legend.
Figure 37:
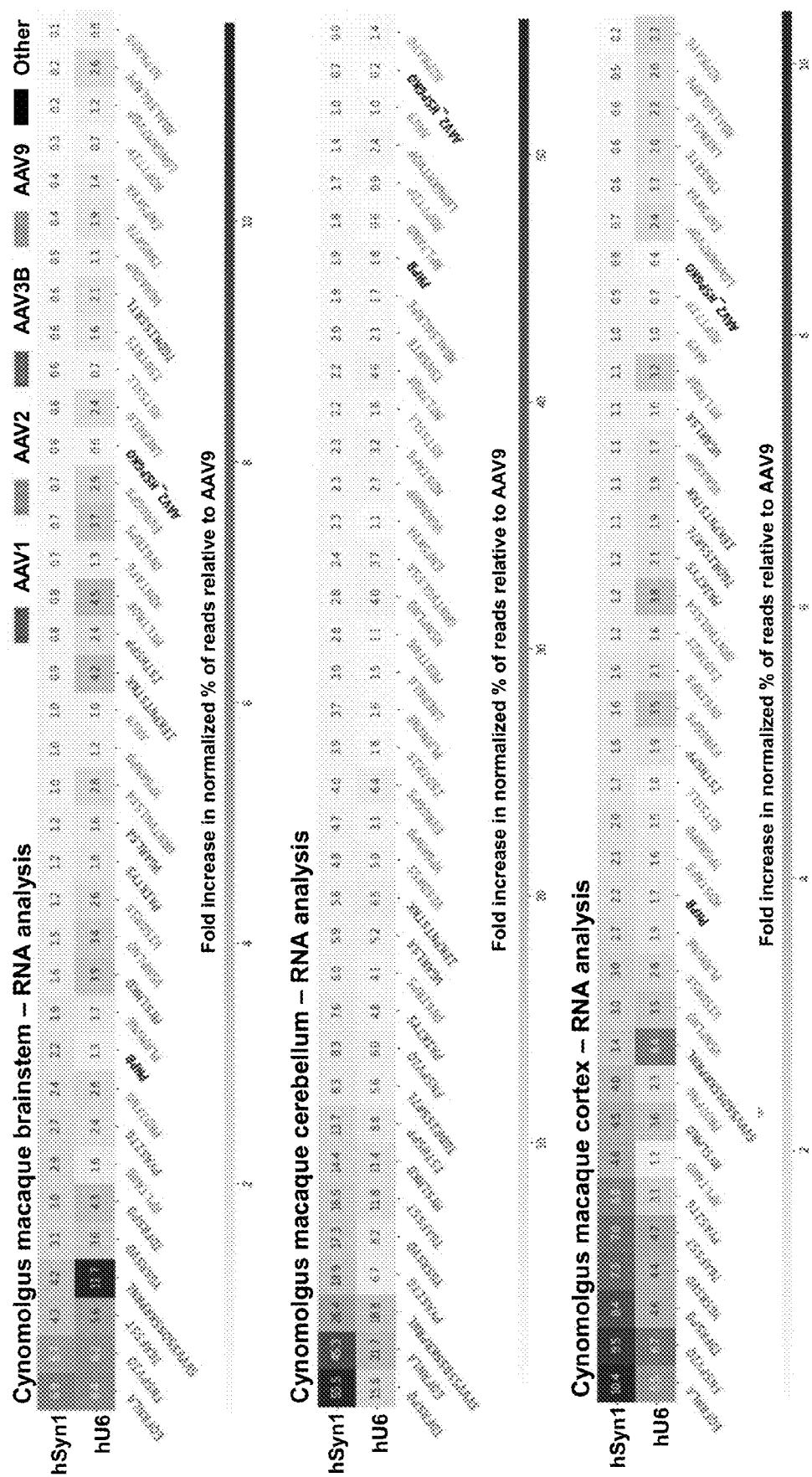
FIG. 37 shows the evaluation of the barcoded AAV variants and control serotypes wild-type AAV9, PHP.B, and AAV2_HSPGKO in vivo after intrathecal administration in non-human primates (cynomolgus macaques). Data shown are from analysis of total RNA isolated from NHP tissues. The data are aggregated according to the following CNS regions: brainstem (medulla, midbrain, pons, substantia nigra), cerebellum (cerebellum, cerebellar vermis), and cortex (entorhinal cortex, frontal cortex, fronto-orbital gyrus, fusiform gyrus, lateral orbital gyrus, medial orbital gyrus, motor cortex, parahippocampal gyrus, parietal cortex, parietal-visual cortex, posterior cingulate gyrus, sensory cortex, somatosensory cortex, temporal cortex, visual cortex). The plotted results show the fold increase in the normalized percentage of reads for each serotype compared to wild-type AAV9.
Figure 38:
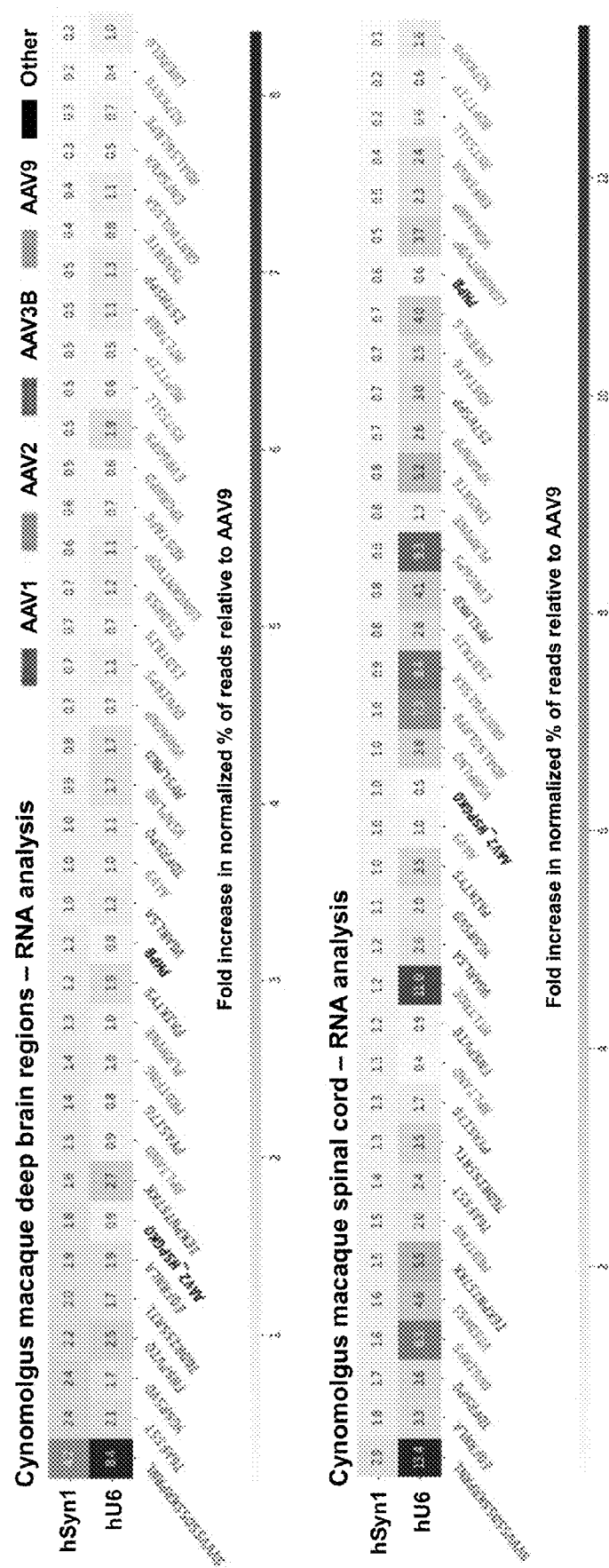
FIG. 38 shows the evaluation of the barcoded AAV variants and control serotypes wild-type AAV9, PHP.B, and AAV2_HSPGKO in vivo after intrathecal administration in non-human primates (cynomolgus macaques). Data shown are from analysis of total RNA isolated from NHP tissues. The data are aggregated according to the following CNS regions: deep brain regions (amygdala, caudate nucleus, hippocampus, hypothalamus, putamen, thalamus) and spinal cord (cervical, thoracic, and lumbar). The plotted results show the fold increase in the normalized percentage of reads for each serotype compared to wild-type AAV9.

In cynomolgus macaques, the RNA analysis results (FIG. 35), based on hSyn1 barcode measurements of transcripts expressed in neuronal cells, show a distribution of performance with many AAV variants based on peptide insertions into AAV3B, AAV2, and AAV1 disclosed herein exhibiting high performance relative to the AAV9 benchmark. Generally, the performance of AAV variants based on AAV9 was lower. In cynomolgus macaques, the hU6 barcode measurements of transcripts expressed in all cell types show a distribution of performance with many AAV variants based on peptide insertions into AAV3B, AAV2, and AAV1 disclosed herein exhibiting high performance relative to the AAV9 benchmark. Generally, the performance of AAV variants based on AAV9 was lower. Fold improvement of the serotypes disclosed herein compared to the AAV9 benchmark are plotted in FIGS. 37 and 38.

Figure 36:
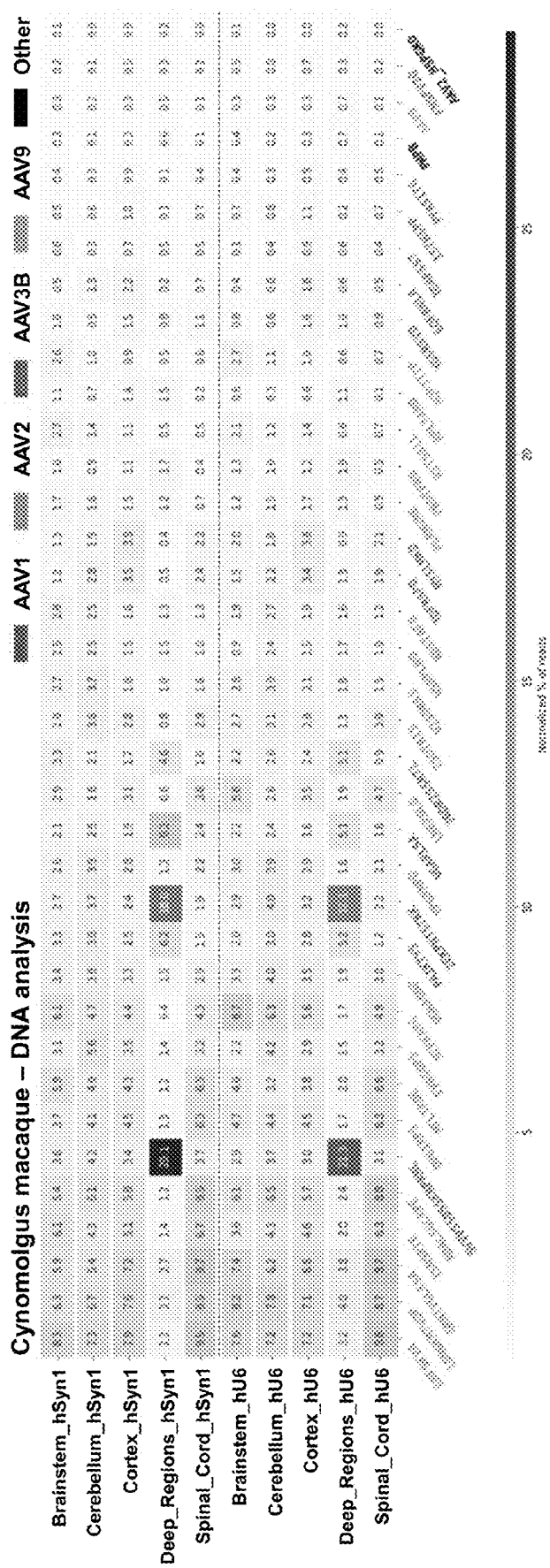
FIG. 36 shows the evaluation of the barcoded AAV variants and control serotypes wild-type AAV9, PHP.B, and AAV2_HSPGKO in vivo after intrathecal administration in non-human primates (cynomolgus macaques). Data shown are from analysis of genomic DNA isolated from NHP tissues. The data are aggregated according to the following CNS regions: brainstem (medulla, pons, substantia nigra), cerebellum, cortex (entorhinal cortex, frontal cortex, motor cortex, parietal cortex, somatosensory cortex, temporal cortex), deep brain regions (caudate nucleus, hippocampus, hypothalamus, putamen, thalamus) and spinal cord (cervical, thoracic, and lumbar). The AAV expression cassette described in FIG. 30 was employed for the pooled evaluation and the distinct barcode quantifications from the pol II neuron-specific hSyn1 promoter and the pol III hU6 ubiquitous promoter are labeled. The values in the heat maps represent the percentage of NGS reads derived from each AAV variant and are rounded to the nearest tenth of a percent. These results were normalized by the frequency of each AAV variant in the pool that was administered. The parental serotype of each AAV variant is colored according to the accompanying figure legend.
Figure 39:
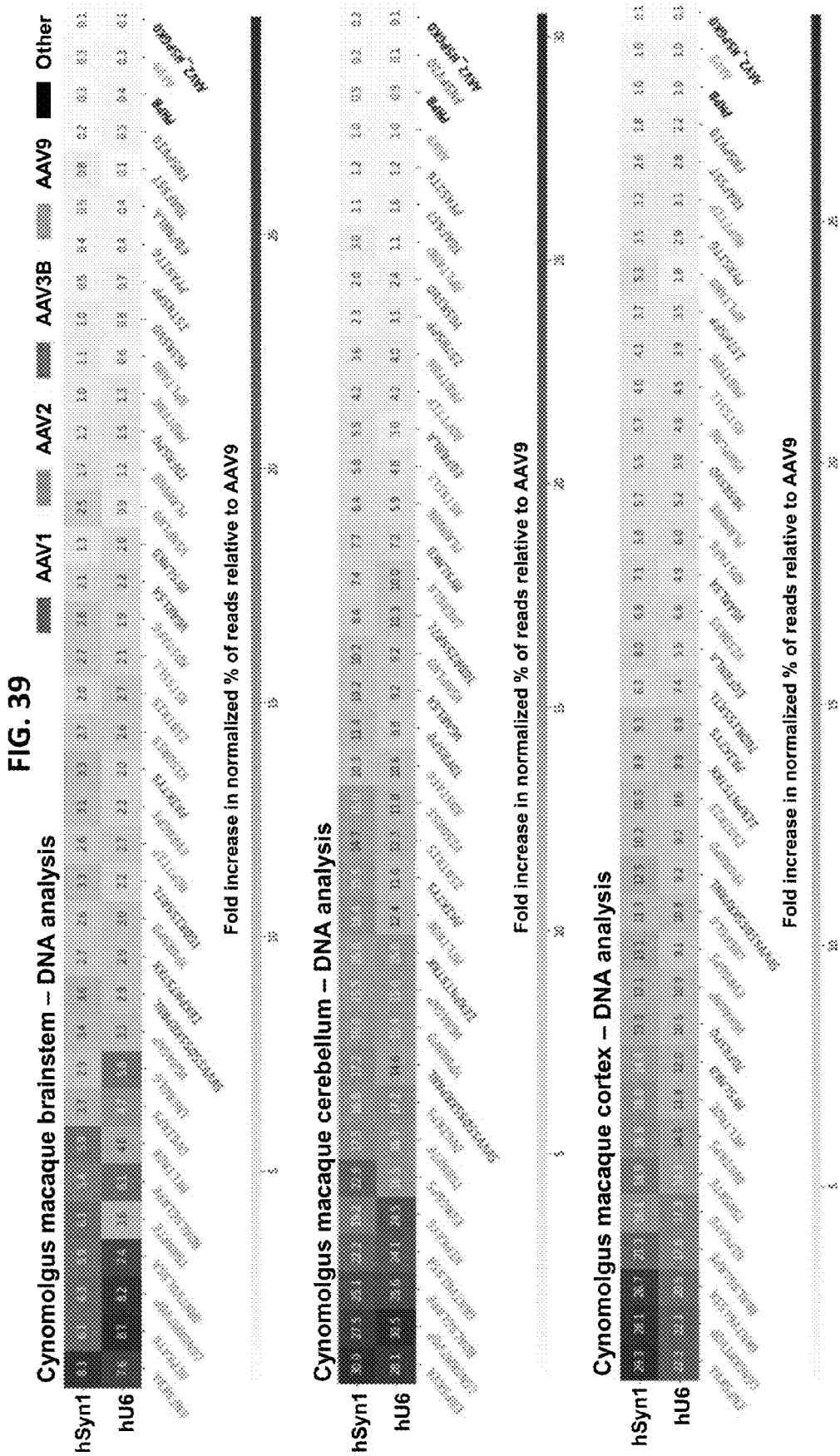
FIG. 39 shows the evaluation of the barcoded AAV variants and control serotypes wild-type AAV9, PHP.B, and AAV2_HSPGKO in vivo after intrathecal administration in non-human primates (cynomolgus macaques). Data shown are from analysis of genomic DNA isolated from NHP tissues. The data are aggregated according to the following CNS regions: brainstem (medulla, pons, substantia nigra), cerebellum, and cortex (entorhinal cortex, frontal cortex, motor cortex, parietal cortex, somatosensory cortex, temporal cortex). The plotted results show the fold increase in the normalized percentage of reads for each serotype compared to wild-type AAV9.
Figure 40:
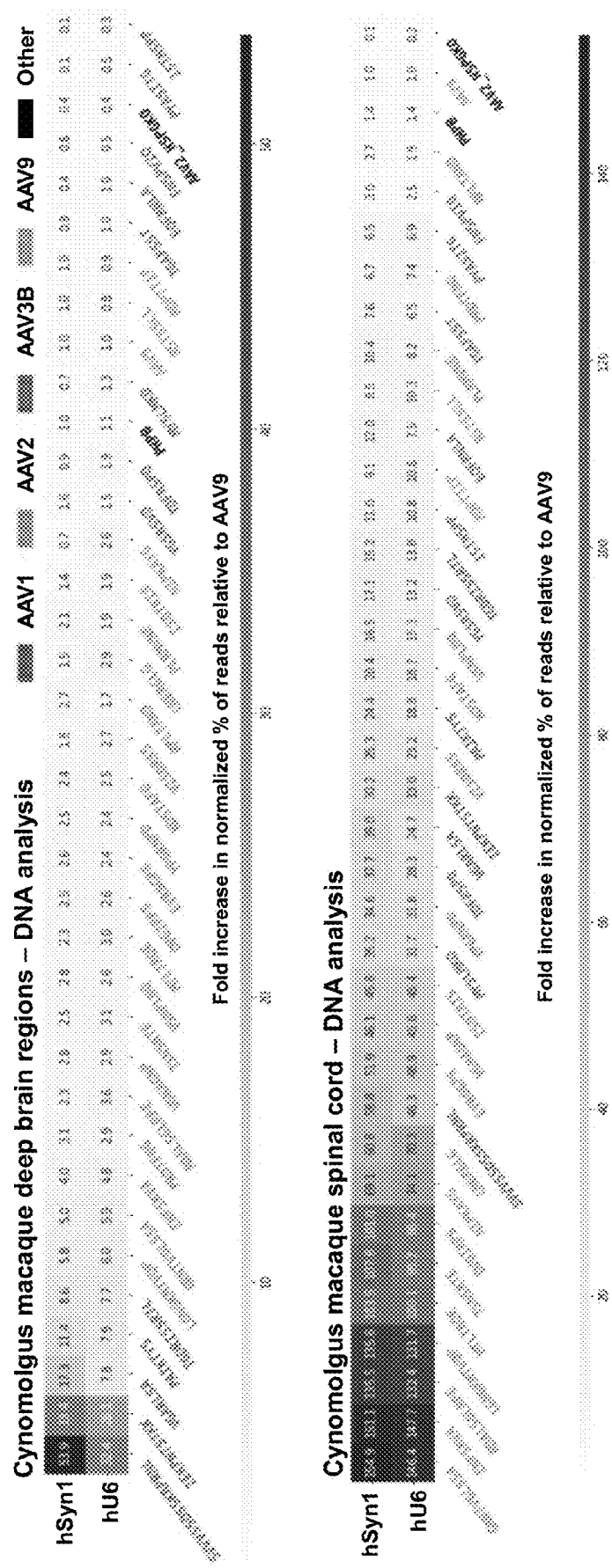
FIG. 40 shows the evaluation of the barcoded AAV variants and control serotypes wild-type AAV9, PHP.B, and AAV2_HSPGKO in vivo after intrathecal administration in non-human primates (cynomolgus macaques). Data shown are from analysis of genomic DNA isolated from NHP tissues. The data are aggregated according to the following CNS regions: deep brain regions (caudate nucleus, hippocampus, hypothalamus, putamen, thalamus) and spinal cord (cervical, thoracic, and lumbar). The plotted results show the fold increase in the normalized percentage of reads for each serotype compared to wild-type AAV9.

In cynomolgus macaques, the DNA analysis results (FIG. 36) based on hSyn1 and hU6 barcode measurements of AAV vector genomes in CNS tissues show a distribution of performance with many AAV variants across all serotypes including engineered variants based on AAV9 exhibiting very high performance relative to the wild-type AAV9 benchmark. Fold improvement of the serotypes disclosed herein compared to the AAV9 benchmark are plotted in FIGS. 39 and 40.

Although the RNA analysis indicates which AAV variants provided highest levels of productive transgene expression in neurons and all CNS cells, it is notable that the DNA analysis suggests there are additional AAVs that are very highly enriched in brain tissue.

Figure 41:
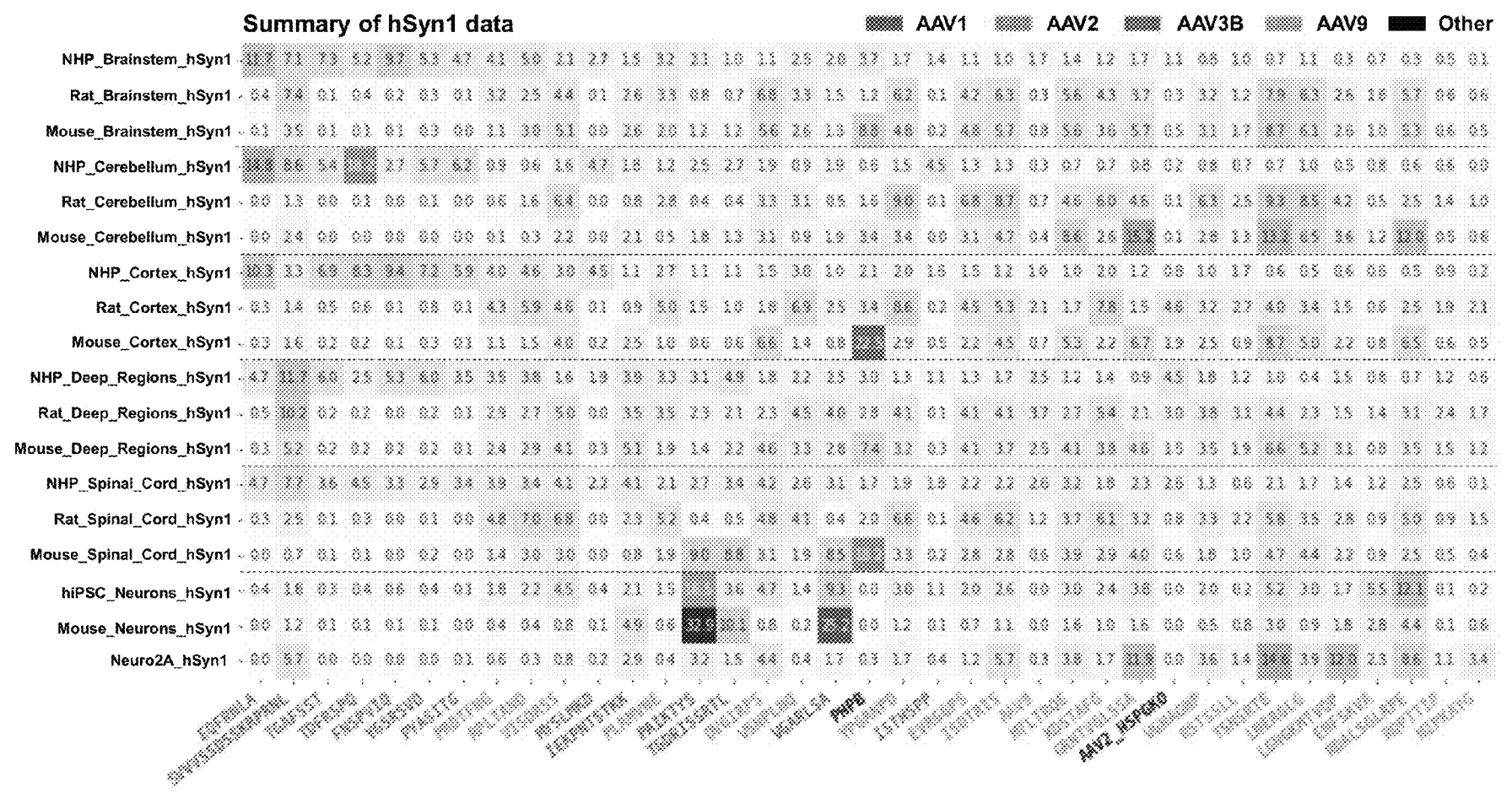
Figure 42:
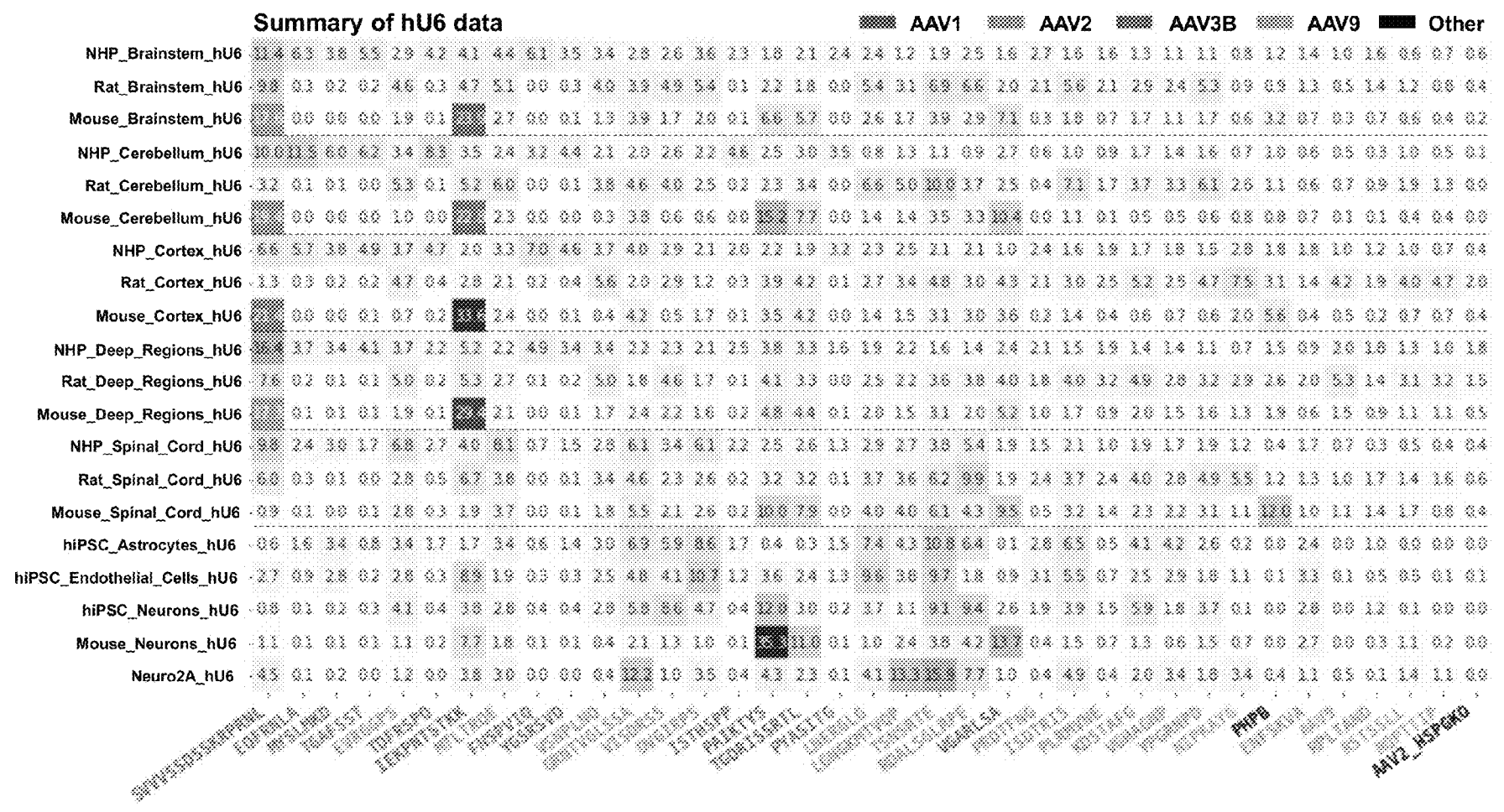

An overview of serotype performance across all cell culture and in vivo evaluations is plotted in FIGS. 41 and 42. The results show differences in transduction across species and highlight the value of performing serotype screening and evaluations in non-human primates.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

Particular embodiments of the disclosure are set forth in the following numbered paragraphs:

1. A method of identifying an AAV capsid variant with a desired characteristic compared to a natural AAV serotype, comprising:
   (i) contacting a cell, cell line, or tissue with a library of AAV variants, wherein each member of the library comprises:
   a) a nucleic acid encoding an AAV variant capsid protein comprising a peptide inserted into a hypervariable and/or surface-exposed loop of the variant capsid protein; and one or more of:
   b) one or more silent mutations in the nucleic acid sequence flanking the peptide insertion site in the AAV variant capsid protein of a);
   c) a nucleic acid encoding a localization signal;
   d) a nucleic acid comprising a barcode; and
   e) a nucleic acid encoding a reporter protein;
   (ii) allowing the AAV variants in said library to transduce the cell, cell line, or tissue;
   (iii) recovering from the cell, cell line, or tissue the AAV variant; and
   (iv) identifying the AAV capsid variant with the desired characteristic.

2. A method of identifying an AAV capsid variant with a desired characteristic compared to a natural AAV serotype, comprising:
   (i) contacting a cell, cell line, or tissue with a library of AAV variants, wherein each member of the library comprises:
   a) an AAV variant capsid protein comprising a peptide inserted into a hypervariable and/or surface-exposed loop of the variant capsid protein; and one or more of:
   b) one or more silent mutations in the nucleic acid encoding the AAV variant capsid protein of a) in the nucleic acid sequence flanking the peptide insertion site;
   c) a nucleic acid encoding a localization signal;
   d) a nucleic acid comprising a barcode; and
   e) a nucleic acid encoding a reporter protein;
   (ii) allowing the AAV variants in said library to transduce the cell, cell line, or tissue;
   (iii) recovering from the cell, cell line, or tissue the AAV variant; and
   (iv) identifying the AAV capsid variant with the desired characteristic.

3. The method of embodiment 1, wherein each member of the library comprises one or more silent mutations in the nucleic acid sequence flanking the peptide insertion site in the AAV variant capsid protein of a).

4. The method of embodiment 2, wherein each member of the library comprises one or more silent mutations in the nucleic acid encoding the AAV variant capsid protein of a) in the nucleic acid sequence flanking the peptide insertion site.

5. The method of any one of embodiments 1-4, wherein each member of the library comprises a nucleic acid encoding a localization signal.

6. The method of any one of embodiments 1-5, wherein each member of the library comprises a nucleic acid comprising a barcode.

7. The method of any one of embodiments 1-6, wherein each member of the library comprises a nucleic acid encoding a reporter protein.

8. The method of any one of embodiments 1-7, wherein the nucleic acid encoding an AAV variant capsid protein, and the nucleic acid encoding a localization signal, the nucleic acid comprising a barcode, and/or the nucleic acid encoding a reporter protein, are located in separate nucleic acid molecules.

9. The method of any one of embodiments 1-7, wherein the nucleic acid encoding an AAV variant capsid protein, the nucleic acid encoding a localization signal, the nucleic acid comprising a barcode, and/or the nucleic acid encoding a reporter protein, are located in one nucleic acid molecule.

10. The method of embodiment 9, wherein the nucleic acid encoding an AAV variant capsid protein, and the nucleic acid encoding a localization signal, the nucleic acid comprising a barcode, and/or the nucleic acid encoding a reporter protein, are linked to each other in any order.

11. The method of embodiment 10, wherein each member of the library comprises: a 5'ITR sequence, the nucleic acid comprising a barcode, the nucleic acid encoding a reporter protein, the nucleic acid encoding an AAV variant capsid protein, and a 3'ITR sequence, in that order.

12. The method of any one of embodiments 1-11, wherein the library of AAV variants comprises AAV variant capsid proteins derived from two or more AAV serotypes.

13. The method of any one of embodiments 1-12, wherein the AAV serotype of the library of AAV variants is selected from one or more of: AAV1, AAV2, AAV3B, AAV5, AAV6, AAV8, AAV9, AAV3, AAV4, AAV7, AAV11, AAVrh10, AAVrh39, and AAVrh74.

14. The method of any one of embodiments 1-13, wherein the nucleic acid encoding the reporter protein and the nucleic acid encoding an AAV variant capsid are each independently operatively linked to a promoter.

15. The method of any one of embodiments 1-14, wherein the desired characteristic is enhanced cell or tissue tropism.

16. A method of identifying an AAV capsid variant with a desired characteristic compared to a natural AAV serotype, comprising:
(i) inserting a plurality of nucleic acids encoding peptides, into a population of nucleic acids encoding a hypervariable and/or surface-exposed loop of an AAV capsid protein to create a library of nucleic acids encoding AAV variant capsid proteins;
(ii) linking each nucleic acid encoding an AAV variant capsid protein in said library to one or more of:
(a) a nucleic acid comprising a barcode,
(b) a nucleic acid encoding a reporter protein, and
(c) a nucleic acid encoding a localization signal;
(iii) manufacturing a library of AAV variants in producer cells by providing adenovirus helper and AAV rep functions in trans;
(iv) purifying the library of AAV variants;
(v) contacting a cell, cell line, or tissue with the library of AAV variants;
(vi) recovering the AAV variants from the target cell, cell line, or tissue; and
(vii) identifying the AAV capsid variant with the desired characteristic.

17. The method of embodiment 16, wherein each nucleic acid encoding an AAV variant capsid protein in said library is linked to a nucleic acid comprising a barcode.

18. The method of any one of embodiments 1-17, wherein each member of the library comprises a first nucleic acid comprising a first barcode and a second nucleic acid comprising a second barcode.

19. The method of embodiment 18, wherein the first nucleic acid comprising the first barcode and the second nucleic acid comprising the second barcode are different.

20. The method of embodiment 18 or 19, wherein the first nucleic acid comprising the first barcode comprises a sequence selected from any one of sequences SEQ ID NO: 111-154.

21. The method of embodiment 18 or 19, wherein the first nucleic acid comprising the first barcode is selected from any one of sequences SEQ ID NO: 111-154.

22. The method of embodiment 18 or 19, wherein the second nucleic acid comprising the second barcode comprises a sequence selected from any one of sequences SEQ ID NO: 155-198.

23. The method of embodiment 18 or 19, wherein the second nucleic acid comprising the second barcode is selected from any one of sequences SEQ ID NO: 155-198.

24. The method of any one of embodiments 18-23, wherein each of the first nucleic acid comprising the first barcode and the second nucleic acid comprising the second barcode is independently operatively linked to a promoter.

25. The method of embodiment 24, wherein the promoter operatively linked to the first nucleic acid comprising the first barcode and the promoter operatively linked to the second nucleic acid comprising the second barcode is each independently an RNA Pol II promoter.

26. The method of embodiment 24, wherein the promoter operatively linked to the first nucleic acid comprising the first barcode and the promoter operatively linked to the nucleic acid comprising the second barcode is each independently an RNA Pol III promoter.

27. The method of embodiment 24, wherein the promoter operatively linked to the first nucleic acid comprising the first barcode is an RNA Pol II promoter and the promoter operatively linked to the second nucleic acid comprising the second barcode is an RNA Pol III promoter.

28. The method of any one of embodiments 25-27, wherein each RNA Pol II promoter is independently selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

29. The method of any one of embodiments 26-27, wherein each RNA Pol III promoter is independently selected from the group consisting of U6 promoter, H1 promoter and 7SK promoter.

30. The method of any one of embodiments 16-29, wherein each nucleic acid encoding an AAV variant capsid protein in said library is linked to a nucleic acid encoding a reporter protein.

31. The method of any one of embodiments 16-30, wherein each nucleic acid encoding an AAV variant capsid protein in said library is linked to a nucleic acid encoding a localization signal.

32. The method of any one of embodiments 16-31, wherein each nucleic acid encoding an AAV variant capsid protein further comprises one or more silent mutations in the nucleic acid sequence flanking the peptide insertion site.

33. The method of any one of embodiments 16-32, wherein step (iv) further comprises combining libraries of variant AAVs based on two or more AAV serotypes to generate a single pool.

34. The method of any one of embodiments 16-33, wherein the population of nucleic acid sequences encoding a hypervariable and/or surface-exposed loop of an AAV capsid protein comprises sequences derived from two or more AAV serotypes.

35. The method of any one of embodiments 16-34, wherein the AAV serotype is selected from one or more of: AAV1, AAV2, AAV3B, AAV5, AAV6, AAV8, AAV9, AAV3, AAV4, AAV7, AAV11, AAVrh10, AAVrh39, and AAVrh74.

36. The method of any one of embodiments 16-35, wherein the helper functions comprise one or more of E2A, E4, VA, E1A, and E1B.

37. The method of any one of embodiments 16-36, wherein the AAV rep function comprises rep78, rep 68, rep 52 and rep40 genes.

38. The method of embodiment 37, wherein the start codon of the rep78 and/or rep68 gene is modified from ACG to ATG.

39. The method of any one of embodiments 16-38, wherein the producer cells are HEK293 cells.

40. The method of any one of embodiments 16-39, wherein the nucleic acid encoding an AAV variant capsid protein, the nucleic acid comprising a barcode, the nucleic acid encoding a reporter protein, and/or a nucleic acid encoding a localization signal are linked to each other in any order.

41. The method of any one of embodiments 16-40, wherein each member of the library comprises: a 5'ITR sequence, the nucleic acid comprising a barcode, the nucleic acid encoding a reporter protein, the nucleic acid encoding an AAV variant capsid protein, and a 3'ITR sequence, in that order.

42. The method of any one of embodiments 16-41, wherein the nucleic acid encoding a reporter protein and the nucleic acid encoding an AAV variant capsid are each independently operatively linked to a promoter.

43. The method of any one of embodiments 16-42, wherein the desired characteristic is enhanced cell or tissue tropism.

44. The method of any one of embodiments 1-43, wherein the peptide has a length of 4-15 amino acids.

45. The method of any one of embodiments 1-44, wherein the peptide has a length of 6-15 amino acids.

46. The method of embodiment 45, wherein the peptide has a length of 7, 10, or 15 amino acids.

47. The method of embodiment 46, wherein the peptide has a length of 7 amino acids.

48. The method of any one of embodiments 1-47, wherein the peptide is inserted into a region selected from the group consisting of VR-I, VR-II, VR-III, VR-IV, VR-V, VR-VI, VR-VII, VR-VIII and VR-IX region of the capsid protein.

49. The method of embodiment 48, wherein the peptide is inserted into the VR-I of the capsid protein.

50. The method of embodiment 48, wherein the peptide is inserted into the VR-IV of the capsid protein.

51. The method of embodiment 48, wherein the peptide is inserted into the VR-VIII of the capsid protein.

52. The method of any one of embodiments 1-49, wherein the peptide is inserted into the capsid protein VP1, VP2, or VP3.

53. The method of any one of embodiments 1-50, wherein the peptide is inserted at a location between amino acid residues 450 and 600 of the capsid protein.

54. The method of any one of embodiments 1-51, wherein
(i) the AAV serotype is AAV1 and the peptide is inserted at amino acid position 590 of the capsid protein,
(ii) the AAV serotype is AAV6 and the peptide is inserted at amino acid position 454 or 590 of the capsid protein,
(iii) the AAV serotype is AAV2 and the peptide is inserted at amino acid position 588 of the capsid protein,
(iv) the AAV serotype is AAV3B and the peptide is inserted at amino acid position 589 of the capsid protein,
(v) the AAV serotype is AAV5 and the peptide is inserted at amino acid position 578 of the capsid protein,
(vi) the AAV serotype is AAV8 and the peptide is inserted at amino acid position 591 of the capsid protein, or
(vii) the AAV serotype is AAV9 and the peptide is inserted at amino acid position 266, 455, or 589 of the capsid protein,
wherein the positions correspond to the numbering of VP1 in the AAV serotype.

55. The method of any one of embodiments 1-54, wherein the reporter protein is a fluorescent protein.

56. The method of embodiment 55, wherein the reporter protein is selected from the group consisting of: EGFP, mCherry, mClover3, mRuby3, mApple, iRFP, tdTomato, mVenus, YFP, RFP, firefly luciferase, and nanoluciferase.

57. The method of any one of embodiments 1-56, wherein the nucleic acid encoding an AAV variant capsid protein is operatively linked to a p40 promoter.

58. The method of any one of embodiments 1-57, wherein the nucleic acid encoding a reporter protein is operatively linked to a cell type and/or tissue specific promoter.

59. The method of embodiment 58, wherein the cell type and/or tissue specific promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

60. The method of embodiment 59, wherein the cell type and/or tissue specific promoter is the hSyn1 promoter.

61. The method of embodiment 60, wherein the cell type and/or tissue specific promoter is the TTR promoter.

62. The method of any one of embodiments 1-61, wherein the reporter protein is fused to the localization signal.

63. The method of embodiment 62, wherein the localization signal is fused N-terminally, C-terminally or both N-terminally and C-terminally to the reporter protein.

64. The method of any one of embodiments 1-63, wherein the localization signal is a nuclear localization signal (NLS), a nuclear envelope binding domain or a histone binding domain.

65. The method of embodiment 64, wherein the NLS is the SV40 NLS.

66. The method of embodiment 64, wherein the nuclear envelope binding domain is a KASH domain.

67. The method of embodiment 64, wherein the histone binding domain is H2B.

68. The method of any one of embodiments 1-67, wherein the nucleic acid comprising the barcode is 5-18 nucleotides long.

69. The method of any one of embodiments 1-68, wherein the nucleic acid comprising the barcode comprises a sequence selected from any one of sequences SEQ ID NO: 111-154.

70. The method of any one of embodiments 1-68, wherein the nucleic acid comprising the barcode comprises a sequence selected from any one of sequences SEQ ID NO: 155-198.

71. The method of any one of embodiments 1-68, wherein the nucleic acid comprising the barcode is selected from any one of sequences SEQ ID NO: 111-154.

72. The method of any one of embodiments 1-68, wherein the nucleic acid comprising the barcode is selected from any one of sequences SEQ ID NO: 155-198.

73. The method of any one of embodiments 1-72, wherein the AAV capsid variant with the desired characteristic is identified through sequencing of the associated one or more barcodes.

74. The method of any one of embodiments 1-73, wherein the AAV capsid variant with the desired characteristic is identified by purification and sequencing of the AAV genome.

75. The method of any one of embodiments 1-74, wherein the cell, cell line or tissue is selected from the group consisting of CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, and oral mucosa.

76. The method of any one of embodiments 1-74, wherein the cell is selected from: neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

77. A library of AAV variants, wherein each member of said library comprises:
  a) a nucleic acid sequence encoding an AAV variant capsid protein comprising a peptide inserted into a hypervariable and/or surface-exposed loop of the variant capsid protein; and one or more of:
  b) one or more silent mutations in the nucleic acid sequence flanking the peptide insertion site in the AAV variant capsid protein of a);
  c) a nucleic acid encoding a localization signal;
  d) a nucleic acid comprising a barcode; and
  e) a nucleic acid encoding a reporter protein.

78. A library of AAV variants, wherein each member of said library comprises:
  a) an AAV variant capsid protein comprising a peptide inserted into a hypervariable and/or surface-exposed loop of the variant capsid protein; and one or more of:
  b) one or more silent mutations in the nucleic acid encoding the AAV variant capsid protein of a) in the nucleic acid sequence flanking the peptide insertion site;
  c) a nucleic acid encoding a localization signal;
  d) a nucleic acid comprising a barcode; and
  e) a nucleic acid encoding a reporter protein.

79. The library of embodiment 77, wherein each member of the library comprises one or more silent mutations in the nucleic acid sequence flanking the peptide insertion site in the AAV variant capsid protein of a).

80. The library of embodiment 78, wherein each member of the library comprises one or more silent mutations in the nucleic acid encoding the AAV variant capsid protein of a) in the nucleic acid sequence flanking the peptide insertion site.

81. The library of any one of embodiments 77-80, wherein each member of the library comprises a nucleic acid encoding a localization signal.

82. The library of any one of embodiments 77-81, wherein each member of the library comprises a nucleic acid comprising a barcode.

83. The library of any one of embodiments 77-82, wherein each member of the library comprises a first nucleic acid comprising a first barcode and a second nucleic acid comprising a second barcode.

84. The library of embodiment 83, wherein the first nucleic acid comprising the first barcode and the second nucleic acid comprising the second barcode are different.

85. The library of embodiment 84, wherein the first nucleic acid comprising the first barcode sequence comprises a sequence selected from any one of sequences SEQ ID NO: 111-154.

86. The library of embodiment 84, wherein the first nucleic acid comprising the first barcode sequence is selected from any one of sequences SEQ ID NO: 111-154.

87. The library of embodiment 84, wherein the second nucleic acid comprising the second barcode sequence comprises a sequence selected from any one of sequences SEQ ID NO: 155-198.

88. The library of embodiment 84, wherein the second nucleic acid comprising the second barcode sequence is selected from any one of sequences SEQ ID NO: 155-198.

89. The library of any one of embodiments 83-88, wherein each of the first nucleic acid comprising the first barcode and the second nucleic acid comprising the second barcode is independently operatively linked to a promoter.

90. The library of embodiment 89, wherein the promoter operatively linked to the first nucleic acid comprising the first barcode and the promoter operatively linked to the second nucleic acid comprising the second barcode is each independently an RNA Pol II promoter.

91. The library of embodiment 89, wherein the promoter operatively linked to the first nucleic acid comprising the first barcode and the promoter operatively linked to the second nucleic acid comprising the second barcode is each independently an RNA Pol III promoter.

92. The library of embodiment 89, wherein the promoter operatively linked to the first nucleic acid comprising the first barcode is operatively linked to an RNA Pol II promoter and the promoter operatively linked to the second nucleic acid comprising the second barcode is an RNA Pol III promoter.

93. The library of any one of embodiments 90-91, wherein the RNA Pol II promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

94. The library of any one of embodiments 91-93, wherein the RNA Pol III promoter is selected from the group consisting of U6 promoter, H1 promoter and 7SK promoter.

95. The library of any one of embodiments 77-94, wherein each member of the library comprises a nucleic acid encoding a reporter protein.

96. The library of any one of embodiments 77-95, wherein the nucleic acid encoding an AAV variant capsid protein, and the nucleic acid encoding a localization signal, the nucleic acid comprising a barcode, and/or the nucleic acid encoding a reporter protein, are located in separate nucleic acid molecules.

97. The library of any one of embodiments 77-95, wherein the nucleic acid encoding an AAV variant capsid protein, the nucleic acid encoding a localization signal, the nucleic acid comprising a barcode, and/or the nucleic acid encoding a reporter protein, are located in one nucleic acid molecule.

98. The library of embodiment 97, wherein the nucleic acid encoding an AAV variant capsid protein, and the nucleic acid encoding a localization signal, the nucleic acid comprising a barcode, and/or the nucleic acid encoding a reporter protein, are linked to each other in any order.

99. The library of embodiment 97, wherein each member of the library comprises: a 5'ITR sequence, the nucleic acid comprising a barcode, the nucleic acid encoding a reporter protein, the nucleic acid encoding an AAV variant capsid protein, and a 3'ITR sequence, in that order.

100. The library of any one of embodiments 77-99, wherein the AAV variants are derived from one or more of:

AAV1, AAV2, AAV3B, AAV5, AAV6, AAV8, AAV9, AAV3, AAV4, AAV7, AAV11, AAVrh10, AAVrh39, and AAVrh74.

101. The library of embodiment 100, wherein the library of AAV variants comprises AAV variant capsid proteins derived from two or more AAV serotypes.

102. The library of any one of embodiments 77-101, wherein the peptide has a length of 4-15 amino acids.

103. The library of embodiment 102, wherein the peptide has a length of 6-15 amino acids.

104. The library of embodiment 103, wherein the peptide has a length of 7, 10, or 15 amino acids.

105. The library of embodiment 104, wherein the peptide has a length of 7 amino acids.

106. The library of any one of embodiments 77-105, wherein the peptide comprises at least 4 contiguous amino acids of an amino acid sequence set forth in any one of SEQ ID NO: 1-32.

107. The library of embodiment 106, wherein the peptide comprises an amino acid sequence set forth in any one of SEQ ID NO: 1-32.

108. The library of any one of embodiments 77-106, wherein the peptide comprises at least 4 contiguous amino acids of an amino acid sequence set forth in any one of SEQ ID NO: 68-110.

109. The library of embodiment 108, wherein the peptide comprises an amino acid sequence set forth in any one of SEQ ID NO: 68-110.

110. The library of any one of embodiments 77-109, wherein the peptide is inserted into a region selected from the group consisting of VR-I, VR-II, VR-III, VR-IV, VR-V, VR-VI, VR-VII, VR-VIII and VR-IX region of the capsid protein.

111. The library of embodiment 110, wherein the peptide is inserted into the VR-I of the capsid protein.

112. The library of embodiment 110, wherein the peptide is inserted into the VR-IV of the capsid protein.

113. The library of embodiment 110, wherein the peptide is inserted into the VR-VIII of the capsid protein.

114. The library of any one of embodiments 77-113, wherein the peptide is inserted into the capsid protein VP1, VP2, or VP3.

115. The library of any one of embodiments 77-114, wherein the peptide is inserted at a location between amino acid residues 450 and 600 of the capsid protein.

116. The library of any one of embodiments 77-115, wherein
(i) the AAV serotype is AAV1 and the peptide is inserted at amino acid position 590 of the capsid protein,
(ii) the AAV serotype is AAV6 and the peptide is inserted at amino acid position 454 or 590 of the capsid protein,
(iii) the AAV serotype is AAV2 and the peptide is inserted at amino acid position 588 of the capsid protein,
(iv) the AAV serotype is AAV3B and the peptide is inserted at amino acid position 589 of the capsid protein,
(v) the AAV serotype is AAV5 and the peptide is inserted at amino acid position 578 of the capsid protein,
(vi) the AAV serotype is AAV8 and the peptide is inserted at amino acid position 591 of the capsid protein, or
(vii) the AAV serotype is AAV9 and the peptide is inserted at amino acid position 266, 455, or 589 of the capsid protein,
wherein the positions correspond to the numbering of VP1 in the AAV serotype.

117. The library of any one of embodiments 77-116, wherein the reporter protein is a fluorescent protein.

118. The library of embodiment 117, wherein the reporter protein is selected from the group consisting of: EGFP, mCherry, mClover3, mRuby3, mApple, iRFP, tdTomato, mVenus, YFP, RFP, firefly luciferase, and nanoluciferase.

119. The library of any one of embodiments 77-118, wherein the nucleic acid encoding an AAV variant capsid protein is operatively linked to a p40 promoter.

120. The library of any one of embodiments 77-119, wherein the nucleic acid encoding a reporter protein is operatively linked to a cell type and/or tissue specific promoter.

121. The library of embodiment 120, wherein the cell type and/or tissue specific promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

122. The library of embodiment 121, wherein the cell type and/or tissue specific promoter is the hSyn1 promoter.

123. The library of embodiment 121, wherein the cell type and/or tissue specific promoter is the TTR promoter.

124. The library of any one of embodiments 77-123, wherein the reporter protein is fused to the localization signal.

125. The library of embodiment 124, wherein the localization signal is fused N-terminally, C-terminally or both N-terminally and C-terminally to the reporter protein.

126. The library of any one of embodiments 77-125, wherein the localization signal is a nuclear localization signal (NLS), a nuclear envelope binding domain or a histone binding domain.

127. The library of embodiment 126, wherein the NLS is the SV40 NLS.

128. The library of embodiment 126, wherein the nuclear envelope binding domain is a KASH domain.

129. The library of embodiment 126, wherein the histone binding domain is H2B.

130. The library of any one of embodiments 77-129, wherein the nucleic acid comprising the barcode is 5-18 nucleotides long.

131. The library of any one of embodiments 77-130, wherein the nucleic acid comprising the barcode comprises a sequence selected from any one of sequences SEQ ID NO: 111-154.

132. The library of any one of embodiments 77-130, wherein the nucleic acid comprising the barcode comprises a sequence selected from any one of sequences SEQ ID NO: 155-198.

133. The library of any one of embodiments 77-132, wherein the nucleic acid comprising the barcode is selected from any one of sequences SEQ ID NO: 111-154.

134. The library of any one of embodiments 77-132, wherein the nucleic acid comprising the barcode is selected from any one of sequences SEQ ID NO: 155-198.

135. An AAV variant comprising:
a) a nucleic acid sequence encoding an AAV variant capsid protein comprising a peptide inserted into a hypervariable and/or surface-exposed loop of the variant capsid protein; and one or more of:
b) one or more silent mutations in the nucleic acid sequence flanking the peptide insertion site in the AAV variant capsid protein of a);
c) a nucleic acid encoding a localization signal;
d) a nucleic acid comprising a barcode; and
e) a nucleic acid encoding a reporter protein.

136. An AAV variant comprising:
  a) an AAV variant capsid protein comprising a peptide inserted into a hypervariable and/or surface-exposed loop of the variant capsid protein; and one or more of:
  b) one or more silent mutations in the nucleic acid encoding the AAV variant capsid protein of a) in the nucleic acid sequence flanking the peptide insertion site;
  c) a nucleic acid encoding a localization signal;
  d) a nucleic acid comprising a barcode; and
  e) a nucleic acid encoding a reporter protein.

137. The variant of embodiment 135, wherein the variant comprises one or more silent mutations in the nucleic acid sequence flanking the peptide insertion site in the AAV variant capsid protein of a).

138. The variant of embodiment 136, wherein the variant comprises one or more silent mutations in the nucleic acid encoding the AAV variant capsid protein of a) in the nucleic acid sequence flanking the peptide insertion site.

139. The variant of any one of embodiments 135-136, wherein the variant comprises a nucleic acid encoding a localization signal.

140. The variant of any one of embodiment 135-139, wherein the variant comprises a nucleic acid comprising a barcode.

141. The variant of any one of embodiments 138-139, wherein the variant comprises a first nucleic acid comprising a first barcode and a second nucleic acid comprising a second barcode.

142. The variant of embodiment 141, wherein the first nucleic acid comprising the first barcode and the second nucleic acid comprising the second barcode are different.

143. The variant of embodiment 142, wherein the first nucleic acid comprising the first barcode sequence comprises a sequence selected from any one of sequences SEQ ID NO: 111-154.

144. The variant of embodiment 142, wherein the first nucleic acid comprising the first barcode sequence is selected from any one of sequences SEQ ID NO: 111-154.

145. The variant of embodiment 142, wherein the second nucleic acid comprising the second barcode sequence comprises a sequence selected from any one of sequences SEQ ID NO: 155-198.

146. The variant of embodiment 142, wherein the second nucleic acid comprising the second barcode sequence is selected from any one of sequences SEQ ID NO: 155-198.

147. The variant of any one of embodiments 142-146, wherein each of the first nucleic acid comprising the first barcode and the second nucleic acid comprising the second barcode is independently operatively linked to a promoter.

148. The variant of embodiment 147, wherein the promoter operatively linked to the first nucleic acid comprising the first barcode and the promoter operatively linked to the second nucleic acid comprising the second barcode is each independently an RNA Pol II promoter.

149. The variant of embodiment 147, wherein the promoter operatively linked to the first nucleic acid comprising the first barcode and the promoter operatively linked to the second nucleic acid comprising the second barcode is each independently an RNA Pol III promoter.

150. The variant of embodiment 147, wherein the promoter operatively linked to the first nucleic acid comprising the first barcode is operatively linked to an RNA Pol II promoter and the promoter operatively linked to the second nucleic acid comprising the second barcode is an RNA Pol III promoter.

151. The variant of any one of embodiments 148-150, wherein the RNA Pol II promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

152. The variant of any one of embodiments 149-151, wherein the RNA Pol III promoter is selected from the group consisting of U6 promoter, H1 promoter and 7SK promoter.

153. The variant of any one of embodiment 135-152, wherein the variant comprises a nucleic acid encoding a reporter protein.

154. The variant of any one of embodiments 135-153, wherein the nucleic acid encoding an AAV variant capsid protein, and the nucleic acid encoding a localization signal, the nucleic acid comprising a barcode, and/or the nucleic acid encoding a reporter protein, are located in separate nucleic acid molecules.

155. The variant of any one of embodiments 135-154, wherein the nucleic acid encoding an AAV variant capsid protein, the nucleic acid encoding a localization signal, the nucleic acid comprising a barcode, and/or the nucleic acid encoding a reporter protein, are located in one nucleic acid molecule.

156. The variant of embodiment 155, wherein the nucleic acid encoding an AAV variant capsid protein, and the nucleic acid encoding a localization signal, the nucleic acid comprising a barcode, and/or the nucleic acid encoding a reporter protein, are linked to each other in any order.

157. The variant of embodiment 156, wherein the variant comprises: a 5'ITR sequence, the nucleic acid comprising a barcode, the nucleic acid encoding a reporter protein, the nucleic acid encoding an AAV variant capsid protein, and a 3'ITR sequence, in that order.

158. The variant of any one of embodiments 135-157, wherein the AAV variant is derived from the group consisting of: AAV1, AAV2, AAV3B, AAV5, AAV6, AAV8, AAV9, AAV3, AAV4, AAV7, AAV11, AAVrh10, AAVrh39, and AAVrh74.

159. The variant of any one of embodiments 135-158, wherein the peptide has a length of 4-15 amino acids.

160. The variant of embodiment 159, wherein the peptide has a length of 6-15 amino acids.

161. The variant of embodiment 160, wherein the peptide has a length of 7, 10, or 15 amino acids.

162. The variant of embodiment 161, wherein the peptide has a length of 7 amino acids.

163. The variant of any one of embodiments 135-162, wherein the inserted peptide comprises at least 4 contiguous amino acids of an amino acid sequence set forth in any one of SEQ ID NO: 1-32.

164. The variant of embodiment 163, wherein the peptide comprises an amino acid sequence set forth in any one of SEQ ID NO: 1-32.

165. The variant of any one of embodiments 135-162, wherein the inserted peptide comprises at least 4 contiguous amino acids of an amino acid sequence set forth in any one of SEQ ID NO: 68-110.

166. The variant of embodiment 165, wherein the peptide comprises an amino acid sequence set forth in any one of SEQ ID NO: 68-110.

167. The variant of any one of embodiments 135-166, wherein the peptide is inserted into a region selected from the group consisting of VR-I, VR-II, VR-III, VR-IV, VR-V, VR-VI, VR-VII, VR-VIII and VR-IX region of the capsid protein.

168. The variant of embodiment 167, wherein the peptide is inserted into the VR-I of the capsid protein.

169. The variant of embodiment 167, wherein the peptide is inserted into the VR-IV of the capsid protein.

170. The variant of embodiment 168, wherein the peptide is inserted into VR-VIII of the capsid protein.

171. The variant of any one of embodiments 135-170, wherein the peptide is inserted into the capsid protein VP1, VP2, or VP3.

172. The variant of any one of embodiments 135-171, wherein the peptide is inserted at a location between amino acid residues 450 and 600 of the capsid protein.

173. The variant of any one of embodiments 135-172, wherein
  (i) the AAV serotype is AAV1 and the peptide is inserted at amino acid position 590 of the capsid protein,
  (ii) the AAV serotype is AAV6 and the peptide is inserted at amino acid position 454 or 590 of the capsid protein,
  (iii) the AAV serotype is AAV2 and the peptide is inserted at amino acid position 588 of the capsid protein,
  (iv) the AAV serotype is AAV3B and the peptide is inserted at amino acid position 589 of the capsid protein,
  (v) the AAV serotype is AAV5 and the peptide is inserted at amino acid position 578 of the capsid protein,
  (vi) the AAV serotype is AAV8 and the peptide is inserted at amino acid position 591 of the capsid protein, or
  (vii) the AAV serotype is AAV9 and the peptide is inserted at amino acid position 266, 455, or 589 of the capsid protein, wherein the positions correspond to the numbering of VP1 in the AAV serotype.

174. The variant of any one of embodiments 135-173, wherein the reporter protein is a fluorescent protein.

175. The variant of embodiment 174, wherein the reporter protein is selected from the group consisting of: EGFP, mCherry, mClover3, mRuby3, mApple, iRFP, tdTomato, mVenus, YFP, RFP, firefly luciferase, and nanoluciferase.

176. The variant of any one of embodiments 135-175, wherein the nucleic acid encoding an AAV variant capsid protein is operatively linked to a p40 promoter.

177. The variant of any one of embodiments 138-176, wherein the nucleic acid encoding a reporter protein is operatively linked to a cell type and/or tissue specific promoter.

178. The variant of embodiment 177, wherein the cell type and/or tissue specific promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

179. The variant of embodiment 178, wherein the cell type and/or tissue specific promoter is the hSyn1 promoter.

180. The variant of embodiment 178, wherein the cell type and/or tissue specific promoter is the TTR promoter.

181. The variant of any one of embodiments 135-180, wherein the reporter protein is fused to the localization signal.

182. The variant of embodiment 181, wherein the localization signal is fused N-terminally, C-terminally or both N-terminally and C-terminally to the reporter protein.

183. The variant of any one of embodiments 135-182, wherein the localization signal is a nuclear localization signal (NLS), a nuclear envelope binding domain or a histone binding domain.

184. The variant of embodiment 183, wherein the NLS is the SV40 NLS.

185. The variant of embodiment 183, wherein the nuclear envelope binding domain is a KASH domain.

186. The variant of embodiment 183, wherein the histone binding domain is H2B.

187. The variant of any one of embodiments 135-186, wherein the nucleic acid comprising the barcode is 5-18 nucleotides long.

188. The variant of any one of embodiments 135-187, wherein the nucleic acid comprising the barcode comprises a sequence selected from any one of sequences SEQ ID NO: 111-154.

189. The variant of embodiment 188, wherein the nucleic acid comprising the barcode is selected from any one of sequences SEQ ID NO: 111-154.

190. The variant of any one of embodiments 135-187, wherein the nucleic acid comprising the barcode comprises a sequence selected from any one of sequences SEQ ID NO: 155-198.

191. The variant of embodiment 190, wherein the nucleic acid comprising the barcode is selected from any one of sequences SEQ ID NO: 155-198.

192. The variant of any one of embodiments 135-191, wherein the AAV variant is derived from AAV1.

193. The variant of embodiment 192, wherein the variant comprises a peptide comprising an amino acid sequence selected from the group consisting of any one of SEQ ID NO: 68 to SEQ ID NO: 75.

194. The variant of embodiment 192, wherein the variant comprises a peptide comprising an amino acid sequence selected from the group consisting of SEQ ID NO: 1, SEQ ID NO: 2 and SEQ ID NO: 3.

195. The variant of embodiment 192, wherein the variant comprises a peptide comprising the amino acid sequence SEQ ID NO: 71.

196. The variant of any one of embodiments 135-191, wherein the AAV variant is derived from AAV2.

197. The variant of embodiment 196, wherein the variant comprises a peptide comprising an amino acid sequence selected from the group consisting of any one of SEQ ID NO: 90 to SEQ ID NO: 110.

198. The variant of embodiment 196, wherein the variant comprises a peptide comprising any one of the sequences selected from the group consisting of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

199. The variant of embodiment 196, wherein the variant comprises a peptide comprising an amino acid sequence selected from the group consisting of any one of SEQ ID NO: 4-7.

200. The variant of any one of embodiments 135-191, wherein the AAV variant is derived from AAV3B.

201. The variant of embodiment 200, wherein the variant comprises a peptide comprising any one of the sequences selected from the group consisting of SEQ ID NO: 78, SEQ ID NO: 80, SEQ ID NO: 77, SEQ ID NO: 79, SEQ ID NO: 76 and SEQ ID NO: 83.

202. The variant of embodiment 200, wherein the variant comprises a peptide comprising an amino acid sequence selected from the group consisting of any one of SEQ ID NO: 8 to SEQ ID NO: 11.

203. The variant of any one of embodiments 135-191, wherein the AAV variant is derived from AAV5.

204. The variant of embodiment 203, wherein the variant comprises a peptide comprising an amino acid sequence selected from the group consisting of any one of SEQ ID NO: 28 to SEQ ID NO: 32.

205. The variant of any one of embodiments 135-191, wherein the AAV variant is derived from AAV6.

206. The variant of embodiment 205, wherein the variant comprises a peptide comprising an amino acid sequence selected from the group consisting of consisting of any one of SEQ ID NO: 19 to SEQ ID NO: 27.

207. The variant of any one of embodiments 135-191, wherein the AAV variant is derived from AAV9.

208. The variant of embodiment 207, wherein the variant comprises a peptide comprising an amino acid sequence selected from the group consisting of any one of SEQ ID NO: 12 to SEQ ID NO: 18.

209. The variant of embodiment 207, wherein the variant comprises a peptide comprising an amino acid sequence selected from the group consisting of any one of SEQ ID NO: 86 to SEQ ID NO: 89.

210. The variant of embodiment 207, wherein the variant comprises a peptide comprising the sequence SEQ ID NO: 89.

211. A nucleic acid molecule comprising:
a) a nucleic acid sequence encoding an AAV variant capsid protein comprising a peptide inserted into a hypervariable and/or surface-exposed loop of the variant capsid protein; and one or more of:
b) a nucleic acid sequence encoding a variant capsid protein comprising one or more silent mutations in the nucleotide sequence flanking the peptide insertion site in the hypervariable and/or surface-exposed loop of the variant capsid protein;
c) a nucleic acid sequence encoding a localization signal;
d) a nucleic acid sequence comprising a barcode; and
e) a nucleic acid sequence encoding a reporter protein.

212. The nucleic acid molecule of embodiment 211, wherein the nucleic acid sequence encoding an AAV variant capsid protein comprises one or more silent mutations in the nucleic acid sequence flanking the peptide insertion site in the AAV variant capsid protein of a).

213. The nucleic acid molecule of embodiment 212, wherein the nucleic acid molecule comprises a nucleic acid encoding a localization signal.

214. The nucleic acid molecule of embodiment 212, wherein the nucleic acid molecule comprises a nucleic acid comprising a barcode.

215. The nucleic acid molecule of embodiments 211-214, wherein the nucleic acid molecule comprises a first nucleic acid comprising a first barcode and a second nucleic acid comprising a second barcode.

216. The nucleic acid molecule of embodiment 215, wherein the first nucleic acid comprising the first barcode and the second nucleic acid comprising the second barcode are different.

217. The nucleic acid molecule of embodiment 216, wherein the first nucleic acid comprising the first barcode sequence comprises a sequence selected from any one of sequences SEQ ID NO: 111-154.

218. The nucleic acid molecule of embodiment 217, wherein the first nucleic acid comprising the first barcode sequence is selected from any one of sequences SEQ ID NO: 111-154.

219. The nucleic acid molecule of embodiment 216, wherein the second nucleic acid comprising the second barcode sequence comprises a sequence selected from any one of sequences SEQ ID NO: 155-198.

220. The nucleic acid molecule of embodiment 217, wherein the second nucleic acid comprising the second barcode sequence is selected from any one of sequences SEQ ID NO: 155-198.

221. The nucleic acid molecule of any one of embodiments 215-220, wherein each of the first nucleic acid comprising the first barcode and the second nucleic acid comprising the second barcode is independently operatively linked to a promoter.

222. The nucleic acid molecule of embodiment 221, wherein the promoter operatively linked to the first nucleic acid comprising the first barcode and the promoter operatively linked to the second nucleic acid comprising the second barcode is each independently an RNA Pol II promoter.

223. The nucleic acid molecule of embodiment 221, wherein the promoter operatively linked to the first nucleic acid comprising the first barcode and the promoter operatively linked to the second nucleic acid comprising the second barcode is each independently an RNA Pol III promoter.

224. The nucleic acid molecule of embodiment 221, wherein the promoter operatively linked to the first nucleic acid comprising the first barcode is operatively linked to an RNA Pol II promoter and the promoter operatively linked to the second nucleic acid comprising the second barcode is an RNA Pol III promoter.

225. The nucleic acid molecule of any one of embodiments 222-224, wherein the RNA Pol II promoter is selected from the group consisting of: human synapsin promoter (hSyn1), transthyretin promoter (TTR), cytokeratin 18, cytokeratin 19, unc-45 myosin chaperon B (unc45b) promoter, cardiac troponin T (cTnT) promoter, glial fibrillary acidic protein (GFAP) promoter, myelin basic protein (MBP) promoter, and methyl CpG-binding protein 2 (Mecp2) promoter.

226. The nucleic acid molecule of any one of embodiments 223-224, wherein the RNA Pol III promoter is selected from the group consisting of U6 promoter, H1 promoter and 7SK promoter.

227. The nucleic acid molecule of any one of embodiments 211-226, where the nucleic acid molecule comprises a nucleic acid encoding a reporter protein.

228. The nucleic acid molecule of any one of embodiments 211-227, wherein the AAV variants are derived from one or more of: AAV1, AAV2, AAV3B, AAV5, AAV6, AAV8, AAV9, AAV3, AAV4, AAV7, AAV11, AAVrh10, AAVrh39, and AAVrh74.

229. The nucleic acid molecule of any one of embodiments 211-228, wherein the inserted peptide has a length of 4-15 amino acids.

230. The nucleic acid molecule of embodiment 229, wherein the inserted peptide comprises at least 4 contiguous amino acids of an amino acid sequence set forth in any one of SEQ ID NO: 1-32.

231. The nucleic acid molecule of embodiment 229, wherein the inserted peptide comprises at least 4 contiguous amino acids of an amino acid sequence set forth in any one of SEQ ID NO: 68-110.

232. The nucleic acid molecule of any one of embodiments 211-231, wherein the nucleic acid encoding a reporter protein is operatively linked to a cell type and/or tissue specific promoter.

233. The nucleic acid molecule of embodiment 232, wherein the cell type and/or tissue specific promoter is the hSyn1 promoter.

234. The nucleic acid molecule of any one of embodiments 211-233, wherein the nucleic acid comprising the barcode comprises a sequence selected from any one of sequences SEQ ID NO: 111-154.

235. The nucleic acid molecule of any one of embodiments 211-233, wherein the nucleic acid comprising the barcode comprises a sequence selected from any one of sequences SEQ ID NO: 155-198.

236. Use of an AAV variant according to any one of embodiments 135-210 to deliver a transgene to a target cell or tissue.

237. An AAV vector comprising a nucleic acid molecule encoding a peptide that comprises at least 4 contiguous amino acids of an amino acid sequence set forth in any one of SEQ ID NO: 1-32.

238. The AAV vector of embodiment 237, wherein the nucleic acid encodes a peptide that comprises an amino acid sequence set forth in any one of SEQ ID NO: 1-32.

239. The AAV vector of embodiment 237 or 238, wherein the nucleic acid encodes a peptide having a sequence of any of one of SEQ ID NO: 1-32.

240. An AAV vector comprising a nucleic acid molecule encoding a peptide that comprises at least 4 contiguous amino acids of an amino acid sequence set forth in any one of SEQ ID NO:68-110.

241. The AAV vector of embodiment 240, wherein the nucleic acid encodes a peptide that comprises an amino acid sequence set forth in any one of SEQ ID NO: 68-110.

242. The AAV vector of embodiment 240 or 241, wherein the nucleic acid encodes a peptide having the sequence of any of one of SEQ ID NO: 68-110.

243. The AAV vector of embodiment 240, wherein the nucleic acid encodes a peptide that comprises an amino acid sequence set forth in any one of SEQ ID NO: 71, 76-80, 83, 89, 91, 94-96, 101-103 and 106.

244. The AAV vector of any one of embodiments 237-243, wherein the peptide is a part of a capsid protein.

245. The AAV vector of embodiment 244, wherein the capsid protein is VP1, VP2, or VP3.

246. The AVV vector of any one of embodiments 237-245, wherein the peptide is inserted at a location between amino acid residues 450 and 600 of the capsid protein.

247. The AAV vector of embodiment 246, wherein the peptide is inserted at
  (i) amino acid position 590 of an AAV1 capsid protein,
  (ii) amino acid position 454 or 590 of an AAV6 capsid protein,
  (iii) amino acid position 588 of an AAV2 capsid protein,
  (iv) amino acid position 589 of an AAV3B capsid protein,
  (v) amino acid position 578 of an AAV5 capsid protein,
  (vi) amino acid position 591 of the an AAV8 capsid protein, or
  (vi) amino acid position 266, 455, or 589 of an AAV9 capsid protein,
  wherein the positions correspond to the numbering of VP1 in the AAV serotype.

248. A pharmaceutical composition comprising the AAV vector of any one of embodiments 237-247 and a pharmaceutically acceptable carrier.

249. A peptide comprising an amino acid sequence set forth in any one of SEQ ID NO: 1-32.

250. A peptide comprising an amino acid sequence set forth in any one of SEQ ID NO: 68-110.

251. A peptide comprising an amino acid sequence set forth in any one of SEQ ID NO: 71, 76-80, 83, 89, 91, 94-96, 101-103 and 106.

252. A peptide comprising an amino acid sequence set forth in any one of SEQ ID NO: 71, 76-80, 83 and 94-96.

253. A peptide comprising an amino acid sequence set forth in any one of SEQ ID NO: 89, 91, 101-103 and 106.

254. A peptide comprising an amino acid sequence set forth in any one of SEQ ID NO: 68 to SEQ ID NO: 75.

255. A peptide comprising an amino acid sequence set forth in any one of SEQ ID NO: 1, SEQ ID NO: 2 and SEQ ID NO: 3.

256. A peptide comprising an amino acid sequence set forth in SEQ ID NO: 71.

257. A peptide comprising an amino acid sequence set forth in any one of SEQ ID NO: 90 to SEQ ID NO: 110.

258. A peptide comprising an amino acid sequence set forth in any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

259. A peptide comprising an amino acid sequence set forth in any one of SEQ ID NO: 4-7.

260. A peptide comprising an amino acid sequence set forth in any one of SEQ ID NO: 78, SEQ ID NO: 80, SEQ ID NO: 77, SEQ ID NO: 79, SEQ ID NO: 76 and SEQ ID NO: 83.

261. A peptide comprising an amino acid sequence set forth in any one of SEQ ID NO: 8 to SEQ ID NO: 11.

262. A peptide comprising an amino acid sequence set forth in any one of SEQ ID NO: 28 to SEQ ID NO: 32.

263. A peptide comprising an amino acid sequence set forth in any one of SEQ ID NO: 19 to SEQ ID NO: 27.

264. A peptide comprising an amino acid sequence set forth in any one of SEQ ID NO: 12 to SEQ ID NO: 18.

265. A peptide comprising an amino acid sequence set forth in any one of SEQ ID NO: 86 to SEQ ID NO: 89.

266. A peptide comprising an amino acid sequence set forth in SEQ ID NO: 89.

267. The peptide of any one of embodiments 249-266, wherein the peptide is part of an AAV vector.

268. The peptide of embodiment 267, wherein the peptide is part of a capsid protein of the AAV vector.

269. A nucleic acid molecule encoding the peptide of any one of embodiments 249-268.

270. A capsid protein comprising a peptide comprising at least 4 contiguous amino acids of an amino acid sequence set forth in any one of SEQ ID NO: 1-32.

271. A capsid protein comprising a peptide comprising at least 4 contiguous amino acids of an amino acid sequence set forth in any one of SEQ ID NO:68-110.

272. The capsid protein of embodiment 270, wherein the peptide comprises the amino acid sequence set forth in any one of SEQ ID NO: 1-32.

273. The capsid protein of embodiment 271, wherein the peptide comprises the amino acid sequence set forth in any one of SEQ ID NO: 68-110.

274. The capsid protein of embodiment 270, comprising the amino acid sequence set forth in any one of SEQ ID NO: 1-32.

275. The capsid protein of embodiment 271, comprising the amino acid sequence set forth in any one of SEQ ID NO:68-110.

276. The capsid protein of embodiment 271, wherein the peptide comprises an amino acid sequence set forth in any one of SEQ ID NO: 71, 76-80, 83, 89, 91, 94-96, 101-103 and 106.

277. The capsid protein of embodiment 271, wherein the peptide comprises an amino acid sequence set forth in any one of SEQ ID NO: 71, 76-80, 83 and 94-96.

278. The capsid protein of embodiment 271, wherein the peptide comprises an amino acid sequence set forth in any one of SEQ ID NO: 89, 91, 101-103 and 106.

279. The capsid protein of embodiment 271, wherein the peptide comprises an amino acid sequence set forth in any one of SEQ ID NO: 68 to SEQ ID NO: 75.

280. The capsid protein of embodiment 270, wherein the peptide comprises an amino acid sequence set forth in any one of SEQ ID NO: 1, SEQ ID NO: 2 and SEQ ID NO: 3.

281. The capsid protein of embodiment 271, wherein the peptide comprises an amino acid sequence set forth in SEQ ID NO: 71.

282. The capsid protein of embodiment 271, wherein the peptide comprises an amino acid sequence set forth in any one of SEQ ID NO: 90 to SEQ ID NO: 110.

283. The capsid protein of embodiment 271, wherein the peptide comprises an amino acid sequence set forth in any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

284. The capsid protein of embodiment 270, wherein the peptide comprises an amino acid sequence set forth in any one of SEQ ID NO: 4-7.

285. The capsid protein of embodiment 271, wherein the peptide comprises an amino acid sequence set forth in any one of SEQ ID NO: 78, SEQ ID NO: 80, SEQ ID NO: 77, SEQ ID NO: 79, SEQ ID NO: 76 and SEQ ID NO: 83.

286. The capsid protein of embodiment 270, wherein the peptide comprises an amino acid sequence set forth in any one of SEQ ID NO: 8 to SEQ ID NO: 11.

287. The capsid protein of embodiment 270, wherein the peptide comprises an amino acid sequence set forth in any one of SEQ ID NO: 28 to SEQ ID NO: 32.

288. The capsid protein of embodiment 270, wherein the peptide comprises an amino acid sequence set forth in any one of SEQ ID NO: 19 to SEQ ID NO: 27.

289. The capsid protein of embodiment 270, wherein the peptide comprises an amino acid sequence set forth in any one of SEQ ID NO: 12 to SEQ ID NO: 18.

290. The capsid protein of embodiment 271, wherein the peptide comprises an amino acid sequence set forth in any one of SEQ ID NO: 86 to SEQ ID NO: 89.

291. The capsid protein of embodiment 271, wherein the peptide comprises an amino acid sequence set forth in SEQ ID NO: 89.

292. A nucleic acid molecule encoding the capsid protein of any one of embodiments 269-291.

293. A method of delivering a nucleic acid to a target cell or tissue of a subject, comprising: administering a composition comprising an AAV vector according to any one of embodiments 237-247.

294. The method of embodiment 293, wherein the capsid protein comprises an amino acid sequence set forth in any one of SEQ ID NO: 1-32.

295. The method of embodiment 293, wherein the capsid protein comprises an amino acid sequence set forth in any one of SEQ ID NO:68-110.

296. The method of any one of embodiments 293-295, wherein the target cell, cell line or tissue is selected from the group consisting of CNS, heart, lung, trachea, esophagus, muscle, bone, cartilage, stomach, pancreas, intestine, liver, bladder, kidney, ureter, urethra, uterus, fallopian tube, ovary, testes, prostate, eye, blood, lymph, and oral mucosa.

297. The method of any one of embodiments 293-295, wherein the target cell is selected from the group consisting of neurons, glial cells, astrocytes, oligodendroglia, microglia, Schwann cells, ependymal cells, hepatocytes, stellate fat storing cells, Kupffer cells, liver endothelial cells, epithelial cells, cardiomyocytes, smooth muscle cells, T-cells, B cells, hematopoietic stem cells, and embryonic stem cells.

298. The method of embodiment 296, wherein the target cell or tissue is from liver.

299. The method of embodiment 296, wherein the target cell or tissue is from CNS.

300. A pharmaceutical composition comprising the variant of any one of embodiments 135-211 and a pharmaceutically acceptable carrier.

301. The library of embodiment 116, wherein a peptide comprising the amino acid sequence of any one of SEQ ID NO: 1-32 is inserted at amino acid position 590 of the capsid protein of an AAV1 serotype.

302. The library of embodiment 116, wherein a peptide comprising the amino acid sequence of any one of SEQ ID NO: 68-110 is inserted at amino acid position 590 of the capsid protein of an AAV1 serotype.

304. The library of embodiment 302, wherein the peptide comprises an amino acid sequence of any one of SEQ ID NO: 68-75.

305. The library of embodiment 302, wherein the peptide comprises the amino acid sequence SEQ ID NO: 71.

306. The library of embodiment 301, wherein the peptide comprises an amino acid sequence selected from the group consisting of any one of SEQ ID NO: 1, SEQ ID NO: 2 and SEQ ID NO: 3.

307. The library of embodiment 116, wherein a peptide comprising the amino acid sequence of any one of SEQ ID NO: 1-32 is inserted at amino acid position 454 of the capsid protein of an AAV6 serotype.

308. The library of embodiment 116, wherein a peptide comprising the amino acid sequence of any one of SEQ ID NO: 68-110 is inserted at amino acid position 454 of the capsid protein of an AAV6 serotype.

309. The library of embodiment 116, wherein a peptide comprising the amino acid sequence of any one of SEQ ID NO: 1-32 is inserted at amino acid position 590 of the capsid protein of an AAV6 serotype.

310. The library of embodiment 116, wherein a peptide comprising the amino acid sequence of any one of SEQ ID NO: 68-110 is inserted at amino acid position 590 of the capsid protein of an AAV6 serotype.

311. The library of any one of embodiments 307 and 309, wherein the peptide comprises an amino acid sequence of any one of SEQ ID NO: 19 to SEQ ID NO: 27.

312. The library of embodiment 116, wherein a peptide comprising the amino acid sequence of any one of SEQ ID NO: 1-32 is inserted at amino acid position 588 of the capsid protein of an AAV2 serotype.

313. The library of embodiment 116, wherein a peptide comprising the amino acid sequence of any one of SEQ ID NO: 68-110 is inserted at amino acid position 588 of the capsid protein of an AAV2 serotype.

314. The library of embodiment 313, wherein the peptide comprises an amino acid sequence selected from the group consisting of any one of SEQ ID NO: 90 to SEQ ID NO: 110.

315. The library of embodiments 313, wherein the peptide comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

316. The library of embodiments 312, wherein the peptide comprises an amino acid sequence selected from the group consisting of any one of SEQ ID NO: 4-7.

317. The library of embodiment 116, wherein a peptide comprising the amino acid sequence of any one of SEQ ID NO: 1-32 is inserted at amino acid position 589 of the capsid protein of an AAV3B serotype.

318. The library of embodiment 116, wherein a peptide comprising the amino acid sequence of any one of SEQ ID NO: 68-110 is inserted at amino acid position 589 of the capsid protein of an AAV3B serotype.

319. The library of embodiment 318, wherein the peptide comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83.

320. The library of embodiment 317, wherein the peptide comprises an amino acid sequence selected from the group consisting of any one of SEQ ID NO: 8 to SEQ ID NO: 11.

321. The library of embodiment 116, wherein a peptide comprising the amino acid sequence of any one of SEQ ID NO: 1-32 is inserted at amino acid position 578 of the capsid protein of an AAV5 serotype.

322. The library of embodiment 116, wherein a peptide comprising the amino acid sequence of any one of SEQ ID NO: 68-110 is inserted at amino acid position 578 of the capsid protein of an AAV5 serotype.

323. The library of embodiment 321, wherein the peptide comprises an amino acid sequence selected from the group consisting of any one SEQ ID NO: 28 to SEQ ID NO: 32.

324. The library of embodiment 116, wherein a peptide comprising the amino acid sequence of any one of SEQ ID NO: 1-32 is inserted at amino acid position 591 of the capsid protein of an AAV8 serotype.

325. The library of embodiment 116, wherein a peptide comprising the amino acid sequence of any one of SEQ ID NO: 68-110 is inserted at amino acid position 591 of the capsid protein of an AAV8 serotype.

326. The library of embodiment 116, wherein a peptide comprising the amino acid sequence of any one of SEQ ID NO: 1-32 is inserted at amino acid position 266 of the capsid protein of an AAV9 serotype.

327. The library of embodiment 116, wherein a peptide comprising the amino acid sequence of any one of SEQ ID NO: 68-110 is inserted at amino acid position 266 of the capsid protein of an AAV9 serotype.

328. The library of embodiment 116, wherein a peptide comprising the amino acid sequence of any one of SEQ ID NO: 1-32 is inserted at amino acid position 455 of the capsid protein of an AAV9 serotype.

329. The library of embodiment 116, wherein a peptide comprising the amino acid sequence of any one of SEQ ID NO: 68-110 is inserted at amino acid position 455 of the capsid protein of an AAV9 serotype.

330. The library of embodiment 116, wherein a peptide comprising the amino acid sequence of any one of SEQ ID NO: 1-32 is inserted at amino acid position 589 of the capsid protein of an AAV9 serotype.

331. The library of embodiment 116, wherein a peptide comprising the amino acid sequence of any one of SEQ ID NO: 68-110 is inserted at amino acid position 589 of the capsid protein of an AAV9 serotype.

332. The library of any one of embodiments 326, 328, and 330, wherein the peptide comprises an amino acid sequence selected from the group consisting of any one of SEQ ID NO: 12 to SEQ ID NO: 18.

333. The library of any one of embodiments 327, 329, and 331, wherein the peptide comprises an amino acid sequence selected from the group consisting of any one of SEQ ID NO: 86 to SEQ ID NO: 89.

334. The library of any one of embodiments 327, 329, and 331, wherein the peptide comprises the sequence of SEQ ID NO: 89.

335. The AAV variant of embodiment 173, wherein a peptide comprising the amino acid sequence of any one of SEQ ID NO: 1-32 is inserted at amino acid position 590 of the capsid protein of an AAV1 serotype.

336. The AAV variant of embodiment 173, wherein a peptide comprising the amino acid sequence of any one of SEQ ID NO: 68-110 is inserted at amino acid position 590 of the capsid protein of an AAV1 serotype.

337. The AAV variant of embodiment 336, wherein the peptide comprises an amino acid sequence selected from the group consisting of any one of SEQ ID NO: 68 to SEQ ID NO: 75.

338. The AAV variant of embodiment 336, wherein the peptide comprises the amino acid sequence SEQ ID NO: 71.

339. The AAV variant of embodiment 335, wherein the peptide comprises an amino acid sequence selected from the group consisting of any one of SEQ ID NO: 1, SEQ ID NO: 2 and SEQ ID NO: 3.

340. The AAV variant of embodiment 173, wherein a peptide comprising the amino acid sequence of any one of SEQ ID NO: 1-32 is inserted at amino acid position 454 of the capsid protein of an AAV6 serotype.

341. The AAV variant of embodiment 173, wherein a peptide comprising the amino acid sequence of any one of SEQ ID NO: 68-110 is inserted at amino acid position 454 of the capsid protein of an AAV6 serotype.

342. The AAV variant of embodiment 173, wherein a peptide comprising the amino acid sequence of any one of SEQ ID NO: 1-32 is inserted at amino acid position 590 of the capsid protein of an AAV6 serotype.

343. The AAV variant of embodiment 173, wherein a peptide comprising the amino acid sequence of any one of SEQ ID NO: 68-110 is inserted at amino acid position 590 of the capsid protein of an AAV6 serotype.

344. The AAV variant of any one of embodiments 340 and 342, wherein the peptide comprises an amino acid sequence selected from the group consisting of any one of SEQ ID NO: 19 to SEQ ID NO: 27.

345. The AAV variant of embodiment 173, wherein a peptide comprising the amino acid sequence of SEQ ID NO: 1-32 is inserted at amino acid position 588 of the capsid protein of an AAV2 serotype.

346. The AAV variant of embodiment 173, wherein a peptide comprising the amino acid sequence of SEQ ID NO: 68-110 is inserted at amino acid position 588 of the capsid protein of an AAV2 serotype.

347. The AAV variant of embodiment 346, wherein the peptide comprises an amino acid sequence selected from the group consisting of any one of SEQ ID NO: 90 to SEQ ID NO: 110.

348. The AAV variant of embodiments 346, wherein the peptide comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

349. The AAV variant of embodiments 345, wherein the peptide comprises an amino acid sequence selected from the group consisting of any one of SEQ ID NO: 4-7.

350. The AAV variant of embodiment 173, wherein a peptide comprising the amino acid sequence of any one of SEQ ID NO: 1-32 is inserted at amino acid position 589 of the capsid protein of an AAV3B serotype.

351. The AAV variant of embodiment 173, wherein a peptide comprising the amino acid sequence of any one of SEQ ID NO: 68-110 is inserted at amino acid position 589 of the capsid protein of an AAV3B serotype.

352. The AAV variant of embodiment 351, wherein the peptide comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83.

353. The AAV variant of embodiment 350, wherein the peptide comprises an amino acid sequence selected from the group consisting of any one of SEQ ID NO: 8 to SEQ ID NO: 11.

354. The AAV variant of embodiment 173, wherein a peptide comprising the amino acid sequence of any one of SEQ ID NO: 1-32 is inserted at amino acid position 578 of the capsid protein of an AAV5 serotype.

355. The AAV variant of embodiment 173, wherein a peptide comprising the amino acid sequence of any one of SEQ ID NO: 68-110 is inserted at amino acid position 578 of the capsid protein of an AAV5 serotype.

356. The AAV variant of embodiment 354, wherein the peptide comprises an amino acid sequence selected from the group consisting of any one SEQ ID NO: 28 to SEQ ID NO: 32.

357. The AAV variant of embodiment 173, wherein a peptide comprising the amino acid sequence of any one of SEQ ID NO: 1-32 is inserted at amino acid position 591 of the capsid protein of an AAV8 serotype.

358. The AAV variant of embodiment 173, wherein a peptide comprising the amino acid sequence of any one of SEQ ID NO: 68-110 is inserted at amino acid position 591 of the capsid protein of an AAV8 serotype.

359. The AAV variant of embodiment 173, wherein a peptide comprising the amino acid sequence of any one of SEQ ID NO: 1-32 is inserted at amino acid position 266 of the capsid protein of an AAV9 serotype.

360. The AAV variant of embodiment 173, wherein a peptide comprising the amino acid sequence of any one of SEQ ID NO: 68-110 is inserted at amino acid position 266 of the capsid protein of an AAV9 serotype.

361. The AAV variant of embodiment 173, wherein a peptide comprising the amino acid sequence of any one of SEQ ID NO: 1-32 is inserted at amino acid position 455 of the capsid protein of an AAV9 serotype.

362. The AAV variant of embodiment 173, wherein a peptide comprising the amino acid sequence of any one of SEQ ID NO: 68-110 is inserted at amino acid position 455 of the capsid protein of an AAV9 serotype.

363. The AAV variant of embodiment 173, wherein a peptide comprising the amino acid sequence of any one of SEQ ID NO: 1-32 is inserted at amino acid position 589 of the capsid protein of an AAV9 serotype.

364. The AAV variant of embodiment 173, wherein a peptide comprising the amino acid sequence of any one of SEQ ID NO: 68-110 is inserted at amino acid position 589 of the capsid protein of an AAV9 serotype.

365. The AAV variant of any one of embodiments 359, 361, and 363, wherein the peptide comprises an amino acid sequence selected from the group consisting of any one of SEQ ID NO: 12 to SEQ ID NO: 18.

366. The AAV variant of any one of embodiments 360, 362, and 364, wherein the peptide comprises an amino acid sequence selected from the group consisting of any one of SEQ ID NO: 86 to SEQ ID NO: 89.

367. The AAV variant of any one of embodiments 360, 362, and 364, wherein the peptide comprises the sequence of SEQ ID NO: 89.

368. The AAV vector of embodiment 247, wherein a peptide comprising the amino acid sequence of any one of SEQ ID NO: 1-32 is inserted at amino acid position 590 of the capsid protein of an AAV1 serotype.

369. The AAV vector of embodiment 247, wherein a peptide comprising the amino acid sequence of any one of SEQ ID NO: 68-110 is inserted at amino acid position 590 of the capsid protein of an AAV1 serotype.

370. The AAV vector of embodiment 369, wherein the peptide comprises an amino acid sequence selected from the group consisting of any one of SEQ ID NO: 68 to SEQ ID NO: 75.

371. The AAV vector of embodiment 369, wherein the peptide comprises the amino acid sequence SEQ ID NO: 71.

372. The AAV vector of embodiment 368, wherein the peptide comprises an amino acid sequence selected from the group consisting of any one of SEQ ID NO: 1, SEQ ID NO: 2 and SEQ ID NO: 3.

373. The AAV vector of embodiment 247, wherein a peptide comprising the amino acid sequence of any one of SEQ ID NO: 1-32 is inserted at amino acid position 454 of the capsid protein of an AAV6 serotype.

374. The AAV vector of embodiment 247, wherein a peptide comprising the amino acid sequence of any one of SEQ ID NO: 68-110 is inserted at amino acid position 454 of the capsid protein of an AAV6 serotype.

375. The AAV vector of embodiment 247, wherein a peptide comprising the amino acid sequence of any one of SEQ ID NO: 1-32 is inserted at amino acid position 590 of the capsid protein of an AAV6 serotype.

376. The AAV vector of embodiment 247, wherein a peptide comprising the amino acid sequence of any one of SEQ ID NO: 68-110 is inserted at amino acid position 590 of the capsid protein of an AAV6 serotype.

377. The AAV vector of any one of embodiments 373 and 375, wherein the peptide comprises an amino acid sequence selected from the group consisting of any one of SEQ ID NO: 19 to SEQ ID NO: 27.

378. The AAV vector of embodiment 247, wherein a peptide comprising the amino acid sequence of any one of SEQ ID NO: 1-32 is inserted at amino acid position 588 of the capsid protein of an AAV2 serotype.

379. The AAV vector of embodiment 247, wherein a peptide comprising the amino acid sequence of any one of SEQ ID NO: 68-110 is inserted at amino acid position 588 of the capsid protein of an AAV2 serotype.

380. The AAV vector of embodiment 379, wherein the peptide comprises an amino acid sequence selected from the group consisting of any one of SEQ ID NO: 90 to SEQ ID NO: 110.

381. The AAV vector of embodiments 379, wherein the peptide comprises an amino acid sequence selected from the group consisting of any one of SEQ ID NO: 95, SEQ ID NO: 94, SEQ ID NO: 96, SEQ ID NO: 101, SEQ ID NO: 103, SEQ ID NO: 106, SEQ ID NO: 91 and SEQ ID NO: 102.

382. The AAV vector of embodiments 378, wherein the peptide comprises an amino acid sequence selected from the group consisting of any one of SEQ ID NO: 4-7.

383. The AAV vector of embodiment 247, wherein a peptide comprising the amino acid sequence of any one of SEQ ID NO: 1-32 is inserted at amino acid position 589 of the capsid protein of an AAV3B serotype.

384. The AAV vector of embodiment 247, wherein a peptide comprising the amino acid sequence of any one of SEQ ID NO: 68-110 is inserted at amino acid position 589 of the capsid protein of an AAV3B serotype.

385. The AAV vector of embodiment 384, wherein the peptide comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83.

386. The AAV vector of embodiment 383, wherein the peptide comprises an amino acid sequence selected from the group consisting of any one of SEQ ID NO: 8 to SEQ ID NO: 11.

387. The AAV vector of embodiment 247, wherein a peptide comprising the amino acid sequence of any one of SEQ ID NO: 1-32 is inserted at amino acid position 578 of the capsid protein of an AAV5 serotype.

388. The AAV vector of embodiment 247, wherein a peptide comprising the amino acid sequence of any one of SEQ ID NO: 68-110 is inserted at amino acid position 578 of the capsid protein of an AAV5 serotype.

389. The AAV vector of embodiment 387, wherein the peptide comprises an amino acid sequence selected from the group consisting of any one SEQ ID NO: 28 to SEQ ID NO: 32.

390. The AAV vector of embodiment 247, wherein a peptide comprising the amino acid sequence of any one of SEQ ID NO: 1-32 is inserted at amino acid position 591 of the capsid protein of an AAV8 serotype.

391. The AAV vector of embodiment 247, wherein a peptide comprising the amino acid sequence of any one of SEQ ID NO: 68-110 is inserted at amino acid position 591 of the capsid protein of an AAV8 serotype.

392. The AAV vector of embodiment 247, wherein a peptide comprising the amino acid sequence of any one of SEQ ID NO: 1-32 is inserted at amino acid position 266 of the capsid protein of an AAV9 serotype.

393. The AAV vector of embodiment 247, wherein a peptide comprising the amino acid sequence of any one of SEQ ID NO: 68-110 is inserted at amino acid position 266 of the capsid protein of an AAV9 serotype.

394. The AAV vector of embodiment 247, wherein a peptide comprising the amino acid sequence of any one of SEQ ID NO: 1-32 is inserted at amino acid position 455 of the capsid protein of an AAV9 serotype.

395. The AAV vector of embodiment 247, wherein a peptide comprising the amino acid sequence of any one of SEQ ID NO: 68-110 is inserted at amino acid position 455 of the capsid protein of an AAV9 serotype.

396. The AAV vector of embodiment 247, wherein a peptide comprising the amino acid sequence of any one of SEQ ID NO: 1-32 is inserted at amino acid position 589 of the capsid protein of an AAV9 serotype.

397. The AAV vector of embodiment 247, wherein a peptide comprising the amino acid sequence of any one of SEQ ID NO: 68-110 is inserted at amino acid position 589 of the capsid protein of an AAV9 serotype.

398. The AAV vector of any one of embodiments 392, 394, and 396, wherein the peptide comprises an amino acid sequence selected from the group consisting of any one of SEQ ID NO: 12 to SEQ ID NO: 18.

399. The AAV vector of any one of embodiments 393, 395, and 397, wherein the peptide comprises an amino acid sequence selected from the group consisting of any one of SEQ ID NO: 86 to SEQ ID NO: 89.

400. The AAV vector of any one of embodiments 393, 395, and 397, wherein the peptide comprises the sequence of SEQ ID NO: 89.

401. A capsid protein comprising an inserted peptide, wherein the peptide is inserted at
  (i) amino acid position 590 of an AAV1 capsid protein,
  (ii) amino acid position 454 or 590 of an AAV6 capsid protein,
  (iii) amino acid position 588 of an AAV2 capsid protein,
  (iv) amino acid position 589 of an AAV3B capsid protein,
  (v) amino acid position 578 of an AAV5 capsid protein,
  (vi) amino acid position 591 of the an AAV8 capsid protein, or
  (vi) amino acid position 266, 455, or 589 of an AAV9 capsid protein,
  wherein the positions correspond to the numbering of VP1 in the AAV serotype.

402. The capsid protein of embodiment 401, wherein a peptide comprising the amino acid sequence of any one of SEQ ID NO: 1-32 is inserted at amino acid position 590 of the capsid protein of an AAV1 serotype.

403. The capsid protein of embodiment 401, wherein a peptide comprising the amino acid sequence of any one of SEQ ID NO: 68-110 is inserted at amino acid position 590 of the capsid protein of an AAV1 serotype.

404. The capsid protein of embodiment 403, wherein the peptide comprises an amino acid sequence selected from the group consisting of any one of SEQ ID NO: 68 to SEQ ID NO: 75.

405. The capsid protein of embodiment 403, wherein the peptide comprises the amino acid sequence SEQ ID NO: 71.

406. The capsid protein of embodiment 402, wherein the peptide comprises an amino acid sequence selected from the group consisting of any one of SEQ ID NO: 1, SEQ ID NO: 2 and SEQ ID NO: 3.

407. The capsid protein of embodiment 401, wherein a peptide comprising the amino acid sequence of any one of SEQ ID NO: 1-32 is inserted at amino acid position 454 of the capsid protein of an AAV6 serotype.

408. The capsid protein of embodiment 401, wherein a peptide comprising the amino acid sequence of any one of SEQ ID NO: 68-110 is inserted at amino acid position 454 of the capsid protein of an AAV6 serotype.

409. The capsid protein of embodiment 401, wherein a peptide comprising the amino acid sequence of any one of SEQ ID NO: 1-32 is inserted at amino acid position 590 of the capsid protein of an AAV6 serotype.

410. The capsid protein of embodiment 401, wherein a peptide comprising the amino acid sequence of any one of SEQ ID NO: 68-110 is inserted at amino acid position 590 of the capsid protein of an AAV6 serotype.

411. The capsid protein of any one of embodiments 407 and 409, wherein the peptide comprises an amino acid sequence selected from the group consisting of any one of SEQ ID NO: 19 to SEQ ID NO: 27.

412. The capsid protein of embodiment 401, wherein a peptide comprising the amino acid sequence of any one of SEQ ID NO: 1-32 is inserted at amino acid position 588 of the capsid protein of an AAV2 serotype.

413. The capsid protein of embodiment 401, wherein a peptide comprising the amino acid sequence of any one of SEQ ID NO: 68-110 is inserted at amino acid position 588 of the capsid protein of an AAV2 serotype.

414. The capsid protein of embodiment 413, wherein the peptide comprises an amino acid sequence selected from the group consisting of any one of SEQ ID NO: 90 to SEQ ID NO: 110.

415. The capsid protein of embodiments 413, wherein the peptide comprises an amino acid sequence selected from the group consisting of any one of SEQ ID NO: 95, SEQ ID NO:

94, SEQ ID NO: 96, SEQ ID NO: 101, SEQ ID NO: 103, SEQ ID NO: 106, SEQ ID NO: 91 and SEQ ID NO: 102.

416. The capsid protein of embodiments 412, wherein the peptide comprises an amino acid sequence selected from the group consisting of any one of SEQ ID NO: 4-7.

417. The capsid protein of embodiment 401, wherein a peptide comprising the amino acid sequence of any one of SEQ ID NO: 1-32 is inserted at amino acid position 589 of the capsid protein of an AAV3B serotype.

418. The capsid protein of embodiment 401, wherein a peptide comprising the amino acid sequence of any one of SEQ ID NO: 68-110 is inserted at amino acid position 589 of the capsid protein of an AAV3B serotype.

419. The capsid protein of embodiment 418, wherein the peptide comprises an amino acid sequence selected from the group consisting of any one of SEQ ID NO: 78, SEQ ID NO: 80, SEQ ID NO: 77, SEQ ID NO: 79, SEQ ID NO: 76 and SEQ ID NO: 83.

420. The capsid protein of embodiment 417, wherein the peptide comprises an amino acid sequence selected from the group consisting of any one of SEQ ID NO: 8 to SEQ ID NO: 11.

421. The capsid protein of embodiment 401, wherein a peptide comprising the amino acid sequence of any one of SEQ ID NO: 1-32 is inserted at amino acid position 578 of the capsid protein of an AAV5 serotype.

422. The capsid protein of embodiment 401, wherein a peptide comprising the amino acid sequence of any one of SEQ ID NO: 68-110 is inserted at amino acid position 578 of the capsid protein of an AAV5 serotype.

423. The capsid protein of embodiment 421, wherein the peptide comprises an amino acid sequence selected from the group consisting of any one SEQ ID NO: 28 to SEQ ID NO: 32.

424. The capsid protein of embodiment 401, wherein a peptide comprising the amino acid sequence of SEQ ID NO: 1-32 is inserted at amino acid position 591 of the capsid protein of an AAV8 serotype.

425. The capsid protein of embodiment 401, wherein a peptide comprising the amino acid sequence of any one of SEQ ID NO: 68-110 is inserted at amino acid position 591 of the capsid protein of an AAV8 serotype.

426. The capsid protein of embodiment 401, wherein a peptide comprising the amino acid sequence of any one of SEQ ID NO: 1-32 is inserted at amino acid position 266 of the capsid protein of an AAV9 serotype.

427. The capsid protein of embodiment 401, wherein a peptide comprising the amino acid sequence of any one of SEQ ID NO: 68-110 is inserted at amino acid position 266 of the capsid protein of an AAV9 serotype.

428. The capsid protein of embodiment 401, wherein a peptide comprising the amino acid sequence of any one of SEQ ID NO: 1-32 is inserted at amino acid position 455 of the capsid protein of an AAV9 serotype.

429. The capsid protein of embodiment 401, wherein a peptide comprising the amino acid sequence of any one of SEQ ID NO: 68-110 is inserted at amino acid position 455 of the capsid protein of an AAV9 serotype.

430. The capsid protein of embodiment 401, wherein a peptide comprising the amino acid sequence of any one of SEQ ID NO: 1-32 is inserted at amino acid position 589 of the capsid protein of an AAV9 serotype.

431. The capsid protein of embodiment 401, wherein a peptide comprising the amino acid sequence of any one of SEQ ID NO: 68-110 is inserted at amino acid position 589 of the capsid protein of an AAV9 serotype.

432. The capsid protein of any one of embodiments 426, 428, and 430, wherein the peptide comprises an amino acid sequence selected from the group consisting of any one of SEQ ID NO: 12 to SEQ ID NO: 18.

433. The capsid protein of any one of embodiments 427, 429, and 431, wherein the peptide comprises an amino acid sequence selected from the group consisting of any one of SEQ ID NO: 86 to SEQ ID NO: 89.

434. The capsid protein of any one of embodiments 427, 429, and 431, wherein the peptide comprises the sequence of SEQ ID NO: 89.

435. A nucleic acid molecule encoding the capsid protein of any one of embodiments 401 to 434.

The invention claimed is:

1. An AAV capsid protein comprising at least 4 contiguous amino acids of an amino acid sequence set forth in any one of SEQ ID NO: 1-32 or at least 4 contiguous amino acids of an amino acid sequence set forth in any one of SEQ ID NO: 68-110.

2. The AAV capsid protein of claim 1, wherein the AAV capsid protein comprises serotype AAV1, AAV2, AAV3B, AAV5, AAV6, AAV8, AAV9, AAV3, AAV4, AAV7, AAV11, AAVrh10, AAVrh39, or AAVrh74.

3. The AAV capsid protein of claim 2, wherein the AAV capsid protein comprises serotype AAV2.

4. The AAV capsid protein of claim 3, wherein the AAV capsid comprises SEQ ID NO: 207.

5. The AAV capsid protein of claim 4, wherein the AAV capsid comprises SEQ ID NO: 90.

6. The AAV capsid protein of claim 5, wherein SEQ ID NO: 90 is inserted into SEQ ID NO: 207 at a hypervariable and/or surface exposed loop of the AAV capsid protein.

7. The AAV capsid protein of claim 6, wherein SEQ ID NO: 90 is inserted into SEQ ID NO: 207 at amino acid position 588.

8. The AAV capsid of claim 2, wherein SEQ ID NO: 90 is inserted into any one of the serotypes AAV1, AAV3B, AAV5, AAV6, AAV8, AAV9, AAV3, AAV4, AAV7, AAV11, AAVrh10, AAVrh39, and AAVrh74.

9. The AAV capsid of claim 8, wherein AAV1 comprises SEQ ID NO: 206, and wherein SEQ ID NO: 90 is inserted into serotype AAV1 at amino acid position 590.

10. The AAV capsid of claim 8, wherein AAV3b comprises SEQ ID NO: 208, and wherein SEQ ID NO: 90 is inserted into serotype AAV3b at amino acid position 589.

11. The AAV capsid of claim 8, wherein AAV5 comprises SEQ ID NO: 209, and wherein SEQ ID NO: 90 is inserted into serotype AAV5 at amino acid position 578.

12. The AAV capsid of claim 8, wherein AAV6 comprises SEQ ID NO: 210, and wherein SEQ ID NO: 90 is inserted into AAV6 serotype at amino acid position 454 or 590.

13. The AAV capsid protein of claim 8, wherein AAV8 comprises SEQ ID NO: 211, and wherein SEQ ID NO: 90 is inserted into AAV8 serotype at amino acid position 591.

14. The AAV capsid protein of claim 8, wherein AAV9 comprises SEQ ID NO: 212, and wherein SEQ ID NO: 90 is inserted into any one of amino acid positions 266, 455, or 589.

15. The AAV capsid of claim 3, wherein SEQ ID NO: 90 is inserted into serotype AAV2.

16. An AAV capsid protein, comprising an amino acid sequence set forth in any one of SEQ ID NO: 1-32 or in any one of SEQ ID NO: 68-110, wherein the amino acid sequence is inserted into the AAV capsid protein between amino acid positions 450 and 600.

17. The AAV capsid protein of claim 16, wherein the amino acid sequence is inserted into the AAV capsid protein at amino acid position 588.

18. The AAV capsid protein of claim 16, wherein the amino acid sequence comprises SEQ ID NO: 90.

19. The AAV capsid protein of claim 16, wherein the AAV capsid protein comprises serotype AAV1, AAV2, AAV3B, AAV5, AAV6, AAV8, AAV9, AAV3, AAV4, AAV7, AAV11, AAVrh10, AAVrh39, or AAVrh74.

20. An AAV capsid protein, comprising an amino acid sequence set forth in any one of SEQ ID NO: 1-32 or in any one of SEQ ID NO: 68-110, wherein the amino acid sequence is inserted into the AAV capsid protein at amino acid position 266, 454, 455, 578, 588, 589, 590, or 591.

* * * * *